(12) United States Patent
Guo et al.

(10) Patent No.: US 10,415,038 B2
(45) Date of Patent: Sep. 17, 2019

(54) COMPOUNDS AND METHODS FOR MODULATING TMPRSS6 EXPRESSION

(71) Applicant: Ionis Pharmaceuticals, Inc., Carlsbad, CA (US)

(72) Inventors: Shuling Guo, Carlsbad, CA (US); Mariam Aghajan, San Diego, CA (US); Eric E. Swayze, Encinitas, CA (US)

(73) Assignee: Ionis Pharmaceuticals, Inc., Carlsbad, CA (US)

(*) Notice: Subject to any disclaimer, the term of this patent is extended or adjusted under 35 U.S.C. 154(b) by 52 days.

(21) Appl. No.: 15/562,843

(22) PCT Filed: Apr. 4, 2016

(86) PCT No.: PCT/US2016/025883
§ 371 (c)(1),
(2) Date: Sep. 28, 2017

(87) PCT Pub. No.: WO2016/161429
PCT Pub. Date: Oct. 6, 2016

(65) Prior Publication Data
US 2018/0105817 A1    Apr. 19, 2018

Related U.S. Application Data

(60) Provisional application No. 62/142,986, filed on Apr. 3, 2015.

(51) Int. Cl.
*C12N 15/113* (2010.01)
*A61K 47/54* (2017.01)
*A61P 7/06* (2006.01)
*A61P 7/00* (2006.01)
*C07H 21/00* (2006.01)
*C12N 5/00* (2006.01)

(52) U.S. Cl.
CPC ........ *C12N 15/1137* (2013.01); *A61K 47/549* (2017.08); *A61P 7/00* (2018.01); *A61P 7/06* (2018.01); *C07H 21/00* (2013.01); *C12N 15/113* (2013.01); *C12N 15/1138* (2013.01); *C12Y 304/21109* (2013.01); *C12N 2310/11* (2013.01); *C12N 2310/14* (2013.01); *C12N 2310/315* (2013.01); *C12N 2310/321* (2013.01); *C12N 2310/3231* (2013.01); *C12N 2310/334* (2013.01); *C12N 2310/341* (2013.01); *C12N 2310/351* (2013.01); *C12N 2310/3525* (2013.01); *C12N 2310/3527* (2013.01)

(58) Field of Classification Search
None
See application file for complete search history.

(56) References Cited

U.S. PATENT DOCUMENTS

| | | |
|---|---|---|
| 5,801,154 A | 9/1998 | Baracchini et al. |
| 6,268,490 B1 | 7/2001 | Imanishi et al. |
| 6,525,191 B1 | 2/2003 | Ramasamy |
| 6,582,908 B2 | 6/2003 | Fodor et al. |
| 6,670,461 B1 | 12/2003 | Wengel et al. |
| 6,770,748 B2 | 8/2004 | Imanishi et al. |
| 6,794,499 B2 | 9/2004 | Wengel et al. |
| 7,034,133 B2 | 4/2006 | Wengel et al. |
| 7,053,207 B2 | 5/2006 | Wengel |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,547,684 B2 | 6/2009 | Seth et al. |
| 7,691,997 B2 | 4/2010 | Khvorova et al. |
| 7,696,345 B2 | 4/2010 | Allerson et al. |
| 7,777,022 B2 | 8/2010 | Bentwich et al. |
| 7,834,170 B2 | 11/2010 | Khvorova et al. |
| 7,888,497 B2 | 2/2011 | Bentwich et al. |
| 8,090,542 B2 | 1/2012 | Khvorova et al. |
| 8,106,022 B2 | 1/2012 | Manoharan et al. |
| 8,178,503 B2 | 5/2012 | Rigoutsos et al. |
| 8,501,805 B2 | 8/2013 | Seth et al. |
| 8,530,640 B2 | 9/2013 | Seth et al. |
| 8,546,556 B2 | 10/2013 | Seth et al. |
| 9,175,290 B2 | 11/2015 | Bumcrot et al. |
| 9,725,722 B2 * | 8/2017 | Guo .................... C12Y 304/21 |
| 9,783,806 B2 | 10/2017 | Butler et al. |

(Continued)

FOREIGN PATENT DOCUMENTS

| WO | WO 2016/137923 | 9/1916 |
|---|---|---|
| WO | WO 1998/039352 | 9/1998 |

(Continued)

OTHER PUBLICATIONS

Adams et al., "Hemochromatosis and iron-overload screening in a racially diverse population." N Engl. J. Med. (2005) 352(17): 1769-1778.

(Continued)

*Primary Examiner* — Sean McGarry
(74) *Attorney, Agent, or Firm* — Grant IP, Inc.

(57) ABSTRACT

Disclosed herein are compositions and compounds comprising modified oligonucleotides for modulating TMPRSS6 and modulating an iron accumulation disease, disorder and/or condition in an individual in need thereof. Iron accumulation diseases in an individual such as polycythemia, hemochromatosis or β-thalassemia can be treated, ameliorated, delayed or prevented with the administration of antisense compounds targeted to TMPRSS6.

29 Claims, No Drawings
Specification includes a Sequence Listing.

(56) References Cited

U.S. PATENT DOCUMENTS

| | | | |
|---|---|---|---|
| 9,885,047 B2* | 2/2018 | Guo | C12Y 304/21 |
| 2001/0053519 A1 | 12/2001 | Fodor et al. | |
| 2003/0228597 A1 | 12/2003 | Cowsert et al. | |
| 2004/0171570 A1 | 9/2004 | Allerson et al. | |
| 2005/0054027 A1 | 3/2005 | Harris et al. | |
| 2005/0130923 A1 | 6/2005 | Bhat et al. | |
| 2007/0031844 A1 | 2/2007 | Khvorova et al. | |
| 2007/0134655 A1 | 6/2007 | Bentwich | |
| 2008/0039618 A1 | 2/2008 | Allerson et al. | |
| 2009/0012281 A1 | 1/2009 | Swayze et al. | |
| 2010/0184643 A1 | 7/2010 | Goldfarb et al. | |
| 2011/0152351 A1 | 6/2011 | Pandey et al. | |
| 2012/0087862 A1 | 4/2012 | Hood et al. | |
| 2014/0106981 A1 | 4/2014 | Hood et al. | |
| 2014/0194489 A1 | 7/2014 | Bumcrot et al. | |
| 2014/0309286 A1 | 10/2014 | Guo | |
| 2015/0232836 A1 | 8/2015 | Krieg et al. | |
| 2016/0145626 A1 | 5/2016 | Butler et al. | |
| 2016/0145629 A1 | 5/2016 | Butler et al. | |

FOREIGN PATENT DOCUMENTS

| | | |
|---|---|---|
| WO | WO 1999/014226 | 3/1999 |
| WO | WO 2003/004602 | 1/2003 |
| WO | WO 2004/106356 | 12/2004 |
| WO | WO 2005/021570 | 3/2005 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2011/085271 | 7/2011 |
| WO | WO 2012/135246 | 10/2012 |
| WO | WO 2013/070786 | 5/2013 |
| WO | WO 2013/173635 | 11/2013 |
| WO | WO 2014/179620 | 11/2014 |
| WO | WO 2014/179625 | 11/2014 |
| WO | WO 2014/190157 | 11/2014 |
| WO | WO 2015/021457 | 2/2015 |

OTHER PUBLICATIONS

Ahmad et al., "Decreased liver hepcidin expression in the Hfe knockout mouse." Blood Cells Mol Dis. (2002) 29(3): 361-366.

Albaek et al., "Analogues of a Locked Nucleic Acid with Three-Carbon 2',4'-Linkages: Synthesis by Ring-Closing Metathesis and Influence on Nucleic Acid Duplex Stability and Structure" J. Org. Chem. (2006) 71: 7731-7740.

Allen et al., "Iron-Overload—Related Disease in HFE Hereditary Hemochromatosis" N. Engl. J. Med. (2008) 358(3): 221-230.

Altmann et al., "Second-generation antisense oligonucleotides: structure-activity relationships and the design of improved signal-transduction inhibitors" Biochem Soc Trans. (1996) 24: 630-637.

Altmann et al., "Second Generation of Antisense Oligonucleotides: From Nuclease Resistance to Biological Efficacy in Animals" Chimia (1996) 50: 168-176.

Altmann et al., "Second Generation Antisense Oligonucleotides—Inhibition of PKC-α and c-raf Kinase Expression by Chimeric Oligonucleotides Incorporating 6"-Substituted Carbocyclic Nucleosides and 2"-O-Ethylene Glycol Substituted Ribonucleosides" Nucleosides Nucleotides (1997) 16(7-9): 917-926.

Andrews, "Disorders of Iron Metabolism" N Engl J Med (1999) 341: 1986-1995.

Andriopoulos et al., "BMP6 is a key endogenous regulator of hepcidin expression and iron metabolism" Nat Genet. (2009) 41: 482-487.

Babitt et al., "Bone morphogenetic protein signaling by hemojuvelin regulates hepcidin expression" Nat Genet. (2006) 38(5): 531-539.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J Biol Chem. (1997) 272: 11944-12000.

Bennett et al., "RNA targeting therapeutics: molecular mechanisms of antisense oligonucleotides as a therapeutic platform." Annu Rev Pharmacol Toxicol. (2010) 50: 259-293.

Bennett et al., "Antisense oligonucleotides as a tool for gene functionalization and target validation.", Biochimica et Biophysica Acta (1999) 1489:19-30.

Braasch et al., "Locked nucleic acid (LNA): fine-tuning the recognition of DNA and RNA" Chem. Biol. (2001) 8:1-7.

Branch et al., "A good antisense molecule is hard to find," TIBS (1998) 23:45-50.

Brissot et al., "Current approaches to the management of hemochromatosis." Hematology Am Soc Hematol Educ Program. (2006) 36-41.

Camaschella, "Understanding iron homeostasis through genetic analysis of hemochromatosis and related disorders" Blood (2005) 106(12): 3710-3717.

Camaschella et al., "Rare Types of Genetic Hemochromatosis" Acta Haematol (2009) 122(2-3): 140-145.

Carroll et al., "Hereditary hemochromatosis is characterized by a clinically definable arthropathy that correlates with iron load." Arthritis Rheum. (2011) 63(1): 286-294.

Chen et al., "Resolving the distinct stages in erythroid differentiation based on dynamic changes in membrane protein expression during erythropoiesis." PNAS (2009) 106(41): 17413-17418.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Ciavatta et al., "Mouse model of human beta zero thalassemia: targeted deletion of the mouse beta maj- and beta min-globin genes in embryonic stem cells" PNAS (1995) 92(20): 9259-9263.

Corradini et al., "BMP6 treatment compensates for the molecular defect and ameliorates hemochromatosis in Hfe knockout mice." Gastroenterology (2010) 139(5): 1721-1729.

Cox et al., "Posttranscriptional regulation of chimeric human transferrin genes by iron." Biochemistry (1993) 32(18): 4738-4745.

Crooke et al., "Basic Principles of Antisense Therapeutics" Antisense Research and Application (1998) Chapter 1:1-50.

Du et al., "The serine protease TMPRSS6 is required to sense iron deficiency." Science (2008) 320(5879): 1088-1092.

Elayadi et al., "Application of PNA and LNA oligomers to chemotherapy" Curr. Opinion Invens. Drugs (2001) 2:558-561.

Enns et al., "Neogenin interacts with matriptase-2 to facilitate hemojuvelin cleavage." J Biol Chem. (2012) 287(42): 35104-35117.

Feder et al., "A novel MHC class I-like gene is mutated in patients with hereditary haemochromatosis." Nat Genet. (1996) 13(4): 399-408.

Feder et al., "The hemochromatosis founder mutation in HLA-H disrupts beta2-microglobulin interaction and cell surface expression." J Biol Chem. (1997) 272(22): 14025-14028.

Finberg et al., "Mutations in TMPRSS6 cause iron-refractory iron deficiency anemia (IRIDA)." Nat Genet. (2008) 40(5): 569-571.

Finberg et al., "Tmprss6 is a genetic modifier of the Hfe-hemochromatosis phenotype in mice." Blood (2011) 117(17): 4590-4599.

Finberg et al., "Tmprss6, an inhibitor of hepatic Bmp/Smad signaling, is required for Hepcidin suppression and iron loading in a mouse model of beta-thalassemia" Blood (ASH Annual Meeting Abstracts) 2010 (116) Oral Session: Abstract #164.

Finberg et al., "Down-regulation of Bmp/Smad signaling by Tmprss6 is required for maintenance of systemic iron homeostasis." Blood (2010) 115(18): 3817-3826.

Finch et al., "Perspectives in iron metabolism." N Engl J Med. (1982) 306(25): 1520-1528.

Freier et al., "The ups and downs of nucleic acid duplex stability: structure-stability studies on chemically-modified DNA:RNA duplexes" Nucleic Acids Research (1997) 25(22):4429-4443.

Frieden et al., "Expanding the design horizon of antisense oligonucleotides with alpha-L-LNA" Nucleic Acids Research (2003) 31(21):6365-6372.

(56) References Cited

OTHER PUBLICATIONS

Ganz, "Hepcidin and its role in regulating systemic iron metabolism." Hematology Am Soc Hematol Educ Program. (2006) 507: 29-35.
Ganz et al., "Hepcidin and disorders of iron metabolism." Annu Rev Med. (2011) 62: 347-360.
Gardenghi et al., "Increased Hepcidin Expression in Mice Affected by β-Thalassemia Reduces Iron Overload with No Effect on Anemia." Blood (ASH Annual Meeting Abstracts) (2008) 112: Abstract 128.
Gardenghi et al., "Hepcidin as a therapeutic tool to limit iron overload and improve anemia in β-thalassemic mice." J Clin Invest. (2010) 120(12): 4466-4477.
Gardenghi et al., "Anemia, ineffective erythropoiesis, and hepcidin: interacting factors in abnormal iron metabolism leading to iron overload in β-thalassemia." Hematol Oncol Clin North Am. (2010) 24(6): 1089-1107.
Gautschi et al., "Activity of a Novel bcl-2/bcl-xL-Bispecific Antisense Oligonucleotide Against Tumors of Diverse Histologic Origins" J Natl Cancer Inst. (2001) 93(6): 463-471.
Ginzburg et al., "β-thalassemia: a model for elucidating the dynamic regulation of ineffective erythropoiesis and iron metabolism" Blood (2011) 118(16): 4321-4330.
Guo et al., "Reducing TMPRSS6 ameliorates hemochromatosis and β-thalassemia in mice" J Clin Invest. (2013) 123(4): 1531-1541.
Hooper et al., "Mouse matriptase-2: identification, characterization and comparative mRNA expression analysis with mouse hepsin in adult and embryonic tissues." Biochem J. (2003) 373(pt 3): 689-702.
Huang et al., "A mouse model of juvenile hemochromatosis." J Clin Invest. (2005) 115(8): 2187-2191.
Huang et al., "Iron overload and diabetes risk: a shift from glucose to Fatty Acid oxidation and increased hepatic glucose production in a mouse model of hereditary hemochromatosis." Diabetes (2011) 60(1): 80-87.
Kawabata et al., "Expression of hepcidin is down-regulated in TfR2 mutant mice manifesting a phenotype of hereditary hemochromatosis." Blood (2005) 105(1): 376-381.
Kemna et al., "Mass spectrometry-based hepcidin measurements in serum and urine: analytical aspects and clinical implications." Clin Chem. (2007) 53(4): 620-628.
Koshkin et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition" Tetrahedron (1998) 54: 3607-3630.
Krause et al., "LEAP-1, a novel highly disulfide-bonded human peptide, exhibits antimicrobial activity." FEBS Lett. (2000) 480(2-3): 147-150.
Kumar et al., "The first analogues of LNA (locked nucleic acids): phosphorothioate-LNA and 2'-thio-LNA." Bioorg. Med. Chem. Lett. (1998) 8(16): 2219-2222.
Leumann et al., "DNA Analogues: From Supramolecular Principles to Biological Properties" Bioorganic & Medicinal Chemistry (2002) 10:841-854.
Li et al., "Transferrin therapy ameliorates disease in beta-thalassemic mice." Nat Med. (2010) 16(2): 177-182.
Libani et al., "Decreased differentiation of erythroid cells exacerbates ineffective erythropoiesis in beta-thalassemia." Blood (2008) 112(3): 875-885.
Maher et al., "Comparative hybrid arrest by tandem antisense oligodeoxyribonucleotides or oligodeoxyribonucleoside methylphosphonates" Nuc Acid Res. (1988) 16(8): 3341-3358.
Martin et al., "Ein neuer Zugang zu 2'-O-Alkylribonucleosiden und Eigenschaften deren Oligonucleotide" Helv Chim Acta (1995) 78: 486-504.
Maxson et al., "Matriptase-2- and proprotein convertase-cleaved forms of hemojuvelin have different roles in the down-regulation of hepcidin expression." J Biol Chem. (2010) 285(50): 39021-39028.
Melis et al., "A mutation in the TMPRSS6 gene, encoding a transmembrane serine protease that suppresses hepcidin production, in familial iron deficiency anemia refractory to oral iron" Hematologica (2008) 93(10): 1473-1479.
Nai et al., "Deletion of TMPRSS6 attenuates the phenotype in a mouse model of β-thalassemia." Blood (2012) 119(21): 5021-5029.
Nemeth et al., "Regulation of iron metabolism by hepcidin." Annu Rev Nutr. (2006) 26: 323-342.
Nemeth et al., "Hepcidin regulates cellular iron efflux by binding to ferroportin and inducing its internalization." Science (2004) 306(5704): 2090-2093.
New England Biolabs 1998/99 Catalog (cover page and pp. 121 and 284).
Niederkofler et al., "Hemojuvelin is essential for dietary iron sensing, and its mutation leads to severe iron overload." J Clin Invest. (2005) 115(8): 2180-2186.
Nyblom et al., "High AST/ALT ratio may indicate advanced alcoholic liver disease rather than heavy drinking" Alcohol & Alcoholism (2004) 39(4): 336-339.
Orum et al., "Locked nucleic acids: A promising molecular family for gene-function analysis and antisense drug development" Curr. Opinion Mol. Ther. (2001) 3:239-243.
Papanikolaou et al., "Mutations in HFE2 cause iron overload in chromosome 1q-linked juvenile hemochromatosis." Nat. Genet. (2004) 36(1): 77-82.
Park et al., "Hepcidin, a urinary antimicrobial peptide synthesized in the liver." J Biol Chem. (2001) 276(11): 7806-7810.
Parrow et al., "Prospects for a hepcidin mimic to treat β-thalassemia and hemochromatosis." Expert Rev Hematol. (2011) 4(3): 233-235.
Pietrangelo, "Non-HFE hemochromatosis." Semin Liver Dis. (2005) 25(4): 450-460.
Pippard et al., "Iron absorption and loading in beta-thalassaemia intermedia." Lancet. (1979) 2(8147): 819-821.
Preza et al., "Minihepcidins are rationally designed small peptides that mimic hepcidin activity in mice and may be useful for the treatment of iron overload." J Clin Invest. (2011) 121(12): 4880-4888.
Quistorff et al., "Preparation of isolated rat liver hepatocytes." Methods Mol Biol. (1990) 5: 151-160.
Rajeev, "Conjugation Strategies for In Vitro siRNA Delivery" 8th Annual Meeting of the Oligonucleotide Therapeutics Society (2012).
Ramm et al., "Iron homeostasis, hepatocellular injury, and fibrogenesis in hemochromatosis: the role of inflammation in a noninflammatory liver disease." Semin Liver Dis. (2010) 30(3): 271-287.
Ramos et al., "Enhanced erythropoiesis in Hfe-KO mice indicates a role for Hfe in the modulation of erythroid iron homeostasis." Blood (2011) 117(4): 1379-1389.
Ramos et al., "Minihepcidins prevent iron overload in a hepcidin-deficient mouse model of severe hemochromatosis." Blood (2012) 120(18): 3829-3836.
Ramsay et al. "Matriptase-2 (TMPRSS6): a proteolytic regulator of iron homeostasis." Haematologica (2009) 94(6): 840-849.
Reynolds et al., "Rational siRNA design for RNA interference" Nature Biotechnology (2004) 22(3):326-330.
Rivella, "Ineffective erythropoiesis and thalassemias." Curr Opin Hematol. (2009) 16(3): 187-194.
Rivella, "The role of ineffective erythropoiesis in non-transfusion-dependent thalassemia." Blood Rev. (2012) 26 Suppl 1: S12-15.
Roy et al., "Hepcidin antimicrobial peptide transgenic mice exhibit features of the anemia of inflammation." Blood (2007) 109(9): 4038-4044.
Sanghvi et al., "Heterocyclic Base Modifications in Nucleic Acids and Their Applications in Antisense Oligonucleotides" Antisense Research and Applications (1993) pp. 273-288.
Schmidt et al., "An RNAi therapeutic targeting Tmprss6 decreases iron overload in Hfe(−/−) mice and ameliorates anemia and iron overload in murine β-thalassemia intermedia." Blood. (2013) 121(7): 1200-1208.
Siek et al., "Direct serum total iron-binding capacity assay suitable for automated analyzers." Clin. Chem. (2002) 48(1): 161-166.
Silvestri et al., "The serine protease matriptase-2 (TMPRSS6) inhibits hepcidin activation by cleaving membrane hemojuvelin." Cell Metab. (2008) 8(6): 502-511.

(56) References Cited

OTHER PUBLICATIONS

Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.
Singh et al, "A Review of Antisense Therapeutic Interventions for Molecular Biological Targets in Various Diseases" Int'l Journal of Pharmacology (2011) 7(3):294-315.
Sisay et al., "Identification of the first low-molecular-weight inhibitors of matriptase-2" J Med Chem. (2010) 53(15): 5523-5535.
Spasic et al., "Hfe acts in hepatocytes to prevent hemochromatosis." Cell Metab. (2008) 7(2): 173-178.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Taher et al., "Recent advances and treatment challenges in patients with non-transfusion-dependent thalassemia." Blood Rev. (2012) 26 Suppl 1:S1-2.
Taher et al., "Contemporary approaches to treatment of beta-thalassemia intermedia." Blood Rev. (2012) 26 Suppl 1:S24-27.
Tanno et al., "Iron Loading and Overloading due to Ineffective Eryhtropoiesis" Adv Hematol. (2010) Article ID 358283, 1-8.
Velasco et al., "Matriptase-2, a membrane-bound mosaic serine proteinase predominantly expressed in human liver and showing degrading activity against extracellular matrix proteins." J. Biol. Chem. (2002) 277(40): 37637-37646.
Wahlestedt et al., "Potent and nontoxic antisense oligonucleotides containing locked nucleic acids." PNAS (2000) 97(10): 5633-5638.
Weatherall, "The definition and epidemiology of non-transfusion-dependent thalassemia." Blood Rev. (2012) 26 Suppl 1: S3-6.
Woolf et al., "Specificity of antisense oligonucleotides in vivo." PNAS (1992) 89(16): 7305-7309.
Yamanishi et al., "Total Iron-binding Capacity Calculated from Serum Transferrin Concentration or Serum Iron Concentration and Unsaturated Iron-binding Capacity" Clin. Chem. (2003) 49: 175-178.
Yang et al., "A mouse model for beta 0-thalassemia." PNAS (1995) 92(25): 11608-11612.
Zhou et al., "Fine tuning of electrostatics around the internucleotidic phosphate through incorporation of modified 2',4'-carbocyclic-LNAs and -ENAs leads to significant modulation of antisense properties." J. Org. Chem. (2009) 74(1): 118-134.
Zhou et al., "HFE gene knockout produces mouse model of hereditary hemochromatosis" PNAS (1998) 95: 2492-2497.
European Search Report for application EP 12847024.2 dated May 8, 2015.
International Search Report for application PCT/US12/63970 dated Apr. 19, 2013.
EP Search Report for 16774409.3 dated Oct. 25, 2018.

\* cited by examiner

COMPOUNDS AND METHODS FOR MODULATING TMPRSS6 EXPRESSION

SEQUENCE LISTING

The present application is being filed along with a Sequence Listing in electronic format. The Sequence Listing is provided as a file entitled BIOL0271USASEQ_ST25.txt created Sep. 19, 2017, which is 148 kb in size. The information in the electronic format of the sequence listing is incorporated herein by reference in its entirety.

FIELD OF THE INVENTION

The present invention provides methods, compounds, and compositions for modulating TMPRSS6 expression for the purpose of reducing iron accumulation in an animal.

BACKGROUND OF THE INVENTION

Maintenance of iron balance in human beings is delicate because of the limited capacity of the human physiology for iron absorption and excretion (Finch, C. A. and Huebers, H. N. Engl. J. Med. 1982. 306: 1520-1528). Iron deficiency is a widespread disorder and results from any condition in which dietary iron intake does not meet the body's demands. Often, pathological blood loss contributes to negative iron balance. Iron overload is also a common condition, and may result from a genetic cause, for example, mutations of different genes of iron metabolism (Camaschella, C. Blood. 2005. 106: 3710-3717). The hepatic peptide hormone, hepcidin plays a key role in body iron metabolism as it controls iron absorption and recycling (Ganz, T. Am. Soc. Hematol. Educ. Program 2006. 507: 29-35; Kemna, E. H. et al., Clin. Chem. 2007. 53: 620-628). Several proteins, including HFE (hemochromatosis protein) (Ahmad, K. A. et al., Blood Cells Mol Dis. 2002. 29: 361), transferrin receptor 2 (Kawabata, H. et al., Blood 2005. 105: 376), and hemojuvelin (Papanikolaou, G. et al., Nat. Genet. 2004. 36: 77) also regulate the body's iron levels.

Transmembrane protease, serine 6 (TMPRSS6) is a type II transmembrane serine protease and is expressed primarily in the liver (Velasco, G. et al., J. Biol. Chem. 2002. 277: 37637-37646). Mutations in TMPRSS6 have been implicated in iron deficiency anemia (Finberg, K. E. et al., Nat. Genet. 2008. 40: 569-571), where the level of hepcidin was found to be unusually elevated. A study of a human population with microcytic anemia found that loss-of-function mutations in the TMPRSS6 gene lead to overproduction of hepcidin, which, in turn, lead to defective iron absorption and utilization (Melis, M. A. et al., Hematologica 2008. 93: 1473-1479). TMPRSS6 participates in a transmembrane signaling pathway triggered by iron deficiency and suppresses diverse pathways of Hamp activation, the gene that encodes hepcidin (Du, X. et al., Science 2008. 320: 1088-1092). Heterozygous loss of TMPRSS6 in HFE$^{-/-}$ mice reduces systemic iron overload, while homozygous loss of TMPRSS6 in HFE$^{-/-}$ mice causes systemic iron deficiency and elevated hepatic expression of hepcidin (Finberg, K. E. et al., Blood 2011. 117: 4590-4599).

An example of an iron overload disorder is Hemochromatosis. Hemochromatosis (e.g. hemochromatosis type 1 or hereditary hemochromatosis) is a disorder that results in excess intestinal absorption of dietary iron from the gastrointestinal tract (Allen, K. J. et al., N. Engl. J. Med. 2008. 358: 221-230). This results in a pathological increase in total body iron stores. Excess iron accumulates in tissues and organs, particularly the liver, adrenal glands, heart, skin, gonads, joints and pancreas, and disrupt their normal function. Secondary complications, such as cirrhosis (Ramm, G. A. and Ruddell, R. G. Semin. Liver Dis. 2010. 30: 271-287), polyarthropathy (Carroll, G. J. et al., Arthritis Rheum. 2011. 63: 286-294), adrenal insufficiency, heart failure and diabetes (Huang, J. et al., Diabetes 2011. 60: 80-87) are common. Another example of an iron overload disorder is β-thalassemia, where patients can develop iron overload caused by ineffective erythropoiesis or transfusions to treat β-thalassemia.

To date, therapeutic strategies to treat iron overload disorders have been limited. Nucleic acid inhibitors such as siRNA and antisense oligonucleotides have been suggested or developed, but none of the compounds directly targeting TMPRSS6 (PCT Publications WO2014/076195, WO2012/135246, WO2014/190157, WO2005/0032733, WO 2013/070786 and WO2013/173635; U.S. Pat. No. 8,090,542; Schmidt et al. Blood. 2013, 121 (7):1200-8) have been approved for treating iron overload disorders. Accordingly, there is an unmet need for highly potent and tolerable compounds to inhibit TMPRSS6. The invention disclosed herein relates to the discovery of novel, highly potent inhibitors of TMPRSS6 expression and their use in treatment.

All documents, or portions of documents, cited in this application, including, but not limited to, patents, patent applications, articles, books, and treatises, are hereby expressly incorporated-by-reference for the portions of the document discussed herein, as well as in their entirety.

SUMMARY OF THE INVENTION

Provided herein are compositions, compounds and methods for modulating the levels of TMPRSS6 mRNA and/or protein in an animal. Provided herein are compositions, compounds and methods for lowering TMPRSS6 levels.

Certain embodiments disclosed herein provide a compound comprising a modified oligonucleotide targeting a nucleic acid sequence encoding TMPRSS6. In certain embodiments, the compound targets a TMPRSS6 sequence as shown in the nucleobase sequences of any of SEQ ID NOs: 1-6.

Certain embodiments disclosed herein provide a compound comprising a modified oligonucleotide consisting of 12 to 30 linked nucleosides and comprising a nucleobase sequence comprising a portion of at least 8 contiguous nucleobases complementary to an equal length portion of nucleobases 3162 to 3184 of SEQ ID NO: 1, wherein the nucleobase sequence of the modified oligonucleotide is at least 80% complementary to SEQ ID NO: 1.

Certain embodiments disclosed herein provide a compound comprising a modified oligonucleotide consisting of 12 to 30 linked nucleosides and having a nucleobase sequence comprising at least 8 contiguous nucleobases of any of the nucleobase sequences of SEQ ID NOs: 23, 36, 37, 63, 77.

Certain embodiments disclosed herein provide a compound comprising a modified oligonucleotide with the following formula:

3
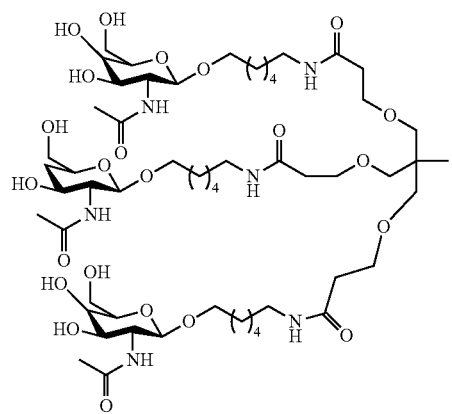
4
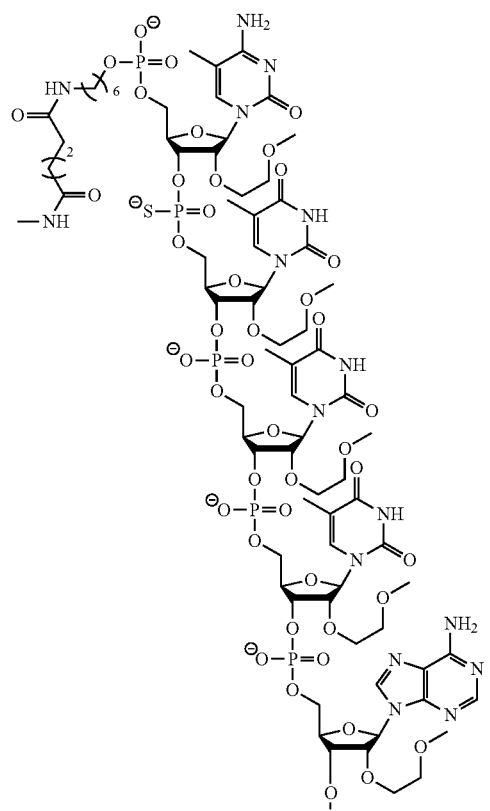
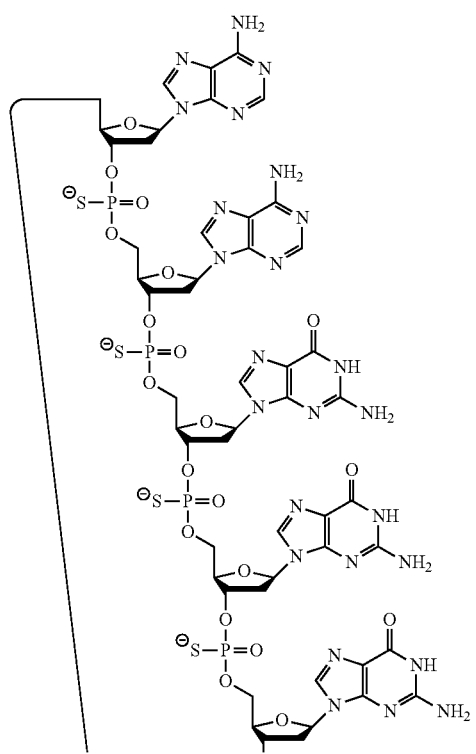

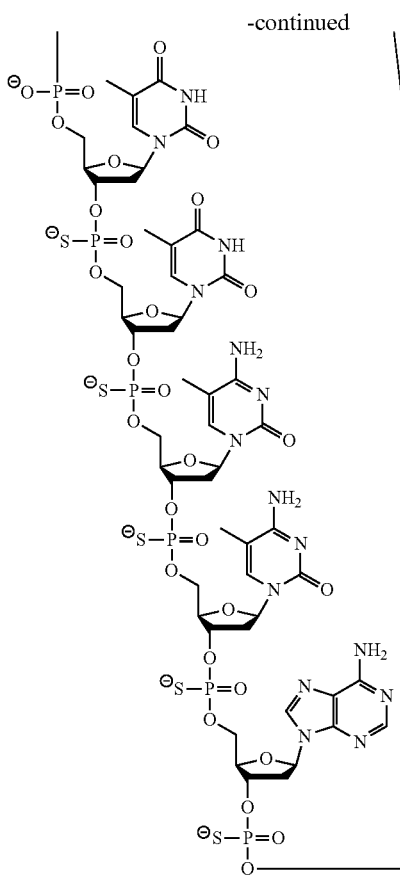
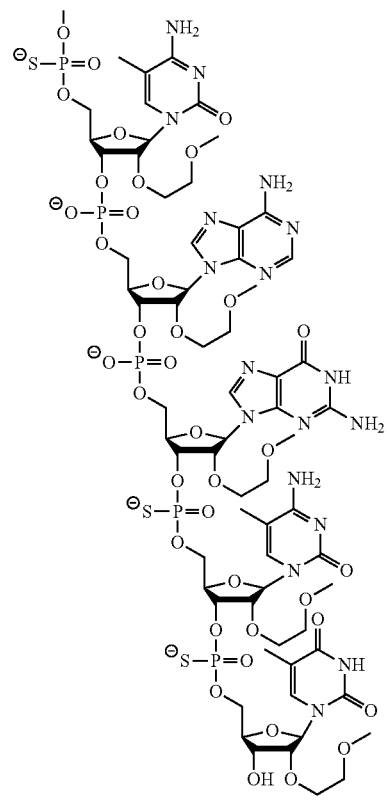
Certain embodiments disclosed herein provide a compound comprising a modified oligonucleotide with the following formula:
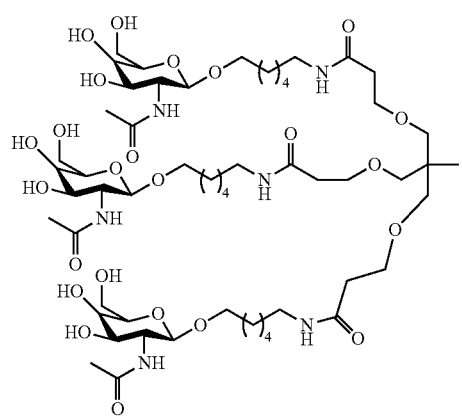

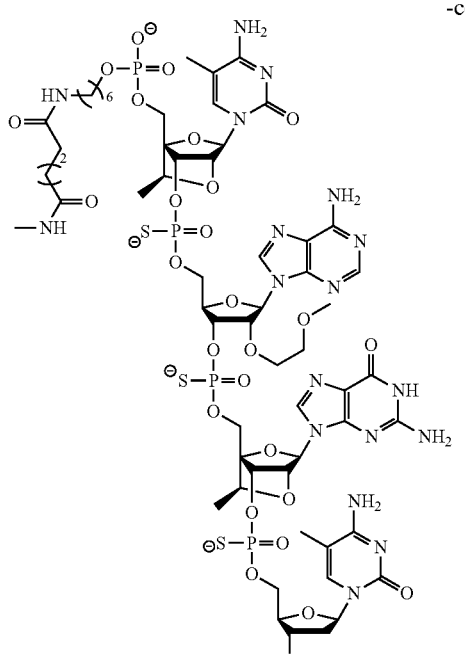
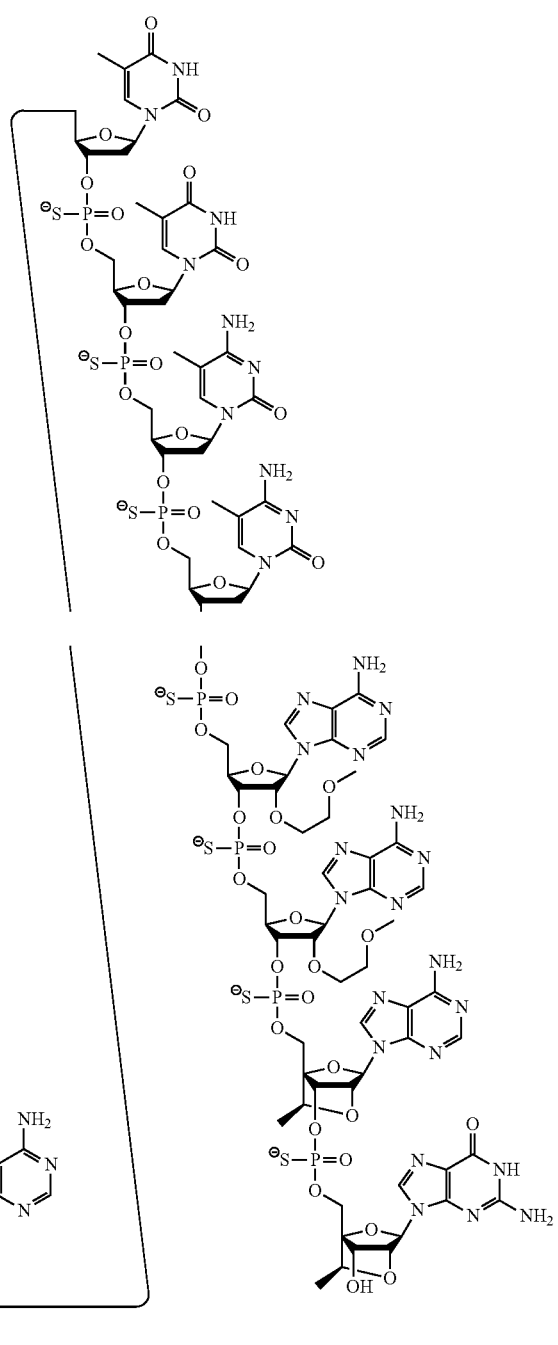

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"5-methylcytosine" means a cytosine modified with a methyl group attached to the 5' position. A 5-methylcytosine is a modified nucleobase.

"About" means within ±10% of a value. For example, if it is stated, "a marker may be increased by about 50%", it is implied that the marker may be increased between 45%-55%.

"Active pharmaceutical agent" or "Pharmaceutical agent" means the substance or substances in a pharmaceutical composition that provide a therapeutic benefit when administered to an individual. For example, in certain embodiments, an antisense oligonucleotide targeted to TMPRSS6 is an active pharmaceutical agent.

"Active target region" or "target region" means a region to which one or more active antisense compounds is targeted.

"Active antisense compounds" means antisense compounds that reduce target nucleic acid levels or protein levels.

"Administered concomitantly" refers to the co-administration of two agents in any manner in which the pharmacological effects of both are manifest in the patient time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to administering by a medical professional and self-administering.

"Agent" means an active substance that can provide a therapeutic benefit when administered to an animal. "First Agent" means a therapeutic compound provided herein. For example, a first agent is an antisense oligonucleotide targeting TMPRSS6. "Second agent" means a second therapeutic compound described herein. For example, a second agent can be a second antisense oligonucleotide targeting TMPRSS6 or a non-TMPRSS6 target. Alternatively, a second agent can be a compound other than an antisense oligonucleotide.

"Amelioration" or "ameliorate" refers to a lessening of at least one indicator, marker, sign, or symptom of an associated disease, disorder and/or condition. In certain embodiments, amelioration includes a delay or slowing in the progression of one or more indicators of a condition, disorder and/or disease. The severity of indicators may be determined by subjective or objective measures, which are known to those skilled in the art.

"Anemia" is a disease characterized by a lower than normal number of red blood cells (erythrocytes) in the blood, usually measured by a decrease in the amount of hemoglobin. The cause of anemia can include chronic inflammation, chronic kidney disease, kidney dialysis treatment, genetic (hereditary) disorders, chronic infection, acute infection, cancer and cancer treatments. Altered iron homeostasis and/or erythropoiesis in these diseases, disorders and/or conditions can also result in decreased erythrocyte production. Clinical signs of anemia include low serum iron (hypoferremia), low hemoglobin levels, low hematocrit levels, decreased red blood cells, decreased reticulocytes, increased soluble transferrin receptor and iron restricted erythropoiesis. Examples of anemia include thalassemias (i.e. α-thalassemia, β-thalassemia (minor, intermedia and major) and δ-thalassemia), sickle cell anemia, aplastic anemia, Fanconi anemia, Diamond Blackfan anemia, Shwachman Diamond syndrome, red cell membrane disorders, glucose-6-phosphate dehydrogenase deficiency, hereditary hemorrhagic telangiectasia, hemolytic anemia, anemia of chronic disease and the like.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furosyl ring modified by the bridging of two non-geminal ring atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

"Blood transfusion" refers to the process of receiving blood products into one's circulation intravenously. Transfusions are used in a variety of medical disease, disorder and/or conditions to replace lost blood components.

"Cap structure" or "terminal cap moiety" means chemical modifications, which have been incorporated at either terminus of an antisense compound.

"cEt" or "constrained ethyl" means a bicyclic sugar moiety comprising a bridge connecting the 4'-carbon and the 2'-carbon, wherein the bridge has the formula: 4'-CH(CH$_3$)—O-2'.

"Constrained ethyl nucleoside" (also cEt nucleoside) means a nucleoside comprising a bicyclic sugar moiety comprising a 4'-CH(CH$_3$)—O-2' bridge.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses concomitant, parallel or sequential administration.

"Complementarity" means the capacity for pairing between nucleobases of a first nucleic acid and a second nucleic acid. In certain embodiments, the first nucleic acid is an antisense compound and the second nucleic acid is a target nucleic acid.

"Contiguous nucleobases" means nucleobases immediately adjacent to each other.

"Deoxyribonucleotide" means a nucleotide having a hydrogen at the 2' position of the sugar portion of the nucleotide. Deoxyribonucleotides may be modified with any of a variety of substituents.

"Diluent" means an ingredient in a composition that lacks pharmacological activity, but is pharmaceutically necessary or desirable. For example, the diluent in an injected composition may be a liquid, e.g. phosphate buffered saline (PBS).

"Dosage unit" means a form in which a pharmaceutical agent is provided, e.g. pill, tablet, or other dosage unit known in the art. In certain embodiments, a dosage unit is a vial containing lyophilized antisense oligonucleotide. In certain embodiments, a dosage unit is a vial containing reconstituted antisense oligonucleotide.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

"Fully complementary" or "100% complementary" means that each nucleobase of a nucleobase sequence of a first nucleic acid has a complementary nucleobase in a second nucleobase sequence of a second nucleic acid. In certain embodiments, the first nucleic acid is an antisense compound and the second nucleic acid is a target nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap segment" and the external regions may be referred to as "wing segments."

"Gap-widened" means a chimeric antisense compound having a gap segment of 12 or more contiguous 2'-deoxynucleosides positioned between and immediately adjacent to 5' and 3' wing segments having from one to six nucleosides.

"Hemochromatosis" is a disorder of iron metabolism that results in excess iron being absorbed from the gastrointestinal tract, leading to excess iron accumulation and deposition in various tissues of the body. Primary or hereditary or classic hemochromatosis is caused by a genetic mutation, for example, in the HFE gene. Subjects with this disease have excess amounts of iron, which is absorbed in the gastrointestinal tract and builds up in the body tissues, particularly in the liver. Secondary or acquired hemochromatosis can be caused by frequent blood transfusions, high oral or parenteral intake of iron supplements, or a secondary effect of other diseases.

"Hematopoiesis" refers to the formation of cellular components of the blood, derived from hematopoietic stem cells. These stem cells reside in the medulla of the bone marrow and have the unique ability to give rise to all the different mature blood cell types.

"Hemolysis" refers to the rupturing of erythrocytes or red blood cells and the release of their contents into surrounding fluid. Hemolysis in an animal may occur due to a large number of medical conditions, including bacterial infection, parasitic infection, autoimmune disorders and genetic disorders.

"Hepcidin" refers to both an mRNA as well as a protein encoded by the mRNA that is produced by hepatocytes in response to inflammation or to rising levels of iron in the blood. The primary role of hepcidin is to regulate blood iron levels by facilitating a decrease in these blood iron levels. Hepcidin expression is increased in conditions of acute and chronic inflammation resulting in decreased iron availability for erythropoiesis. "Hepcidin" is also referred to as hepcidin antimicrobial peptide; HAMP; HAMP 1; HEPC; HFE2; LEAP-1; LEAP1; and liver-expressed antimicrobial peptide.

"Hereditary anemia" refers to anemia which is caused by a hereditary condition that causes red blood cells in the body to die faster than normal, be ineffective in transporting oxygen from the lungs to the different parts of the body, or not be created at all. Examples include, but are not limited to, sickle cell anemia, thalassemia, Fanconi anemia, Diamond Blackfan anemia, Shwachman Diamond syndrome, red cell membrane disorders, glucose-6-phosphate dehydrogenase deficiency, or hereditary hemorrhagic telangiectasia.

"HFE" refers to the human hemochromatosis gene or protein.

"HFE gene mutation" refers to mutations in the HFE gene, which may result in hereditary hemochromatosis.

"Hybridization" means the annealing of complementary nucleic acid molecules. In certain embodiments, complementary nucleic acid molecules include an antisense compound and a target nucleic acid.

"Identifying an animal at risk for or having a disease, disorder and/or condition associated with excess accumulation of iron" means identifying an animal having been diagnosed with a disease, disorder and/or condition or identifying an animal predisposed to develop a disease, disorder and/or condition associated with excess accumulation of iron. For example, an animal can be predisposed to develop a disease, disorder and/or condition associated with excess accumulation of iron if the animal has a family history of hemochromatosis. Such identification may be accomplished by any method including evaluating an animal's medical history and standard clinical tests or assessments.

"Immediately adjacent" means that there are no intervening elements between the immediately adjacent elements.

"Individual" or "subject" or "animal" means a human or non-human animal selected for treatment or therapy.

"Inhibiting the expression or activity" refers to a reduction or blockade of the expression or activity of a RNA or protein and does not necessarily indicate a total elimination of expression or activity.

"Internucleoside linkage" refers to the chemical bond between nucleosides.

"Intravenous administration" means administration into a vein.

"Iron accumulation" or "iron overload" indicates accumulation and deposition of iron in the body from any cause. The most common causes are hereditary causes, transfusional iron overload, which can result from repeated blood transfusions, or excessive dietary iron intake.

"Iron supplements" refer to supplements prescribed for a medical reason to treat iron deficiency in a patient. Iron can be supplemented by the oral route or given parenterally.

"Linked nucleosides" means adjacent nucleosides which are bonded together.

"Marker" or "biomarker" is any measurable and quantifiable biological parameter that serves as an index for health- or physiology-related assessments. For example, an increase in the percentage saturation of transferrin, an increase in iron levels, or a decrease in hepcidin levels can be considered markers of an iron overload disease, disorder and/or condition.

"MCH" refers to "mean corpuscular hemoglobin" or "mean cell hemoglobin", a value to express the average mass of hemoglobin (Hb) per red blood cell in a sample of blood.

"MCV" refers to "mean corpuscular volume" or "mean cell volume", a value to express the average red blood cell size.

"Mismatch" or "non-complementary nucleobase" or "MM" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. For example, a modified nucleobase can be 5-methylcytosine.

An "unmodified nucleobase" means the purine bases adenine (A) and guanine (G), and the pyrimidine bases thymine (T), cytosine (C), and uracil (U).

"Modified nucleoside" means a nucleoside having, independently, a modified sugar moiety and/or modified nucleobase.

"Modified nucleotide" means a nucleotide having, independently, a modified sugar moiety, modified internucleoside linkage, and/or modified nucleobase.

"Modified oligonucleotide" means an oligonucleotide comprising a modified internucleoside linkage, a modified sugar, and/or a modified nucleobase.

"Modified sugar" refers to a substitution or change from a natural sugar. For example, a modified sugar can be 2'-MOE.

"Modulating" refers to changing or adjusting a feature in a cell, tissue, organ or organism. For example, modulating TMPRSS6 level can mean to increase or decrease the level of TMPRSS6 mRNA or TMPRSS6 protein in a cell, tissue, organ or organism. A "modulator" effects the change in the cell, tissue, organ or organism. For example, a TMPRSS6 antisense oligonucleotide can be a modulator that increases or decreases the amount of TMPRSS6 mRNA or TMPRSS6 protein in a cell, tissue, organ or organism.

"Monomer" refers to a single unit of an oligomer. Monomers include, but are not limited to, nucleosides and nucleotides, whether naturally occurring or modified.

"Motif" means the pattern of chemically distinct regions in an antisense compound.

"Mutations" refer to changes in a nucleic acid sequence. Mutations can be caused in a variety of ways including, but not limited to, radiation, viruses, transposons and mutagenic chemicals, as well as errors that occur during meiosis, DNA replication, RNA transcription and post-transcriptional processing. Mutations can result in several different changes in sequence; they can have either no effect, alter the product of a gene, or prevent the gene from functioning properly or completely. For example, HFE mutation can lead to the improper functioning of the gene product, leading to excess iron absorption in the intestines.

"Myelodysplastic syndrome" refers to a diverse collection of hematological medical disease, disorder and/or conditions that involve ineffective production of the myeloid class of blood cells. The syndrome is caused by disorders of the stem cells in the bone marrow. In myelodysplastic syndrome, hematopoiesis is ineffective and the number and quality of blood cells decline irreversibly, further impairing blood production. As a result, patients with myelodysplastic syndrome develop severe anemia and require frequent blood transfusions.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound; such as, for example, nucleoside mimetics having morpholino, cyclohexenyl, cyclohexyl, tetrahydropyranyl, bicyclo or tricyclo sugar mimetics e.g. non furanose sugar units.

"Nucleotide" means a nucleoside having a phosphate group covalently linked to the sugar portion of the nucleoside.

"Nucleotide mimetic" includes those structures used to replace the nucleoside and the linkage at one or more positions of an oligomeric compound; such as, for example, peptide nucleic acids or morpholinos (morpholinos linked by —N(H)—C(=O)—O— or other non-phosphodiester linkage).

"Oligomeric compound" or "oligomer" refers to a polymeric structure comprising two or more sub-structures (monomers) and capable of hybridizing to a region of a nucleic acid molecule. In certain embodiments, oligomeric compounds are oligonucleosides. In certain embodiments, oligomeric compounds are oligonucleotides. In certain embodiments, oligomeric compounds are antisense compounds. In certain embodiments, oligomeric compounds are antisense oligonucleotides. In certain embodiments, oligomeric compounds are chimeric oligonucleotides.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intra-arterial administration, intraperitoneal administration, or intracranial administration, e.g., intrathecal or intracerebroventricular administration. Administration can be continuous, or chronic, or short or intermittent.

"Peptide" refers to a molecule formed by linking at least two amino acids by amide bonds. Peptide refers to polypeptides and proteins.

"Percentage saturation of transferrin" refers to the ratio of serum iron to total iron binding capacity multiplied by 100. Of the transferrin molecules that are available to bind iron, this value tells a clinician how much serum iron are actually bound.

"Pharmaceutical composition" means a mixture of substances suitable for administering to an individual. For example, a pharmaceutical composition may comprise one or more active pharmaceutical agents and a sterile aqueous solution.

"Pharmaceutically acceptable carrier" means a medium or diluent that does not interfere with the structure of the oligonucleotide. Certain of such carriers enable pharmaceutical compositions to be formulated as, for example, tablets, pills, dragees, capsules, liquids, gels, syrups, slurries, suspension and lozenges for the oral ingestion by a subject. For example, a pharmaceutically acceptable carrier can be a sterile aqueous solution, such as PBS.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Polycythemia" refers to a condition of increased red blood cells (RBCs) in a specified volume due to either an increase in red blood cell numbers (absolute polycythemia) or a decrease in plasma volume (relative polycythemia). Blood volume to red blood cell proportions can be measured as Hematocrit (Hct) levels. The increased proportion of RBCs can make the blood viscous which can lead to slower blood flow through the circulatory system and potential formation of blood clots. Slower blood flow can decrease oxygen transport to cells, tissue and/or organs leading to diseases, disorders or conditions such as angina or heart failure. Formation of blood clots in the circulatory system can lead to cell, tissue and/or organ damage leading to diseases, disorders or conditions such as myocardial infarction or stroke. Treatment for polycythemia includes phlebotomy or drugs to decrease RBC production (e.g., INF-α, hydroxyurea, anagrelide). Examples of polycythemia include, but is not limited to, polycythemia vera (PCV), polycythemia rubra vera (PRV) and erythremia. In certain instances, polycythemia can progress into erythroid leukemia in a subject.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset, development, or progression of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity with a target nucleic acid to induce a desired effect, while exhibiting minimal or no effects on non-target nucleic acids under conditions in which specific binding is desired, i.e. under physiological conditions in the case of in vivo assays and therapeutic treatments.

"Subcutaneous administration" means administration just below the skin.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Thalassemia" refers to a subgroup of anemias (e.g., α-thalassemia, β-thalassemia, δ-thalassemia, non-transfusion dependent thalassemia (NTDT)) caused by the formation of abnormal hemoglobin molecules leading to the destruction or degradation of red blood cells. Complications of thalassemia include excess iron (i.e. iron overload in the blood either from the thalassemia itself or from frequent transfusions to treat the thalassemia), increased risk of infection, bone deformities, enlarged spleens (i.e. splenomegaly), slowed growth rates and heart problems (e.g., congestive heart failure and arrhythmias).

"Therapeutically effective amount" means an amount of a pharmaceutical agent that provides a therapeutic benefit to an animal.

"TMPRSS6" (also known as "matriptase-2") refers to any nucleic acid or protein of TMPRSS6.

"TMPRSS6 nucleic acid" means any nucleic acid encoding TMPRSS6. For example, in certain embodiments, a TMPRSS6 nucleic acid includes a DNA sequence encoding TMPRSS6, a RNA sequence transcribed from DNA encoding TMPRSS6 (including genomic DNA comprising introns and exons), and a mRNA sequence encoding TMPRSS6. "TMPRSS6 mRNA" means a mRNA encoding a TMPRSS6 protein.

"TMPRSS6 specific inhibitor" refers to any agent capable of specifically inhibiting the expression of TMPRSS6 gene, TMPRSS6 RNA and/or TMPRSS6 protein at the molecular level. For example, TMPRSS6 specific inhibitors include nucleic acids (including antisense compounds), peptides, antibodies, small molecules, and other agents capable of inhibiting the level of TMPRSS6. In certain embodiments, by specifically modulating TMPRSS6, TMPRSS6 specific inhibitors may affect components of the iron accumulation pathway.

"Treat" refers to administering a pharmaceutical composition to an animal in order to effect an alteration or improvement of a disease, disorder, or condition in the animal. In certain embodiments, one or more pharmaceutical compositions can be administered to the animal.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleotide) or a DNA nucleotide (i.e. β-D-deoxyribonucleotide).

Certain Embodiments

In certain embodiments disclosed herein, TMPRSS6 has the sequence as set forth in: GenBank Accession No. NM_153609.2 (incorporated herein as SEQ ID NO: 1); the complement of GENBANK Accession NT_011520.12 truncated from Ser. No. 16/850,000 to Ser. No. 16/897,000 (incorporated herein as SEQ ID NO: 2); GENBANK Accession CR456446.1 (incorporated herein as SEQ ID NO: 3); GENBANK Accession No. BC039082.1 (incorporated herein as SEQ ID NO: 4); GENBANK Accession No. AY358398.1 (incorporated herein as SEQ ID NO: 5); and GENBANK Accession No. DB081153.1 (incorporated herein as SEQ ID NO: 6).

Certain embodiments disclosed herein provide a compound comprising a modified oligonucleotide targeting a nucleic acid sequence encoding TMPRSS6. In certain embodiments, the compound targets a TMPRSS6 sequence as shown in the nucleobase sequences of any of SEQ ID NOs: 1-6.

Certain embodiments disclosed herein provide a compound comprising a modified oligonucleotide consisting of 12 to 30 linked nucleosides having a nucleobase sequence comprising at least 8, least 9, least 10, least 11, at least 12, least 13, at least 14, at least 15, at least 16, least 17, least 18, least 19, or 20 contiguous nucleobases complementary to an equal length portion of SEQ ID NOs: 1-6.

Certain embodiments disclosed herein provide a compound comprising a modified oligonucleotide consisting of 12 to 30 linked nucleosides having a nucleobase sequence comprising a portion of at least 8 contiguous nucleobases complementary to an equal length portion of nucleobases 3162 to 3184 of SEQ ID NO: 1, wherein the nucleobase sequence of the modified oligonucleotide is at least 80% complementary to SEQ ID NO: 1.

Certain embodiments disclosed herein provide a compound comprising a modified oligonucleotide consisting of 12 to 30 linked nucleosides having a nucleobase sequence comprising a portion of at least 8 contiguous nucleobases complementary to an equal length portion of nucleobases 1286 to 1305 of SEQ ID NO: 1, wherein the nucleobase sequence of the modified oligonucleotide is at least 80% complementary to SEQ ID NO: 1.

Certain embodiments disclosed herein provide a compound comprising a modified oligonucleotide consisting of 12 to 30 linked nucleosides having a nucleobase sequence comprising a portion of at least 8, at least 9, at least 10, at least 11, at least 12, at least 13, at least 14, at least 15, at least 16, at least 17, at least 18, at least 19, or at least 20 contiguous nucleobases complementary to an equal length portion of nucleobases 3162 to 3184 of SEQ ID NO: 1, wherein the nucleobase sequence of the modified oligonucleotide is at least 80% complementary to SEQ ID NO: 1.

Certain embodiments disclosed herein provide a compound comprising a modified oligonucleotide consisting of 12 to 30 linked nucleosides having a nucleobase sequence comprising a portion of at least 8, at least 9, at least 10, at least 11, at least 12, at least 13, at least 14, at least 15, at least 16, at least 17, at least 18, at least 19, or at least 20 contiguous nucleobases complementary to an equal length portion of nucleobases 1286 to 1305 of SEQ ID NO: 1, wherein the nucleobase sequence of the modified oligonucleotide is at least 80% complementary to SEQ ID NO: 1.

Certain embodiments disclosed herein provide a compound comprising a modified oligonucleotide consisting of 12 to 30 linked nucleosides having a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 7-85.

Certain embodiments disclosed herein provide a compound comprising a modified oligonucleotide consisting of 12 to 30 linked nucleosides having a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 23, 36, 37, 63, 77.

Certain embodiments disclosed herein provide a compound comprising a modified oligonucleotide consisting of 12 to 30 linked nucleosides having a nucleobase sequence comprising at least 8, at least 9, at least 10, at least 11, at least 12, at least 13, at least 14, at least 15, at least 16, at least 17, at least 18, at least 19, or 20 contiguous nucleobases of SEQ ID NO: 36.

Certain embodiments disclosed herein provide a compound comprising a modified oligonucleotide consisting of 12 to 30 linked nucleosides having a nucleobase sequence comprising at least 8, at least 9, at least 10, at least 11, at least 12, at least 13, at least 14, at least 15, at least 16, at least 17, at least 18, at least 19, or 20 contiguous nucleobases of SEQ ID NO: 77.

In certain embodiments, the nucleobase sequence of the modified oligonucleotide is at least 70%, at least 75%, at least 80%, at least 85%, at least 90%, at least 95%, at least 96%, at least 97%, at least 98%, or at least 99% complementary to an equal length portion of any of SEQ ID NOs: 1-6. In certain embodiments, the modified oligonucleotide comprises a nucleobase sequence 100% complementary to an equal length portion of any of SEQ ID NOs: 1-6.

In certain embodiments, the compound comprises a modified oligonucleotide consisting of 8 to 80, 20 to 80, 10 to 50, 20 to 35, 10 to 30, 12 to 30, 15 to 30, 16 to 30, 20 to 30, 20 to 29, 20 to 28, 20 to 27, 20 to 26, 20 to 25, 20 to 24, 20 to 23, 20 to 22, 20 to 21, 15 to 25, 16 to 25, 15 to 24, 16 to 24, 17 to 24, 18 to 24, 19 to 24, 19 to 22, 16 to 21, 18 to 21 or 16 to 20 linked nucleobases. In certain embodiments, the compound comprises a modified oligonucleotide consisting of 16 linked nucleosides. In certain embodiments, the compound comprises a modified oligonucleotide consisting of 20 linked nucleosides.

In certain embodiments, the compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobases in length, or a range defined by any two of the above values.

In certain embodiments, the modified oligonucleotide is single-stranded.

In certain embodiments, the modified oligonucleotide comprises at least one modified internucleoside linkage. In certain embodiments, the modified internucleoside linkage is a phosphorothioate internucleoside linkage. In certain embodiments, at least one modified internucleoside linkage is a phosphorothioate internucleoside linkage. In certain embodiments, each modified internucleoside linkage is a phosphorothioate internucleoside linkage.

In certain embodiments, the modified oligonucleotide comprises at least one nucleoside comprising a modified sugar. In certain embodiments, at least one modified sugar comprises a bicyclic sugar. In certain embodiments, at least one modified sugar comprises a 2'-O-methoxyethyl, a constrained ethyl, a 3'-fluoro-HNA or a 4'-(CH$_2$)$_n$—O-2' bridge, wherein n is 1 or 2.

In certain embodiments, the modified oligonucleotide comprises at least one nucleoside comprising a modified nucleobase. In certain embodiments, the modified nucleobase is a 5-methylcytosine.

In certain embodiments, the modified oligonucleotide comprises a conjugate group. In certain embodiments, the conjugate is a carbohydrate moiety. In certain embodiments, the conjugate is a GalNAc moiety. In certain embodiments, the GalNAc is 5'-Trishexylamino-(THA)-C6 GalNAc$_3$. In certain embodiments, the conjugate has the formula

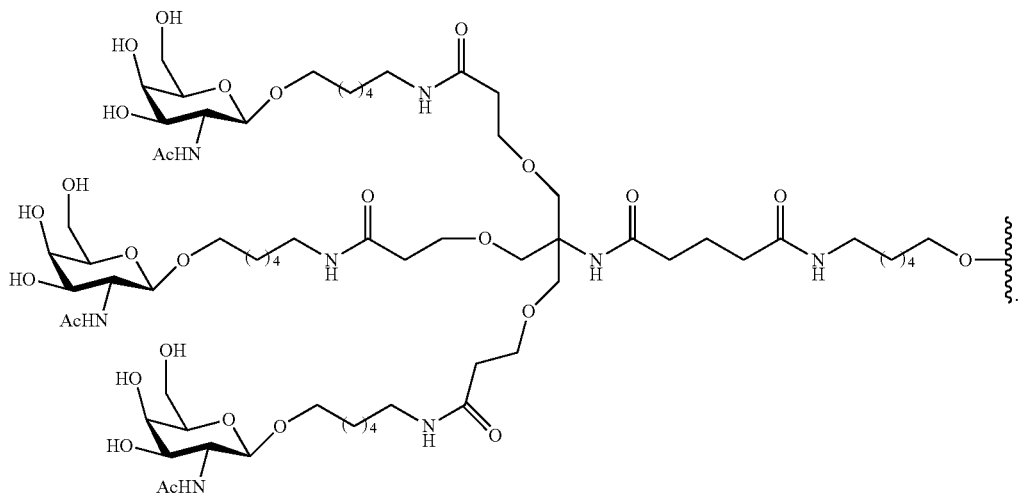

In certain embodiments, the compound comprises a modified oligonucleotide consisting of 12 to 30 linked nucleosides and targeted to or complementary to an equal length portion of region 3162 to 3184 of SEQ ID NO: 1, wherein the modified oligonucleotide comprises: (a) a gap segment consisting of linked deoxynucleosides; (b) a 5' wing segment consisting of linked nucleosides; and (c) a 3' wing segment consisting of linked nucleosides; wherein the gap segment is positioned immediately adjacent to and between the 5' wing segment and the 3' wing segment and wherein each nucleoside of each wing segment comprises a modified sugar. In certain embodiments, the modified oligonucleotide further comprises at least one phosphorothioate internucleoside linkage. In certain embodiments, the modified oligonucleotide further comprises a GalNAc conjugate. In certain embodiments, the conjugate is a 5'-Trishexylamino-(THA)-C6 GalNAc$_3$ conjugate.

In certain embodiments, the compound comprises a modified oligonucleotide consisting of 12 to 30 linked nucleosides and targeted to or complementary to an equal length portion of region 1286 to 1305 of SEQ ID NO: 1, wherein the modified oligonucleotide comprises: (a) a gap segment consisting of linked deoxynucleosides; (b) a 5' wing segment consisting of linked nucleosides; and (c) a 3' wing segment consisting of linked nucleosides; wherein the gap segment is positioned immediately adjacent to and between the 5' wing segment and the 3' wing segment and wherein each nucleoside of each wing segment comprises a modified sugar. In certain embodiments, the modified oligonucleotide further comprises at least one phosphorothioate internucleoside linkage. In certain embodiments, the modified oligonucleotide further comprises a GalNAc conjugate. In certain embodiments, the conjugate is a 5'-Trishexylamino-(THA)-C6 GalNAc₃ conjugate.

In certain embodiments, the compound comprises a modified oligonucleotide consisting of 20 linked nucleosides and targeted to or complementary to an equal length portion of region 3162 to 3181 of SEQ ID NO: 1, wherein the modified oligonucleotide comprises: (a) a gap segment consisting of ten linked deoxynucleosides; (b) a 5' wing segment consisting of five linked nucleosides; and (c) a 3' wing segment consisting of five linked nucleosides; wherein the gap segment is positioned immediately adjacent to and between the 5' wing segment and the 3' wing segment, wherein each nucleoside of each wing segment comprises a 2'-O-methoxyethyl sugar, wherein at least one internucleoside linkage is a phosphorothioate linkage and wherein each cytosine residue is a 5-methylcytosine. In certain embodiments, the modified oligonucleotide further comprises a GalNAc conjugate. In certain embodiments, the conjugate is a 5'-Trishexylamino-(THA)-C6 GalNAc₃ conjugate.

In certain embodiments, the compound comprises a modified oligonucleotide consisting of 16 linked nucleosides and targeted to or complementary to an equal length portion of region 3169 to 3184 of SEQ ID NO: 1, wherein the modified oligonucleotide comprises: (a) a gap segment consisting of nine linked deoxynucleosides; (b) a 5' wing segment consisting of three linked nucleosides; and (c) a 3' wing segment consisting of four linked nucleosides; wherein the gap segment is positioned immediately adjacent to and between the 5' wing segment and the 3' wing segment, wherein each nucleoside of each wing segment comprises a modified sugar, wherein each internucleoside linkage is a phosphorothioate linkage and wherein each cytosine residue is a 5-methylcytosine. In certain embodiments, the modified oligonucleotide further comprises a GalNAc conjugate. In certain embodiments, the conjugate is a 5'-Trishexylamino-(THA)-C6 GalNAc₃ conjugate.

In certain embodiments, the compound comprising a modified oligonucleotide consisting of 20 linked nucleosides and having a nucleobase sequence comprising at least 8 contiguous nucleobases of SEQ ID NO: 36, wherein the modified oligonucleotide comprises: (a) a gap segment consisting of ten linked deoxynucleosides; (b) a 5' wing segment consisting of five linked nucleosides; and (c) a 3' wing segment consisting of five linked nucleosides; wherein the gap segment is positioned immediately adjacent to and between the 5' wing segment and the 3' wing segment, wherein each nucleoside of each wing segment comprises a 2'-O-methoxyethyl sugar, wherein at least one internucleoside linkage is a phosphorothioate linkage and wherein each cytosine residue is a 5-methylcytosine. In certain embodiments, the modified oligonucleotide further comprises a GalNAc conjugate. In certain embodiments, the conjugate is a 5'-Trishexylamino-(THA)-C6 GalNAc₃ conjugate.

In certain embodiments, the compound comprising a modified oligonucleotide consisting of 16 linked nucleosides and having a nucleobase sequence comprising at least 8 contiguous nucleobases of SEQ ID NO: 77, wherein the modified oligonucleotide comprises: (a) a gap segment consisting of nine linked deoxynucleosides; (b) a 5' wing segment consisting of three linked nucleosides; and (c) a 3' wing segment consisting of four linked nucleosides; wherein the gap segment is positioned immediately adjacent to and between the 5' wing segment and the 3' wing segment, wherein each nucleoside of each wing segment comprises a modified sugar, wherein each internucleoside linkage is a phosphorothioate linkage and wherein each cytosine residue is a 5-methylcytosine. In certain embodiments, the modified oligonucleotide further comprises a GalNAc conjugate. In certain embodiments, the conjugate is a 5'-Trishexylamino-(THA)-C6 GalNAc₃ conjugate.

Certain embodiments disclosed herein provide a compound comprising a modified oligonucleotide according to the following formula: mCes Teo Teo Teo Aeo Tds Tds mCds mCds Ads Ads Ads Gds Gds Gds mCeo Aeo Ges mCes Te (SEQ ID NO: 36); wherein, A is an adenine, mC is a 5-methylcytosine, G is a guanine, T is a thymine, e is a 2'-O-methoxyethyl modified nucleoside, d is a 2'-deoxynucleoside, and s is a phosphorothioate internucleoside linkage. In certain embodiments, the modified oligonucleotide further comprises a GalNAc conjugate. In certain embodiments, the conjugate is a 5'-Trishexylamino-(THA)-C6 GalNAc₃ conjugate.

Certain embodiments disclosed herein provide a compound comprising a modified oligonucleotide with the following formula:

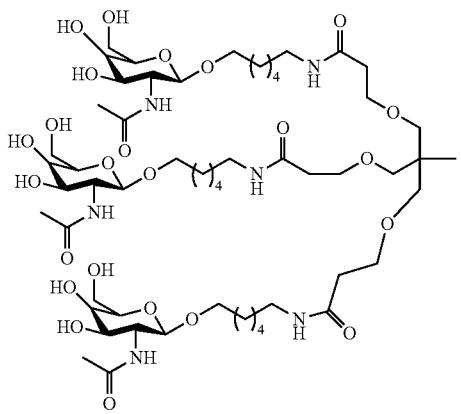

23                                    24
-continued
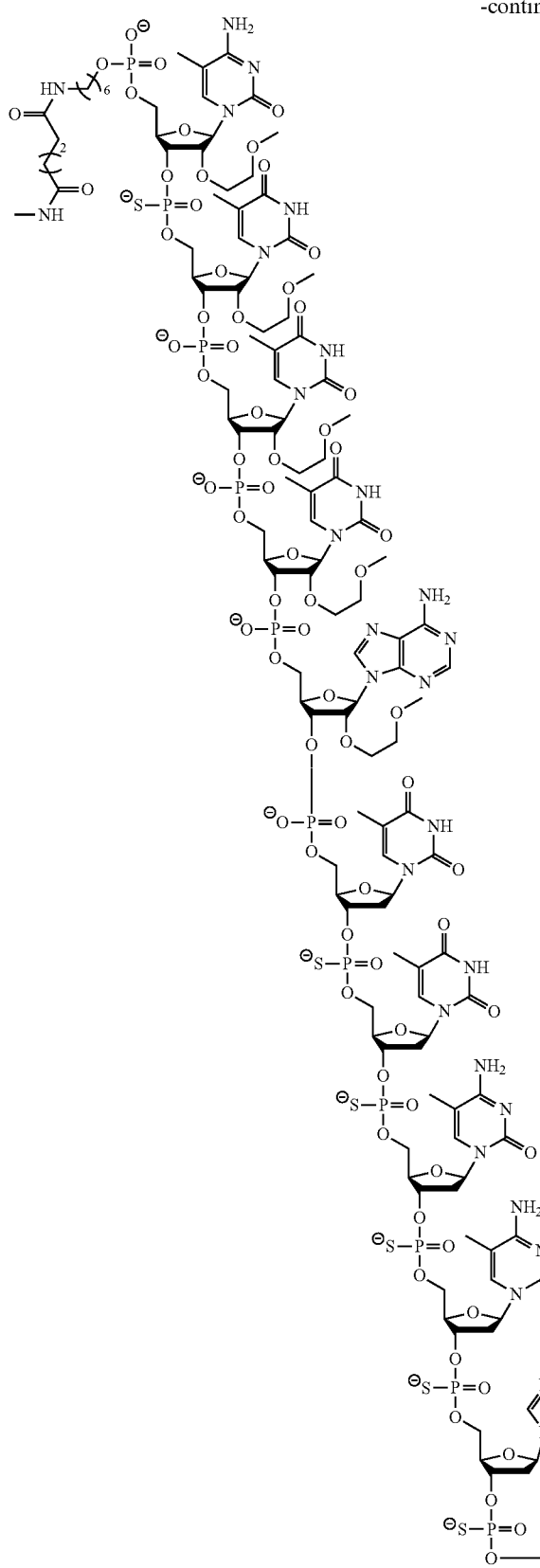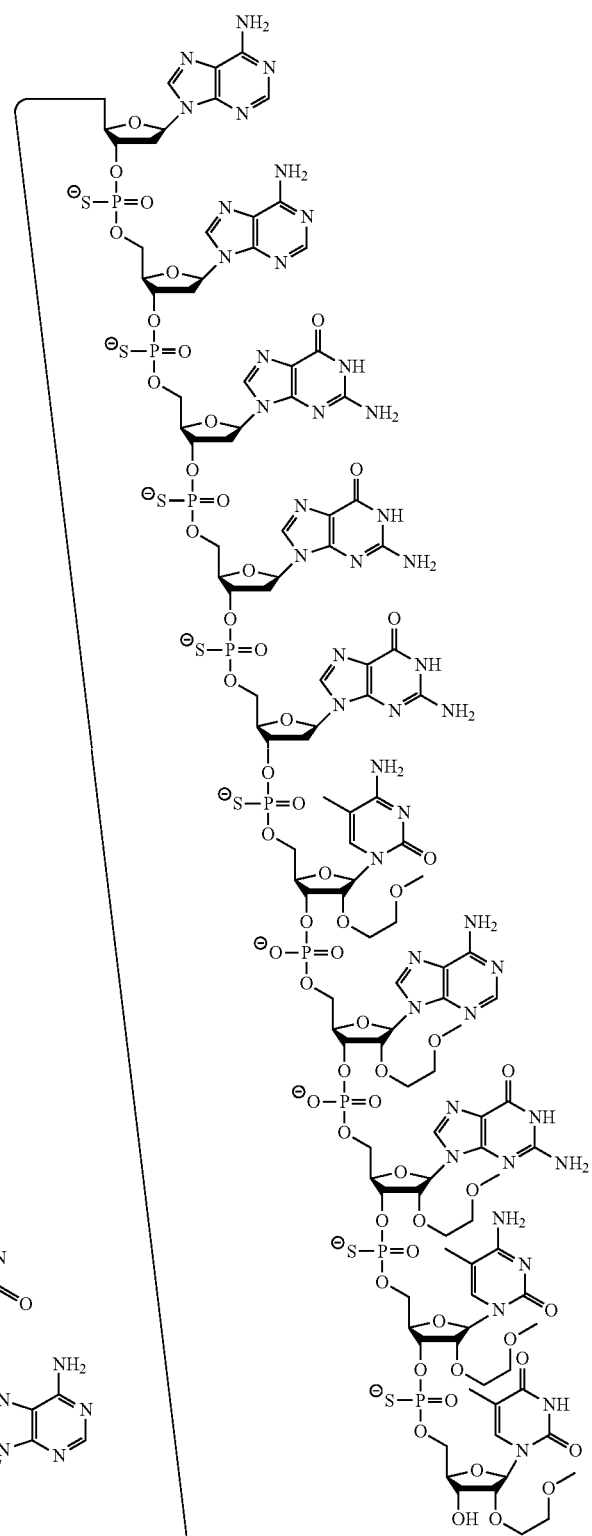
Certain embodiments disclosed herein provide a compound comprising a modified oligonucleotide according to the following formula: mCks Aes Gks mCds Tds Tds Tds Ads Tds Tds mCds mCds Aes Aes Aks Gk (SEQ ID NO:

77); wherein, A is an adenine, mC is a 5-methylcytosine, G is a guanine, T is a thymine, e is a 2'-O-methoxyethyl modified nucleoside, d is a 2'-deoxynucleoside, s is a phosphorothioate internucleoside linkage, and k is a cEt. In certain embodiments, the modified oligonucleotide further comprises a GalNAc conjugate. In certain embodiments, the conjugate is a 5'-Trishexylamino-(THA)-C6 GalNAc$_3$ conjugate.

Certain embodiments disclosed herein provide a compound comprising a modified oligonucleotide with the following formula:

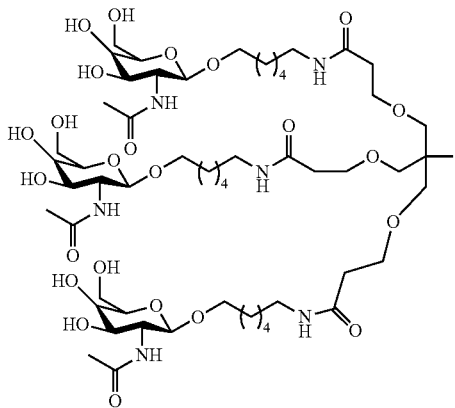

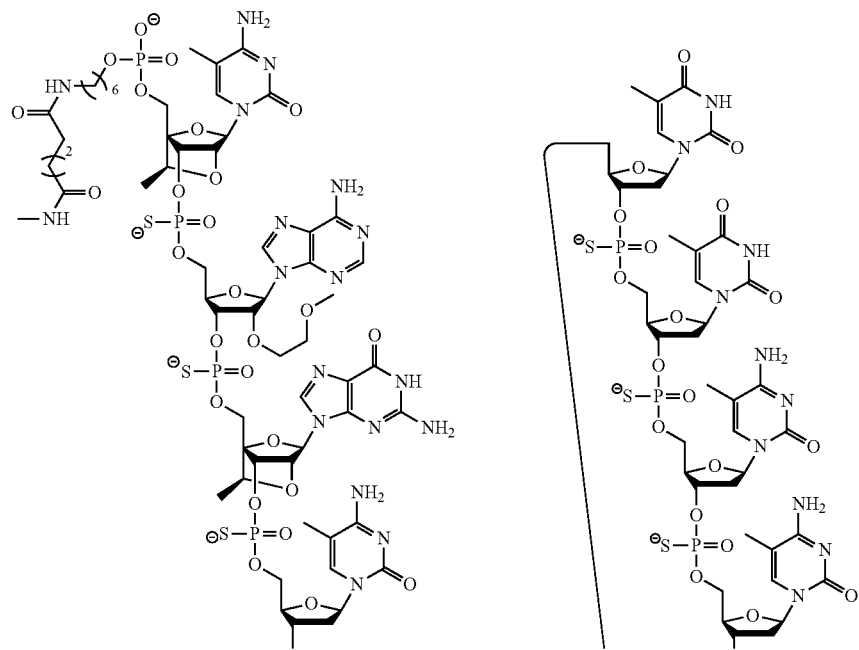

-continued

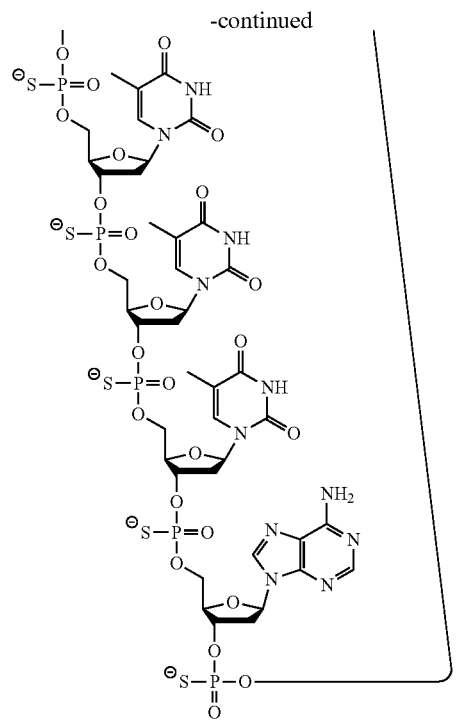
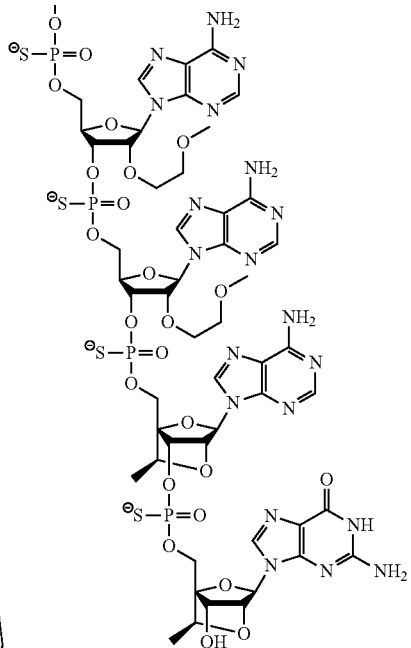

In certain embodiments, the compounds or compositions disclosed herein comprise a salt of the modified oligonucleotide.

In certain embodiments, the compounds or compositions disclosed herein further comprise a pharmaceutically acceptable carrier or diluent.

In certain embodiments, the animal is a human.

Certain embodiments provide a composition or compound comprising a modified oligonucleotide as described herein, wherein the viscosity level is less than 40 cP. In certain embodiments, the composition has a viscosity level less than 15 cP. In certain embodiments, the composition has a viscosity level less than 12 cP. In certain embodiments, the composition has a viscosity level less than 10 cP.

Certain embodiments disclosed herein provide compounds and compositions comprising a modified oligonucleotide targeting TMPRSS6 for use in reducing TMPRSS6 in a cell, tissue, organ or animal.

Certain embodiments disclosed herein provide compounds and compositions comprising a modified oligonucleotide targeting TMPRSS6 for use in reducing iron levels in a cell, tissue, organ or animal. In certain embodiments, the compounds and compositions reduce serum iron levels. In certain embodiments, the compounds and compositions reduce liver iron levels. In certain embodiments, the compounds and compositions reduce iron absorption. In certain embodiments, the compounds and compositions reduce iron overload or accumulation. In certain embodiments, reducing iron overload/accumulation ameliorates, treats, prevents or delays a disease, disorder or condition related to iron overload.

Certain embodiments disclosed herein provide compounds and compositions comprising a modified oligonucleotide targeting TMPRSS6 for use in increasing hepcidin levels, such as mRNA or protein expression levels, in an animal.

Certain embodiments disclosed herein provide compounds and compositions comprising a modified oligonucleotide targeting TMPRSS6 for use in decreasing the percentage saturation of transferrin in an animal. In certain embodiments, decreasing transferrin saturation leads to a decrease in iron supply for erythropoiesis. In certain embodiments, the decrease in erythropoiesis treats, prevents, delays the onset of, ameliorates, and/or reduces polycythemia, or symptom thereof, in the animal. In certain embodiments, the polycythemia is polycythemia vera. In certain embodiments, treatment with the modified oligonucleotide targeting TMPRSS6 prevents or delays the polycythemia from progressing into erythroid leukemia.

Certain embodiments disclosed herein provide compounds and compositions comprising a modified oligonucleotide targeting TMPRSS6 for reducing iron accumulation in an animal. In certain embodiments, compounds and compositions comprising a modified oligonucleotide targeting TMPRSS6 are used for treating, preventing, slowing the progression, delaying the onset of, ameliorating and/or reducing a disease, disorder and/or condition, or symptom thereof, associated with the excess accumulation of iron in an animal.

In certain embodiments, the iron accumulation is the result of, or cause of, a disease, disorder or condition in the animal. In certain embodiments, the disease, disorder or condition is ineffective erythropoiesis, polycythemia, hemochromatosis or anemia. In certain embodiments, the hemochromatosis is hereditary hemochromatosis. In certain embodiments, the anemia is hereditary anemia, myelodysplastic syndrome or severe chronic hemolysis. In certain embodiments, the hereditary anemia is sickle cell anemia, thalassemia, Fanconi anemia, Diamond Blackfan anemia, Shwachman Diamond syndrome, red cell membrane disorders, glucose-6-phosphate dehydrogenase deficiency, or hereditary hemorrhagic telangiectasia. In certain embodiments, the thalassemia is β-thalassemia. In certain embodiments, the β-thalassemia is β-thalassemia major, β-thalassemia intermedia or β-thalassemia minor. In certain embodiments, the disease, disorder or condition is associated with mutations in the HFE gene. In other embodiments, the disease is associated with mutations in the hemojuvelin gene. In other embodiments, the disease is associated with mutations in the hepcidin gene.

In certain embodiments, the iron accumulation is the result of a therapy to treat a disease, disorder or condition in the animal. In certain embodiments, the therapy is phlebotomy or transfusion therapy. In certain embodiments, the disease, disorder and/or condition may be due to multiple blood transfusions. In certain embodiments, multiple transfusions may lead to polycythemia. In certain embodiments, multiple blood transfusions are associated with the animal having anemia. Examples of anemia requiring multiple blood transfusions are hereditary anemia, myelodysplastic syndrome and severe chronic hemolysis.

In certain embodiments, the disease, disorder and/or condition is associated with excess parenteral iron supplement intake or excess dietary iron intake.

In certain embodiments, provided are compounds and compositions comprising a modified oligonucleotide targeting TMPRSS6 for use in therapy. In certain embodiments, the compounds and compositions comprising a modified oligonucleotide targeting TMPRSS6 are administered to an animal in a therapeutically effective amount.

In certain embodiments, provided are compounds and compositions comprising a modified oligonucleotide targeting TMPRSS6 for use in the preparation of a medicament. In certain embodiments, the medicament is used for treating, preventing, slowing the progression, delaying the onset of, and/or reducing a disease, disorder and/or condition, or symptom thereof, associated with excess accumulation of iron in an animal.

In certain embodiments, the composition or compound comprising a modified oligonucleotide targeting TMPRSS6 is co-administered with one or more second agent(s). In certain embodiments the second agent is an iron chelator or a hepcidin agonist. In further embodiments, the iron chelator includes FBS0701 (FerroKin), Exjade, Desferal or Deferiprone (DFP). In certain embodiments, the second agent is a second antisense compound. In further embodiments, the second antisense compound targets TMPRSS6. In other embodiments, the second antisense compound targets a non-TMPRSS6 compound. In other embodiments, the composition or compound comprising a modified oligonucleotide targeting TMPRSS6 is administered before, during or after phlebotomy or transfusion therapy.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound can be "antisense" to a target nucleic acid, meaning that it is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to TMPRSS6 nucleic acid is 10 to 30 nucleotides in length. In other words, antisense compounds are from 10 to 30 linked nucleobases. In other embodiments, the antisense compound comprises a modified oligonucleotide consisting of 8 to 80, 10 to 80, 12 to 50, 15 to 30, 18 to 24, 19 to 22, or 20 linked nucleobases. In certain such embodiments, the antisense compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobases in length, or a range defined by any two of the above values. In some embodiments, the antisense compound is an antisense oligonucleotide.

In certain embodiments, the antisense compound comprises a shortened or truncated modified oligonucleotide. The shortened or truncated modified oligonucleotide can have a single nucleoside deleted from the 5' end (5' truncation), the central portion or alternatively from the 3' end (3' truncation). A shortened or truncated oligonucleotide can have two or more nucleosides deleted from the 5' end, two or more nucleosides deleted from the central portion or alternatively can have two or more nucleosides deleted from the 3' end. Alternatively, the deleted nucleosides can be dispersed throughout the modified oligonucleotide, for example, in an antisense compound having one or more nucleoside deleted from the 5' end, one or more nucleoside deleted from the central portion and/or one or more nucleoside deleted from the 3' end.

When a single additional nucleoside is present in a lengthened oligonucleotide, the additional nucleoside can be located at the 5' end, 3' end or central portion of the oligonucleotide. When two or more additional nucleosides are present, the added nucleosides can be adjacent to each other, for example, in an oligonucleotide having two nucleosides added to the 5' end (5' addition), to the 3' end (3' addition) or the central portion, of the oligonucleotide. Alternatively, the added nucleoside can be dispersed throughout the antisense compound, for example, in an oligonucleotide having one or more nucleoside added to the 5' end, one or more nucleoside added to the 3' end, and/or one or more nucleoside added to the central portion.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Certain Antisense Compound Motifs and Mechanisms

In certain embodiments, antisense compounds have chemically modified subunits arranged in patterns, or motifs, to confer to the antisense compounds properties such as enhanced inhibitory activity, increased binding affinity for a target nucleic acid, or resistance to degradation by in vivo nucleases. Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may confer another desired property e.g., serve as a substrate for the cellular endonuclease RNase H, which cleaves the RNA strand of an RNA:DNA duplex.

Antisense activity may result from any mechanism involving the hybridization of the antisense compound (e.g., oligonucleotide) with a target nucleic acid, wherein the hybridization ultimately results in a biological effect. In certain embodiments, the amount and/or activity of the target nucleic acid is modulated. In certain embodiments, the amount and/or activity of the target nucleic acid is reduced. In certain embodiments, hybridization of the antisense compound to the target nucleic acid ultimately results in target nucleic acid degradation. In certain embodiments, hybridization of the antisense compound to the target nucleic acid does not result in target nucleic acid degradation. In certain such embodiments, the presence of the antisense compound hybridized with the target nucleic acid (occupancy) results in a modulation of antisense activity. In certain embodiments, antisense compounds having a particular chemical motif or pattern of chemical modifications are particularly suited to exploit one or more mechanisms. In certain embodiments, antisense compounds function through more than one mechanism and/or through mechanisms that have not been elucidated. Accordingly, the antisense compounds described herein are not limited by particular mechanism.

Antisense mechanisms include, without limitation, RNase H mediated antisense; RNAi mechanisms, which utilize the RISC pathway and include, without limitation, siRNA, ssRNA and microRNA mechanisms; and occupancy based mechanisms. Certain antisense compounds may act through more than one such mechanism and/or through additional mechanisms.

RNase H-Mediated Antisense

In certain embodiments, antisense activity results at least in part from degradation of target RNA by RNase H. RNase H is a cellular endonuclease that cleaves the RNA strand of an RNA:DNA duplex. It is known in the art that single-stranded antisense compounds which are "DNA-like" elicit RNase H activity in mammalian cells. Accordingly, antisense compounds comprising at least a portion of DNA or DNA-like nucleosides may activate RNase H, resulting in cleavage of the target nucleic acid. In certain embodiments, antisense compounds that utilize RNase H comprise one or more modified nucleosides. In certain embodiments, such antisense compounds comprise at least one block of 1-8 modified nucleosides. In certain such embodiments, the modified nucleosides do not support RNase H activity. In certain embodiments, such antisense compounds are gapmers, as described herein. In certain such embodiments, the gap of the gapmer comprises DNA nucleosides. In certain such embodiments, the gap of the gapmer comprises DNA-like nucleosides. In certain such embodiments, the gap of the gapmer comprises DNA nucleosides and DNA-like nucleosides.

Certain antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE and 2'-O—CH$_3$, among others), and bicyclic sugar modified nucleosides (such bicyclic sugar modified nucleosides may include those having a constrained ethyl). In certain embodiments, nucleosides in the wings may include several modified sugar moieties, including, for example 2'-MOE and bicyclic sugar moieties such as constrained ethyl (cEt) or LNA. In certain embodiments, wings may include several modified and unmodified sugar moieties. In certain embodiments, wings may include various combinations of 2'-MOE nucleosides, bicyclic sugar moieties such as constrained ethyl nucleosides or LNA nucleosides, and 2'-deoxynucleosides.

Each distinct region may comprise uniform sugar moieties, variant, or alternating sugar moieties. The wing-gap-wing motif is frequently described as "X-Y-Z", where "X" represents the length of the 5'-wing, "Y" represents the length of the gap, and "Z" represents the length of the 3'-wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X-Y-Z" has a configuration such that the gap is positioned immediately adjacent to each of the 5'-wing and the 3' wing. Thus, no intervening nucleotides exist between the 5'-wing and gap, or the gap and the 3'-wing. Any of the antisense compounds described herein can have a gapmer motif. In certain embodiments, "X" and "Z" are the same; in other embodiments they are different. In certain embodiments, "Y" is between 8 and 15 nucleosides. X, Y, or Z can be any of 1, 2, 3, 4, 5, 6, 7, 8, 9, 10, 11, 12, 13, 14, 15, 16, 17, 18, 19, 20, 25, 30 or more nucleosides.

In certain embodiments, the antisense compound targeted to a TMPRSS6 nucleic acid has a gapmer motif in which the gap consists of 6, 7, 8, 9, 10, 11, 12, 13, 14, 15, or 16 linked nucleosides.

In certain embodiments, the antisense oligonucleotide has a sugar motif described by Formula A as follows: $(J)_m$-$(B)_n$-$(J)_p$-$(B)_r$-$(A)_t$-$(D)_g$-$(A)_v$-$(B)_w$-$(J)_x$-$(B)_y$-$(J)_z$ wherein:
each A is independently a 2'-substituted nucleoside;
each B is independently a bicyclic nucleoside;
each J is independently either a 2'-substituted nucleoside or a 2'-deoxynucleoside;
each D is a 2'-deoxynucleoside;
m is 0-4; n is 0-2; p is 0-2; r is 0-2; t is 0-2; v is 0-2; w is 0-4; x is 0-2; y is 0-2; z is 0-4; g is 6-14; provided that:

at least one of m, n, and r is other than 0;
at least one of w and y is other than 0;
the sum of m, n, p, r, and t is from 2 to 5; and
the sum of v, w, x, y, and z is from 2 to 5.

RNAi Compounds

In certain embodiments, antisense compounds are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). In certain embodiments, antisense compounds comprise modifications that make them particularly suited for such mechanisms.

i. ssRNA Compounds

In certain embodiments, antisense compounds including those particularly suited for use as single-stranded RNAi compounds (ssRNA) comprise a modified 5'-terminal end. In certain such embodiments, the 5'-terminal end comprises a modified phosphate moiety. In certain embodiments, such modified phosphate is stabilized (e.g., resistant to degradation/cleavage compared to unmodified 5'-phosphate). In certain embodiments, such 5'-terminal nucleosides stabilize the 5'-phosphorous moiety. Certain modified 5'-terminal nucleosides may be found in the art, for example in WO 2011/139702.

In certain embodiments, the 5'-nucleoside of an ssRNA compound has Formula IIc:

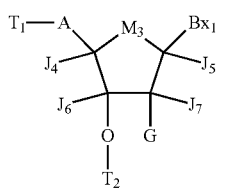

IIc wherein:
$T_1$ is an optionally protected phosphorus moiety;
$T_2$ is an internucleoside linking group linking the compound of Formula IIc to the oligomeric compound;
A has one of the formulas:

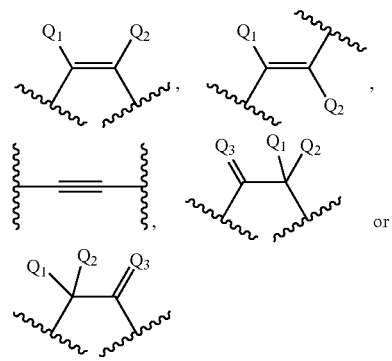

$Q_1$ and $Q_2$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or $N(R_3)(R_4)$;
$Q_3$ is O, S, $N(R_5)$ or $C(R_6)(R_7)$;

each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;
$M_3$ is O, S, $NR_{14}$, $C(R_{15})(R_{16})$, $C(R_{15})(R_{16})C(R_{17})(R_{18})$, $C(R_{15})=C(R_{17})$, $OC(R_{15})(R_{16})$ or $OC(R_{15})(Bx_2)$;
$R_{14}$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
$R_{15}$, $R_{16}$, $R_{17}$ and $R_{18}$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
$Bx_1$ is a heterocyclic base moiety;
or if $Bx_2$ is present then $Bx_2$ is a heterocyclic base moiety and $Bx_1$ is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
$J_4$, $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
or $J_4$ forms a bridge with one of $J_5$ or $J_7$ wherein said bridge comprises from 1 to 3 linked biradical groups selected from O, S, $NR_{19}$, $C(R_{20})(R_{21})$, $C(R_{20})=C(R_{21})$, $C[=C(R_{20})(R_{21})]$ and $C(=O)$ and the other two of $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
each $R_{19}$, $R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
G is H, OH, halogen or $O-[C(R_8)(R_9)]_n-[(C=O)_m-X_1]_j-Z$;
each $R_8$ and $R_9$ is, independently, H, halogen, $C_1$-$C_6$ alkyl or substituted $C_1$-$C_6$ alkyl;
$X_1$ is O, S or $N(E_1)$;
Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;
$E_1$, $E_2$ and $E_3$ are each, independently, H, $C_1$-$C_6$ alkyl or substituted $C_1$-$C_6$ alkyl;
n is from 1 to about 6;
m is 0 or 1;
j is 0 or 1;
each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=X_2)N(J_1)(J_2)$;
$X_2$ is O, S or $NJ_3$;
each $J_1$, $J_2$ and $J_3$ is, independently, H or $C_1$-$C_6$ alkyl;
when j is 1 then Z is other than halogen or $N(E_2)(E_3)$; and
wherein said oligomeric compound comprises from 8 to 40 monomeric subunits and is hybridizable to at least a portion of a target nucleic acid.

In certain embodiments, $M_3$ is O, CH=CH, $OCH_2$ or $OC(H)(Bx_2)$. In certain embodiments, $M_3$ is O.

In certain embodiments, $J_4$, $J_5$, $J_6$ and $J_7$ are each H. In certain embodiments, $J_4$ forms a bridge with one of $J_5$ or $J_7$.

In certain embodiments, A has one of the formulas:

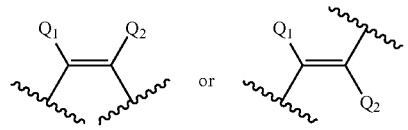

wherein:

$Q_1$ and $Q_2$ are each, independently, H, halogen, $C_1$-$C_6$ alkyl, substituted $C_1$-$C_6$ alkyl, $C_1$-$C_6$ alkoxy or substituted $C_1$-$C_6$ alkoxy. In certain embodiments, $Q_1$ and $Q_2$ are each H. In certain embodiments, $Q_1$ and $Q_2$ are each, independently, H or halogen. In certain embodiments, $Q_1$ and $Q_2$ is H and the other of $Q_1$ and $Q_2$ is F, $CH_3$ or $OCH_3$.

In certain embodiments, $T_1$ has the formula:

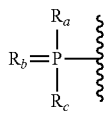

wherein:

$R_a$ and $R_c$ are each, independently, protected hydroxyl, protected thiol, $C_1$-$C_6$ alkyl, substituted $C_1$-$C_6$ alkyl, $C_1$-$C_6$ alkoxy, substituted $C_1$-$C_6$ alkoxy, protected amino or substituted amino; and $R_b$ is O or S. In certain embodiments, $R_b$ is O and $R_a$ and $R_c$ are each, independently, $OCH_3$, $OCH_2CH_3$ or $CH(CH_3)_2$.

In certain embodiments, G is halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH=$CH_2$, $O(CH_2)_2$—$OCH_3$, $O(CH_2)_2$—$SCH_3$, $O(CH_2)_2$—$OCF_3$, $O(CH_2)_3$—$N(R_{10})(R_{11})$, $O(CH_2)_2$—O $N(R_{10})(R_{11})$, $O(CH_2)_2$—$O(CH_2)_2$—$N(R_{10})(R_{11})$, $OCH_2C$(=O)—$N(R_{10})(R_{11})$, $OCH_2C$(=O)—$N(R_{12})$—$(CH_2)_2$—$N(R_{10})(R_{11})$ or $O(CH_2)_2$—$N(R_{12})$—C(=$NR_{13}$)[$N(R_{10})(R_{11})$] wherein $R_{10}$, $R_{11}$, $R_{12}$ and $R_{13}$ are each, independently, H or $C_1$-$C_6$ alkyl. In certain embodiments, G is halogen, $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—O$(CH_2)_2$—$N(CH_3)_2$, $OCH_2C$(=O)—$N(H)CH_3$, $OCH_2C$(=O)—$N(H)$—$(CH_2)_2$—$N(CH_3)_2$ or $OCH_2$—$N(H)$—C(=NH)$NH_2$. In certain embodiments, G is F, $OCH_3$ or $O(CH_2)_2$—$OCH_3$. In certain embodiments, G is $O(CH_2)_2$—$OCH_3$.

In certain embodiments, the 5'-terminal nucleoside has Formula IIe:

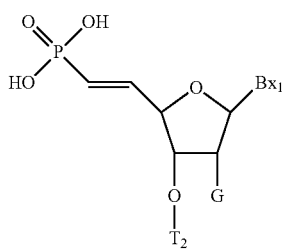

IIe

In certain embodiments, antisense compounds, including those particularly suitable for ssRNA comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having uniform sugar modifications. In certain such embodiments, each nucleoside of the region comprises the same RNA-like sugar modification. In certain embodiments, each nucleoside of the region is a 2'-F nucleoside. In certain embodiments, each nucleoside of the region is a 2'-OMe nucleoside. In certain embodiments, each nucleoside of the region is a 2'-MOE nucleoside. In certain embodiments, each nucleoside of the region is a cEt nucleoside. In certain embodiments, each nucleoside of the region is an LNA nucleoside. In certain embodiments, the uniform region constitutes all or essentially all of the oligonucleotide. In certain embodiments, the region constitutes the entire oligonucleotide except for 1-4 terminal nucleosides.

In certain embodiments, oligonucleotides comprise one or more regions of alternating sugar modifications, wherein the nucleosides alternate between nucleotides having a sugar modification of a first type and nucleotides having a sugar modification of a second type. In certain embodiments, nucleosides of both types are RNA-like nucleosides. In certain embodiments the alternating nucleosides are selected from: 2'-OMe, 2'-F, 2'-MOE, LNA, and cEt. In certain embodiments, the alternating modifications are 2'-F and 2'-OMe. Such regions may be contiguous or may be interrupted by differently modified nucleosides or conjugated nucleosides.

In certain embodiments, the alternating region of alternating modifications each consist of a single nucleoside (i.e., the pattern is $(AB)_xA_y$ wherein A is a nucleoside having a sugar modification of a first type and B is a nucleoside having a sugar modification of a second type; x is 1-20 and y is 0 or 1). In certain embodiments, one or more alternating regions in an alternating motif includes more than a single nucleoside of a type. For example, oligonucleotides may include one or more regions of any of the following nucleoside motifs:

AABBAA;
ABBABB;
AABAAB;
ABBABAABB;
ABABAA;
AABABAB;
ABABAA;
ABBAABBABABAA;
BABBAABBABABAA; or
ABABBAABBABABAA;

wherein A is a nucleoside of a first type and B is a nucleoside of a second type. In certain embodiments, A and B are each selected from 2'-F, 2'-OMe, BNA, and MOE.

In certain embodiments, oligonucleotides having such an alternating motif also comprise a modified 5' terminal nucleoside, such as those of formula IIc or IIe.

In certain embodiments, oligonucleotides comprise a region having a 2-2-3 motif. Such regions comprises the following motif:

$$-(A)_2-(B)_x-(A)_2-(C)_y-(A)_3-$$

wherein: A is a first type of modified nucleoside;

B and C, are nucleosides that are differently modified than A, however, B and C may have the same or different modifications as one another;

x and y are from 1 to 15.

In certain embodiments, A is a 2'-OMe modified nucleoside. In certain embodiments, B and C are both 2'-F modified nucleosides. In certain embodiments, A is a 2'-OMe modified nucleoside and B and C are both 2'-F modified nucleosides.

In certain embodiments, oligonucleosides have the following sugar motif:

$$5'-(Q)-(AB)_xA_y-(D)_z$$

wherein:

Q is a nucleoside comprising a stabilized phosphate moiety. In certain embodiments, Q is a nucleoside having Formula IIc or IIe;

A is a first type of modified nucleoside;

B is a second type of modified nucleoside;

D is a modified nucleoside comprising a modification different from the nucleoside adjacent to it. Thus, if y is 0, then D must be differently modified than B and if y is 1, then D must be differently modified than A. In certain embodiments, D differs from both A and B.

X is 5-15;
Y is 0 or 1;
Z is 0-4.

In certain embodiments, oligonucleosides have the following sugar motif:

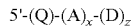

wherein:

Q is a nucleoside comprising a stabilized phosphate moiety. In certain embodiments, Q is a nucleoside having Formula IIc or IIe;

A is a first type of modified nucleoside;

D is a modified nucleoside comprising a modification different from A.

X is 11-30;
Z is 0-4.

In certain embodiments A, B, C, and D in the above motifs are selected from: 2'-OMe, 2'-F, 2'-MOE, LNA, and cEt. In certain embodiments, D represents terminal nucleosides. In certain embodiments, such terminal nucleosides are not designed to hybridize to the target nucleic acid (though one or more might hybridize by chance). In certain embodiments, the nucleobase of each D nucleoside is adenine, regardless of the identity of the nucleobase at the corresponding position of the target nucleic acid. In certain embodiments the nucleobase of each D nucleoside is thymine.

In certain embodiments, antisense compounds, including those particularly suited for use as ssRNA comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least one block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Oligonucleotides having any of the various sugar motifs described herein, may have any linkage motif. For example, the oligonucleotides, including but not limited to those described above, may have a linkage motif selected from non-limiting the table below:

| 5' most linkage | Central region | 3'-region |
|---|---|---|
| PS | Alternating PO/PS | 6 PS |
| PS | Alternating PO/PS | 7 PS |
| PS | Alternating PO/PS | 8 PS | ii. siRNA compounds

In certain embodiments, antisense compounds are double-stranded RNAi compounds (siRNA). In such embodiments, one or both strands may comprise any modification motif described above for ssRNA. In certain embodiments, ssRNA compounds may be unmodified RNA. In certain embodiments, siRNA compounds may comprise unmodified RNA nucleosides, but modified internucleoside linkages.

Several embodiments relate to double-stranded compositions wherein each strand comprises a motif defined by the location of one or more modified or unmodified nucleosides. In certain embodiments, compositions are provided comprising a first and a second oligomeric compound that are fully or at least partially hybridized to form a duplex region and further comprising a region that is complementary to and hybridizes to a nucleic acid target. It is suitable that such a composition comprise a first oligomeric compound that is an antisense strand having full or partial complementarity to a nucleic acid target and a second oligomeric compound that is a sense strand having one or more regions of complementarity to and forming at least one duplex region with the first oligomeric compound.

The compositions of several embodiments modulate gene expression by hybridizing to a nucleic acid target resulting in loss of its normal function. In some embodiments, the target nucleic acid is TMPRSS6. In certain embodiment, the degradation of the targeted TMPRSS6 is facilitated by an activated RISC complex that is formed with compositions of the invention.

Several embodiments are directed to double-stranded compositions wherein one of the strands is useful in, for example, influencing the preferential loading of the opposite strand into the RISC (or cleavage) complex. The compositions are useful for targeting selected nucleic acid molecules and modulating the expression of one or more genes. In some embodiments, the compositions of the present invention hybridize to a portion of a target RNA resulting in loss of normal function of the target RNA.

Certain embodiments are drawn to double-stranded compositions wherein both the strands comprises a hemimer motif, a fully modified motif, a positionally modified motif or an alternating motif. Each strand of the compositions of the present invention can be modified to fulfil a particular role in for example the siRNA pathway. Using a different motif in each strand or the same motif with different chemical modifications in each strand permits targeting the antisense strand for the RISC complex while inhibiting the incorporation of the sense strand. Within this model, each strand can be independently modified such that it is enhanced for its particular role. The antisense strand can be modified at the 5'-end to enhance its role in one region of the RISC while the 3'-end can be modified differentially to enhance its role in a different region of the RISC.

The double-stranded oligonucleotide molecules can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The double-stranded oligonucleotide molecules can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double-stranded structure, for example wherein the double-stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the double-stranded oligonucleotide molecule are complementary to the target nucleic acid or a portion thereof). Alternatively, the double-stranded oligonucleotide is assembled from a single oligonucleotide, where the self-complementary sense and antisense regions of the siRNA are linked by means of a nucleic acid based or non-nucleic acid-based linker(s).

The double-stranded oligonucleotide can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The double-stranded oligonucleotide can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNAi.

In certain embodiments, the double-stranded oligonucleotide comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions. In certain embodiments, the double-stranded oligonucleotide comprises nucleotide sequence that is complementary to nucleotide sequence of a target gene. In another embodiment, the double-stranded oligonucleotide interacts with nucleotide sequence of a target gene in a manner that causes inhibition of expression of the target gene.

As used herein, double-stranded oligonucleotides need not be limited to those molecules containing only RNA, but further encompasses chemically modified nucleotides and non-nucleotides. In certain embodiments, the short interfering nucleic acid molecules lack 2'-hydroxy (2'-OH) containing nucleotides. In certain embodiments short interfering nucleic acids optionally do not include any ribonucleotides (e.g., nucleotides having a 2'-OH group). Such double-stranded oligonucleotides that do not require the presence of ribonucleotides within the molecule to support RNAi can however have an attached linker or linkers or other attached or associated groups, moieties, or chains containing one or more nucleotides with 2'-OH groups. Optionally, double-stranded oligonucleotides can comprise ribonucleotides at about 5, 10, 20, 30, 40, or 50% of the nucleotide positions. As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, double-stranded oligonucleotides can be used to epigenetically silence genes at both the post-transcriptional level and the pre-transcriptional level. In a non-limiting example, epigenetic regulation of gene expression by siRNA molecules of the invention can result from siRNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

It is contemplated that compounds and compositions of several embodiments provided herein can target TMPRSS6 by a dsRNA-mediated gene silencing or RNAi mechanism, including, e.g., "hairpin" or stem-loop double-stranded RNA effector molecules in which a single RNA strand with self-complementary sequences is capable of assuming a double-stranded conformation, or duplex dsRNA effector molecules comprising two separate strands of RNA. In various embodiments, the dsRNA consists entirely of ribonucleotides or consists of a mixture of ribonucleotides and deoxynucleotides, such as the RNA/DNA hybrids disclosed, for example, by WO 00/63364, filed Apr. 19, 2000, or U.S. Ser. No. 60/130,377, filed Apr. 21, 1999. The dsRNA or dsRNA effector molecule may be a single molecule with a region of self-complementarity such that nucleotides in one segment of the molecule base pair with nucleotides in another segment of the molecule. In various embodiments, a dsRNA that consists of a single molecule consists entirely of ribonucleotides or includes a region of ribonucleotides that is complementary to a region of deoxyribonucleotides. Alternatively, the dsRNA may include two different strands that have a region of complementarity to each other.

In various embodiments, both strands consist entirely of ribonucleotides, one strand consists entirely of ribonucleotides and one strand consists entirely of deoxyribonucleotides, or one or both strands contain a mixture of ribonucleotides and deoxyribonucleotides. In certain embodiments, the regions of complementarity are at least 70, 80, 90, 95, 98, or 100% complementary to each other and to a target nucleic acid sequence. In certain embodiments, the region of the dsRNA that is present in a double-stranded conformation includes at least 19, 20, 21, 22, 23, 24, 25, 26, 27, 28, 29, 30, 50, 75, 100, 200, 500, 1000, 2000 or 5000 nucleotides or includes all of the nucleotides in a cDNA or other target nucleic acid sequence being represented in the dsRNA. In some embodiments, the dsRNA does not contain any single stranded regions, such as single stranded ends, or the dsRNA is a hairpin. In other embodiments, the dsRNA has one or more single stranded regions or overhangs. In certain embodiments, RNA/DNA hybrids include a DNA strand or region that is an antisense strand or region (e.g, has at least 70, 80, 90, 95, 98, or 100% complementarity to a target nucleic acid) and an RNA strand or region that is a sense strand or region (e.g, has at least 70, 80, 90, 95, 98, or 100% identity to a target nucleic acid), and vice versa.

In various embodiments, the RNA/DNA hybrid is made in vitro using enzymatic or chemical synthetic methods such as those described herein or those described in WO 00/63364, filed Apr. 19, 2000, or U.S. Ser. No. 60/130,377, filed Apr. 21, 1999. In other embodiments, a DNA strand synthesized in vitro is complexed with an RNA strand made in vivo or in vitro before, after, or concurrent with the transformation of the DNA strand into the cell. In yet other embodiments, the dsRNA is a single circular nucleic acid containing a sense and an antisense region, or the dsRNA includes a circular nucleic acid and either a second circular nucleic acid or a linear nucleic acid (see, for example, WO 00/63364, filed Apr. 19, 2000, or U.S. Ser. No. 60/130,377, filed Apr. 21, 1999.) Exemplary circular nucleic acids include lariat structures in which the free 5' phosphoryl group of a nucleotide becomes linked to the 2' hydroxyl group of another nucleotide in a loop back fashion.

In other embodiments, the dsRNA includes one or more modified nucleotides in which the 2' position in the sugar contains a halogen (such as fluorine group) or contains an alkoxy group (such as a methoxy group) which increases the half-life of the dsRNA in vitro or in vivo compared to the corresponding dsRNA in which the corresponding 2' position contains a hydrogen or an hydroxyl group. In yet other embodiments, the dsRNA includes one or more linkages between adjacent nucleotides other than a naturally-occurring phosphodiester linkage. Examples of such linkages include phosphoramide, phosphorothioate, and phosphorodithioate linkages. The dsRNAs may also be chemically modified nucleic acid molecules as taught in U.S. Pat. No. 6,673,661. In other embodiments, the dsRNA contains one or two capped strands, as disclosed, for example, by WO 00/63364, filed Apr. 19, 2000, or U.S. Ser. No. 60/130,377, filed Apr. 21, 1999.

In other embodiments, the dsRNA can be any of the at least partially dsRNA molecules disclosed in WO 00/63364, as well as any of the dsRNA molecules described in U.S. Provisional Application 60/399,998; and U.S. Provisional Application 60/419,532, and PCT/US2003/033466, the teaching of which is hereby incorporated by reference. Any of the dsRNAs may be expressed in vitro or in vivo using the methods described herein or standard methods, such as those described in WO 00/63364.

Occupancy

In certain embodiments, antisense compounds are not expected to result in cleavage or the target nucleic acid via RNase H or to result in cleavage or sequestration through the RISC pathway. In certain such embodiments, antisense activity may result from occupancy, wherein the presence of the hybridized antisense compound disrupts the activity of the target nucleic acid. In certain such embodiments, the antisense compound may be uniformly modified or may comprise a mix of modifications and/or modified and unmodified nucleosides.

Target Nucleic Acids, Target Regions and Nucleotide Sequences

Nucleotide sequences that encode TMPRSS6 include, without limitation, the following: GENBANK Accession NM_153609.2 (incorporated herein as SEQ ID NO: 1), the complement of GENBANK Accession NT_011520.12 truncated from Ser. No. 16/850,000 to Ser. No. 16/897,000 (incorporated herein as SEQ ID NO: 2), GENBANK Accession CR456446.1 (incorporated herein as SEQ ID NO: 3), GENBANK Accession No. BC039082.1 (incorporated herein as SEQ ID NO: 4), GENBANK Accession No. AY358398.1 (incorporated herein as SEQ ID NO: 5), or GENBANK Accession No. DB081153.1 (incorporated herein as SEQ ID NO: 6). In certain embodiments, an antisense compound described herein targets a nucleic acid sequence encoding TMPRSS6. In certain embodiments, an antisense compound described herein targets the sequence of any of SEQ ID NOs: 1-6.

It is understood that the sequence set forth in each SEQ ID NO in the examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for TMPRSS6 can be obtained by accession number from sequence databases such as NCBI and such information is incorporated herein by reference. In certain embodiments, a target region may encompass the sequence from a 5' target site of one target segment within the target region to a 3' target site of another target segment within the target region.

In certain embodiments, a "target segment" is a smaller, sub-portion of a target region within a nucleic acid. For example, a target segment can be the sequence of nucleotides of a target nucleic acid to which one or more antisense compound is targeted. "5' target site" refers to the 5'-most nucleotide of a target segment. "3' target site" refers to the 3'-most nucleotide of a target segment.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in TMPRSS6 mRNA levels are indicative of inhibition of TMPRSS6 expression. Reductions in levels of a TMPRSS6 protein are also indicative of inhibition of TMPRSS6 expression. Further, phenotypic changes are indicative of inhibition of TMPRSS6 expression. For example, an increase in hepcidin expression levels can be indicative of inhibition of TMPRSS6 expression. In another example, a decrease in iron accumulation in tissues can be indicative of inhibition of TMPRSS6 expression. In another example, an increase in the percentage of saturation of transferrin can be indicative of inhibition of TMPRSS6 expression.

Hybridization

In some embodiments, hybridization occurs between an antisense compound disclosed herein and a TMPRSS6 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art (Sambrook and Russell, Molecular Cloning: A Laboratory Manual, $3^{rd}$ Ed., 2001). In certain embodiments, the antisense compounds provided herein are specifically hybridizable with a TMPRSS6 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a TMPRSS6 nucleic acid).

Non-complementary nucleobases between an antisense compound and a TMPRSS6 nucleic acid may be tolerated provided that the antisense compound remains able to specifically hybridize to the TMPRSS6 nucleic acid. Moreover, an antisense compound may hybridize over one or more segments of a TMPRSS6 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least 70%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% complementary to a TMPRSS6 nucleic acid, a target region, target segment, or specified portion thereof. Percent complementarity of an antisense compound with a target nucleic acid can be determined using routine methods. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention.

Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, antisense compound may be fully complementary to a TMPRSS6 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a TMPRSS6 nucleic acid, or specified portion thereof.

In certain embodiments, antisense compounds that are, or are up to, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a TMPRSS6 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, at least a 10, at least an 11, at least a 12, at least a 13, at least a 14, at least a 15, at least a 16, at least a 17, at least an 18, at least a 19, at least a 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, at least 75%, at least 80%, at least 85%, at least 90%, at least 95%, at least 96%, at least 97%, at least 98%, at least 99% or 100% identical to one or more of the antisense compounds or SEQ ID NOs, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a TMPRSS6 nucleic acid comprise one or more modified internucleoside linkages. In certain embodiments, at least one of the modified internucleoside linkages are phosphorothioate linkages. In certain embodiments, each internucleoside linkage of an antisense compound is a phosphorothioate internucleoside linkage.

Modified Sugar Moieties

Antisense compounds of the invention can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substituent groups (including 5' and 2' substituent groups, bridging of non-geminal ring atoms to form bicyclic nucleic acids (BNA), replacement of the ribosyl ring oxygen atom with S, N(R), or C($R_1$)($R_2$) (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-$OCH_3$, 2'-$OCH_2CH_3$, 2'-$OCH_2CH_2F$ and 2'-$O(CH_2)_2OCH_3$ substituent groups. The substituent at the 2' position can also be selected from allyl, amino, azido, thio, O—$C_1$-$C_{10}$ alkyl, $OCF_3$, $OCH_2F$, $O(CH_2)_2SCH_3$, $O(CH_2)_2$—O—N($R_m$)($R_n$), O—$CH_2$—C(=O)—N($R_m$)($R_n$), and O—$CH_2$—C(=O)—N(R)—$(CH_2)_2$—N($R_m$)($R_n$), where each $R_j$, $R_m$ and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'-($CH_2$)—O-2' (LNA); 4'-($CH_2$)—S-2; 4'-($CH_2$)$_2$—O-2' (ENA); 4'-CH($CH_3$)—O-2' (cEt) and 4'-CH($CH_2OCH_3$)—O-2' (and analogs thereof see U.S. Pat. No. 7,399,845, issued on Jul. 15, 2008); 4'-C($CH_3$)($CH_3$)—O-2' (and analogs thereof see PCT/US2008/068922 published as WO/2009/006478, published Jan. 8, 2009); 4'-$CH_2$—N($OCH_3$)-2' (and analogs thereof see PCT/US2008/064591 published as WO/2008/150729, published Dec. 11, 2008); 4'-$CH_2$—O—N($CH_3$)-2' (see published U.S. Patent Application US2004-0171570, published Sep. 2, 2004); 4'-$CH_2$—N(R)—O-2', wherein R is H, $C_1$-$C_{12}$ alkyl, or a protecting group (see U.S. Pat. No. 7,427,672, issued on Sep. 23, 2008); 4'-$CH_2$—C(H)($CH_3$)-2' (see Zhou et al., *J. Org. Chem.*, 2009, 74, 118-134); and 4'-$CH_2$—C(=$CH_2$)-2' (and analogs thereof see PCT/US2008/066154 published as WO 2008/154401, published on Dec. 8, 2008).

Further bicyclic nucleosides have been reported in published literature (see for example: Srivastava et al., *J. Am. Chem. Soc.*, 2007, 129 (26) 8362-8379; Frieden et al., *Nucleic Acids Research*, 2003, 21, 6365-6372; Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; Wahlestedt et al., *Proc. Natl. Acad. Sci. U.S.A.*, 2000, 97, 5633-5638; Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J. Org. Chem.*, 1998, 63, 10035-10039; U.S. Pat. Nos. 7,399,845; 7,053,207; 7,034,133; 6,794,499; 6,770,748; 6,670,461; 6,525,191; 6,268,490; U.S. Patent Publication Nos.: US2008-0039618; US2007-0287831; US2004-0171570; U.S. patent application Ser. Nos. 12/129,154; 61/099,844; 61/097,787; 61/086,231; 61/056,564; 61/026,998; 61/026,995; 60/989,574; International applications WO 2007/134181; WO 2005/021570; WO 2004/106356; WO 99/14226; and PCT International Applications Nos.: PCT/US2008/068922; PCT/US2008/066154; and PCT/US2008/064591). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

As used herein, "monocyclic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

In certain embodiments, bicyclic sugar moieties of BNA nucleosides include, but are not limited to, compounds having at least one bridge between the 4' and the 2' carbon atoms of the pentofuranosyl sugar moiety including without limitation, bridges comprising 1 or from 1 to 4 linked groups independently selected from —[C($R_a$)($R_b$)]$_n$—, —C($R_a$)=C($R_b$)—, —C($R_a$)=N—, —C(=N$R_a$)—, —C(=O)—, —C(=S)—, —O—, —Si($R_a$)$_2$—, —S(=O)$_x$—, and —N($R_a$)—; wherein: x is 0, 1, or 2; n is 1, 2, 3, or 4; each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is, —[C($R_a$)($R_b$)]$_n$—, —[C($R_a$)($R_b$)]$_n$—O—, —C($R_aR_b$)—N(R)—O— or —C($R_aR_b$)—O—N(R)—. In certain embodiments, the bridge is 4'-$CH_2$-2', 4'-($CH_2$)$_2$-2', 4'-($CH_2$)$_3$-2', 4'-$CH_2$—O-2', 4'-($CH_2$)$_2$—O-2', 4'-$CH_2$—O—N(R)-2' and 4'-$CH_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-($CH_2$)—O-2' bridge, may be in the α-L configuration or in the β-D configuration. Previously, α-L-methyleneoxy (4'-$CH_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include those having a 4' to 2' bridge wherein such bridges include without limitation, α-L-4'-($CH_2$)—O-2', β-D-4'-$CH_2$—O-2', 4'-($CH_2$)$_2$—O—N(R)-2', 4'-$CH_2$—N(R)—O-2', 4'-CH (CH$_3$)—O-2', 4'-CH$_2$—S-2', 4'CH$_2$—N(R)-2', 4'-CH$_2$—CH(CH$_3$)-2', and 4'-(CH$_2$)$_3$-2', wherein R is H, a protecting group or C$_1$-C$_{12}$ alkyl.

In certain embodiment, bicyclic nucleosides have the formula:

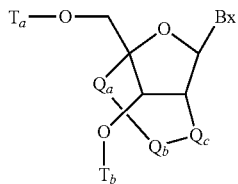

wherein:
Bx is a heterocyclic base moiety;
-Q$_a$-Q$_b$-Q$_c$- is —CH$_2$—N(R$_c$)—CH$_2$—, —C(=O)—N(R$_c$)—CH$_2$—, —CH$_2$—O—N(R$_c$)—, —CH$_2$—N(R$_c$)—O— or —N(R$_c$)—O—CH$_2$;
R$_c$ is C$_1$-C$_{12}$ alkyl or an amino protecting group; and
T$_a$ and T$_b$ are each, independently H, a hydroxyl protecting group, a conjugate group, a reactive phosphorus group, a phosphorus moiety or a covalent attachment to a support medium.

In certain embodiments, bicyclic nucleosides have the formula:

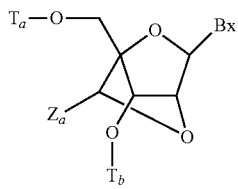

wherein:
Bx is a heterocyclic base moiety;
T$_a$ and T$_b$ are each, independently H, a hydroxyl protecting group, a conjugate group, a reactive phosphorus group, a phosphorus moiety or a covalent attachment to a support medium;
Z$_a$ is C$_1$-C$_6$ alkyl, C$_2$-C$_6$ alkenyl, C$_2$-C$_6$ alkynyl, substituted C$_1$-C$_6$ alkyl, substituted C$_2$-C$_6$ alkenyl, substituted C$_2$-C$_6$ alkynyl, acyl, substituted acyl, substituted amide, thiol or substituted thiol.

In one embodiment, each of the substituted groups, is, independently, mono or poly substituted with substituent groups independently selected from halogen, oxo, hydroxyl, OJ$_c$, NJ$_c$J$_d$, SJ$_c$, N$_3$, OC(=X)J$_c$, and NJ$_e$C(=X)NJ$_c$J$_d$, wherein each J$_c$, J$_d$ and J$_e$ is, independently, H, C$_1$-C$_6$ alkyl, or substituted C$_1$-C$_6$ alkyl and X is O or NJ$_c$.

In certain embodiments, bicyclic nucleosides have the formula:

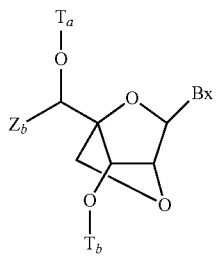

wherein:
Bx is a heterocyclic base moiety;
T$_a$ and T$_b$ are each, independently H, a hydroxyl protecting group, a conjugate group, a reactive phosphorus group, a phosphorus moiety or a covalent attachment to a support medium;
Z$_b$ is C$_1$-C$_6$ alkyl, C$_2$-C$_6$ alkenyl, C$_2$-C$_6$ alkynyl, substituted C$_1$-C$_6$ alkyl, substituted C$_2$-C$_6$ alkenyl, substituted C$_2$-C$_6$ alkynyl or substituted acyl (C(=O)—).

In certain embodiments, bicyclic nucleosides have the formula:

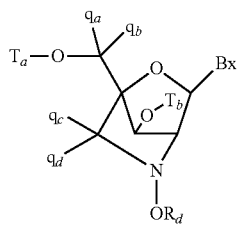

wherein:
Bx is a heterocyclic base moiety;
T$_a$ and T$_b$ are each, independently H, a hydroxyl protecting group, a conjugate group, a reactive phosphorus group, a phosphorus moiety or a covalent attachment to a support medium;
R$_d$ is C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl or substituted C$_2$-C$_6$ alkynyl;
each q$_a$, q$_b$, q$_c$ and q$_d$ is, independently, H, halogen, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl or substituted C$_2$-C$_6$ alkynyl, C$_1$-C$_6$ alkoxyl, substituted C$_1$-C$_6$ alkoxyl, acyl, substituted acyl, C$_1$-C$_6$ aminoalkyl or substituted C$_1$-C$_6$ aminoalkyl;

In certain embodiments, bicyclic nucleosides have the formula:

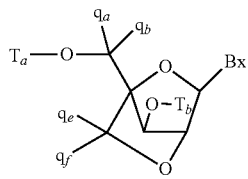

wherein:
Bx is a heterocyclic base moiety;
T$_a$ and T$_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O-C(=O)NJ_jJ_k$, $N(H)C(=NH)NJ_jJ_k$, $N(H)C(=O)NJ_jJ_k$ or $N(H)C(=S)NJ_jJ_k$;

or $q_e$ and $q_f$ together are $=C(q_g)(q_h)$;

$q_g$ and $q_h$ are each, independently, H, halogen, $C_1$-$C_{12}$ alkyl or substituted $C_1$-$C_{12}$ alkyl.

The synthesis and preparation of adenine, cytosine, guanine, 5-methyl-cytosine, thymine and uracil bicyclic nucleosides having a 4'-$CH_2$-O-2' bridge, along with their oligomerization, and nucleic acid recognition properties have been described (Koshkin et al., *Tetrahedron*, 1998, 54, 3607-3630). The synthesis of bicyclic nucleosides has also been described in WO 98/39352 and WO 99/14226.

Analogs of various bicyclic nucleosides that have 4' to 2' bridging groups such as 4'-$CH_2$-O-2' and 4'-$CH_2$-S-2', have also been prepared (Kumar et al., *Bioorg. Med. Chem. Lett.*, 1998, 8, 2219-2222). Preparation of oligodeoxyribonucleotide duplexes comprising bicyclic nucleosides for use as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides have the formula:

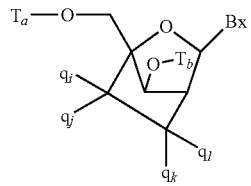

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O-C(=O)NJ_jJ_k$, $N(H)C(=NH)NJ_jJ_k$, $N(H)C(=O)NJ_jJ_k$ or $N(H)C(=S)NJ_jJ_k$; and $q_i$ and $q_j$ or $q_l$ and $q_k$ together are $=C(q_g)(q_h)$, wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-$(CH_2)_3$-2' bridge and the alkenyl analog bridge 4'-CH=CH-$CH_2$-2' have been described (Frier et al., *Nucleic Acids Research*, 1997, 25 (22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.* 2007, 129 (26), 8362-8379).

In certain embodiments, bicyclic nucleosides include, but are not limited to, (A) α-L-methyleneoxy (4'-$CH_2$-O-2') BNA, (B) β-D-methyleneoxy (4'-$CH_2$-O-2') BNA, (C) ethyleneoxy (4'-$(CH_2)_2$-O-2') BNA, (D) aminooxy (4'-$CH_2$-O-N(R)-2') BNA, (E) oxyamino (4'-$CH_2$-N(R)-O-2') BNA, (F) methyl(methyleneoxy) (4'-$CH(CH_3)$-O-2') BNA (also referred to as constrained ethyl or cEt), (G) methylene-thio (4'-$CH_2$-S-2') BNA, (H) methylene-amino (4'-$CH_2$-N(R)-2') BNA, (I) methyl carbocyclic (4'-$CH_2$-$CH(CH_3)$-2') BNA, (J) propylene carbocyclic (4'-$(CH_2)_3$-2') BNA, and (K) vinyl BNA as depicted below.

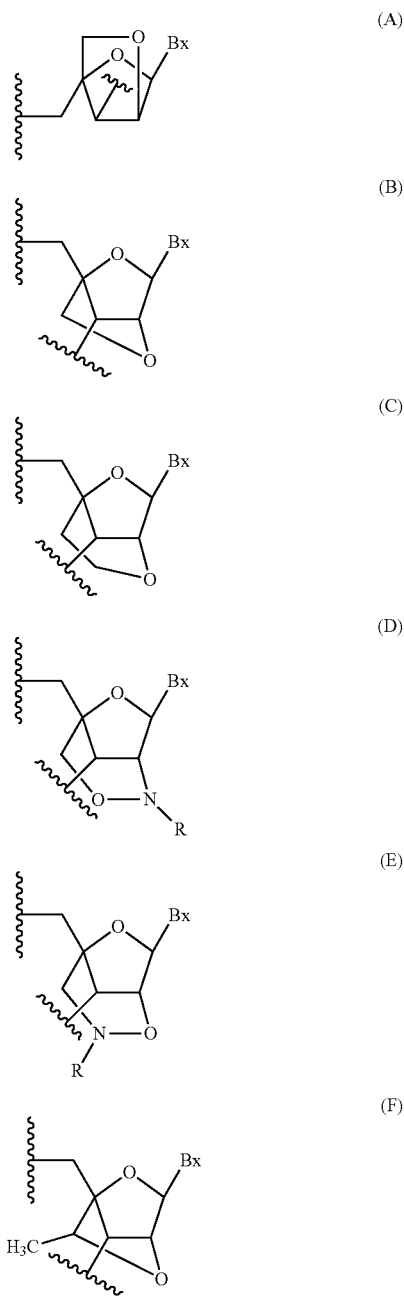

53
-continued

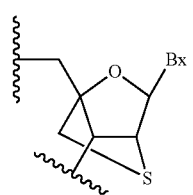
(G)

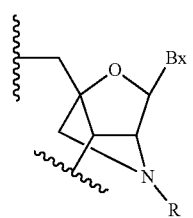
(H)

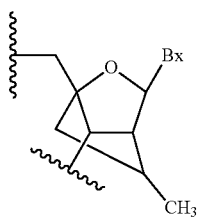
(I)

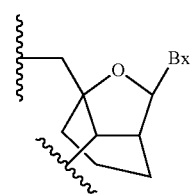
(J)

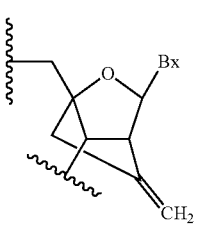
(K)

wherein Bx is the base moiety and R is, independently, H, a protecting group, $C_1$-$C_6$ alkyl or $C_1$-$C_6$ alkoxy.

As used herein, the term "modified tetrahydropyran nucleoside" or "modified THP nucleoside" means a nucleoside having a six-membered tetrahydropyran "sugar" substituted for the pentofuranosyl residue in normal nucleosides and can be referred to as a sugar surrogate. Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854) or fluoro HNA (F-HNA) having a tetrahydropyranyl ring system as illustrated below.

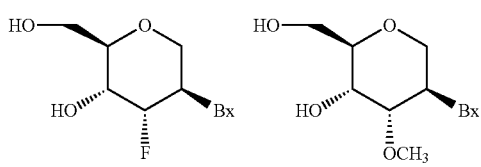

54
-continued

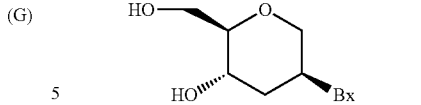

In certain embodiment, sugar surrogates are selected having the formula:

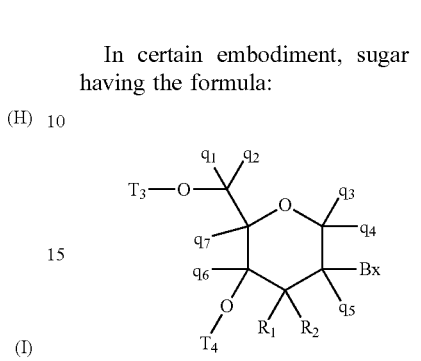

wherein:

Bx is a heterocyclic base moiety; $T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to an oligomeric compound or oligonucleotide and the other of $T_3$ and $T_4$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides are provided wherein one of $R_1$ and $R_2$ is F. In certain embodiments, $R_1$ is fluoro and $R_2$ is H; $R_1$ is methoxy and $R_2$ is H, and $R_1$ is methoxyethoxy and $R_2$ is H.

In certain embodiments, sugar surrogates comprise rings having more than 5 atoms and more than one heteroatom. For example nucleosides comprising morpholino sugar moieties and their use in oligomeric compounds has been reported (see for example: Braasch et al., *Biochemistry*, 2002, 41, 4503-4510; and U.S. Pat. Nos. 5,698,685; 5,166, 315; 5,185,444; and 5,034,506). As used here, the term "morpholino" means a sugar surrogate having the following formula:

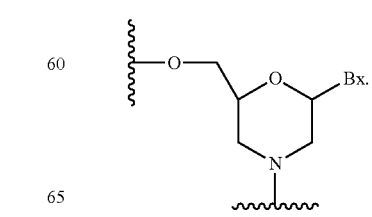

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129 (26), 8362-8379).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.*, 2008, 130 (6), 1979-1984; Horvath et al., *Tetrahedron Letters*, 2007, 48, 3621-3623; Nauwelaerts et al., *J. Am. Chem. Soc.*, 2007, 129 (30), 9340-9348; Gu et al. *Nucleosides, Nucleotides & Nucleic Acids*, 2005, 24 (5-7), 993-998; Nauwelaerts et al., *Nucleic Acids Research*, 2005, 33 (8), 2452-2463; Robeyns et al., *Acta Crystallographica, Section F: Structural Biology and Crystallization Communications*, 2005, F61 (6), 585-586; Gu et al., *Tetrahedron*, 2004, 60 (9), 2111-2123; Gu et al., *Oligonucleotides*, 2003, 13 (6), 479-489; Wang et al., *J. Org. Chem.*, 2003, 68, 4499-4505; Verbeure et al., *Nucleic Acids Research*, 2001, 29 (24), 4941-4947; Wang et al., *J. Org. Chem.*, 2001, 66, 8478-82; Wang et al., *Nucleosides, Nucleotides & Nucleic Acids*, 2001, 20 (4-7), 785-788; Wang et al., *J. Am. Chem.*, 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

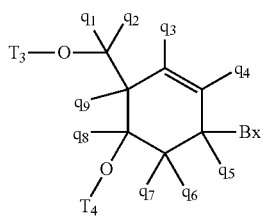

X wherein independently for each of said at least one cyclohexenyl nucleoside analog of Formula X:
Bx is a heterocyclic base moiety;
T$_3$ and T$_4$ are each, independently, an internucleoside linking group linking the cyclohexenyl nucleoside analog to an antisense compound or one of T$_3$ and T$_4$ is an internucleoside linking group linking the tetrahydropyran nucleoside analog to an antisense compound and the other of T$_3$ and T$_4$ is H, a hydroxyl protecting group, a linked conjugate group, or a 5'- or 3'-terminal group; and
q$_1$, q$_2$, q$_3$, q$_4$, q$_5$, q$_6$, q$_7$, q$_8$ and q$_9$ are each, independently, H, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl or other sugar substituent group.

Many other monocyclic, bicyclic and tricyclic ring systems are known in the art and are suitable as sugar surrogates that can be used to modify nucleosides for incorporation into oligomeric compounds as provided herein (see for example review article: Leumann, Christian J. *Bioorg. & Med. Chem.*, 2002, 10, 841-854). Such ring systems can undergo various additional substitutions to further enhance their activity.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[(CH$_2$)$_n$O]$_m$CH$_3$, O(CH$_2$)$_n$NH$_2$, O(CH$_2$)$_n$CH$_3$, O(CH$_2$)$_n$F, O(CH$_2$)$_n$ONH$_2$, OCH$_2$C(=O)N(H)CH$_3$, and O(CH$_2$)$_n$ON[(CH$_2$)$_n$CH$_3$]$_2$, where n and m are from 1 to about 10. Other 2'-substituent groups can also be selected from: C$_1$-C$_{12}$ alkyl, substituted alkyl, alkenyl, alkynyl, alkaryl, aralkyl, O-alkaryl or O-aralkyl, SH, SCH$_3$, OCN, Cl, Br, CN, F, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926). As used herein, "2'-modified" or "2'-substituted" refers to a nucleoside comprising a sugar comprising a substituent at the 2' position other than H or OH. 2'-modified nucleosides, include, but are not limited to, nucleosides with non-bridging 2' substituents, such as allyl, amino, azido, thio, O-allyl, O—C$_1$-C$_{10}$ alkyl, —OCF$_3$, O—(CH$_2$)$_2$—O—CH$_3$, 2'-O(CH$_2$)$_2$SCH$_3$, O—(CH$_2$)$_2$—O—N(R$_m$)(R$_n$), or O—CH$_2$—C(=O)—N (R$_m$)(R$_n$), where each R$_m$ and R$_n$ is, independently, H or substituted or unsubstituted C$_1$-C$_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position of the sugar ring.

As used herein, "2'-OMe" or "2'-OCH₃", "2'-O-methyl" or "2'-methoxy" each refers to a nucleoside comprising a sugar comprising an —OCH₃ group at the 2' position of the sugar ring.

As used herein, "MOE" or "2'-MOE" or "2'-OCH₂CH₂OCH₃" or "2'-O-methoxyethyl" each refers to a nucleoside comprising a sugar comprising a —OCH₂CH₂OCH₃ group at the 2' position of the sugar ring.

Methods for the preparations of modified sugars are well known to those skilled in the art. Some representative U.S. patents that teach the preparation of such modified sugars include without limitation, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005, and each of which is herein incorporated by reference in its entirety.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH(CH₃)—O-2') bridging group. In certain embodiments, the (4'-CH(CH₃)—O-2') modified nucleosides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH₃) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to a TMPRSS6 nucleic acid comprise one or more modified nucleobases. In certain embodiments, gap-widened antisense oligonucleotides targeted to a TMPRSS6 nucleic acid comprise one or more modified nucleobases. In certain embodiments, at least one of the modified nucleobases is 5-methylcytosine. In certain embodiments, each cytosine is a 5-methylcytosine.

Compositions and Methods for Formulating Pharmaceutical Compositions

Antisense oligonucleotides may be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to a TMPRSS6 nucleic acid can be utilized in pharmaceutical compositions by combining the antisense compound with a suitable pharmaceutically acceptable diluent or carrier. A pharmaceutically acceptable diluent includes water e.g., water-for-injection (WFI). A pharmaceutically acceptable diluent includes saline e.g., phosphate-buffered saline (PBS). Water or saline is a diluent suitable for use in compositions to be delivered parenterally. Accordingly, in one embodiment, employed in the methods described herein is a pharmaceutical composition comprising an antisense compound targeted to a TMPRSS6 nucleic acid and a pharmaceutically acceptable diluent. In certain embodiments, the pharmaceutically acceptable diluent is water or saline. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure herein is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

Pharmaceutically acceptable salts of the compounds described herein may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002). Sodium salts of antisense oligonucleotides are useful and are well accepted for therapeutic administration to humans. Accordingly, in one embodiment the compounds described herein are in the form of a sodium salt.

A prodrug can include the incorporation of additional nucleosides at one or both ends of an antisense compound which are cleaved by endogenous nucleases within the body, to form the active antisense compound.

Dosing

In certain embodiments, pharmaceutical compositions are administered according to a dosing regimen (e.g., dose, dose frequency, and duration) wherein the dosing regimen can be selected to achieve a desired effect. The desired effect can be, for example, reduction of TMPRSS6 or the prevention, reduction, amelioration or slowing the progression of a disease, disorder or condition associated with TMPRSS6.

In certain embodiments, the variables of the dosing regimen are adjusted to result in a desired concentration of pharmaceutical composition in a subject. "Concentration of pharmaceutical composition" as used with regard to dose regimen can refer to the compound, oligonucleotide, or active ingredient of the pharmaceutical composition. For example, in certain embodiments, dose and dose frequency are adjusted to provide a tissue concentration or plasma concentration of a pharmaceutical composition at an amount sufficient to achieve a desired effect.

Dosing is dependent on severity and responsiveness of the disease state to be treated, with the course of treatment lasting from several days to several months, or until a cure is effected or a diminution of the disease state is achieved. Dosing is also dependent on drug potency and metabolism. In certain embodiments, dosage is from 0.01 µg to 100 mg per kg of body weight, or within a range of 0.001 mg to 1000 mg dosing, and may be given once or more daily, weekly, biweekly, monthly, quarterly, semi-annually or yearly, or even once every 2 to 20 years. Following successful treatment, it may be desirable to have the patient undergo maintenance therapy to prevent the recurrence of the disease state, wherein the oligonucleotide is administered in maintenance doses, ranging from 0.01 g to 100 mg per kg of body weight, once or more daily, to once every 20 years or ranging from 0.001 mg to 1000 mg dosing.

Administration

The compounds or pharmaceutical compositions of the present invention can be administered in a number of ways depending upon whether local or systemic treatment is desired and upon the area to be treated. Administration can be inhaled (i.e., pulmonary), enteral (i.e., enteric), parenteral or topical.

In certain embodiments, the compounds and compositions as described herein are administered parenterally. Parenteral administration includes, but is not limited to, intravenous, intra-arterial, subcutaneous, intraperitoneal, intraocular, intramuscular, intracranial, intrathecal, intramedullary, intraventricular or intratumoral injection or infusion. Parenteral administration also includes intranasal administration.

In certain embodiments, parenteral administration is by infusion. Infusion can be chronic or continuous or short or intermittent. In certain embodiments, infused pharmaceutical agents are delivered with a pump.

In certain embodiments, parenteral administration is by injection. The injection can be delivered with a syringe or a pump. In certain embodiments, the injection is a bolus injection. In certain embodiments, the injection is administered directly to a tissue or organ.

In certain embodiments, formulations for parenteral administration can include sterile aqueous solutions which can also contain buffers, diluents and other suitable additives such as, but not limited to, penetration enhancers, carrier compounds and other pharmaceutically acceptable carriers or excipients.

In certain embodiments, the compounds and compositions as described herein are administered enterally. Enteric administration includes, but is not limited to, oral, transmucosal, intestinal or rectal (e.g., suppository, enema). In certain embodiments, formulations for enteral administration of the compounds or compositions can include, but is not limited to, pharmaceutical carriers, excipients, powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In certain embodiments, enteral formulations are those in which compounds provided herein are administered in conjunction with one or more penetration enhancers, surfactants and chelators.

In certain embodiments, administration includes pulmonary administration. In certain embodiments, pulmonary administration comprises delivery of aerosolized oligonucleotide to the lung of a subject by inhalation. Following inhalation by a subject of aerosolized oligonucleotide, oligonucleotide distributes to cells of both normal and inflamed lung tissue, including alveolar macrophages, eosinophils, epithelium, blood vessel endothelium, and bronchiolar epithelium. A suitable device for the delivery of a pharmaceutical composition comprising a modified oligonucleotide includes, but is not limited to, a standard nebulizer device. Additional suitable devices include dry powder inhalers or metered dose inhalers.

In certain embodiments, pharmaceutical compositions are administered to achieve local rather than systemic exposures. For example, pulmonary administration delivers a pharmaceutical composition to the lung, with minimal systemic exposure.

Conjugated Antisense Compounds

In certain embodiments, the oligonucleotides or oligomeric compounds as provided herein are modified by covalent attachment of one or more conjugate groups. In general, conjugate groups modify one or more properties of the attached oligonucleotide or oligomeric compound including but not limited to pharmacodynamics, pharmacokinetics, stability, binding, absorption, cellular distribution, cellular uptake, charge and clearance. As used herein, "conjugate group" means a radical group comprising a group of atoms that are attached to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties. Conjugate groups are routinely used in the chemical arts and can include a conjugate linker that covalently links the conjugate group to an oligonucleotide or oligomeric compound. In certain embodiments, conjugate groups include a cleavable moiety that covalently links the conjugate group to an oligonucleotide or oligomeric compound. In certain embodiments, conjugate groups include a conjugate linker and a cleavable moiety to covalently link the conjugate group to an oligonucleotide or oligomeric compound. In certain embodiments, a conjugate group has the general formula:

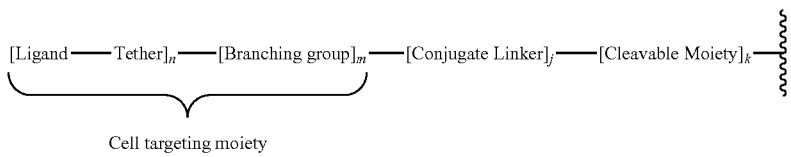

Cell targeting moiety wherein n is from 1 to about 3, m is 0 when n is 1 or m is 1 when n is 2 or 3, j is 1 or 0, k is 1 or 0 and the sum of j and k is at least one.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

Conjugate groups are shown herein as radicals, providing a bond for forming covalent attachment to an oligomeric compound such as an oligonucleotide. In certain embodiments, the point of attachment on the oligomeric compound is at the 3'-terminal nucleoside or modified nucleoside. In certain embodiments, the point of attachment on the oligomeric compound is the 3'-oxygen atom of the 3'-hydroxyl group of the 3' terminal nucleoside or modified nucleoside. In certain embodiments, the point of attachment on the oligomeric compound is at the 5'-terminal nucleoside or modified nucleoside. In certain embodiments the point of attachment on the oligomeric compound is the 5'-oxygen atom of the 5'-hydroxyl group of the 5'-terminal nucleoside or modified nucleoside. In certain embodiments, the point of attachment on the oligomeric compound is at any reactive site on a nucleoside, a modified nucleoside or an internucleoside linkage.

As used herein, "cleavable moiety" and "cleavable bond" mean a cleavable bond or group of atoms that is capable of being split or cleaved under certain physiological conditions. In certain embodiments, a cleavable moiety is a cleavable bond. In certain embodiments, a cleavable moiety comprises a cleavable bond. In certain embodiments, a cleavable moiety is a group of atoms. In certain embodiments, a cleavable moiety is selectively cleaved inside a cell or sub-cellular compartment, such as a lysosome. In certain embodiments, a cleavable moiety is selectively cleaved by endogenous enzymes, such as nucleases. In certain embodiments, a cleavable moiety comprises a group of atoms having one, two, three, four, or more than four cleavable bonds.

In certain embodiments, conjugate groups comprise a cleavable moiety. In certain such embodiments, the cleavable moiety covalently attaches the oligomeric compound to the conjugate linker. In certain such embodiments, the cleavable moiety covalently attaches the oligomeric compound to the cell-targeting moiety.

In certain embodiments, a cleavable bond is selected from among: an amide, a polyamide, an ester, an ether, one or both esters of a phosphodiester, a phosphate ester, a carbamate, a di-sulfide, or a peptide. In certain embodiments, a cleavable bond is one of the esters of a phosphodiester. In certain embodiments, a cleavable bond is one or both esters of a phosphodiester. In certain embodiments, the cleavable moiety is a phosphodiester linkage between an oligomeric compound and the remainder of the conjugate group. In certain embodiments, the cleavable moiety comprises a phosphodiester linkage that is located between an oligomeric compound and the remainder of the conjugate group. In certain embodiments, the cleavable moiety comprises a phosphate or phosphodiester. In certain embodiments, the cleavable moiety is attached to the conjugate linker by either a phosphodiester or a phosphorothioate linkage. In certain embodiments, the cleavable moiety is attached to the conjugate linker by a phosphodiester linkage. In certain embodiments, the conjugate group does not include a cleavable moiety.

In certain embodiments, the cleavable moiety is a cleavable nucleoside or a modified nucleoside. In certain embodiments, the nucleoside or modified nucleoside comprises an optionally protected heterocyclic base selected from a purine, substituted purine, pyrimidine or substituted pyrimidine. In certain embodiments, the cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine.

In certain embodiments, the cleavable moiety is 2'-deoxy nucleoside that is attached to either the 3' or 5'-terminal nucleoside of an oligomeric compound by a phosphodiester linkage and covalently attached to the remainder of the conjugate group by a phosphodiester or phosphorothioate linkage. In certain embodiments, the cleavable moiety is 2'-deoxy adenosine that is attached to either the 3' or 5'-terminal nucleoside of an oligomeric compound by a phosphodiester linkage and covalently attached to the remainder of the conjugate group by a phosphodiester or phosphorothioate linkage. In certain embodiments, the cleavable moiety is 2'-deoxy adenosine that is attached to the 3'-oxygen atom of the 3'-hydroxyl group of the 3'-terminal nucleoside or modified nucleoside by a phosphodiester linkage. In certain embodiments, the cleavable moiety is 2'-deoxy adenosine that is attached to the 5'-oxygen atom of the 5'-hydroxyl group of the 5'-terminal nucleoside or modified nucleoside by a phosphodiester linkage. In certain embodiments, the cleavable moiety is attached to a 2'-position of a nucleoside or modified nucleoside of an oligomeric compound.

As used herein, "conjugate linker" in the context of a conjugate group means a portion of a conjugate group comprising any atom or group of atoms that covalently link the cell-targeting moiety to the oligomeric compound either directly or through the cleavable moiety. In certain embodiments, the conjugate linker comprises groups selected from alkyl, amino, oxo, amide, disulfide, polyethylene glycol, ether, thioether (—S—) and hydroxylamino (—O—N(H)—). In certain embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus linking group. In certain embodiments, the conjugate linker comprises at least one phosphodiester group. In certain embodiments, the conjugate linker includes at least one neutral linking group.

In certain embodiments, the conjugate linker is covalently attached to the oligomeric compound. In certain embodiments, the conjugate linker is covalently attached to the oligomeric compound and the branching group. In certain embodiments, the conjugate linker is covalently attached to the oligomeric compound and a tethered ligand. In certain embodiments, the conjugate linker is covalently attached to the cleavable moiety. In certain embodiments, the conjugate linker is covalently attached to the cleavable moiety and the branching group. In certain embodiments, the conjugate linker is covalently attached to the cleavable moiety and a tethered ligand. In certain embodiments, the conjugate linker includes one or more cleavable bonds. In certain embodiments, the conjugate group does not include a conjugate linker.

As used herein, "branching group" means a group of atoms having at least 3 positions that are capable of forming covalent linkages to two or more tether-ligands and the remainder of the conjugate group. In general a branching group provides a plurality of reactive sites for connecting tethered ligands to the oligomeric compound through the conjugate linker and/or the cleavable moiety. In certain embodiments, the branching group comprises groups selected from alkyl, amino, oxo, amide, disulfide, polyethylene glycol, ether, thioether and hydroxylamino groups. In certain embodiments, the branching group comprises a branched aliphatic group comprising groups selected from alkyl, amino, oxo, amide, disulfide, polyethylene glycol, ether, thioether and hydroxylamino groups. In certain such embodiments, the branched aliphatic group comprises groups selected from alkyl, amino, oxo, amide and ether groups. In certain such embodiments, the branched aliphatic group comprises groups selected from alkyl, amino and ether groups. In certain such embodiments, the branched aliphatic group comprises groups selected from alkyl and ether groups. In certain embodiments, the branching group comprises a mono or polycyclic ring system.

In certain embodiments, the branching group is covalently attached to the conjugate linker. In certain embodiments, the branching group is covalently attached to the cleavable moiety. In certain embodiments, the branching group is covalently attached to the conjugate linker and each of the tethered ligands. In certain embodiments, the branching group comprises one or more cleavable bond. In certain embodiments, the conjugate group does not include a branching group.

In certain embodiments, conjugate groups as provided herein include a cell-targeting moiety that has at least one tethered ligand. In certain embodiments, the cell-targeting moiety comprises two tethered ligands covalently attached to a branching group. In certain embodiments, the cell-targeting moiety comprises three tethered ligands covalently attached to a branching group.

As used herein, "tether" means a group of atoms that connect a ligand to the remainder of the conjugate group. In certain embodiments, each tether is a linear aliphatic group comprising one or more groups selected from alkyl, substituted alkyl, ether, thioether, disulfide, amino, oxo, amide, phosphodiester and polyethylene glycol groups in any combination. In certain embodiments, each tether is a linear aliphatic group comprising one or more groups selected from alkyl, ether, thioether, disulfide, amino, oxo, amide and polyethylene glycol groups in any combination. In certain embodiments, each tether is a linear aliphatic group comprising one or more groups selected from alkyl, substituted alkyl, phosphodiester, ether and amino, oxo, amide groups in any combination. In certain embodiments, each tether is a linear aliphatic group comprising one or more groups selected from alkyl, ether and amino, oxo, amide groups in any combination. In certain embodiments, each tether is a linear aliphatic group comprising one or more groups selected from alkyl, amino and oxo groups in any combination. In certain embodiments, each tether is a linear aliphatic group comprising one or more groups selected from alkyl and oxo groups in any combination. In certain embodiments, each tether is a linear aliphatic group comprising one or more groups selected from alkyl and phosphodiester in any combination. In certain embodiments, each tether comprises at least one phosphorus linking group or neutral linking group.

In certain embodiments, tethers include one or more cleavable bond. In certain embodiments, each tethered ligand is attached to a branching group. In certain embodiments, each tethered ligand is attached to a branching group through an amide group. In certain embodiments, each tethered ligand is attached to a branching group through an ether group. In certain embodiments, each tethered ligand is attached to a branching group through a phosphorus linking group or neutral linking group. In certain embodiments, each tethered ligand is attached to a branching group through a phosphodiester group. In certain embodiments, each tether is attached to a ligand through either an amide or an ether group. In certain embodiments, each tether is attached to a ligand through an ether group.

In certain embodiments, each tether comprises from about 8 to about 20 atoms in chain length between the ligand and the branching group. In certain embodiments, each tether comprises from about 10 to about 18 atoms in chain length between the ligand and the branching group. In certain embodiments, each tether comprises about 13 atoms in chain length.

In certain embodiments, the present disclosure provides ligands wherein each ligand is covalently attached to the remainder of the conjugate group through a tether. In certain embodiments, each ligand is selected to have an affinity for at least one type of receptor on a target cell. In certain embodiments, ligands are selected that have an affinity for at least one type of receptor on the surface of a mammalian liver cell. In certain embodiments, ligands are selected that have an affinity for the hepatic asialoglycoprotein receptor (ASGP-R). In certain embodiments, each ligand is a carbohydrate. In certain embodiments, each ligand is, independently selected from galactose, N-acetyl galactoseamine, mannose, glucose, glucosamone and fucose. In certain embodiments, each ligand is N-acetyl galactoseamine (GalNAc). In certain embodiments, the targeting moiety comprises 1 to 3 ligands. In certain embodiments, the targeting moiety comprises 3 ligands. In certain embodiments, the targeting moiety comprises 2 ligands. In certain embodiments, the targeting moiety comprises 1 ligand. In certain embodiments, the targeting moiety comprises 3 N-acetyl galactoseamine ligands. In certain embodiments, the targeting moiety comprises 2 N-acetyl galactoseamine ligands. In certain embodiments, the targeting moiety comprises 1 N-acetyl galactoseamine ligand.

In certain embodiments, each ligand is a carbohydrate, carbohydrate derivative, modified carbohydrate, multivalent carbohydrate cluster, polysaccharide, modified polysaccharide, or polysaccharide derivative. In certain embodiments, each ligand is an amino sugar or a thio sugar. For example, amino sugars may be selected from any number of compounds known in the art, for example glucosamine, sialic acid, α-D-galactosamine, N-Acetylgalactosamine, 2-acetamido-2-deoxy-D-galactopyranose (GalNAc), 2-Amino-3-O—[(R)-1-carboxyethyl]-2-deoxy-β-D-glucopyranose β-muramic acid), 2-Deoxy-2-methylamino-L-glucopyranose, 4,6-Dideoxy-4-formamido-2,3-di-O-methyl-D-mannopyranose, 2-Deoxy-2-sulfoamino-D-glucopyranose and N-sulfo-D-glucosamine, and N-Glycoloyl-α-neuraminic acid. For example, thio sugars may be selected from the group consisting of 5-Thio-β-D-glucopyranose, Methyl 2,3,4-tri-O-acetyl-1-thio-6-O-trityl-α-D-glucopyranoside, 4-Thio-β-D-galactopyranose, and ethyl 3,4,6,7-tetra-O-acetyl-2-deoxy-1,5-dithio-α-D-gluco-heptopyranoside.

In certain embodiments, conjugate groups as provided herein comprise a carbohydrate cluster. As used herein, "carbohydrate cluster" means a portion of a conjugate group wherein two or more carbohydrate residues are attached to a branching group through tether groups. (see, e.g., Maier et al., "Synthesis of Antisense Oligonucleotides Conjugated to a Multivalent Carbohydrate Cluster for Cellular Targeting," *Bioconjugate Chemistry*, 2003, (14): 18-29, which is incorporated herein by reference in its entirety, or Rensen et al., "Design and Synthesis of Novel N-Acetylgalactosamine-Terminated Glycolipids for Targeting of Lipoproteins to the Hepatic Asiaglycoprotein Receptor," *J. Med. Chem.* 2004, (47): 5798-5808, for examples of carbohydrate conjugate clusters).

As used herein, "modified carbohydrate" means any carbohydrate having one or more chemical modifications relative to naturally occurring carbohydrates.

As used herein, "carbohydrate derivative" means any compound which may be synthesized using a carbohydrate as a starting material or intermediate.

As used herein, "carbohydrate" means a naturally occurring carbohydrate, a modified carbohydrate, or a carbohydrate derivative.

In certain embodiments, conjugate groups are provided wherein the cell-targeting moiety has the formula:

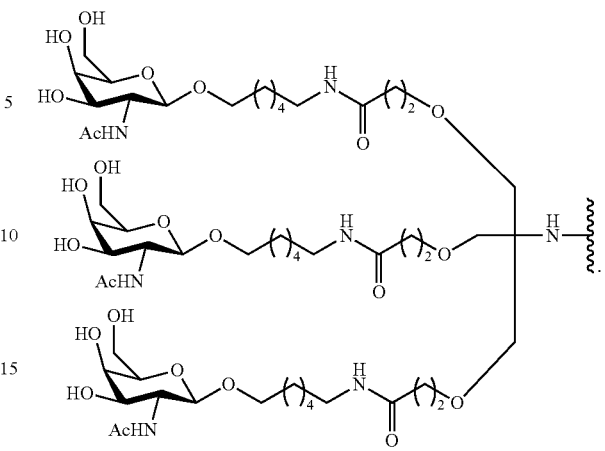

In certain embodiments, conjugate groups are provided wherein the cell-targeting moiety has the formula:

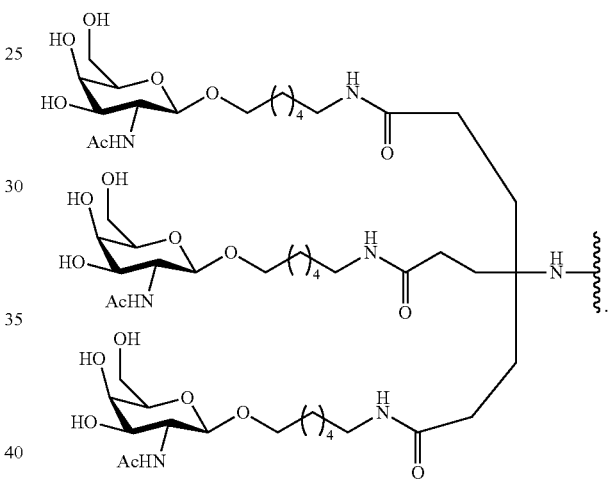

In certain embodiments, conjugate groups are provided wherein the cell-targeting moiety has the formula:

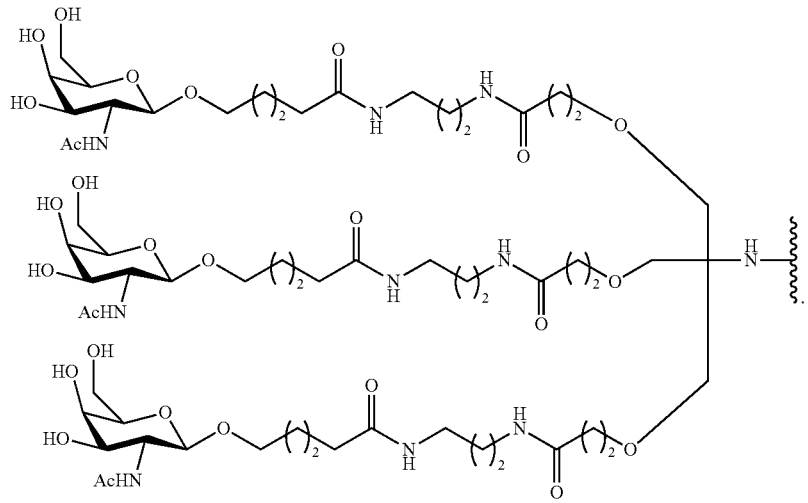

In certain embodiments, conjugate groups have the formula:

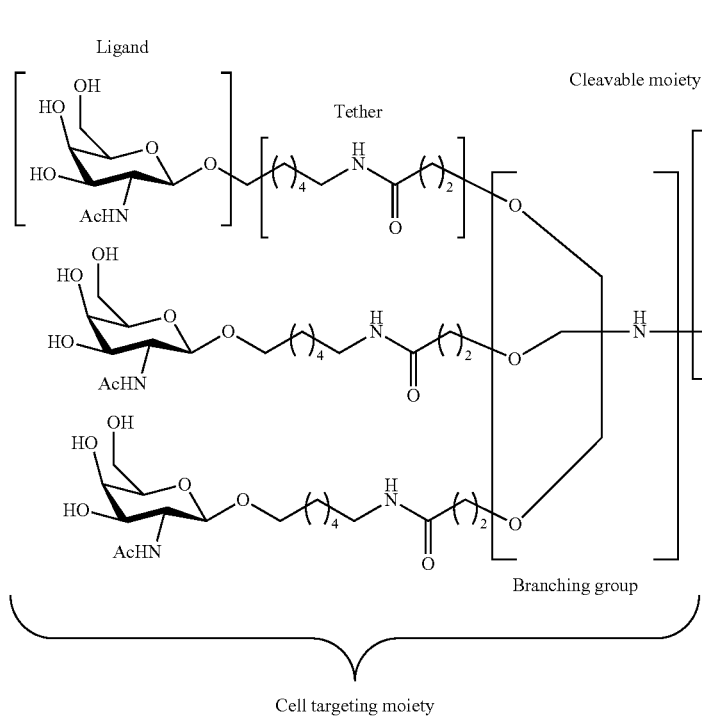

Cell targeting moiety

Representative United States patents, United States patent application publications, and international patent application publications that teach the preparation of certain of the above noted conjugate groups, conjugated oligomeric compounds such as antisense compounds comprising a conjugate group, tethers, conjugate linkers, branching groups, ligands, cleavable moieties as well as other modifications include without limitation, U.S. Pat. Nos. 5,994,517, 6,300, 319, 6,660,720, 6,906,182, 7,262,177, 7,491,805, 8,106,022, 7,723,509, US 2006/0148740, US 2011/0123520, WO 2013/033230 and WO 2012/037254, each of which is incorporated by reference herein in its entirety.

Representative publications that teach the preparation of certain of the above noted conjugate groups, conjugated oligomeric compounds such as antisense compounds comprising a conjugate group, tethers, conjugate linkers, branching groups, ligands, cleavable moieties as well as other modifications include without limitation, BIESSEN et al., "The Cholesterol Derivative of a Triantennary Galactoside with High Affinity for the Hepatic Asialoglycoprotein Receptor: a Potent Cholesterol Lowering Agent" J. Med. Chem. (1995) 38:1846-1852, BIESSEN et al., "Synthesis of Cluster Galactosides with High Affinity for the Hepatic Asialoglycoprotein Receptor" J. Med. Chem. (1995) 38:1538-1546, LEE et al., "New and more efficient multivalent glyco-ligands for asialoglycoprotein receptor of mammalian hepatocytes" Bioorganic & Medicinal Chemistry (2011) 19:2494-2500, RENSEN et al., "Determination of the Upper Size Limit for Uptake and Processing of Ligands by the Asialoglycoprotein Receptor on Hepatocytes in Vitro and in Vivo" J. Biol. Chem. (2001) 276 (40):37577-37584, RENSEN et al., "Design and Synthesis of Novel N-Acetylgalactosamine-Terminated Glycolipids for Targeting of Lipoproteins to the Hepatic Asialoglycoprotein Receptor" J. Med. Chem. (2004) 47:5798-5808, SLIEDREGT et al., "Design and Synthesis of Novel Amphiphilic Dendritic Galactosides for Selective Targeting of Liposomes to the Hepatic Asialoglycoprotein Receptor" J. Med. Chem. (1999) 42:609-618, and Valentijn et al., "Solid-phase synthesis of lysine-based cluster galactosides with high affinity for the Asialoglycoprotein Receptor" Tetrahedron, 1997, 53 (2), 759-770, each of which is incorporated by reference herein in its entirety.

In certain embodiments, conjugate groups include without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-

237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

Some nonlimiting examples of conjugate linkers include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other connugate linkers include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a non-limiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3' end of an oligomeric compound, but before one or more terminal group nucleosides. In certain embodiments, conjugate groups are placed within a terminal group.

Cell Culture and Antisense Compounds Treatment

The effects of antisense compounds on the level, activity or expression of TMPRSS6 nucleic acids can be tested in vitro in a variety of cell types. Cell types used for such analyses are available from commercial vendors (e.g., American Type Culture Collection, Manassas, Va.; Zen-Bio, Inc., Research Triangle Park, N.C.; Clonetics Corporation, Walkersville, Md.) and cells are cultured according to the vendor's instructions using commercially available reagents (e.g., Invitrogen Life Technologies, Carlsbad, Calif.). Illustrative cell types include, but are not limited to, HepG2 cells, Hep3B cells, Huh7 (hepatocellular carcinoma) cells, primary hepatocytes, A549 cells, GM04281 fibroblasts and LLC-MK2 cells.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE 2000® (Invitrogen, Carlsbad, Calif.). Antisense oligonucleotide is mixed with LIPOFECTAMINE 2000® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Another reagent used to introduce antisense oligonucleotides into cultured cells includes Cytofectin® (Invitrogen, Carlsbad, Calif.). Antisense oligonucleotide is mixed with Cytofectin® in OPTI-MEM® 1 reduced serum medium (Invitrogen, Carlsbad, Calif.) to achieve the desired concentration of antisense oligonucleotide and a Cytofectin® concentration that typically ranges 2 to 12 ug/mL per 100 nM antisense oligonucleotide.

Another reagent used to introduce antisense oligonucleotides into cultured cells includes Oligofectamine™ (Invitrogen Life Technologies, Carlsbad, Calif.). Antisense oligonucleotide is mixed with Oligofectamine™ in Opti-MEM™-1 reduced serum medium (Invitrogen Life Technologies, Carlsbad, Calif.) to achieve the desired concentration of oligonucleotide with an Oligofectamine™ to oligonucleotide ratio of approximately 0.2 to 0.8 μL per 100 nM.

Another reagent used to introduce antisense oligonucleotides into cultured cells includes FuGENE 6 (Roche Diagnostics Corp., Indianapolis, Ind.). Antisense oligomeric compound was mixed with FuGENE 6 in 1 mL of serum-free RPMI to achieve the desired concentration of oligonucleotide with a FuGENE 6 to oligomeric compound ratio of 1 to 4 μL of FuGENE 6 per 100 nM.

Another technique used to introduce antisense oligonucleotides into cultured cells includes electroporation (Sambrook and Russell in *Molecular Cloning. A Laboratory Manual.* Third Edition. Cold Spring Harbor laboratory Press, Cold Spring Harbor, N.Y. 2001).

Cells are treated with antisense oligonucleotides by routine methods. Cells are typically harvested 16-24 hours after antisense oligonucleotide treatment, at which time RNA or protein levels of target nucleic acids are measured by methods known in the art and described herein (Sambrook and Russell in *Molecular Cloning. A Laboratory Manual.* Third Edition. Cold Spring Harbor laboratory Press, Cold Spring Harbor, N.Y. 2001). In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art (Sambrook and Russell in *Molecular Cloning. A Laboratory Manual.* Third Edition. Cold Spring Harbor laboratory Press, Cold Spring Harbor, N.Y. 2001). Antisense oligonucleotides are typically used at concentrations ranging from 1 nM to 300 nM when transfected with LIPOFECTAMINE2000®, Lipofectin or Cytofectin. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art (Sambrook and Russell, Molecular Cloning: A Laboratory Manual, $3^{rd}$ Ed., 2001). RNA is prepared using methods well known in the art, for example, using the TRIZOL® Reagent (Invitrogen, Carlsbad, Calif.) according to the manufacturer's recommended protocols.

Analysis of Inhibition of Target Levels or Expression

Inhibition of levels or expression of a TMPRSS6 nucleic acid can be assayed in a variety of ways known in the art (Sambrook and Russell, Molecular Cloning: A Laboratory Manual, $3^{rd}$ Ed., 2001). For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT, real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN® (Invitrogen, Inc. Carlsbad, Calif.). Cyclophilin A expression is quantified by real time PCR, by being run simultaneously with the target, multiplexing, or separately. Total RNA is quantified using RIBOGREEN® RNA quantification reagent (Invitrogen, Inc. Eugene, Oreg.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to a TMPRSS6 nucleic acid. Methods for designing real-time PCR probes and primers are well known in the art, and may include the use of software such as PRIMER EXPRESS® Software (Applied Biosystems, Foster City, Calif.).

Analysis of Protein Levels

Antisense inhibition of TMPRSS6 nucleic acids can be assessed by measuring TMPRSS6 protein levels. Protein levels of TMPRSS6 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS) (Sambrook and Russell, Molecular Cloning: A Laboratory Manual, $3^{rd}$ Ed., 2001). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art.

In Vivo Testing of Antisense Compounds

Antisense compounds, for example, antisense oligonucleotides, are tested in animals to assess their ability to inhibit expression of TMPRSS6 and produce phenotypic changes, such as, reduced accumulation of iron in the body. Testing can be performed in normal animals, or in experimental disease models. For administration to animals, antisense oligonucleotides are formulated in a pharmaceutically acceptable diluent, such as sterile water-for-injection or phosphate-buffered saline. Administration includes parenteral routes of administration, such as intraperitoneal, intravenous, and subcutaneous. Calculation of antisense oligonucleotide dosage and dosing frequency depends upon factors such as route of administration and animal body weight. In one embodiment, following a period of treatment with antisense oligonucleotides, RNA is isolated from liver tissue and changes in TMPRSS6 nucleic acid expression are measured. Changes in TMPRSS6 protein levels can also be measured. Changes in TMPRSS6 expression can be measured by determining the level of hepcidin expression, plasma levels of iron and percentage saturation of transferrin present in the animal.

Certain Indications

Provided are compositions, compounds and methods for treating an individual comprising administering to the individual one or more compositions or compounds described herein. In certain embodiments, compositions, compounds and methods are provided for reducing TMPRSS6 expression in the individual. In certain embodiments, compositions, compounds and methods are provided for treating the individual by administering to the individual a therapeutically effective amount of a composition or compound comprising an antisense oligonucleotide targeted to a TMPRSS6 nucleic acid. In certain embodiments, the antisense compound targeted to a TMPRSS6 reduces TMPRSS6. In certain embodiments, the individual in need of TMPRSS6 reduction has, or is at risk for, an iron accumulation disease, disorder or condition. In certain embodiments, compositions, compounds and methods described herein are provided herein for use in reducing iron levels in an individual.

In certain embodiments, the iron accumulation is the result of a therapy to treat a disease, disorder or condition in the individual. In certain embodiments, the therapy is transfusion therapy. In certain embodiments, multiple transfusions may lead to polycythemia. In further embodiments, multiple blood transfusions are associated with the animal having anemia. Examples of anemia requiring multiple blood transfusions are hereditary anemia, myelodysplastic syndrome and severe chronic hemolysis. Examples of hereditary anemia include, but are not limited to, sickle cell anemia, thalassemia, Fanconi anemia, Diamond Blackfan anemia, Shwachman Diamond syndrome, red cell membrane disorders, glucose-6-phosphate dehydrogenase deficiency, or hereditary hemorrhagic telangiectasia. In certain embodiments, the thalassemia is β-thalassemia. In certain embodiments, the β-thalassemia is HbE/β-thalassemia, β-thalassemia major, β-thalassemia intermedia or β-thalassemia minor.

In certain embodiments, the iron accumulation is due to a disease, disorder or condition in the individual. In certain embodiments, the disease, disorder or condition is hereditary hemochromatosis or thalassemia. In certain embodiments, the thalassemia is non-transfusion dependent thalassemia (NTDT) or β-thalassemia. In certain embodiments, the β-thalassemia is HbE/β-thalassemia, β-thalassemia major, β-thalassemia intermedia or β-thalassemia minor.

In certain embodiments, the disease, disorder and/or condition is associated with excess parenteral iron supplement intake or excess dietary iron intake.

Provided herein are compositions, compounds and methods for increasing hepcidin levels, such as mRNA or protein expression levels. In certain embodiments, provided are antisense compounds targeting TMPRSS6 as described herein for use in increasing hepcidin levels, such as mRNA or protein expression levels.

Provided herein are compositions, compounds and methods for decreasing the percentage saturation of transferrin in an animal. In certain embodiments, provided are antisense compounds targeting TMPRSS6 as described herein for use in decreasing the percentage saturation of transferrin in an animal. In certain embodiments, decreasing transferrin saturation leads to a decrease in iron supply for erythropoiesis. In certain embodiments, the decrease in erythropoiesis treats, prevents, delays the onset of, ameliorates, and/or reduces polycythemia, or symptom thereof, in the animal. In certain embodiments, provided are antisense compounds targeting TMPRSS6 as described herein for use in treating, preventing, delaying the onset of, ameliorating, and/or reducing polycythemia, or symptom thereof, in the animal. In certain embodiments, the polycythemia is polycythemia vera. In certain embodiments, treatment with the antisense compound targeting TMPRSS6 prevents or delays the polycythemia from progressing into erythroid leukemia.

In certain embodiments, administration of a therapeutically effective amount of an antisense compound targeted to a TMPRSS6 nucleic acid in an individual is accompanied by monitoring of TMPRSS6 levels to determine the individual's response to the antisense compound. In certain embodiments, administration of a therapeutically effective amount of an antisense compound targeted to a TMPRSS6 nucleic acid in an individual is accompanied by monitoring the levels of hepcidin in the individual. In certain embodiments, administration of a therapeutically effective amount of an antisense compound targeted to a TMPRSS6 nucleic acid in an individual is accompanied by monitoring the levels of iron in the individual. In certain embodiments, administration of a therapeutically effective amount of an antisense compound targeted to a TMPRSS6 nucleic acid in an individual is accompanied by evaluating the percentage saturation of transferrin in the individual. An individual's response to administration of the antisense compound is used by a physician to determine the amount and duration of therapeutic intervention.

Provided herein are pharmaceutical compositions comprising an antisense compound targeted to TMPRSS6 for use in the preparation of a medicament for treating a patient suffering from, or susceptible to, an iron accumulation disease, disorder or condition.

In certain embodiments, the methods described herein include administering an antisense compound comprising a modified oligonucleotide having at least an 8, 9, 10, 11, 12, 13, 14, 15, 16, 17, 18, 19 or 20 contiguous nucleobase portion complementary to a TMPRSS6 nucleic acid.

Certain Combination Therapies

In certain embodiments, a first agent comprising a composition or compound provided herein is co-administered with one or more secondary agents. In certain embodiments, such second agents are designed to treat the same iron accumulation disease, disorder or condition as the first agent described herein. In certain embodiments, such second agents are designed to treat a different disease, disorder, or condition as the first agent described herein. In certain embodiments, such second agents are designed to treat an undesired side effect of one or more composition or compound as described herein. In certain embodiments, such first agents are designed to treat an undesired side effect of a second agent. In certain embodiments, second agents are co-administered with the first agent to treat an undesired effect of the first agent. In certain embodiments, second agents are co-administered with the first agent to produce a combinational effect. In certain embodiments, second agents are co-administered with the first agent to produce a synergistic effect. In certain embodiments, the co-administration of the first and second agents permits use of lower dosages than would be required to achieve a therapeutic or prophylactic effect if the agents were administered as independent therapy. In certain embodiments, the dose of a co-administered second agent is the same as the dose that would be administered if the second agent was administered alone. In certain embodiments, the dose of a co-administered second agent is lower than the dose that would be administered if the second agent was administered alone. In certain embodiments, the dose of a co-administered second agent is greater than the dose that would be administered if the second agent was administered alone.

In certain embodiments, a first agent and one or more second agents are administered at the same time. In certain embodiments, the first agent and one or more second agents are administered at different times. In certain embodiments, the second agent is administered prior to administration of the first agent. In certain embodiments, the second agent is administered following administration of the first agent. In certain embodiments, the first agent and one or more second agents are prepared together in a single pharmaceutical formulation. In certain embodiments, the first agent and one or more second agents are prepared separately.

In certain embodiments, second agents include, but are not limited to, nucleic acid compounds. Such nucleic acid compounds can include a siRNA, a ribozyme or an antisense compound targeting TMPRSS6 or another target.

In certain embodiments, second agents include, but are not limited to, non-antisense compounds such as iron chelators, transferrin, bone morphogenetic proteins 6 (BMP6), hepcidin agonists, stem cells, antibodies targeting TMPRSS6 or fetal hemoglobin (HbF)-raising agents. In further embodiments, iron chelators are selected from, but not limited to, FBS0701 (FerroKin), Exjade, Desferal, and Deferiprone. In certain embodiments, HBF-raising agents include 5-hydroxyl urea, short chain fatty acid (SCFA) derivatives (e.g., HQK1001), DNA methyltransferase inhibitors (e.g., decitabine) or histone deacetylase (HDAC) inhibitors (e.g., Zolina, Panobinostat).

In certain embodiments, a second agent includes, but is not limited to, phlebotomy or transfusion therapy. In certain embodiments, the first agent is administered at the same time as phlebotomy or transfusion therapy. In certain embodiments, the first agent is administered prior to phlebotomy or transfusion therapy. In certain embodiments, the first agent is administered following phlebotomy or transfusion therapy. In certain embodiments, administration of a composition or compound provided herein decreases the frequency of phlebotomy or transfusion in an individual. In certain embodiments, administration of a composition or compound provided herein increases the frequency of phlebotomy or transfusion in an individual. In certain embodiments, administration of a composition or compound provided herein decreases the length of time required for phlebotomy or transfusion.

Certain Compounds

Preferred antisense compounds with beneficial properties that enhance their use as therapeutic treatments in humans are demonstrated in the examples herein. For brevity, only the studies that contributed to the selection of the preferred antisense compounds are described. A non-exhaustive summary of the examples is provided below for ease of reference.

About 2200 antisense compounds with a MOE gapmer motif or a cEt containing motif targeting human TMPRSS6 were designed and screened in Hep3B cells for their effect on human TMPRSS6 mRNA after administering a single dose to the cells. Example 1 shows representative single dose screening data for over 100 potent antisense compounds that were selected for further studies.

Of the approximately 2200 antisense compounds tested with a single dose in vitro, about 100 antisense compounds were chosen for testing in dose-dependent inhibition studies to determine their half maximal inhibitory concentration ($IC_{50}$) in Hep3B cells (Example 2).

About 77 antisense compounds were further selected, based on their potency in dose response and/or single dose studies, for study in CD-1 mice to determine tolerability (e.g., plasma chemistry markers, body weight and organ weight) of the antisense compound (Examples 3-4) in mice.

Of the approximately 77 antisense compounds tested in CD-1 mice for tolerability, about 48 antisense compounds were chosen for study in Sprague-Dawley rats to determine tolerability in rats (Example 5).

Base on the rat tolerability study, about 32 antisense compounds were selected for in vivo potency testing in human TMPRSS6 transgenic (huTMPRSS6 tg) mice (Example 6).

Antisense compounds identified as potent and tolerable in mice studies were assessed for cross-reactivity to a rhesus monkey TMPRSS6 gene sequence (Example 7). Although the antisense compounds in the studies described herein were tested in cynomolgus monkeys (Example 11), the cynomolgus monkey TMPRSS6 sequence was not available for comparison to the sequences of the antisense compounds, therefore the sequences of the antisense compounds were compared to that of the closely related rhesus monkey. About seven antisense compounds were found to have no mismatches with the rhesus TMPRSS6 gene sequence.

Based on the results of the mice potency and tolerability studies, and homology to the rhesus monkey sequence, the sequences of seven antisense compounds (585774, 585683, 585775, 630718, 647477, 647449, 647420) from the prior studies were selected for further chemical modification to make them more potent in reducing TMPRSS6 levels. Eight new antisense compounds with a GalNAc conjugate (702843, 705051, 705052, 705053, 706940, 706941, 706942, 706943) were designed based on the seven original antisense compounds (Example 7).

The eight GalNAc conjugated antisense compounds were tested in mice: for tolerability in CD-1 mice (e.g., body weights, organ weights, liver metabolic markers (e.g., ALT, AST and bilirubin), kidney metabolic markers (e.g., BUN and creatinine), histology, hematology parameters (e.g., blood cell counts and hematocrit), and the like were measured (Example 8); and, for potency in human TMPRSS6 transgenic mice (Example 9).

The eight GalNAc conjugated antisense compounds were also assessed for viscosity and seven of the eight were found to have a favorable viscosity level while one was found to have a borderline acceptable viscosity level (Example 10).

Based on the favorable profile seen in the mice and in vitro viscosity studies, the eight GalNAc conjugated antisense compounds were further tested for potency in reducing TMPRSS6, tolerability and for their effect on iron parameters (e.g., hepcidin levels, serum iron and transferrin saturation) in cynomolgus monkeys (Example 11). The eight GalNAc conjugated antisense compounds were generally found to be potent and tolerable in cynomolgus monkeys. Antisense compounds 705051, 702843, 706942 and 706943 were found to be especially potent in reducing TMPRSS6, serum iron and transferrin saturation.

Accordingly, provided herein are antisense compounds with any one or more characteristics that are beneficial for their use as a therapeutic agent. In certain embodiments, provided herein are antisense compounds comprising a modified oligonucleotide as described herein targeted to, or specifically hybridizable with, a region of nucleotides selected from any of SEQ ID NOs: 1-6.

In certain embodiments, certain antisense compounds as described herein are efficacious by virtue of their potency in inhibiting TMPRSS6 expression. In certain embodiments, the compounds or compositions inhibit TMPRSS6 by at least 40%, at least 45%, at least 50%, at least 55%, at least 60%, at least 65%, at least 70%, at least 75%, at least 80%, at least 85%, at least 90% or at least 95%.

In certain embodiments, certain antisense compounds as described herein are efficacious by virtue of an in vitro $IC_{50}$ of less than 20 µM, less than 10 µM, less than 8 µM, less than 5 µM, less than 2 µM, less than 1 µM, less than 0.9 µM, less than 0.8 µM, less than 0.7 µM, less than 0.6 µM, or less than 0.5 µM when tested in human cells, for example, in the Hep3B cell line (as described in Example 2).

In certain embodiments, certain antisense compounds as described herein are efficacious by virtue of a median effective dose ($ED_{50}$) of ≤5 mpk/wk, ≤4 mpk/wk, ≤3 mpk/wk, ≤2 mpk/wk or ≤1 mpk/wk in vivo. In certain embodiments, preferred antisense compounds having an $ED_{50} \le 1$ mpk/wk include antisense compounds 702843, 706940, 706942 and 706943 as described in Example 8.

In certain embodiments, certain antisense compounds as described herein are efficacious by virtue of having a viscosity of less than 40 cP, less than 35 cP, less than 30 cP, less than 25 cP, less than 20 cP, less than 15 cP, or less than 10 cP as described in Example 9. Oligonucleotides having a viscosity greater than 40 cP would have less than optimal viscosity.

In certain embodiments, certain antisense compounds as described herein are highly tolerable, as demonstrated by the in vivo tolerability measurements described in the examples. In certain embodiments, the certain antisense compounds as described herein are highly tolerable, as demonstrated by having an increase in ALT and/or AST value of no more than 3 fold, 2 fold or 1.5 fold over saline treated animals.

In certain embodiments, certain antisense compounds as described herein are efficacious by virtue of having one or more of an inhibition potency of greater than 50%, an $ED_{50} \le 1$ mpk/wk, a viscosity of less than 40 cP, and no more than a 3 fold increase in ALT and/or AST in transgenic mice.

In certain embodiments, ISIS 702843 (SEQ ID NO: 36) is preferred. This compound was found to be a potent inhibitor in TMPRSS6 transgenic mice and a very tolerable antisense compound in CD-1 mice. In mice it had less than a 3 fold increase in ALT and/or AST levels over saline treated animals. It had an acceptable viscosity of about 33 cP and an $ED_{50} \le 1$ mpk/wk in huTMPRSS6 transgenic mice. Also, in monkeys, it was among the most potent compounds in inhibiting TMPRSS6.

In certain embodiments, ISIS 705051 (SEQ ID NO: 36) is preferred. This compound was found to be a potent inhibitor in TMPRSS6 transgenic mice and a very tolerable antisense compound in CD-1 mice. In mice it had less than a 3 fold increase in ALT and/or AST levels over saline treated animals. It had an acceptable viscosity of about 23 cP and an $ED_{50} \le 3$ mpk/wk in huTMPRSS6 transgenic mice. Also, in monkeys, it was among the most potent compounds in inhibiting TMPRSS6.

In certain embodiments, ISIS 706942 (SEQ ID NO: 77) is preferred. This compound was found to be a potent inhibitor in TMPRSS6 transgenic mice and a very tolerable antisense compound in CD-1 mice. In mice it had less than a 3 fold increase in ALT and/or AST levels over saline treated animals. It had an acceptable viscosity of about 20 cP and an $ED_{50} \leq 1$ mpk/wk in huTMPRSS6 transgenic mice. Also, in monkeys, it was among the most potent compounds in inhibiting TMPRSS6.

In certain embodiments, ISIS 706943 (SEQ ID NO: 77) is preferred. This compound was found to be a potent inhibitor in TMPRSS6 transgenic mice and a very tolerable antisense compound in CD-1 mice. In huTMPRSS6 transgenic mice it had less than a 3 fold increase in ALT and/or AST levels over saline treated animals. It had an acceptable viscosity of about 19 cP and an $ED_{50} \leq 1$ mpk/wk in huTMPRSS6 transgenic mice. Also, in monkeys, it was among the most potent compounds in inhibiting TMPRSS6.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Oligonucleotides Targeting Human Type II Transmembrane Serine Protease 6 (TMPRSS6)

Approximately 2200 newly designed chimeric antisense oligonucleotides were designed as 5-10-5 MOE gapmers or cET containing gapmers.

The 5-10-5 MOE gapmers were designed as oligonucleotides 20 nucleosides in length, wherein the central gap segment comprises ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines.

The cET containing gapmers were designed with varied deoxy, MOE, and (S)-cEt gapmer motifs. The deoxy, MOE and (S)-cEt oligonucleotides are 16 nucleosides in length wherein the nucleosides have either a MOE sugar modification, an (S)-cEt sugar modification, or a deoxyribose. The 'Chemistry' column in Table 3 describes the sugar modifications of each oligonucleotide. 'k' indicates an (S)-cEt sugar modification; 'd' indicates deoxyribose; and 'e' indicates a MOE modification. Unless otherwise specified, the internucleoside linkages throughout each gapmer are phosphorothioate (P=S) linkages. All cytosine residues throughout each gapmer are 5-methylcytosines.

"Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human TMPRSS6 mRNA, designated herein as SEQ ID NO: 1 (GENBANK Accession No. NM_153609.2) or the human TMPRSS6 genomic sequence, designated herein as SEQ ID NO: 2 (the complement of GENBANK Accession No. NT_011520.12 truncated from nucleotide 16850000 to Ser. No. 16/897, 000). In the tables below, 'n/a' indicates that the antisense oligonucleotide does not target that particular gene sequence with 100% complementarity.

The 2200 chimeric antisense oligonucleotides were tested for their single dose effects on TMPRSS6 mRNA in vitro. Antisense oligonucleotides were tested at least once in a series of experiments that had similar culture conditions.

A representative result for about 110 potent antisense oligonucleotides out of the 2200 tested is presented in Tables 1-3 shown below. These potent antisense oligonucleotides were selected for further studies as described below.

Table 1 shows the percent inhibition of TMPRSS6 mRNA by 5-10-5 MOE gapmers. Cultured Hep3B cells at a density of about 20,000 cells per well were transfected using electroporation with 4,500 nM antisense oligonucleotide. After a treatment period of approximately 24 hours, RNA was isolated from the cells and TMPRSS6 mRNA levels were measured by quantitative real-time PCR. Human primer probe set RTS3840 (forward sequence CAAAGCCCA-GAAGATGCTCAA, designated herein as SEQ ID NO: 92; reverse sequence GGAATAGACGGAGCTGGAGTTG, designated herein as SEQ ID NO: 93; probe sequence ACCAGCACCCGCCTGGGAACTT, designated herein as SEQ ID NO: 94) was used to measure mRNA levels. TMPRSS6 mRNA levels were adjusted according to total RNA content, as measured by RIBOGREEN®. Results are presented as percent inhibition of TMPRSS6, relative to untreated control cells.

TABLE 1

Inhibition of TMPRSS6 mRNA by 5-10-5 MOE gapmers targeting SEQ ID NO: 1 and/or 2

| ISIS NO | Sequence | SEQ ID NO: 1 Start Site | SEQ ID NO: 1 Stop Site | SEQ ID NO: 2 Start Site | SEQ ID NO: 2 Stop Site | % Inhibition | SEQ ID NO |
|---|---|---|---|---|---|---|---|
| 585604 | CCATCACCTCCGTCCCCCTG | 178 | 197 | 7011 | 7030 | 58 | 7 |
| 585606 | TCCGCTTCCTCGCCATCACC | 190 | 209 | 7023 | 7042 | 51 | 8 |
| 585608 | TTTTCTCTTGGAGTCCTCAC | 233 | 252 | 7066 | 7085 | 52 | 9 |
| 585609 | GCTTTTCTCTTGGAGTCCTC | 235 | 254 | 7068 | 7087 | 79 | 10 |

TABLE 1-continued

Inhibition of TMPRSS6 mRNA by 5-10-5 MOE gapmers targeting SEQ ID NO: 1 and/or 2

| ISIS NO | Sequence | SEQ ID NO: 1 Start Site | SEQ ID NO: 1 Stop Site | SEQ ID NO: 2 Start Site | SEQ ID NO: 2 Stop Site | % Inhibition | SEQ ID NO |
|---|---|---|---|---|---|---|---|
| 585611 | CCGGGCTTTTCTCTTGGAGT | 239 | 258 | 7072 | 7091 | 58 | 11 |
| 585626 | GGCTTTGGCGGTTTCACTGC | 449 | 468 | 11948 | 11967 | 79 | 12 |
| 585629 | GAGCATCTTCTGGGCTTTGG | 461 | 480 | N/A | N/A | 80 | 13 |
| 585631 | CCTTGAGCATCTTCTGGGCT | 465 | 484 | N/A | N/A | 84 | 14 |
| 585649 | AGTGCCTGCACCACCTCGGG | 616 | 635 | 14372 | 14391 | 79 | 15 |
| 585651 | CAGCAGTGCCTGCACCACCT | 620 | 639 | 14376 | 14395 | 70 | 16 |
| 585653 | TCCTCCACCAGCAGTGCCTG | 628 | 647 | 14384 | 14403 | 49 | 17 |
| 585654 | AGCTCCTCCACCAGCAGTGC | 631 | 650 | 14387 | 14406 | 64 | 18 |
| 585655 | CAGCAGCTCCTCCACCAGCA | 635 | 654 | 14391 | 14410 | 66 | 19 |
| 585667 | GCTGTGCAGGCCCTTCTTCC | 1049 | 1068 | 24044 | 24063 | 52 | 20 |
| 585668 | GTAGTAGCTGTGCAGGCCCT | 1055 | 1074 | 24050 | 24069 | 61 | 21 |
| 585682 | ACGGCAAATCATACTTCTGC | 1284 | 1303 | 26044 | 26063 | 60 | 22 |
| 585683 | GCACGGCAAATCATACTTCT | 1286 | 1305 | 26046 | 26065 | 58 | 23 |
| 585684 | CCCTGGGTGCACGGCAAATC | 1294 | 1313 | 26054 | 26073 | 58 | 24 |
| 585698 | CAAACGCAGTTTCTCTCATC | 1567 | 1586 | N/A | N/A | 52 | 25 |
| 585699 | TGCAAACGCAGTTTCTCTCA | 1569 | 1588 | N/A | N/A | 52 | 26 |
| 585752 | GATCACACCTGTGATGCGGG | 2504 | 2523 | 44266 | 44285 | 48 | 27 |
| 585757 | CTCCTGCCACCACAGGGCCT | 2656 | 2675 | 44418 | 44437 | 70 | 28 |
| 585758 | ACCTCCTGCCACCACAGGGC | 2658 | 2677 | 44420 | 44439 | 69 | 29 |
| 585761 | TGCCATCACTGGAGCAGACA | 2699 | 2718 | 44461 | 44480 | 60 | 30 |
| 585762 | ATCCTCCTGCCATCACTGGA | 2706 | 2725 | 44468 | 44487 | 38 | 31 |
| 585768 | TCCATTCCCAGATCCCAAGT | 2978 | 2997 | 44740 | 44759 | 64 | 32 |
| 585769 | CTTCCATTCCCAGATCCCAA | 2980 | 2999 | 44742 | 44761 | 62 | 33 |
| 585770 | ACCTTCCATTCCCAGATCCC | 2982 | 3001 | 44744 | 44763 | 52 | 34 |
| 585772 | CAAAGGGCAGCTGAGCTCAC | 3154 | 3173 | 44916 | 44935 | 47 | 35 |
| 585774 | CTTTATTCCAAAGGGCAGCT | 3162 | 3181 | 44924 | 44943 | 67 | 36 |
| 585775 | AGCTTTATTCCAAAGGGCAG | 3164 | 3183 | 44926 | 44945 | 68 | 37 |
| 585776 | AGGCAGCTTTATTCCAAAGG | 3168 | 3187 | 44930 | 44949 | 59 | 38 |
| 585777 | GATCAGGCAGCTTTATTCCA | 3172 | 3191 | 44934 | 44953 | 65 | 39 |
| 585831 | AGGAGCGGCCACCGTCCTGT | N/A | N/A | 12340 12371 12562 | 12359 12390 12581 | 45 | 40 |
| 585834 | GGCAGGAGCGGCCACCGTCC | N/A | N/A | 12343 12374 12565 | 12362 12393 12584 | 42 | 41 |
| 585863 | TCCCCCTGAGGCTCTCAGGA | N/A | N/A | 16233 18737 | 16252 18756 | 32 | 42 |
| 585864 | TAAGTCCCCCTGAGGCTCTC | N/A | N/A | 16237 18741 | 16256 18760 | 39 | 43 |

TABLE 1-continued

Inhibition of TMPRSS6 mRNA by 5-10-5 MOE gapmers targeting SEQ ID NO: 1 and/or 2

| ISIS NO | Sequence | SEQ ID NO: 1 Start Site | SEQ ID NO: 1 Stop Site | SEQ ID NO: 2 Start Site | SEQ ID NO: 2 Stop Site | % Inhibition | SEQ ID NO |
|---|---|---|---|---|---|---|---|
| 585906 | AAGACTGTTCCTTCTCCTTT | N/A | N/A | 27990 | 28009 | 44 | 44 |
| 585912 | CAGCTTGTGCCTGCCCAGAG | N/A | N/A | 29208 | 29227 | 45 | 45 |
| 585932 | AGTCTATCTGGCCACAGTGA | N/A | N/A | 32981 | 33000 | 34 | 46 |
| 585937 | GGTCCTTCTTTGAGCCTCAC | N/A | N/A | 34800 | 34819 | 35 | 47 |

Table 2 shows the percent inhibition of TMPRSS6 mRNA by additional 5-10-5 MOE gapmers. Cultured Hep3B cells at a density of about 20,000 cells per well were transfected using electroporation with 5,000 nM antisense oligonucleotide. After a treatment period of approximately 24 hours, RNA was isolated from the cells and TMPRSS6 mRNA levels were measured by quantitative real-time PCR. Human primer probe set RTS3840 was used to measure mRNA levels. TMPRSS6 mRNA levels were adjusted according to total RNA content, as measured by RIBOGREEN®. Results are presented as percent inhibition of TMPRSS6, relative to untreated control cells.

Table 3 shows the percent inhibition of TMPRSS6 mRNA by cEt containing gapmers from a series of experiments. Cultured Hep3B cells at a density of about 20,000 cells per well were transfected using electroporation with 2,000 nM antisense oligonucleotide. After a treatment period of approximately 24 hours, RNA was isolated from the cells and TMPRSS6 mRNA levels were measured by quantitative real-time PCR. Human primer probe set RTS3840 was used to measure mRNA levels. TMPRSS6 mRNA levels were adjusted according to total RNA content, as measured by RIBOGREEN®. Results are presented as percent inhibition of TMPRSS6, relative to untreated control cells.

TABLE 2

Inhibition of TMPRSS6 mRNA by 5-10-5 MOE gapmers targeting SEQ ID NO: 1 and/or 2

| ISIS NO | Sequence | SEQ ID NO: 1 Start Site | SEQ ID NO: 1 Stop Site | SEQ ID NO: 2 Start Site | SEQ ID NO: 2 Stop Site | % Inhibition | SEQ ID NO |
|---|---|---|---|---|---|---|---|
| 591466 | CCTCAGGTCACCACTTGCTG | 2533 | 2552 | 44295 | 44314 | 63 | 48 |
| 591491 | GCCACCTCCTGCCACCACAG | 2661 | 2680 | 44423 | 44442 | 72 | 49 |
| 591492 | ATGCCACCTCCTGCCACCAC | 2663 | 2682 | 44425 | 44444 | 59 | 50 |
| 591514 | CTCCATCCTCCTGCCATCAC | 2710 | 2729 | 44472 | 44491 | 59 | 51 |
| 591536 | GCAGCTGAGCTCACCTCCCA | 3148 | 3167 | 44910 | 44929 | 68 | 52 |
| 591537 | GGCAGCTGAGCTCACCTCCC | 3149 | 3168 | 44911 | 44930 | 75 | 53 |
| 591549 | GGCAGCTTTATTCCAAAGGG | 3167 | 3186 | 44929 | 44948 | 69 | 54 |
| 591550 | CAGGCAGCTTTATTCCAAAG | 3169 | 3188 | 44931 | 44950 | 76 | 55 |
| 591552 | ATCAGGCAGCTTTATTCCAA | 3171 | 3190 | 44933 | 44952 | 66 | 56 |
| 591578 | CCACTGGCCCTGGGTGCACG | 1301 | 1320 | 26061 | 26080 | 65 | 57 |
| 591579 | TCCACTGGCCCTGGGTGCAC | 1302 | 1321 | 26062 | 26081 | 68 | 58 |

TABLE 3

Inhibition of TMPRSS6 mRNA by cEt containing gapmers targeting SEQ ID NO: 1 and/or 2

| ISIS NO | Sequence | SEQ ID NO: 1 Start Site | SEQ ID NO: 1 Stop Site | SEQ ID NO: 2 Start Site | SEQ ID NO: 2 Stop Site | Chemistry | % Inhibition | SEQ ID NO |
|---|---|---|---|---|---|---|---|---|
| 615840 | CTTTTGGCTTACAGTG | 3057 | 3072 | 44819 | 44834 | ekk-d10-kke | 59 | 59 |
| 615884 | GCTGAGCTCACCTCCC | 3149 | 3164 | 44911 | 44926 | ekk-d10-kke | 70 | 60 |
| 615898 | TATTCCAAAGGGCAGC | 3163 | 3178 | 44925 | 44940 | ekk-d10-kke | 69 | 61 |
| 615901 | CTTTATTCCAAAGGGC | 3166 | 3181 | 44928 | 44943 | ekk-d10-kke | 68 | 62 |
| 615903 | AGCTTTATTCCAAAGG | 3168 | 3183 | 44930 | 44945 | ekk-d10-kke | 70 | 63 |
| 615909 | TCAGGCAGCTTTATTC | 3174 | 3189 | 44936 | 44951 | ekk-d10-kke | 69 | 64 |
| 615910 | ATCAGGCAGCTTTATT | 3175 | 3190 | 44937 | 44952 | ekk-d10-kke | 69 | 65 |
| 615911 | GATCAGGCAGCTTTAT | 3176 | 3191 | 44938 | 44953 | ekk-d10-kke | 69 | 66 |
| 630497 | ATTCCAAAGGGCAGCT | 3162 | 3177 | 44924 | 44939 | kkk-d10-kkk | 80 | 67 |
| 630689 | CTTACAGTGGCAGCAG | 3050 | 3065 | 44812 | 44827 | kkk-d10-kkk | 71 | 68 |
| 630692 | TGGCTTACAGTGGCAG | 3053 | 3068 | 44815 | 44830 | kkk-d10-kkk | 75 | 69 |
| 630693 | TTGGCTTACAGTGGCA | 3054 | 3069 | 44816 | 44831 | kkk-d10-kkk | 75 | 70 |
| 630696 | CTTTTGGCTTACAGTG | 3057 | 3072 | 44819 | 44834 | kkk-d10-kkk | 66 | 59 |
| 630716 | CTTTATTCCAAAGGGC | 3166 | 3181 | 44928 | 44943 | kkk-d10-kkk | 63 | 62 |
| 630717 | GCTTTATTCCAAAGGG | 3167 | 3182 | 44929 | 44944 | kkk-d10-kkk | 81 | 71 |
| 630718 | AGCTTTATTCCAAAGG | 3168 | 3183 | 44930 | 44945 | kkk-d10-kkk | 84 | 63 |
| 630719 | CAGGCAGCTTTATTCC | 3173 | 3188 | 44935 | 44950 | kkk-d10-kkk | 80 | 72 |
| 630722 | GATCAGGCAGCTTTAT | 3176 | 3191 | 44938 | 44953 | kkk-d10-kkk | 72 | 66 |
| 630725 | TTTGATCAGGCAGCTT | 3179 | 3194 | N/A | N/A | kkk-d10-kkk | 61 | 73 |
| 630726 | TTTTGATCAGGCAGCT | 3180 | 3195 | N/A | N/A | kkk-d10-kkk | 72 | 74 |
| 630727 | TTTTTGATCAGGCAGC | 3181 | 3196 | N/A | N/A | kkk-d10-kkk | 73 | 75 |
| 630794 | ACATCAGGGACGAGAC | 2686 | 2701 | 44448 | 44463 | kk-d8-kekeke | 72 | 76 |
| 647393 | TTATTCCAAAGGGCAG | 3164 | 3179 | 44926 | 44941 | kkk-d10-kkk | 78 | 83 |
| 647394 | TTTATTCCAAAGGGCA | 3165 | 3180 | 44927 | 44942 | kkk-d10-kkk | 77 | 84 |
| 647395 | CAGCTTTATTCCAAAG | 3169 | 3184 | 44931 | 44946 | kkk-d10-kkk | 86 | 77 |
| 647396 | GCAGCTTTATTCCAAA | 3170 | 3185 | 44932 | 44947 | kkk-d10-kkk | 86 | 78 |
| 647397 | GGCAGCTTTATTCCAA | 3171 | 3186 | 44933 | 44948 | kkk-d10-kkk | 85 | 82 |
| 647398 | AGGCAGCTTTATTCCA | 3172 | 3187 | 44934 | 44949 | kkk-d10-kkk | 82 | 79 |
| 647404 | GGCAGCTGAGCTCACC | 3153 | 3168 | 44915 | 44930 | kek-d9-eekk | 76 | 85 |
| 647414 | TATTCCAAAGGGCAGC | 3163 | 3178 | 44925 | 44940 | kek-d9-eekk | 86 | 61 |
| 647419 | AGCTTTATTCCAAAGG | 3168 | 3183 | 44930 | 44945 | kek-d9-eekk | 87 | 63 |
| 647420 | CAGCTTTATTCCAAAG | 3169 | 3184 | 44931 | 44946 | kek-d9-eekk | 83 | 77 |
| 647421 | GCAGCTTTATTCCAAA | 3170 | 3185 | 44932 | 44947 | kek-d9-eekk | 83 | 78 |
| 647423 | AGGCAGCTTTATTCCA | 3172 | 3187 | 44934 | 44949 | kek-d9-eekk | 84 | 79 |
| 647424 | CAGGCAGCTTTATTCC | 3173 | 3188 | 44935 | 44950 | kek-d9-eekk | 78 | 72 |
| 647426 | ATCAGGCAGCTTTATT | 3175 | 3190 | 44937 | 44952 | kek-d9-eekk | 81 | 65 |

TABLE 3-continued

Inhibition of TMPRSS6 mRNA by cEt containing gapmers targeting SEQ ID NO: 1 and/or 2

| ISIS NO | Sequence | SEQ ID NO: 1 Start Site | SEQ ID NO: 1 Stop Site | SEQ ID NO: 2 Start Site | SEQ ID NO: 2 Stop Site | Chemistry | % Inhibition | SEQ ID NO |
|---|---|---|---|---|---|---|---|---|
| 647428 | TGATCAGGCAGCTTTA | 3177 | 3192 | N/A | N/A | kek-d9-eekk | 76 | 80 |
| 647429 | TTGATCAGGCAGCTTT | 3178 | 3193 | N/A | N/A | kek-d9-eekk | 78 | 81 |
| 647442 | ATTCCAAAGGGCAGCT | 3162 | 3177 | 44924 | 44939 | kk-d9-eeekk | 81 | 67 |
| 647446 | CTTTATTCCAAAGGGC | 3166 | 3181 | 44928 | 44943 | kk-d9-eeekk | 79 | 62 |
| 647447 | GCTTTATTCCAAAGGG | 3167 | 3182 | 44929 | 44944 | kk-d9-eeekk | 87 | 71 |
| 647448 | AGCTTTATTCCAAAGG | 3168 | 3183 | 44930 | 44945 | kk-d9-eeekk | 86 | 63 |
| 647449 | CAGCTTTATTCCAAAG | 3169 | 3184 | 44931 | 44946 | kk-d9-eeekk | 89 | 77 |
| 647450 | GCAGCTTTATTCCAAA | 3170 | 3185 | 44932 | 44947 | kk-d9-eeekk | 88 | 78 |
| 647451 | GGCAGCTTTATTCCAA | 3171 | 3186 | 44933 | 44948 | kk-d9-eeekk | 88 | 82 |
| 647453 | CAGGCAGCTTTATTCC | 3173 | 3188 | 44935 | 44950 | kk-d9-eeekk | 77 | 72 |
| 647454 | TCAGGCAGCTTTATTC | 3174 | 3189 | 44936 | 44951 | kk-d9-eeekk | 82 | 64 |
| 647457 | TGATCAGGCAGCTTTA | 3177 | 3192 | N/A | N/A | kk-d9-eeekk | 78 | 80 |
| 647475 | CTTTATTCCAAAGGGC | 3166 | 3181 | 44928 | 44943 | kk-d8-eeeekk | 77 | 62 |
| 647476 | GCTTTATTCCAAAGGG | 3167 | 3182 | 44929 | 44944 | kk-d8-eeeekk | 83 | 71 |
| 647477 | AGCTTTATTCCAAAGG | 3168 | 3183 | 44930 | 44945 | kk-d8-eeeekk | 84 | 63 |
| 647478 | CAGCTTTATTCCAAAG | 3169 | 3184 | 44931 | 44946 | kk-d8-eeeekk | 79 | 77 |
| 647482 | CAGGCAGCTTTATTCC | 3173 | 3188 | 44935 | 44950 | kk-d8-eeeekk | 76 | 72 |
| 647506 | AGCTTTATTCCAAAGG | 3168 | 3183 | 44930 | 44945 | k-d9-kekeke | 89 | 63 |
| 647508 | GCAGCTTTATTCCAAA | 3170 | 3185 | 44932 | 44947 | k-d9-kekeke | 77 | 78 |
| 647514 | GATCAGGCAGCTTTAT | 3176 | 3191 | 44938 | 44953 | k-d9-kekeke | 78 | 66 |
| 647531 | CAGCTTTATTCCAAAG | 3169 | 3184 | 44931 | 44946 | kk-d8-kekeke | 88 | 77 |
| 647532 | GCAGCTTTATTCCAAA | 3170 | 3185 | 44932 | 44947 | kk-d8-kekeke | 77 | 78 |

Example 2: Dose Response of Antisense Oligonucleotides Targeting Human TMPRSS6 in Hep3B Cells About 100 antisense oligonucleotides selected from the about 2200 antisense oligonucleotides tested in single dose experiments described in Example 1 were also tested at various doses in Hep3B cells in studies of in vitro inhibition of human TMPRSS6 mRNA.

For the experiment in Table 4, below, cells were plated at a density of 12,000 cells per well and transfected using electroporation with 0.15 µM, 0.44 µM, 1.33 µM, 4.00 µM and 12.00 µM concentrations of antisense oligonucleotide. After the treatment period of approximately 16 hours, RNA was isolated from the cells and TMPRSS6 mRNA levels were measured by quantitative real-time PCR. Human primer probe set RTS3840 was used to measure mRNA levels. TMPRSS6 mRNA levels were adjusted according to total RNA content, as measured by RIBOGREEN®. Results are presented as percent inhibition of TMPRSS6, relative to untreated control cells. "0" indicate that the antisense oligonucleotide did not reduce TMPRSS6 mRNA levels.

The half maximal inhibitory concentration (IC$_{50}$) of each oligonucleotide is also presented. TMPRSS6 mRNA levels were significantly reduced in a dose-dependent manner in antisense oligonucleotide treated cells.

TABLE 4

Dose response assay with 5-10-5 MOE gapmers

| ISIS No | 0.15 µM | 0.44 µM | 1.33 µM | 4.00 µM | 12.00 µM | IC$_{50}$ (µM) |
|---|---|---|---|---|---|---|
| 585604 | 0 | 0 | 17 | 36 | 63 | 7 |
| 585606 | 0 | 0 | 0 | 0 | 35 | >12 |
| 585608 | 0 | 13 | 6 | 8 | 50 | >12 |
| 585609 | 0 | 10 | 24 | 44 | 68 | 5 |
| 585611 | 0 | 0 | 9 | 33 | 67 | 8 |
| 585626 | 3 | 21 | 27 | 55 | 82 | 3 |
| 585629 | 37 | 45 | 56 | 71 | 83 | 1 |
| 585631 | 29 | 56 | 63 | 70 | 84 | 1 |
| 585649 | 0 | 9 | 35 | 46 | 74 | 4 |
| 585651 | 0 | 18 | 1 | 39 | 75 | 6 |
| 585653 | 10 | 15 | 18 | 42 | 63 | 7 |
| 585654 | 0 | 0 | 25 | 33 | 65 | 8 |

TABLE 4-continued

Dose response assay with 5-10-5 MOE gapmers

| ISIS No | 0.15 µM | 0.44 µM | 1.33 µM | 4.00 µM | 12.00 µM | IC$_{50}$ (µM) |
|---|---|---|---|---|---|---|
| 585655 | 0 | 12 | 15 | 34 | 65 | 8 |
| 585667 | 0 | 0 | 2 | 30 | 52 | >12 |
| 585668 | 11 | 6 | 0 | 43 | 70 | 8 |
| 585682 | 0 | 0 | 0 | 30 | 63 | 11 |
| 585683 | 1 | 9 | 19 | 39 | 77 | 5 |
| 585684 | 6 | 1 | 13 | 21 | 57 | >12 |
| 585698 | 13 | 11 | 37 | 39 | 78 | 4 |
| 585699 | 0 | 8 | 25 | 25 | 65 | 8 |
| 585752 | 0 | 12 | 37 | 34 | 69 | 5 |
| 585757 | 0 | 7 | 16 | 53 | 79 | 4 |
| 585758 | 6 | 0 | 25 | 49 | 71 | 5 |
| 585761 | 2 | 12 | 13 | 39 | 66 | 7 |
| 585762 | 2 | 15 | 26 | 44 | 75 | 4 |
| 585768 | 4 | 0 | 20 | 52 | 76 | 4 |
| 585769 | 0 | 0 | 0 | 42 | 70 | 7 |
| 585770 | 12 | 12 | 42 | 50 | 68 | 3 |
| 585772 | 12 | 12 | 23 | 34 | 56 | 12 |
| 585774 | 15 | 28 | 58 | 68 | 84 | 1 |
| 585775 | 0 | 7 | 28 | 60 | 82 | 3 |
| 585776 | 36 | 24 | 56 | 69 | 86 | 1 |
| 585777 | 15 | 39 | 63 | 76 | 88 | 1 |
| 585831 | 0 | 8 | 3 | 19 | 31 | >12 |
| 585834 | 0 | 10 | 3 | 6 | 32 | >12 |
| 585863 | 7 | 7 | 3 | 0 | 51 | >12 |
| 585864 | 5 | 9 | 19 | 31 | 34 | >12 |
| 585906 | 13 | 2 | 16 | 11 | 29 | >12 |
| 585912 | 20 | 0 | 30 | 33 | 32 | >12 |
| 585932 | 15 | 11 | 25 | 4 | 37 | >12 |
| 585937 | 20 | 33 | 30 | 30 | 43 | >12 |
| 591466 | 0 | 14 | 26 | 39 | 71 | 5 |
| 591491 | 0 | 11 | 23 | 45 | 68 | 5 |
| 591492 | 0 | 0 | 22 | 27 | 64 | 9 |
| 591514 | 0 | 0 | 1 | 41 | 75 | 6 |
| 591536 | 13 | 22 | 34 | 64 | 81 | 2 |
| 591537 | 17 | 44 | 57 | 81 | 88 | 1 |
| 591549 | 21 | 26 | 51 | 72 | 87 | 1 |
| 591550 | 19 | 34 | 65 | 76 | 89 | 1 |
| 591552 | 23 | 49 | 65 | 86 | 90 | 1 |
| 591578 | 0 | 17 | 28 | 45 | 55 | 7 |
| 591579 | 3 | 13 | 47 | 40 | 58 | 6 |

For the experiment in Table 5, below, cells were plated at a density of 5,000 cells per well and transfected using electroporation with 0.19 µM, 0.56 µM, 1.67 µM and 5.0 µM concentrations of antisense oligonucleotide. After the treatment period of approximately 16 hours, RNA was isolated from the cells and TMPRSS6 mRNA levels were measured by quantitative real-time PCR. Human primer probe set RTS3840 was again used to measure mRNA levels. TMPRSS6 mRNA levels were adjusted according to total RNA content, as measured by RIBOGREEN®. Results are presented as percent inhibition of TMPRSS6, relative to untreated control cells.

The half maximal inhibitory concentration (IC$_{50}$) of each oligonucleotide is also presented. TMPRSS6 mRNA levels were significantly reduced in a dose-dependent manner in antisense oligonucleotide treated cells.

TABLE 5

Dose response assay with cEt containing oligonucleotides

| ISIS No | 0.19 µM | 0.56 µM | 1.67 µM | 5.00 µM | IC$_{50}$ (µM) |
|---|---|---|---|---|---|
| 630497 | 28 | 49 | 69 | 86 | 0.6 |
| 647393 | 28 | 42 | 69 | 84 | 0.7 |
| 647394 | 43 | 59 | 67 | 83 | 0.3 |
| 647395 | 11 | 41 | 67 | 83 | 0.9 |
| 647396 | 25 | 47 | 73 | 79 | 0.7 |
| 647397 | 27 | 42 | 70 | 83 | 0.7 |
| 647398 | 27 | 49 | 61 | 84 | 0.7 |
| 647404 | 23 | 47 | 63 | 79 | 0.8 |
| 647414 | 38 | 52 | 72 | 87 | 0.4 |
| 647419 | 45 | 60 | 74 | 84 | 0.3 |
| 647420 | 28 | 52 | 69 | 82 | 0.6 |
| 647421 | 23 | 47 | 68 | 85 | 0.7 |
| 647423 | 23 | 50 | 74 | 81 | 0.7 |
| 647424 | 20 | 48 | 72 | 83 | 0.7 |
| 647426 | 26 | 37 | 67 | 76 | 0.9 |
| 647428 | 25 | 33 | 61 | 83 | 0.9 |
| 647429 | 20 | 32 | 59 | 83 | 1 |
| 647442 | 32 | 51 | 66 | 78 | 0.6 |
| 647446 | 32 | 48 | 73 | 81 | 0.6 |
| 647447 | 29 | 52 | 70 | 81 | 0.6 |
| 647448 | 30 | 56 | 72 | 79 | 0.5 |
| 647449 | 31 | 45 | 71 | 83 | 0.6 |
| 647450 | 32 | 54 | 70 | 82 | 0.5 |
| 647451 | 40 | 62 | 74 | 83 | 0.3 |
| 647453 | 28 | 52 | 68 | 84 | 0.6 |
| 647454 | 32 | 45 | 62 | 84 | 0.7 |
| 647457 | 28 | 46 | 69 | 80 | 0.7 |
| 647475 | 9 | 52 | 63 | 77 | 1 |
| 647476 | 43 | 59 | 70 | 79 | 0.3 |
| 647477 | 48 | 62 | 77 | 83 | 0.2 |
| 647478 | 16 | 41 | 68 | 82 | 0.9 |
| 647482 | 14 | 37 | 73 | 79 | 0.9 |
| 647506 | 37 | 60 | 75 | 83 | 0.4 |
| 647508 | 21 | 39 | 52 | 79 | 1.1 |
| 647514 | 32 | 42 | 63 | 81 | 0.7 |
| 647531 | 25 | 53 | 73 | 80 | 0.6 |
| 647532 | 26 | 49 | 61 | 82 | 0.7 |

For the experiment in Table 6, below, cells were plated at a density of 20,000 cells per well and transfected using electroporation with 0.22 µM, 0.67 µM, 2.00 µM and 6.0 µM concentrations of antisense oligonucleotide. After the treatment period of approximately 16 hours, RNA was isolated from the cells and TMPRSS6 mRNA levels were measured by quantitative real-time PCR. Human primer probe set RTS3840 was used to measure mRNA levels. TMPRSS6 mRNA levels were adjusted according to total RNA content, as measured by RIBOGREEN®. Results are presented as percent inhibition of TMPRSS6, relative to untreated control cells.

The half maximal inhibitory concentration (IC$_{50}$) of each oligonucleotide is also presented. TMPRSS6 mRNA levels were significantly reduced in a dose-dependent manner in antisense oligonucleotide treated cells.

TABLE 6

Dose response assay with cEt containing oligonucleotides

| ISIS No | 0.22 µM | 0.67 µM | 2.00 µM | 6.00 µM | IC$_{50}$ (µM) |
|---|---|---|---|---|---|
| 630497 | 34 | 54 | 81 | 89 | 0.5 |
| 630689 | 43 | 61 | 77 | 87 | 0.3 |
| 630692 | 54 | 64 | 85 | 95 | 0.2 |
| 630693 | 42 | 66 | 75 | 86 | 0.3 |
| 630696 | 20 | 37 | 66 | 82 | 1.1 |
| 630717 | 48 | 73 | 84 | 83 | 0.1 |
| 630718 | 49 | 81 | 88 | 89 | 0.1 |
| 630719 | 42 | 69 | 83 | 95 | 0.3 |
| 630722 | 40 | 56 | 70 | 90 | 0.4 |
| 630726 | 24 | 45 | 64 | 82 | 0.9 |

TABLE 6-continued

Dose response assay with cEt containing oligonucleotides

| ISIS No | 0.22 µM | 0.67 µM | 2.00 µM | 6.00 µM | IC$_{50}$ (µM) |
|---|---|---|---|---|---|
| 630727 | 36 | 57 | 73 | 82 | 0.5 |
| 630794 | 25 | 46 | 71 | 84 | 0.8 |

Example 3: Tolerability of 5-10-5 MOE Gapmers Targeting Human TMPRSS6 in CD1 Mice CD1® mice (Charles River, Mass.) are a multipurpose mice model, frequently utilized for safety and efficacy testing. The mice were treated with about 26 ISIS 5-10-5 MOE gapmer antisense oligonucleotides selected from the tables above and evaluated for changes in the levels of various plasma chemistry markers.

Treatment

Groups of six week old male CD1 mice were injected subcutaneously twice a week for six weeks with 50 mg/kg of ISIS oligonucleotides (100 mg/kg/week dose). One group of male CD1 mice was injected subcutaneously twice a week for 6 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases (ALT and AST), total bilirubin (Tbil), albumin (Alb), creatinine (Creat), and BUN were measured using an automated clinical chemistry analyzer (Hitachi Olympus AU400e, Melville, N.Y.). The results are presented in Table 7. ISIS oligonucleotides that caused changes in the levels of any of the liver or kidney function markers outside the expected range for antisense oligonucleotides were excluded in further studies.

TABLE 7

Plasma chemistry markers in CD1 mice at week six

| ISIS No. | ALT (U/L) | AST (U/L) | BUN (mg/dL) | Creat (mg/dL) | Tbil (mg/dL) | Alb (g/dL) |
|---|---|---|---|---|---|---|
| PBS | 24 | 51 | 27 | 0.17 | 0.17 | 2.9 |
| 585626 | 167 | 155 | 30 | 0.18 | 0.15 | 2.9 |
| 585649 | 263 | 157 | 28 | 0.17 | 0.15 | 3.0 |
| 585653 | 147 | 89 | 28 | 0.18 | 0.39 | 3.4 |
| 585654 | 778 | 300 | 26 | 0.15 | 0.17 | 3.0 |
| 585655 | 1709 | 1353 | 29 | 0.16 | 0.35 | 3.0 |
| 585683 | 45 | 63 | 31 | 0.18 | 0.20 | 3.0 |
| 585698 | 53 | 73 | 34 | 0.21 | 0.19 | 3.0 |
| 585752 | 90 | 99 | 29 | 0.16 | 0.17 | 2.9 |
| 585757 | 246 | 180 | 30 | 0.16 | 0.15 | 2.8 |
| 585758 | 212 | 305 | 28 | 0.18 | 0.28 | 2.9 |
| 585761 | 659 | 439 | 28 | 0.16 | 0.43 | 2.7 |
| 585762 | 597 | 551 | 27 | 0.17 | 0.64 | 3.0 |
| 585768 | 483 | 387 | 26 | 0.18 | 0.19 | 2.7 |
| 585774 | 109 | 126 | 31 | 0.16 | 0.14 | 2.6 |
| 585775 | 60 | 70 | 28 | 0.17 | 0.15 | 2.9 |
| 585776 | 654 | 388 | 27 | 0.17 | 0.13 | 2.9 |
| 585777 | 159 | 200 | 24 | 0.16 | 0.17 | 2.7 |
| 591466 | 46 | 53 | 27 | 0.15 | 0.12 | 3.0 |
| 591491 | 761 | 729 | 28 | 0.18 | 0.25 | 3.2 |
| 591514 | 230 | 215 | 33 | 0.15 | 0.14 | 2.5 |
| 591536 | 540 | 416 | 26 | 0.16 | 0.13 | 3.0 |
| 591537 | 552 | 346 | 27 | 0.17 | 0.16 | 3.0 |
| 591549 | 708 | 488 | 30 | 0.14 | 0.14 | 2.7 |
| 591550 | 294 | 225 | 31 | 0.17 | 0.12 | 2.9 |
| 591552 | 1098 | 680 | 24 | 0.17 | 0.17 | 3.0 |
| 591579 | 135 | 85 | 25 | 0.16 | 0.12 | 2.8 |

Body and Organ Weights

Body weights of all the groups of mice were measured at the start of the experiment, and every week until the end of the study. Liver, spleen and kidney weights were also measured at the end of the study, and the change in body weight and organ weights relative to the PBS control group at baseline are presented in Table 8. ISIS oligonucleotides that caused any changes in organ weights outside the expected range for antisense oligonucleotides were excluded from further studies.

TABLE 8

Body weight and relative organ weights of CD1 mice (in grams) at week six

| ISIS No. | BW change (g) | Relative liver weight (g) | Relative kidney weight (g) | Relative spleen weight (g) |
|---|---|---|---|---|
| PBS | 1.4 | 1.0 | 1.0 | 1.0 |
| 585626 | 1.4 | 1.2 | 0.9 | 1.1 |
| 585649 | 1.3 | 1.2 | 1.0 | 1.1 |
| 585653 | 1.4 | 1.1 | 1.0 | 0.9 |
| 585654 | 1.2 | 1.2 | 1.0 | 1.1 |
| 585655 | 1.3 | 1.4 | 1.0 | 1.3 |
| 585683 | 1.4 | 1.0 | 0.9 | 1.1 |
| 585698 | 1.5 | 1.2 | 1.0 | 1.4 |
| 585752 | 1.3 | 1.1 | 1.0 | 1.3 |
| 585757 | 1.4 | 1.5 | 1.0 | 1.1 |
| 585758 | 1.4 | 1.4 | 0.9 | 1.0 |
| 585761 | 1.1 | 1.4 | 1.0 | 1.3 |
| 585762 | 1.2 | 2.1 | 1.0 | 0.8 |
| 585768 | 1.5 | 1.1 | 1.1 | 1.3 |
| 585774 | 1.5 | 1.1 | 1.0 | 1.1 |
| 585775 | 1.5 | 0.9 | 1.0 | 1.2 |
| 585776 | 1.4 | 1.3 | 1.1 | 1.5 |
| 585777 | 1.4 | 1.2 | 1.1 | 1.5 |
| 591466 | 1.5 | 1.0 | 1.0 | 1.0 |
| 591491 | 1.3 | 1.2 | 1.0 | 1.1 |
| 591514 | 1.4 | 1.1 | 0.9 | 1.5 |
| 591536 | 1.4 | 1.3 | 1.0 | 1.1 |
| 591537 | 1.3 | 1.3 | 0.9 | 1.3 |
| 591549 | 1.4 | 1.2 | 1.0 | 1.5 |
| 591550 | 1.4 | 1.1 | 0.9 | 1.5 |
| 591552 | 1.4 | 1.5 | 1.1 | 1.5 |
| 591579 | 1.5 | 1.0 | 0.9 | 1.1 |

From these tolerability studies, it was observed that most of the 5-10-5 MOE gapmer antisense oligonucleotides were well-tolerated after six weeks of dosing.

Example 4: Tolerability of cEt Containing Oligonucleotides Targeting Human TMPRSS6 in CD1 Mice CD1® mice (Charles River, Mass.) are a multipurpose mice model, frequently utilized for safety and efficacy testing. The mice were treated with about 51 cEt containing antisense oligonucleotides selected from the tables described above, and evaluated for changes in the levels of various plasma chemistry markers.

Treatment

Groups of five- to six-week-old male CD1 mice (n=4 per treatment group) were injected subcutaneously twice a week for six weeks with 25 mg/kg of ISIS oligonucleotides (50 mg/kg/week dose). One group of male CD1 mice was injected subcutaneously twice a week for 6 weeks with PBS. Mice were euthanized 48 hours after the last dose, and organs and plasma were harvested for further analysis. Liver, kidney and spleen were collected for histology, and plasma was collected to measure levels of certain plasma chemistry markers.

The oligonucleotides were split into two test groups with the same conditions and the results are presented to in the tables below.

Plasma Chemistry Markers

To evaluate the effect of ISIS oligonucleotides on liver and kidney function, plasma levels of transaminases, bilirubin, albumin, creatinine, and BUN were measured using an automated clinical chemistry analyzer (Hitachi Olympus AU400e, Melville, N.Y.). The results are presented in Tables 9-10. ISIS oligonucleotides causing changes in the levels of any of the liver or kidney function markers outside the expected range for antisense oligonucleotides were excluded from further studies.

TABLE 9

Plasma chemistry markers in CD1 mice at week six

| ISIS No. | ALT (U/L) | AST (U/L) | BUN (mg/dL) | Creat (mg/dL) | Tbil (mg/dL) | Alb (g/dL) |
|---|---|---|---|---|---|---|
| PBS | 55 | 53 | 24 | 0.1 | 0.2 | 2.7 |
| 615840 | 752 | 636 | 26 | 0.15 | 0.23 | 2.5 |
| 615884 | 1039 | 664 | 25 | 0.17 | 0.17 | 2.8 |
| 615898 | 754 | 420 | 25 | 0.17 | 0.14 | 2.5 |
| 615901 | 118 | 120 | 22 | 0.11 | 0.18 | 2.5 |
| 615903 | 33 | 46 | 22 | 0.12 | 0.18 | 2.5 |
| 615909 | 2042 | 2464 | 49 | 0.16 | 1.19 | 2.7 |
| 615910 | 978 | 1058 | 22 | 0.15 | 1.24 | 2.4 |
| 615911 | 474 | 366 | 23 | 0.14 | 0.34 | 2.4 |
| 630696 | 1117 | 853 | 26 | 0.15 | 0.21 | 2.3 |
| 630716 | 41 | 67 | 25 | 0.13 | 0.14 | 2.4 |
| 630717 | 1005 | 483 | 23 | 0.13 | 0.19 | 2.3 |
| 630718 | 57 | 86 | 25 | 0.13 | 0.13 | 2.4 |
| 630722 | 207 | 168 | 21 | 0.13 | 0.16 | 2.2 |
| 630725 | 1729 | 897 | 20 | 0.12 | 0.15 | 2.2 |
| 630726 | 1330 | 774 | 22 | 0.10 | 0.10 | 2.1 |
| 630727 | 614 | 653 | 23 | 0.10 | 0.13 | 1.6 |
| 630794 | 39 | 78 | 24 | 0.12 | 0.16 | 2.6 |

TABLE 10

Plasma chemistry markers in CD1 mice at week six

| ISIS No. | ALT (U/L) | AST (U/L) | BUN (mg/dL) | Creat (mg/dL) | Tbil (mg/dL) | Alb (g/dL) |
|---|---|---|---|---|---|---|
| PBS | 31.3 | 54.8 | 32.3 | 0.14 | 0.19 | 3.0 |
| 630497 | 429.0 | 297.5 | 31.0 | 0.18 | 0.11 | 2.8 |
| 630689 | 2088.3 | 1306.0 | 34.7 | 0.10 | 0.22 | 2.2 |
| 630692 | 1634.8 | 1402.5 | 30.9 | 0.16 | 0.25 | 3.4 |
| 630693 | 1247.5 | 1193.8 | 33.6 | 0.19 | 0.68 | 2.8 |
| 630719 | 2553.0 | 2594.7 | 28.6 | 0.12 | 2.55 | 3.8 |
| 647414 | 718.5 | 444.0 | 32.7 | 0.13 | 0.12 | 3.0 |
| 647419 | 39.3 | 66.5 | 27.0 | 0.13 | 0.15 | 2.9 |
| 647420 | 90.3 | 100.8 | 30.8 | 0.13 | 0.19 | 3.1 |
| 647421 | 613.3 | 607.3 | 15.5 | 0.09 | 1.61 | 2.6 |
| 647423 | 1290.3 | 807.5 | 29.8 | 0.28 | 0.30 | 3.7 |
| 647424 | 1451.0 | 1198.3 | 25.2 | 0.16 | 0.37 | 3.7 |
| 647426 | 548.5 | 393.0 | 23.7 | 0.12 | 0.16 | 2.7 |
| 647428 | 2658.8 | 2232.8 | 24.8 | 0.21 | 0.52 | 3.0 |
| 647429 | 1306.3 | 725.3 | 23.2 | 0.12 | 0.21 | 2.8 |
| 647442 | 564.8 | 371.5 | 29.7 | 0.08 | 0.13 | 3.0 |
| 647446 | 69.0 | 91.3 | 27.6 | 0.10 | 0.14 | 2.9 |
| 647447 | 61.5 | 76.3 | 27.2 | 0.11 | 0.13 | 2.8 |
| 647448 | 100.8 | 110.5 | 24.4 | 0.10 | 0.14 | 2.9 |
| 647449 | 61.3 | 88.0 | 27.7 | 0.10 | 0.13 | 3.1 |
| 647450 | 1850.8 | 1512.0 | 18.3 | 0.09 | 0.47 | 2.9 |
| 647451 | 1376.3 | 588.3 | 26.0 | 0.15 | 0.29 | 3.7 |
| 647453 | 1774.3 | 1674.5 | 28.8 | 0.16 | 1.24 | 3.7 |
| 647454 | 324.3 | 409.3 | 27.0 | 0.11 | 0.15 | 2.7 |
| 647457 | 1609.0 | 1194.8 | 25.6 | 0.12 | 0.21 | 2.6 |
| 647475 | 40.0 | 80.5 | 25.1 | 0.10 | 0.12 | 2.6 |
| 647476 | 62.0 | 81.0 | 26.1 | 0.11 | 0.14 | 2.8 |
| 647477 | 74.8 | 94.0 | 26.5 | 0.11 | 0.15 | 2.9 |
| 647478 | 62.0 | 88.0 | 28.2 | 0.11 | 0.13 | 3.1 |

TABLE 10-continued

Plasma chemistry markers in CD1 mice at week six

| ISIS No. | ALT (U/L) | AST (U/L) | BUN (mg/dL) | Creat (mg/dL) | Tbil (mg/dL) | Alb (g/dL) |
|---|---|---|---|---|---|---|
| 647482 | 959.8 | 975.8 | 25.8 | 0.11 | 0.19 | 2.9 |
| 647506 | 36.3 | 65.3 | 25.8 | 0.10 | 0.14 | 2.9 |
| 647508 | 49.8 | 93.3 | 26.3 | 0.11 | 0.14 | 3.1 |
| 647514 | 276.0 | 221.8 | 28.3 | 0.11 | 0.17 | 2.9 |
| 647531 | 248.5 | 175.0 | 28.7 | 0.11 | 0.16 | 3.2 |
| 647532 | 156.8 | 180.0 | 21.3 | 0.09 | 0.10 | 3.0 |

Body and Organ Weights

Body weights of all the groups of mice were measured at the start of the experiment, and every week until the end of the study. Liver, spleen and kidney weights were also measured at the end of the study, and the change in body weight and organ weights relative to the PBS control group at baseline are presented in Tables 11-12. ISIS oligonucleotides that caused any changes in organ weights outside the expected range for antisense oligonucleotides were excluded from further studies.

TABLE 11

Body weight and relative organ weights of CD1 mice (in grams) at week six

| ISIS No. | BW change (g) | Relative liver weight (g) | Relative kidney weight (g) | Relative spleen weight (g) |
|---|---|---|---|---|
| PBS | 1.5 | 1 | 1 | 1 |
| 615840 | 1.2 | 1.1 | 1.0 | 0.8 |
| 615884 | 1.4 | 1.5 | 1.1 | 1.2 |
| 615898 | 1.5 | 1.3 | 1.1 | 1.4 |
| 615901 | 1.5 | 1.3 | 1.1 | 2.0 |
| 615903 | 1.4 | 1.1 | 1.1 | 1.2 |
| 615909 | 0.8 | 1.6 | 1.2 | 0.7 |
| 615910 | 1.2 | 1.9 | 1.0 | 2.3 |
| 615911 | 1.5 | 1.4 | 1.1 | 1.6 |
| 630696 | 1.1 | 1.2 | 0.9 | 1.2 |
| 630716 | 1.4 | 1.2 | 1.2 | 1.2 |
| 630717 | 1.2 | 1.4 | 1.0 | 1.7 |
| 630718 | 1.4 | 1.2 | 1.1 | 1.4 |
| 630722 | 1.6 | 1.2 | 1.1 | 1.6 |
| 630725 | 1.3 | 1.2 | 1.1 | 1.8 |
| 630726 | 1.4 | 1.1 | 1.2 | 1.9 |
| 630727 | 1.3 | 1.2 | 1.2 | 3.5 |
| 630794 | 1.4 | 1.0 | 1.1 | 1.1 |

TABLE 12

Body weight and relative organ weights of CD1 mice (in grams) at week six

| ISIS No. | BW change (g) | Relative liver weight (g) | Relative kidney weight (g) | Relative spleen weight (g) |
|---|---|---|---|---|
| PBS | 1.5 | 1 | 1 | 1 |
| 630497 | 1.3 | 1.2 | 1.0 | 1.1 |
| 630689 | 1.6 | 1.3 | 1.0 | 1.4 |
| 630692 | 1.5 | 1.9 | 0.9 | 1.2 |
| 630693 | 1.2 | 1.3 | 0.8 | 0.9 |
| 630719 | 0.8 | 1.4 | 1.1 | 0.4 |
| 647414 | 1.4 | 1.2 | 1.1 | 1.0 |
| 647419 | 1.5 | 1.0 | 1.1 | 1.2 |
| 647420 | 1.4 | 1.1 | 1.0 | 1.4 |
| 647421 | 1.2 | 1.1 | 1.1 | 1.3 |
| 647423 | 1.4 | 1.7 | 1.1 | 1.3 |
| 647424 | 1.1 | 1.8 | 1.2 | 0.6 |
| 647426 | 1.4 | 1.5 | 1.1 | 1.8 |
| 647428 | 1.3 | 1.4 | 1.1 | 1.9 |

TABLE 12-continued

Body weight and relative organ weights of CD1 mice (in grams) at week six

| ISIS No. | BW change (g) | Relative liver weight (g) | Relative kidney weight (g) | Relative spleen weight (g) |
|---|---|---|---|---|
| 647429 | 1.4 | 1.2 | 1.0 | 1.6 |
| 647442 | 1.3 | 1.1 | 1.1 | 1.1 |
| 647446 | 1.4 | 1.2 | 1.2 | 1.4 |
| 647447 | 1.5 | 1.3 | 1.2 | 1.4 |
| 647448 | 1.5 | 1.1 | 1.1 | 1.5 |
| 647449 | 1.5 | 1.1 | 1.1 | 1.6 |
| 647450 | 1.4 | 1.3 | 1.1 | 1.9 |
| 647451 | 1.4 | 1.6 | 1.0 | 1.8 |
| 647453 | 1.2 | 1.8 | 1.4 | 1.5 |
| 647454 | 1.5 | 1.6 | 1.0 | 2.2 |
| 647457 | 1.4 | 1.3 | 1.0 | 1.8 |
| 647475 | 1.4 | 1.2 | 1.1 | 1.5 |
| 647476 | 1.5 | 1.1 | 1.2 | 1.8 |
| 647477 | 1.5 | 1.2 | 1.0 | 1.5 |
| 647478 | 1.6 | 1.1 | 1.0 | 1.2 |
| 647482 | 1.4 | 1.7 | 1.2 | 1.5 |
| 647506 | 1.5 | 1.1 | 1.0 | 1.2 |
| 647508 | 1.6 | 1.0 | 1.0 | 1.2 |
| 647514 | 1.5 | 1.0 | 1.0 | 1.5 |
| 647531 | 1.4 | 1.0 | 1.0 | 1.4 |
| 647532 | 1.5 | 1.3 | 1.1 | 1.4 |

Example 5: Tolerability of Oligonucleotides Targeting Human TMPRSS6 in Sprague-Dawley Rats Sprague-Dawley rats are a multipurpose model used for safety and efficacy evaluations. The rats were treated with about 48 antisense oligonucleotides, found potent in vitro and tolerable in mice from the studies described in the Examples above, and evaluated for changes in the levels of various plasma chemistry markers.

Treatment

Male Sprague-Dawley rats (roughly eight weeks old) were maintained on a 12-hour light/dark cycle and fed ad libitum with Purina normal rat chow, diet 5001. Groups of four Sprague-Dawley rats each were injected subcutaneously once a week for 6 weeks with 100 mg/kg of MOE gapmer; or 50 mg/kg of cEt containing antisense oligonucleotides. One to two days after the final dose, urine protein/creatinine (P/C) ratio was assayed and blood was drawn 3 days after the last dose for hematologic assessments described below. Three days after the last dose, rats were euthanized and organs and plasma were harvested for further analysis.

Plasma Chemistry Markers

To evaluate the effect of ISIS oligonucleotides on liver and kidney function, plasma levels of transaminases (alanine transaminase (ALT) and aspartate transaminase (AST), total bilirubin (Tbil), albumin (Alb), creatinine (Creat), and BUN were measured using an automated clinical chemistry analyzer (Hitachi Olympus AU400e, Melville, N.Y.). The results are presented in Table 13. ISIS oligonucleotides that caused changes in the levels of any of the liver or kidney function markers outside the expected range for antisense oligonucleotides were excluded in further studies.

TABLE 13

Plasma chemistry markers in Sprague-Dawley rats

| ISIS No. | ALT (IU/L) | AST (IU/L) | BUN (mg/dL) | Creat (mg/dL) | Tbil (mg/dL) | Alb (g/dL) |
|---|---|---|---|---|---|---|
| PBS | 60 | 92 | 18 | 0.3 | 0.1 | 3.7 |
| 585626 | 66 | 139 | 25 | 0.4 | 0.1 | 3.2 |
| 585653 | 92 | 154 | 26 | 0.4 | 0.1 | 3.9 |
| 585683 | 73 | 109 | 19 | 0.4 | 0.1 | 3.3 |
| 585698 | 66 | 104 | 22 | 0.4 | 0.1 | 3.4 |
| 585752 | 64 | 145 | 21 | 0.4 | 0.1 | 3.0 |
| 585758 | 113 | 669 | 21 | 0.3 | 0.2 | 2.8 |
| 585774 | 125 | 220 | 25 | 0.4 | 0.2 | 3.2 |
| 585775 | 66 | 117 | 24 | 0.4 | 0.1 | 3.2 |
| 585777 | 302 | 321 | 25 | 0.4 | 0.2 | 3.4 |
| 591466 | 368 | 444 | 22 | 0.4 | 0.2 | 3.1 |
| 591514 | 91 | 218 | 22 | 0.3 | 0.2 | 3.3 |
| 591579 | 484 | 655 | 20 | 0.4 | 0.2 | 3.8 |
| 614954 | 146 | 132 | 26 | 0.1 | 0.2 | 2.8 |
| 615895 | 291 | 383 | 26 | 0.4 | 0.2 | 3.4 |
| 615897 | 1946 | 1467 | 26 | 0.5 | 0.2 | 4.0 |
| 615899 | 70 | 113 | 25 | 0.4 | 0.1 | 3.4 |
| 615900 | 93 | 131 | 26 | 0.4 | 0.1 | 3.1 |
| 615903 | 59 | 70 | 22 | 0.4 | 0.1 | 3.5 |
| 630716 | 57 | 86 | 26 | 0.5 | 0.1 | 3.1 |
| 630718 | 61 | 72 | 23 | 0.4 | 0.1 | 3.4 |
| 630722 | 117 | 153 | 24 | 0.4 | 0.1 | 3.2 |
| 630794 | 90 | 113 | 29 | 0.5 | 0.1 | 3.4 |
| 630800 | 92 | 133 | 25 | 0.4 | 0.1 | 3.6 |
| 630948 | 48 | 77 | 21 | 0.4 | 0.1 | 3.3 |
| 630950 | 79 | 83 | 25 | 0.4 | 0.1 | 3.3 |
| 630952 | 208 | 243 | 31 | 0.4 | 0.2 | 2.9 |
| 630953 | 87 | 135 | 22 | 0.4 | 0.1 | 3.0 |
| 630957 | 110 | 115 | 26 | 0.4 | 0.1 | 3.6 |
| 637749 | 63 | 102 | 25 | 0.1 | 0.2 | 3.2 |
| 647384 | 135 | 158 | 24 | 0.4 | 0.1 | 3.7 |
| 647389 | 243 | 272 | 25 | 0.2 | 0.2 | 3.6 |
| 647391 | 205 | 520 | 27 | 0.0 | 1.1 | 2.1 |
| 647393 | 142 | 172 | 27 | 0.2 | 0.1 | 3.4 |
| 647394 | 391 | 340 | 29 | 0.1 | 0.2 | 2.8 |
| 647395 | 68 | 95 | 24 | 0.1 | 0.1 | 3.2 |
| 647419 | 53 | 66 | 23 | 0.4 | 0.1 | 3.5 |
| 647420 | 56 | 80 | 23 | 0.1 | 0.1 | 3.3 |
| 647446 | 66 | 110 | 23 | 0.2 | 0.1 | 3.4 |
| 647447 | 54 | 67 | 22 | 0.1 | 0.1 | 3.1 |
| 647448 | 55 | 73 | 26 | 0.4 | 0.1 | 3.3 |
| 647449 | 46 | 81 | 24 | 0.4 | 0.1 | 3.2 |
| 647475 | 45 | 78 | 26 | 0.4 | 0.1 | 3.5 |
| 647476 | 52 | 85 | 20 | 0.4 | 0.1 | 3.2 |
| 647477 | 58 | 89 | 24 | 0.5 | 0.1 | 3.5 |
| 647478 | 50 | 82.8 | 22.8 | 0.4 | 0.1 | 3.2 |
| 647506 | 45 | 95.3 | 22.9 | 0.4 | 0.1 | 3.2 |
| 647508 | 73 | 183.3 | 33.3 | 0.3 | 0.1 | 2.5 |
| 647532 | 108 | 179.5 | 47.8 | 0.5 | 0.1 | 1.8 |

TABLE 14

P/C ratio in urine of Sprague-Dawley rats

| | |
|---|---|
| PBS | 1.0 |
| 585626 | 6.7 |
| 585653 | 9.4 |
| 585683 | 7.0 |
| 585698 | 6.2 |
| 585752 | 13.4 |
| 585758 | 11.5 |
| 585774 | 7.5 |
| 585775 | 6.7 |
| 585777 | 7.6 |
| 591466 | 8.0 |
| 591514 | 8.0 |
| 591579 | 7.3 |
| 614954 | 5.2 |
| 615895 | 2.9 |
| 615897 | 4.7 |
| 615899 | 4.2 |
| 615900 | 4.5 |

TABLE 14-continued

P/C ratio in urine of Sprague-Dawley rats

| ISIS No. | P/C |
|---|---|
| 615903 | 5.7 |
| 630716 | 3.9 |
| 630718 | 4.5 |
| 630722 | 4.3 |
| 630794 | 2.3 |
| 630800 | 5.1 |
| 630948 | 2.4 |
| 630950 | 6.3 |
| 630952 | 6.6 |
| 630953 | 4.4 |
| 630957 | 3.8 |
| 637749 | 3.0 |
| 647384 | 2.2 |
| 647389 | 2.4 |
| 647391 | 3.4 |
| 647393 | 3.7 |
| 647394 | 9.9 |
| 647395 | 5.2 |
| 647419 | 5.0 |
| 647420 | 4.9 |
| 647446 | 3.8 |
| 647447 | 3.9 |
| 647448 | 5.6 |
| 647449 | 5.0 |
| 647475 | 4.1 |
| 647476 | 4.6 |
| 647477 | 5.8 |
| 647478 | 4.6 |
| 647506 | 4.7 |
| 647508 | 9.2 |
| 647532 | 49.4 |

Hematology Assays

Blood samples of approximately 1.3 mL of blood were collected from each of the available study animals in tubes containing $K_2$-EDTA and sent to IDEXX Laboratories, Inc. (Fremont, Calif.) for measurement and analysis of red blood cell (RBC) count, white blood cells (WBC) count, individual white blood cell counts—such as that of monocytes, neutrophils, lymphocytes—as well as for platelet count, total hemoglobin content and hematocrit (HCT). The results are presented in Table 15. ISIS oligonucleotides that caused changes in the levels of any of the hematology markers outside the expected range for antisense oligonucleotides were excluded in further studies.

TABLE 15

Hematology markers in Sprague-Dawley rats

| ISIS No. | WBC ($\times 10^3/\mu L$) | RBC ($\times 10^6/\mu L$) | HCT (%) | Lymphocytes (/mm³) | Monocytes (/mm³) | Platelets ($\times 10^3/\mu L$) |
|---|---|---|---|---|---|---|
| PBS | 4.8 | 8.5 | 52.7 | 3567 | 93 | 812 |
| 585626 | 10.1 | 8.3 | 46.9 | 8969 | 252 | 1237 |
| 585653 | 13.8 | 8.2 | 48.3 | 11190 | 359 | 1305 |
| 585683 | 17.8 | 7.9 | 45.7 | 15773 | 557 | 826 |
| 585698 | 16.9 | 7.9 | 46.0 | 15380 | 344 | 761 |
| 585752 | 15.3 | 8.0 | 46.0 | 11396 | 585 | 1158 |
| 585758 | 18.4 | 7.9 | 44.0 | 6369 | 61 | 1548 |
| 585774 | 14.7 | 8.5 | 48.6 | 12818 | 552 | 873 |
| 585775 | 7.3 | 8.4 | 48.4 | 6218 | 219 | 1161 |
| 585777 | 11.2 | 8.1 | 47.1 | 9548 | 175 | 982 |
| 591466 | 14.3 | 8.1 | 45.6 | 12519 | 226 | 812 |
| 591514 | 14.9 | 8.5 | 48.2 | 10993 | 169 | 1157 |
| 591579 | 12.5 | 9.1 | 51.1 | 8540 | 222 | 1080 |
| 614954 | 13.6 | 5.2 | 29.9 | 12186 | 441 | 511 |
| 615895 | 15.2 | 8.0 | 45.9 | 11868 | 603 | 926 |
| 615897 | 14.5 | 7.5 | 43.3 | 10920 | 786 | 902 |
| 615899 | 19.8 | 7.8 | 43.7 | 17319 | 525 | 566 |
| 615900 | 14.0 | 7.1 | 41.0 | 12167 | 267 | 770 |
| 615903 | 9.4 | 8.5 | 51.3 | 7113 | 268 | 687 |
| 630716 | 21.1 | 7.8 | 45.3 | 18994 | 449 | 601 |
| 630718 | 8.9 | 8.9 | 52.5 | 7071 | 269 | 657 |
| 630722 | 17.0 | 9.1 | 51.6 | 13397 | 721 | 693 |
| 630794 | 8.8 | 8.7 | 50.5 | 7098 | 137 | 529 |
| 630800 | 16.6 | 8.0 | 45.3 | 13210 | 478 | 695 |
| 630948 | 7.2 | 8.5 | 50.2 | 5359 | 158 | 670 |
| 630950 | 11.0 | 8.8 | 52.4 | 8833 | 307 | 544 |
| 630952 | 24.2 | 7.7 | 42.8 | 17991 | 798 | 958 |
| 630953 | 25.0 | 6.9 | 42.4 | 20205 | 713 | 662 |
| 630957 | 11.7 | 8.7 | 50.5 | 8913 | 340 | 684 |
| 637749 | 12.8 | 7.5 | 44.7 | 10837 | 765 | 661 |
| 647384 | 14.8 | 9.0 | 54.5 | 11682 | 354 | 642 |
| 647389 | 12.8 | 8.2 | 51.0 | 10621 | 534 | 1075 |
| 647391 | 16.8 | 2.3 | 20.3 | 13574 | 807 | 240 |
| 647393 | 14.5 | 6.9 | 40.8 | 12467 | 423 | 1112 |
| 647394 | 24.9 | 6.5 | 39.6 | 21847 | 1070 | 990 |
| 647395 | 10.4 | 7.4 | 45.2 | 8685 | 515 | 1092 |
| 647419 | 13.8 | 8.3 | 48.5 | 11866 | 257 | 939 |
| 647420 | 11.1 | 8.0 | 47.3 | 9350 | 521 | 1079 |
| 647446 | 5.9 | 7.5 | 44.8 | 4805 | 258 | 1076 |
| 647447 | 10.2 | 7.8 | 47.3 | 8542 | 260 | 1019 |
| 647448 | 10.7 | 7.9 | 45.3 | 9050 | 260 | 933 |
| 647449 | 21.1 | 7.7 | 45.5 | 18809 | 479 | 630 |
| 647475 | 17.4 | 8.3 | 49.0 | 14951 | 562 | 776 |
| 647476 | 14.2 | 8.3 | 47.7 | 12336 | 339 | 979 |

TABLE 15-continued

Hematology markers in Sprague-Dawley rats

| ISIS No. | WBC (×10³/µL) | RBC (×10⁶/µL) | HCT (%) | Lymphocytes (/mm³) | Monocytes (/mm³) | Platelets (×10³/µL) |
|---|---|---|---|---|---|---|
| 647477 | 16.8 | 8.3 | 46.3 | 14089 | 726 | 697 |
| 647478 | 23.7 | 7.4 | 42.9 | 22039 | 440 | 762 |
| 647506 | 12.9 | 7.9 | 45.4 | 11679 | 268 | 711 |
| 647508 | 12.2 | 6.8 | 38.8 | 9800 | 431 | 647 |
| 647532 | 33.1 | 5.3 | 31.0 | 27732 | 963 | 844 |

Body and Organ Weights

Body weights of all the groups of rats were measured at the start of the experiment, and every week until the end of the study. Liver, spleen and kidney weights were also measured at the end of the study, and the change in body weight and organ weights relative to the PBS control group at baseline are presented in Table 16. ISIS oligonucleotides that caused any changes in organ weights outside the expected range for antisense oligonucleotides were excluded from further studies.

TABLE 16

Body weight and relative organ weights of Sprague-Dawley rats (in grams) at week six

| ISIS No. | Liver (g) | Kidney (g) | Spleen (g) | Body weight (g) |
|---|---|---|---|---|
| PBS | 1.0 | 1.0 | 1.0 | 1.8 |
| 585626 | 1.1 | 0.9 | 2.3 | 1.4 |
| 585653 | 1.1 | 1.0 | 2.1 | 1.5 |
| 585683 | 1.1 | 0.9 | 3.3 | 1.4 |
| 585698 | 1.1 | 0.9 | 2.8 | 1.4 |
| 585752 | 1.1 | 0.9 | 2.5 | 1.3 |
| 585758 | 1.5 | 0.9 | 2.3 | 1.2 |
| 585774 | 1.1 | 0.9 | 2.2 | 1.4 |
| 585775 | 1.0 | 0.9 | 1.7 | 1.3 |
| 585777 | 1.0 | 0.9 | 2.3 | 1.4 |
| 591466 | 1.0 | 0.9 | 2.7 | 1.3 |
| 591514 | 1.1 | 1.0 | 2.4 | 1.1 |
| 591579 | 1.0 | 0.8 | 1.9 | 1.3 |
| 614954 | 1.4 | 1.3 | 4.1 | 1.4 |
| 615895 | 1.0 | 1.1 | 1.7 | 1.5 |
| 615897 | 1.3 | 1.1 | 2.1 | 1.7 |
| 615899 | 1.1 | 1.1 | 2.0 | 1.6 |
| 615900 | 1.2 | 1.2 | 2.1 | 1.8 |
| 615903 | 1.2 | 1.0 | 1.5 | 1.9 |
| 630716 | 1.1 | 1.1 | 2.8 | 1.6 |
| 630718 | 1.1 | 1.0 | 2.1 | 1.8 |
| 630722 | 1.2 | 1.2 | 1.6 | 1.5 |
| 630794 | 0.9 | 1.0 | 1.6 | 1.8 |
| 630800 | 1.3 | 1.3 | 2.4 | 1.6 |
| 630948 | 1.0 | 1.1 | 1.7 | 1.9 |
| 630950 | 1.2 | 1.0 | 2.3 | 1.8 |
| 630952 | 1.4 | 1.3 | 2.6 | 1.2 |
| 630953 | 1.4 | 1.2 | 4.2 | 1.6 |
| 630957 | 1.2 | 1.0 | 1.7 | 1.6 |
| 637749 | 1.4 | 1.3 | 4.4 | 1.4 |
| 647384 | 1.0 | 1.0 | 1.1 | 1.7 |
| 647389 | 1.0 | 1.1 | 1.8 | 1.7 |
| 647391 | 1.8 | 1.5 | 13.1 | 1.4 |
| 647393 | 1.3 | 1.1 | 1.8 | 1.6 |
| 647394 | 1.2 | 1.2 | 2.8 | 1.6 |
| 647395 | 1.3 | 1.3 | 1.8 | 1.7 |
| 647419 | 1.3 | 1.1 | 1.6 | 1.8 |
| 647420 | 1.2 | 1.1 | 2.1 | 1.6 |
| 647446 | 1.3 | 1.2 | 2.3 | 1.8 |
| 647447 | 1.1 | 1.1 | 1.9 | 1.7 |
| 647448 | 1.2 | 1.2 | 1.6 | 1.7 |
| 647449 | 1.2 | 1.2 | 1.7 | 1.7 |
| 647475 | 1.2 | 1.1 | 1.5 | 1.7 |
| 647476 | 1.1 | 1.1 | 1.5 | 1.5 |
| 647477 | 1.2 | 1.1 | 1.7 | 1.6 |
| 647478 | 1.2 | 1.3 | 1.8 | 1.7 |
| 647506 | 1.2 | 1.3 | 2.0 | 1.6 |
| 647508 | 1.7 | 2.1 | 2.9 | 1.3 |
| 647532 | 2.0 | 1.7 | 3.7 | 1.3 |

Example 6: Effect of Antisense Inhibition of TMPRSS6 in Transgenic Mouse Model

About 32 antisense oligonucleotides found tolerable in the rat studies above were further evaluated for their ability to reduce human TMPRSS6 mRNA transcript in mice with the human TMPRSS6 transgene ("huTMPRSS6" or "Tg" mice).

Treatment

Eight to sixteen week old male and female huTMPRSS6 transgenic mice were injected subcutaneously with five doses of 6 mg/kg per dose of ISIS antisense oligonucleotides targeting TMPRSS6, administered over a period of two weeks (30 mg/kg total), or with PBS as a control. Each treatment group consisted of 4 animals. Forty-eight hours after the administration of the last dose, blood was drawn from each mouse and the mice were sacrificed and tissues were collected.

RNA Analysis

At the end of the study, RNA was extracted from liver for real-time PCR analysis of liver TMPRSS6 mRNA expression. Results are presented in Table 17 as percent inhibition with respect to PBS treated animals. Human primer probe set RTS4586 (forward sequence TGATAACAGCTGC-CCACTG, designated herein as SEQ ID NO: 86; reverse sequence TCACCTTGAAGGACACCTCT, designated herein as SEQ ID NO: 87; probe sequence AGTTCTGC-CACACCTTGCCCA, designated herein as SEQ ID NO: 88) was used to measure mRNA levels. The mRNA levels were normalized with levels of cyclophilin A, a housekeeping gene, which were determined using primer probe set mCYCLO_24 (forward primer TCGCCGCTTGCTGCA, designated herein as SEQ ID NO: 89; reverse primer ATCG-GCCGTGATGTCGA, designated herein as SEQ ID NO: 90; probe CCATGGTCAACCCCACCGTGTTC, designated herein as SEQ ID NO: 91).

TABLE 17

% inhibition of TMPRSS6 mRNA in transgenic mice liver normalized to PBS expression

| ISIS No | % inhibition |
|---|---|
| 585626 | 57 |
| 585653 | 74 |
| 585683 | 81 |
| 585698 | 59 |

TABLE 17-continued

% inhibition of TMPRSS6 mRNA in transgenic mice liver normalized to PBS expression

| ISIS No | % inhibition |
|---|---|
| 585698 | 59 |
| 585774 | 69 |
| 585775 | 81 |
| 591514 | 73 |
| 615899 | 88 |
| 615900 | 88 |
| 615903 | 97 |
| 630716 | 82 |
| 630718 | 99 |
| 630722 | 92 |
| 630794 | 71 |
| 630800 | 81 |
| 630948 | 65 |
| 630950 | 81 |
| 630957 | 70 |
| 647384 | 66 |
| 647393 | 95 |
| 647395 | 100 |
| 647419 | 99 |
| 647420 | 96 |
| 647446 | 84 |
| 647447 | 89 |
| 647448 | 96 |
| 647449 | 88 |
| 647475 | 84 |
| 647476 | 84 |
| 647477 | 96 |

Example 7: Antisense Compounds Conjugated to GalNAc$_3$ Targeting TMPRSS6

The sequences of selected antisense oligonucleotides targeting TMPRSS6 found potent and tolerable in the examples above were chosen as parent sequences to design new GalNAc$_3$ conjugated antisense compounds targeting human TMPRSS6.

As summarized in Table 18, below, each of the newly designed antisense compounds described in this example had a 5'-Trishexylamino-(THA)-C6 GalNAc$_3$ endcap. ISIS 702843 was a 5-10-5 MOE gapmer having a mixed (phosphorothioate and phosphodiester) backbone ("MBB") with a 5'-Trishexylamino-(THA)-C6 GalNAc$_3$ endcap. ISIS 705051, 705052 and 705053 were 5-10-5 MOE gapmers having a phosphorothioate backbone with a 5'-Trishexylamino-(THA)-C6 GalNAc$_3$ endcap. ISIS 706940 was a 3-10-3 cEt gapmer with all phosphorothioate internucleoside linkages and a 5'-Trishexylamino-(THA)-C6 GalNAc$_3$ endcap; ISIS 706941, 706942 and 706943 are deoxy, MOE, and (S)-cEt containing gapmers having a phosphorothioate backbone with a 5'-Trishexylamino-(THA)-C6 GalNAc$_3$ endcap.

TABLE 18

Eight unconjugated antisense compounds targeting TMPRSS6 mRNA and corresponding GalNAc$_3$ conjugate antisense compounds

| Parent Sequence ISIS# | GalNAc Conjugated ISIS# | Backbone | Length | Sequence | Chemistry | SEQ ID NO |
|---|---|---|---|---|---|---|
| 585774 | 702843 | MBB | 20 | CTTTATTCCAAAGGGCAGCT | 5'-THA GalNAc$_3$ 5-10-5 MOE | 36 |
| 585774 | 705051 | PS | 20 | CTTTATTCCAAAGGGCAGCT | 5'-THA GalNAc$_3$ 5-10-5 MOE | 36 |
| 585683 | 705052 | PS | 20 | GCACGGCAAATCATACTTCT | 5'-THA GalNAc$_3$ 5-10-5 MOE | 23 |
| 585775 | 705053 | PS | 20 | AGCTTTATTCCAAAGGGCAG | 5'-THA GalNAc$_3$ 5-10-5 MOE | 37 |
| 630718 | 706940 | PS | 16 | AGCTTTATTCCAAAGG | 5'-THA GalNAc$_3$ kkk-d10-kkk | 63 |
| 647477 | 706941 | PS | 16 | AGCTTTATTCCAAAGG | 5'-THA GalNAc$_3$ kk-d8-eeeekk | 63 |
| 647449 | 706942 | PS | 16 | CAGCTTTATTCCAAAG | 5'-THA GalNAc$_3$ kk-d9-eeekk | 77 |
| 647420 | 706943 | PS | 16 | CAGCTTTATTCCAAAG | 5'-THA GalNAc$_3$ kek-d9-eekk | 77 |

TABLE 17-continued

% inhibition of TMPRSS6 mRNA in transgenic mice liver normalized to PBS expression

| ISIS No | % inhibition |
|---|---|
| 647478 | 91 |
| 647506 | 91 |

All of the oligonucleotides sequences described in Table 18 were complementary to both human and Rhesus monkey sequences. At the time the studies described herein were undertaken, the cynomolgus monkey genomic sequence for TMPRSS6 was not available in the National Center for Biotechnology Information (NCBI) database; therefore, cross-reactivity of antisense oligonucleotides targeting human TMPRSS6 with the cynomolgus monkey gene sequence could not be confirmed. Instead, the sequences of antisense oligonucleotides were compared to a rhesus monkey sequence for homology. It is expected that ISIS oligonucleotides with homology to the rhesus monkey sequence are fully cross-reactive with the cynomolgus monkey sequence as well.

The antisense oligonucleotides selected for GalNAc conjugation are fully complementary to the rhesus genomic sequence (the complement of GENBANK Accession No. NW_001095180.1, truncated from nucleotides 380000 to 422000, designated herein as SEQ ID NO: 95). The start and stop sites of each oligonucleotide to the rhesus sequence is presented in Table 19 while the start and stop sites of each oligonucleotide to the human sequence is presented in Table 20. "Start site" indicates the 5'-most nucleotide to which the gapmer is targeted in the rhesus monkey or human sequences.

TABLE 19

ASOs complementary to the rhesus TMPRSS6 genomic sequence (SEQ ID NO: 95)

| ISIS No | rhesus Start Site | rhesus Stop Site | Chemistry | Sequence | SEQ ID NO |
|---|---|---|---|---|---|
| 585774 | 40518 | 40537 | 5-10-5 MOE | CTTTATTCCAAAGGGCAGCT | 36 |
| 702843 | 40518 | 40537 | 5'-THA GalNAc3 5-10-5 MOE | CTTTATTCCAAAGGGCAGCT | 36 |
| 705051 | 40518 | 40537 | 5'-THA GalNAc3 5-10-5 MOE | CTTTATTCCAAAGGGCAGCT | 36 |
| 705052 | 22499 | 22518 | 5'-THA GalNAc3 5-10-5 MOE | GCACGGCAAATCATACTTCT | 23 |
| 705053 | 40520 | 40539 | 5'-THA GalNAc3 5-10-5 MOE | AGCTTTATTCCAAAGGGCAG | 37 |
| 630718 | 40524 | 40539 | kkk-10-kkk | AGCTTTATTCCAAAGG | 63 |
| 706940 | 40524 | 40539 | 5'-THA GalNAc3 kkk-10-kkk | AGCTTTATTCCAAAGG | 63 |
| 706941 | 40524 | 40539 | 5'-THA GalNAc3 kk-8-eeeekk | AGCTTTATTCCAAAGG | 63 |
| 706942 | 40525 | 40540 | 5'-THA GalNAc3 kk-9-eeekk | CAGCTTTATTCCAAAG | 77 |
| 706943 | 40525 | 40540 | 5'-THA GalNAc3 kk-9-eeekk | CAGCTTTATTCCAAAG | 77 |

TABLE 20

Sites on TMPRSS6 mRNA (SEQ ID NO: 1) and/or genomic (SEQ ID NO: 2) sequences targeted by GalNAc₃-modified antisense oligonucleotides

| ISIS NO | SEQ ID NO: 1 Start Site | SEQ ID NO: 1 Stop Site | SEQ ID NO: 2 Start Site | SEQ ID NO: 2 Stop Site | SEQ ID NO |
|---|---|---|---|---|---|
| 702843 | 3162 | 3181 | 44924 | 44943 | 36 |
| 705051 | 3162 | 3181 | 44924 | 44943 | 36 |
| 705052 | 1286 | 1305 | 26046 | 26065 | 23 |
| 705053 | 3164 | 3183 | 44926 | 44945 | 37 |
| 706940 | 3168 | 3183 | 44930 | 44945 | 63 |
| 706941 | 3168 | 3183 | 44930 | 44945 | 63 |
| 706942 | 3169 | 3184 | 44931 | 44946 | 77 |
| 706943 | 3169 | 3184 | 44931 | 44946 | 77 |

Example 8: Tolerability of GalNAc3-Modified Antisense Oligonucleotides Targeted to Human TMPRSS6 in CD-1 Mice CD1® mice (Charles River, Mass.) were treated with ISIS GalNAc₃-modified antisense oligonucleotides described in Table 18 above, and evaluated for changes in the levels of various plasma chemistry markers.

Treatment

Groups of six-week-old male CD1 mice (n=4 per treatment group) were injected subcutaneously twice a week for six weeks with 40 mg/kg of ISIS MOE gapmer GalNAc3-modified antisense oligonucleotides (80 mg/kg/week dose) or with 20 mg/kg of ISIS (S)-cEt containing gapmer GalNAc3-modified antisense oligonucleotides described in Table 14 above (40 mg/kg/week dose). One group of male CD1 mice was injected subcutaneously twice a week for 6 weeks with PBS. Mice were euthanized 48 hours after the last dose, and organs and plasma were harvested for further analysis. Liver, kidney, spleen, heart and lung were collected for histology, and plasma was collected to measure levels of certain plasma chemistry markers.

Plasma Chemistry Markers

To evaluate the effect of ISIS GalNAc₃-modified antisense oligonucleotides on liver and kidney function, plasma levels of transaminases, bilirubin, albumin, creatinine, and BUN were measured using an automated clinical chemistry analyzer (Hitachi Olympus AU400e, Melville, N.Y.). The results are presented in Table 21. ISIS oligonucleotides causing changes in the levels of any of the liver or kidney function markers outside the expected range for antisense oligonucleotides were excluded from further studies.

TABLE 21

Plasma chemistry markers in CD1 mice at week six

| ISIS No. | ALT (U/L) | AST (U/L) | BUN (mg/dL) | Creat (mg/dL) | Tbil (mg/dL) | Alb (g/dL) |
|---|---|---|---|---|---|---|
| PBS | 32 | 70 | 27.3 | 0.12 | 0.17 | 2.8 |
| 702843 | 59 | 72 | 28 | 0.17 | 0.16 | 2.9 |
| 705051 | 47 | 73 | 26.6 | 0.16 | 0.17 | 2.8 |
| 705052 | 81 | 94 | 26.3 | 0.16 | 0.17 | 2.8 |
| 705053 | 139 | 129 | 28.2 | 0.17 | 0.18 | 2.9 |
| 706940 | 46 | 66 | 28.1 | 0.18 | 0.14 | 3.0 |
| 706941 | 40 | 57 | 25.5 | 0.18 | 0.16 | 2.9 |
| 706942 | 195 | 145 | 27 | 0.16 | 0.14 | 3.0 |
| 706943 | 178 | 144 | 26.1 | 0.16 | 0.16 | 3.9 |

Body and Organ Weights

Body weights of all groups of mice were measured at the start of the experiment, and every week until the end of the study. Liver, kidney and spleen weights were also measured at the end of the study, and the change in body weight and organ weights relative to the PBS control group at baseline are presented in Table 22. ISIS oligonucleotides that caused any changes in organ weights outside the expected range for antisense oligonucleotides were excluded from further studies.

TABLE 22

Change in body weight and relative organ weights of CD1 mice (in grams) at week six

| ISIS No. | BW change (g) | Relative liver weight (g) | Relative kidney weight (g) | Relative spleen weight (g) |
|---|---|---|---|---|
| PBS | 1.41 | 1.00 | 1.00 | 1.00 |
| 702843 | 1.39 | 1.05 | 1.00 | 1.08 |
| 705051 | 1.38 | 0.98 | 1.00 | 1.05 |
| 705052 | 1.39 | 1.02 | 0.96 | 1.32 |
| 705053 | 1.37 | 1.03 | 0.98 | 1.22 |
| 706940 | 1.31 | 0.97 | 1.01 | 1.16 |
| 706941 | 1.39 | 0.90 | 0.98 | 1.12 |
| 706942 | 1.39 | 1.09 | 1.09 | 1.40 |
| 706943 | 1.44 | 1.06 | 1.02 | 1.08 |

Hematology

To evaluate any effect of ISIS GalNAc$_3$-modified antisense oligonucleotides in CD1 mice on hematologic parameters, blood samples of approximately 1.3 mL of blood was collected from each of the available study animals in tubes containing K$_2$-EDTA. Samples were analyzed for red blood cell (RBC) count, white blood cells (WBC) count, individual white blood cell counts, such as that of monocytes, neutrophils, lymphocytes, as well as for platelet count, hemoglobin content and hematocrit, using an ADVIA120 hematology analyzer (Bayer, USA). The data is presented in Table 23.

The data indicate the oligonucleotides did not cause significant changes in hematologic parameters outside the expected range for antisense oligonucleotides at this dose. Generally, ISIS GalNAc-conjugated antisense oligonucleotides were well tolerated in terms of the hematologic parameters of the mice.

TABLE 23

Blood cell counts in CD1 mice

| ISIS No. | WBC (×10$^3$/μL) | RBC (×10$^6$/μL) | HCT (%) | Lymphocytes (/mm$^3$) | Monocytes (/mm$^3$) | Platelets (×10$^3$/μL) |
|---|---|---|---|---|---|---|
| PBS | 2.9 | 8.9 | 49.9 | 1916.5 | 38.8 | 659.0 |
| 702843 | 4.9 | 8.9 | 48.5 | 3630.0 | 90.3 | 700.5 |
| 705051 | 4.0 | 8.5 | 47.8 | 2961.0 | 80.7 | 781.3 |
| 705052 | 3.2 | 9.3 | 50.7 | 2553.7 | 146.0 | 750.7 |
| 705053 | 5.3 | 9.1 | 49.8 | 3856.0 | 179.5 | 913.3 |
| 706940 | 3.7 | 8.5 | 46.7 | 2591.3 | 154.0 | 935.3 |
| 706941 | 5.5 | 8.8 | 49.9 | 3940.3 | 177.5 | 911.8 |
| 706942 | 5.7 | 9.4 | 51.8 | 4126.3 | 155.3 | 955.7 |
| 706943 | 3.4 | 8.9 | 48.2 | 3067.0 | 0.0 | 1021.3 |

Histological assessment of the GalNAc-conjugated TMPRSS6 antisense compounds in liver, spleen, kidney, heart and lung from the CD-1 Mice was performed. Overall, despite dosing GalNAc$_3$-conjugated antisense oligonucleotides at doses having approximately 8-times more activity in liver than unconjugated oligonucleotides, they were well tolerated and useful compounds for inhibiting TMPRSS6 and are important candidates for the treatment of an iron accumulation disease, disorder or condition.

Example 9: Dose-Response of Antisense Oligonucleotides Targeting TMPRSS6 in huTMPRSS6 Transgenic Mice The eight ISIS GalNAc$_3$-modified antisense oligonucleotides targeting TMPRSS6 (ISIS Nos. 702843, 705051, 705052, 705053, 706940, 706941, 706942 and 706943) as well as two parent compounds (ISIS 585774 and ISIS 630718) were tested and evaluated in a dose-response study for their ability to inhibit human TMPRSS6 mRNA expression in huTMPRSS6 transgenic mice.

Treatment huTMPRSS6 Tg mice were maintained on a 12-hour light/dark cycle and were fed ad libitum normal mouse chow. Animals were acclimated for at least 7 days in the research facility before initiation of the experiment. Antisense oligonucleotides (ASOs) were prepared in buffered saline (PBS) and sterilized by filtering through a 0.2 micron filter. Oligonucleotides were dissolved in 0.9% PBS for injection.

Male and female huTMPRSS6 mice, roughly 3.5 to 4.5 months old, were divided into 44 groups of four mice each (two males and two females in each group). The mice received subcutaneous injections of ISIS oligonucleotide, twice per week for three weeks. One group of mice received subcutaneous injections of PBS twice per week for three weeks. Forty-eight hours after the administration of the last dose, blood was drawn from each mouse and the mice were sacrificed and tissues were collected.

RNA Analysis

At the end of the treatment period, total RNA was extracted from the livers of transgenic mice for quantitative real-time PCR analysis and measurement of human TMPRSS6 mRNA expression. TMPRSS6 mRNA levels were normalized with levels of cyclophilin A, a housekeeping gene, which were determined using mCYCLO_24 primer probe set according to standard protocols. The results below are presented in Table 24 as the average percent of TMPRSS6 mRNA levels for each treatment group, normalized to PBS-treated control and are denoted as "% PBS". Values above 100 were simply noted as "100". Negative values were simply noted as "0".

Human primer probe set RTS4586 (forward sequence TGATAACAGCTGCCCACTG, designated herein as SEQ ID NO: 86; reverse sequence TCACCTTGAAGGACAC-CTCT, designated herein as SEQ ID NO: 87; probe sequence AGTTCTGCCACACCTTGCCCA, designated herein as SEQ ID NO: 88) was used to measure mRNA levels.

TABLE 24

Response to eight ISIS GalNAc₃-conjugated and two unconjugated compounds targeting TMPRSS6 in Tg mice

| Treatment | Dose (mpk/wk) | TMPRSS6 % PBS | TMPRSS6 % Inhibition |
|---|---|---|---|
| 585774 | 100 | 4 | 96 |
|  | 30 | 35 | 65 |
|  | 10 | 99 | 1 |
|  | 3 | 100 | 0 |
| 702843 | 10 | 0 | 100 |
|  | 3 | 16 | 84 |
|  | 1 | 55 | 45 |
|  | 0.3 | 100 | 0 |
| 705051 | 10 | 1 | 99 |
|  | 3 | 68 | 32 |
|  | 1 | 72 | 28 |
|  | 0.3 | 100 | 0 |
| 705052 | 10 | 28 | 72 |
|  | 3 | 23 | 77 |
|  | 1 | 100 | 0 |
|  | 0.3 | 100 | 0 |
| 705053 | 10 | 7 | 93 |
|  | 3 | 30 | 70 |
|  | 1 | 100 | 0 |
|  | 0.3 | 100 | 0 |
| 630718 | 30 | 0 | 100 |
|  | 10 | 37 | 63 |
|  | 3 | 100 | 0 |
|  | 1 | 100 | 0 |
| 706940 | 3 | 0 | 100 |
|  | 1 | 4 | 96 |
|  | 0.3 | 52 | 48 |
|  | 0.1 | 100 | 0 |
| 706941 | 3 | 8 | 92 |
|  | 1 | 71 | 29 |
|  | 0.3 | 100 | 0 |
|  | 0.1 | 100 | 0 |
| 706942 | 3 | 2 | 98 |
|  | 1 | 47 | 53 |
|  | 0.3 | 82 | 18 |
|  | 0.1 | 100 | 0 |
| 706943 | 3 | 2 | 98 |
|  | 1 | 15 | 85 |
|  | 0.3 | 100 | 0 |
|  | 0.1 | 100 | 0 |

Plasma Chemistry Markers

To evaluate the effect of ISIS oligonucleotides on liver and kidney function, serum levels of transaminases, bilirubin and BUN were measured using an automated clinical chemistry analyzer (Hitachi Olympus AU400e, Melville, N.Y.) and presented in Table 25 below. ISIS oligonucleotides causing changes in the levels of any of the liver or kidney function markers outside the expected range for antisense oligonucleotides were excluded from further studies.

TABLE 25

Serum chemistries of eight ISIS GalNAc₃-modified ASOs and two unconjugated compounds targeting TMPRSS6 in transgenic mice

| | Dose (mg/kg/wk) | ALT | AST | BUN |
|---|---|---|---|---|
| PBS | n/a | 39.5 | 64.8 | 40.4 |
| 585774 | 100 | 40.8 | 68.5 | 42.5 |
|  | 30 | 36.5 | 70.8 | 37.2 |
|  | 10 | 38.5 | 59.0 | 38.9 |
|  | 3 | 39.8 | 59.5 | 41.6 |
| 702843 | 10 | 38.3 | 57.3 | 35.6 |
|  | 3 | 41.8 | 65.5 | 38.9 |
|  | 1 | 41.8 | 100.3 | 34.7 |
|  | 0.3 | 43.3 | 65.3 | 38.8 |
| 705051 | 10 | 47.3 | 79.8 | 35.4 |
|  | 3 | 37.0 | 58.5 | 34.9 |
|  | 1 | 33.0 | 57.0 | 35.7 |
|  | 0.3 | 42.0 | 67.5 | 34.6 |
| 705052 | 10 | 34.8 | 61.5 | 33.9 |
|  | 3 | 37.0 | 62.5 | 32.8 |
|  | 1 | 35.8 | 57.8 | 35.1 |
|  | 0.3 | 35.0 | 65.0 | 34.1 |
| 705053 | 10 | 39.0 | 55.8 | 32.4 |
|  | 3 | 35.3 | 62.8 | 38.6 |
|  | 1 | 39.8 | 73.5 | 36.6 |
|  | 0.3 | 39.5 | 73.3 | 37.9 |
| 630718 | 30 | 58.8 | 160.8 | 37.7 |
|  | 10 | 38.3 | 73.0 | 33.8 |
|  | 3 | 39.3 | 92.3 | 32.8 |
|  | 1 | 38.0 | 67.8 | 35.0 |
| 706940 | 3 | 36.3 | 54.8 | 33.7 |
|  | 1 | 39.8 | 65.0 | 35.7 |
|  | 0.3 | 38.3 | 66.8 | 34.9 |
|  | 0.1 | 36.8 | 52.8 | 31.8 |
| 706941 | 3 | 37.5 | 59.0 | 31.6 |
|  | 1 | 34.3 | 75.8 | 32.3 |
|  | 0.3 | 40.5 | 72.8 | 34.9 |
|  | 0.1 | 45.3 | 63.8 | 31.3 |
| 706942 | 3 | 34.3 | 90.5 | 35.8 |
|  | 1 | 36.8 | 58.3 | 32.8 |
|  | 0.3 | 46.8 | 270.0 | 39.8 |
|  | 0.1 | 35.5 | 76.5 | 31.0 |
| 706943 | 3 | 35.5 | 81.3 | 34.6 |
|  | 1 | 33.3 | 71.8 | 31.0 |
|  | 0.3 | 35.0 | 54.5 | 32.2 |
|  | 0.1 | 42.3 | 60.0 | 33.1 |

All GalNAc conjugated ASOs were well-tolerated with no major changes in organ and body weights nor serum transaminase levels.

The half maximal effective dosage ($ED_{50}$) of each ASO was calculated and is presented in Table 26, below.

TABLE 26

Potencies of eight ISIS GalNAc₃-modified ASOs and two unconjugated compounds targeting TMPRSS6

| ISIS # | $ED_{50}$ (mpk/wk) |
|---|---|
| 585774 | 26.0 |
| 702843 | ~1.0 |
| 705051 | 3.7 |
| 705052 | ~2.7 |
| 705053 | ~2.8 |
| 630718 | ~9.7 |
| 706940 | ~0.3 |
| 706941 | 1.3 |
| 706942 | 0.9 |
| 706943 | ~0.9 |

$ED_{50}$ calculations showed that GalNAc-conjugated ASOs are approximately 10-fold more potent than unconjugated ASOs. ISIS 702843 was the most potent GalNAc conjugated 5-10-5 MOE gapmer compound.

Example 10: Viscosity Assessment of Antisense Oligonucleotides Targeting TMPRSS6

The viscosity of the antisense oligonucleotides was measured with the aim of screening out antisense oligonucleotides which have a viscosity more than 40 cP. Oligonucleotides having a viscosity greater than 40 cP would not be optimal for administration to a subject.

ISIS oligonucleotides (32-35 mg) were weighed into a glass vial, 120 µL of water was added and the antisense oligonucleotide was dissolved into solution by heating the vial at 50° C. Part of (75 µL) the pre-heated sample was pipetted to a micro-viscometer (Cambridge). The temperature of the micro-viscometter was set to 25° C. and the viscosity of the sample was measured. Another part (20 µL) of the pre-heated sample was pipetted into 10 mL of water for UV reading at 260 nM at 85° C. (Cary UV instrument). The results are presented in Table 27 and indicate that most of the GalNAc antisense oligonucleotides solutions are optimal in their viscosity under the criterion stated above. Antisense oligonucleotide 706941 was the only antisense oligonucleotide tested that had a viscosity level above 40 cP.

TABLE 27

Viscosity Data for GalNAc-Conjugated ASOs

| ISIS # | Chemistry | cP |
|---|---|---|
| 702843 | 5'-THA GalNAc$_3$ 5-10-5 MOE (MBB) | 33 |
| 705051 | 5'-THA GalNAc$_3$ 5-10-5 MOE (PS) | 23 |
| 705052 | 5'-THA GalNAc$_3$ 5-10-5 MOE (PS) | 16 |
| 705053 | 5'-THA GalNAc$_3$ 5-10-5 MOE (PS) | 26 |
| 706940 | 5'-THA GalNAc$_3$ kkk-10-kkk (PS) | 39 |
| 706941 | 5'-THA GalNAc$_3$ kk-8-eeeekk (PS) | 54 |
| 706942 | 5'-THA GalNAc$_3$ kk-9-eeekk (PS) | 20 |
| 706943 | 5'-THA GalNAc$_3$ kek-9-eekk (PS) | 19 |

Example 11: Antisense Inhibition In Vivo by Oligonucleotides Targeting TMPRSS6 Comprising a GalNAc$_3$ Conjugate in Cynomolgus Monkeys At the time this study was undertaken, the cynomolgus monkey genomic sequence for TMPRSS6 was not available in the National Center for Biotechnology Information (NCBI) database; therefore, cross-reactivity of antisense oligonucleotides targeting human TMPRSS6 with the cynomolgus monkey gene sequence could not be confirmed. Instead, the sequences of antisense oligonucleotides were compared to a rhesus monkey sequence for homology as described in Example 6, above. It is expected that ISIS oligonucleotides with homology to the rhesus monkey sequence are fully cross-reactive with the cynomolgus monkey sequence as well.

The ten human TMPRSS6 antisense oligonucleotides selected for testing in cynomolgus monkey had 0 mismatches with the rhesus genomic sequence (SEQ ID NO: 95) as described in Example 6, above.

Study Design

Ten antisense oligonucleotides were evaluated for efficacy and tolerability, and for their pharmacokinetic profile in the liver and kidney in a 13-week study of antisense inhibition of TMPRSS6 mRNA in male cynomolgus monkeys. The monkeys were treated by subcutaneous administration with the eight ISIS GalNAc$_3$-modified ASOs and two unconjugated parent antisense oligonucleotides antisense oligonucleotides targeting TMPRSS6 as shown in Table 28.

TABLE 28

ASOs compared in cynomolgus monkey studies

| Group | ISIS# | Dose |
|---|---|---|
| 1 | PBS Control | n/a |
| 2 | 585774 | 25 mpk |
| 3 | 705051 | 30 mpk |
| 4 | 705052 | 30 mpk |
| 5 | 705053 | 30 mpk |

TABLE 28-continued

ASOs compared in cynomolgus monkey studies

| Group | ISIS# | Dose |
|---|---|---|
| 6 | 702843 | 30 mpk |
| 7 | 705051 | 5 mpk |
| 8 | 702843 | 5 mpk |
| 9 | 630718 | 23 mpk |
| 10 | 706940 | 30 mpk |
| 11 | 706941 | 30 mpk |
| 12 | 706942 | 30 mpk |
| 13 | 706943 | 30 mpk |
| 14 | 706940 | 5 mpk |

High-dose (30 mpk) groups for the GalNAc-conjugated ASOs assessed toxicity. Low-dose (5 mpk) groups for GalNAc-conjugated ASOs were compared to a corresponding unconjugated parent sequence to assess activity. Groups 2, 3, 6, 7 and 8 are the same sequence, and the mixed backbone (MBB) compound ISIS No. 702843 is tested at both low and high doses, as well as compared to the full phosphorothioate compound ISIS No. 705051 (also tested at both low and high doses). Groups 9, 10, 11 and 14 are the same sequence, and ISIS No. 706940 is tested at both low and high doses.

Treatment

Prior to the study, the monkeys were kept in quarantine during which the animals were observed daily for general health. The monkeys were two to four years old and weighed two to four kg. 56 male cynomolgus monkeys were randomly assigned to 14 treatment groups with four monkeys per group. Monkeys were each injected subcutaneously every other day for the first week, and then once weekly for 11 weeks for a total of 15 doses with ISIS oligonucleotide or PBS using a stainless steel dosing needle and syringe of appropriate size. Tail bleeds were conducted at 1 week prior to the first administration, then again at days 9, 16, 30, 44, 58, 72 and 86.

During the study period, the monkeys were observed twice daily for signs of illness or distress. Any animal experiencing more than momentary or slight pain or distress due to the treatment, injury or illness was treated by the veterinary staff with approved analgesics or agents to relieve the pain after consultation with the Study Director. Any animal in poor health or in a possible moribund condition was identified for further monitoring and possible euthanasia. Scheduled euthanasia of the animals was conducted on day 86. The protocols described in the Example were approved by the Institutional Animal Care and Use Committee (IACUC).

Prior to the first dose and at various time points thereafter, blood draws were performed for clinical pathology endpoints (hematology, clinical chemistry, coagulation, Complement Bb and C3, cytokine and chemokine analyses), and urine chemistry was also measured. At baseline and at the end of the experimental period, certain pharmacology endpoints were measured, such as liver TMPRSS6 mRNA expression, serum hepcidin (Intrinsic LifeSciences, San Diego, Calif.), serum iron and serum transferrin saturation. At the end of the study, body and organ weights, histopathology of tissues and PK analysis of liver and kidney were measured. No significant changes in body weight, cytokine or albumin levels were observed.

TMPRSS6 RNA Analysis

At the end of the study, RNA was extracted from liver for real-time PCR analysis of measurement of mRNA expression of TMPRSS6 using various primer-probe sets. Representative data using the primer probe set RTS3840 is presented in the table below. Results in Table 29 are presented as percent inhibition of TMPRSS6 mRNA relative to saline control, normalized with cyclophilin (mCYCLO_24 primer probe set).

TABLE 29

Reduction of monkey liver TMPRSS6 mRNA after 12-weeks ASO administration

| Treatment | Dose (mg/kg) | % inhibition | Group |
|---|---|---|---|
| 585774 | 25 | 76 | 2 |
| 705051 | 30 | 90 | 3 |
| 705052 | 30 | 64 | 4 |
| 705053 | 30 | 49 | 5 |
| 702843 | 30 | 89 | 6 |
| 705051 | 5 | 77 | 7 |
| 702843 | 5 | 82 | 8 |
| 630718 | 23 | 65 | 9 |
| 706940 | 30 | 71 | 10 |
| 706941 | 30 | 72 | 11 |
| 706942 | 30 | 93 | 12 |
| 706943 | 30 | 91 | 13 |
| 706940 | 5 | 61 | 14 |

ISIS Nos. 705051, 702843, 706942 and 706943 were quite efficacious, demonstrating ≥89% target reduction at 30 mpk after 13-weeks of dosing.

Hepcidin Analysis

Serum hepcidin levels were measured at the time points shown in Table 30 below. Results are presented as percent saline control. "Day −7" indicates one week before the first dose was administered.

TABLE 30

Monkey serum hepcidin levels

| | Dose (mg/kg) | Day −7 | Day 9 | Day 16 | Day 44 | Day 86 |
|---|---|---|---|---|---|---|
| Saline | n/a | 1.0 | 1.0 | 1.0 | 1.0 | 1.0 |
| 585774 | 25 | 0.9 | 1.3 | 1.4 | 1.1 | 1.4 |
| 705051 | 30 | 0.9 | 1.1 | 1.5 | 1.5 | 1.8 |
| 702843 | 30 | 0.9 | 1.2 | 1.2 | 1.3 | 1.9 |
| 706942 | 30 | 0.7 | 1.0 | 1.5 | 1.3 | 1.9 |
| 706943 | 30 | 0.8 | 0.9 | 1.5 | 1.2 | 1.6 |

The table shows that serum hepcidin levels increased over the course of the study.

Serum Iron and Transferrin Saturation Analysis

The averages of the four subjects from each of the 14 treatment groups are presented in Table 31, below. As is shown in Table 31, serum iron levels and transferrin saturation ("Tf sat") were reduced at day 86 in treated groups compared to control.

TABLE 31

Monkey serum iron and transferrin saturation levels at day 86

| Group # | Treatment | Dose (mg/kg) | iron | Tf sat |
|---|---|---|---|---|
| 1 | Saline | n/a | 125.7 | 38.8 |
| 2 | 585774 | 25 | 55.2 | 15.7 |
| 3 | 705051 | 30 | 36.6 | 10.0 |
| 4 | 705052 | 30 | 61.9 | 15.8 |
| 5 | 705053 | 30 | 96.0 | 27.0 |
| 6 | 702843 | 30 | 42.3 | 13.3 |
| 7 | 705051 | 5 | 63.7 | 20.0 |
| 8 | 702843 | 5 | 51.7 | 16.5 |
| 9 | 630718 | 23 | 61.4 | 17.7 |
| 10 | 706940 | 30 | 71.6 | 20.5 |
| 11 | 706941 | 30 | 55.7 | 15.8 |
| 12 | 706942 | 30 | 25.9 | 6.9 |
| 13 | 706943 | 30 | 30.3 | 7.4 |
| 14 | 706940 | 5 | 82.8 | 23.7 |

---

What is claimed is:

1. A compound comprising a modified oligonucleotide consisting of 16 to 23 linked nucleosides having a nucleobase sequence at least 85% complementary to an equal length portion of nucleobases 3162 to 3184 of SEQ ID NO: 1, wherein the modified oligonucleotide is single-stranded.

2. The compound of claim 1, wherein the nucleobase sequence of the modified oligonucleotide is at least 100% complementary to an equal length portion of nucleobases 3162 to 3184 of SEQ ID NO: 1.

3. The compound of claim 1, wherein the nucleobase sequence of the modified oligonucleotide comprises at least 14 contiguous nucleobases of the nucleobase sequences selected from SEQ ID NOs: 63 and 77.

4. The compound of claim 2, wherein the nucleobase sequence of the modified oligonucleotide comprises at least 16 contiguous nucleobases of the nucleobase sequences selected from SEQ ID NOs: 36 and 37.

5. The compound of claim 4, wherein the nucleobase sequence of the modified oligonucleotide is 100% identical to the nucleobase sequence of SEQ ID NO: 36.

6. The compound of claim 1, wherein the modified oligonucleotide comprises at least one modified internucleoside linkage.

7. The compound of claim 6, wherein the at least one modified internucleoside linkage is a phosphorothioate internucleoside linkage.

8. The compound of claim 1, wherein the modified oligonucleotide comprises at least one modified sugar selected from a 2'-O-methoxyethyl modified sugar, a constrained ethyl, a 3'-fluoro-HNA, and a bicyclic sugar having a 4'-$(CH_2)_n$-O-2' bridge, wherein n is 1 or 2.

9. The compound of claim 1, wherein the modified oligonucleotide comprises at least one 5-methylcytosine.

10. The compound of claim 1, wherein the modified oligonucleotide consists of 20 linked nucleosides having a nucleobase sequence comprising at least 16 contiguous nucleobases of SEQ ID NO: 36, wherein the modified oligonucleotide comprises:

a gap segment consisting of ten linked 2'-deoxynucleosides;

a 5' wing segment consisting of five linked nucleosides; and a 3' wing segment consisting of five linked nucleosides wherein the gap segment is positioned between the 5' wing segment and the 3' wing segment, wherein each nucleoside of each wing segment comprises a 2'-O-methoxyethyl sugar, wherein at least one internucleoside linkage is a phosphorothioate linkage, and wherein each cytosine residue is a 5-methylcytosine.

11. The compound of claim 1, comprising a conjugate group conjugated to the modified oligonucleotide, wherein the conjugate group comprises at least one N-acetyl galactosamine (GalNAc).

12. A compound comprising a modified oligonucleotide according to the following formula: mCes Teo Teo Teo Aeo Tds Tds mCds mCds Ads Ads Ads Gds Gds Gds mCeo Aeo Ges mCes Te (SEQ ID NO: 36); wherein, A=an adenine, mC=a 5-methylcytosine G=a guanine, T=a thymine, e=a 2'-O-methoxyethyl modified nucleoside, d=a 2'-deoxynucleoside, and s=a phosphorothioate internucleoside linkage.

13. A compound according to the following structure:
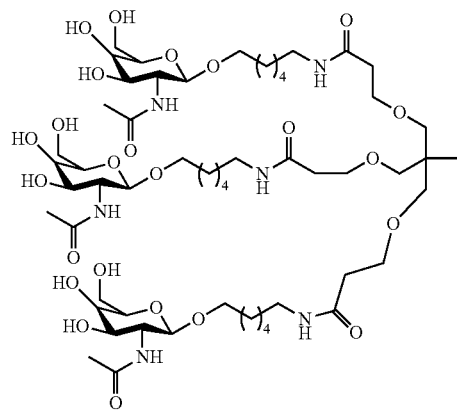
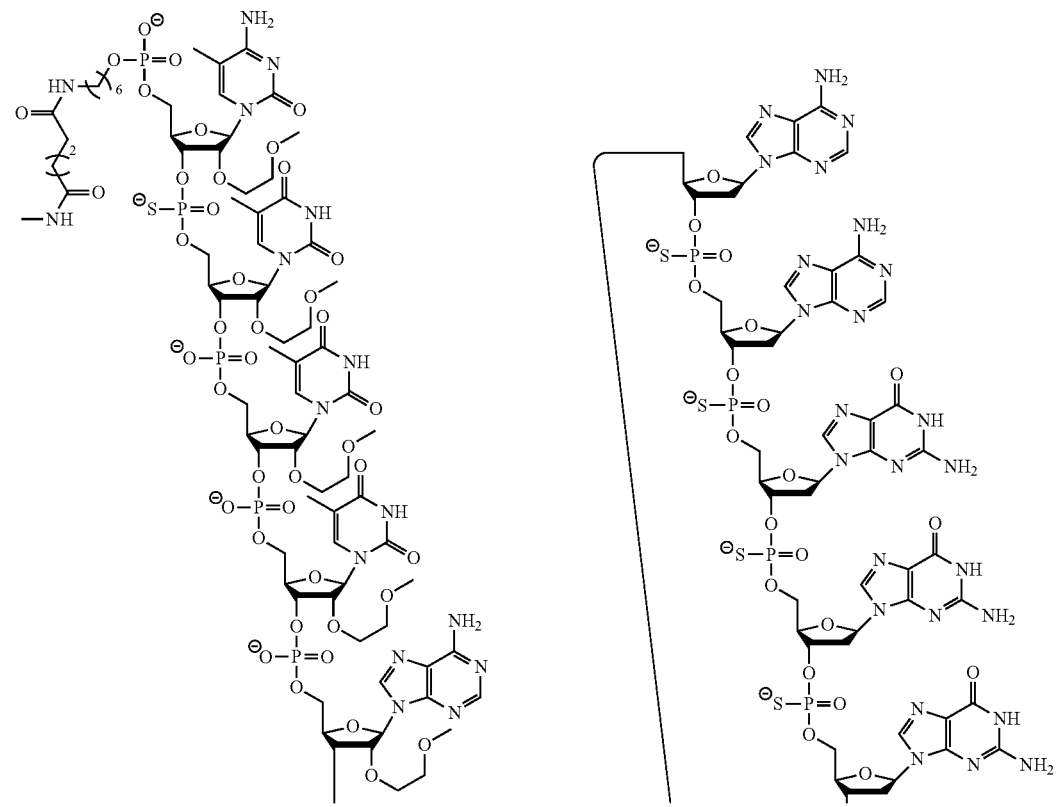

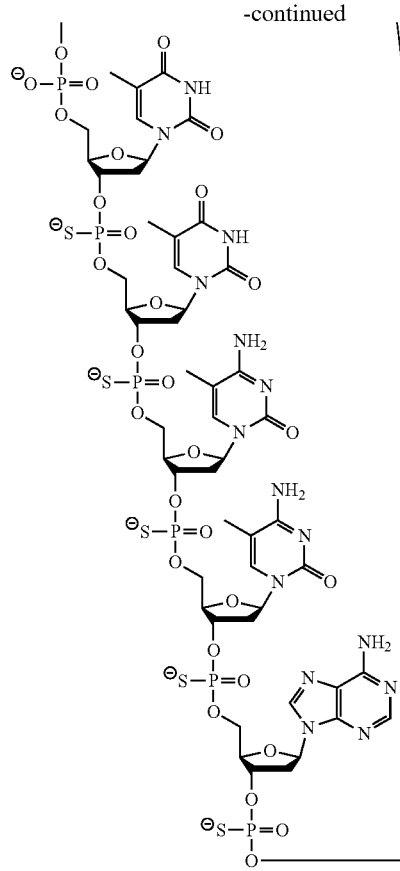
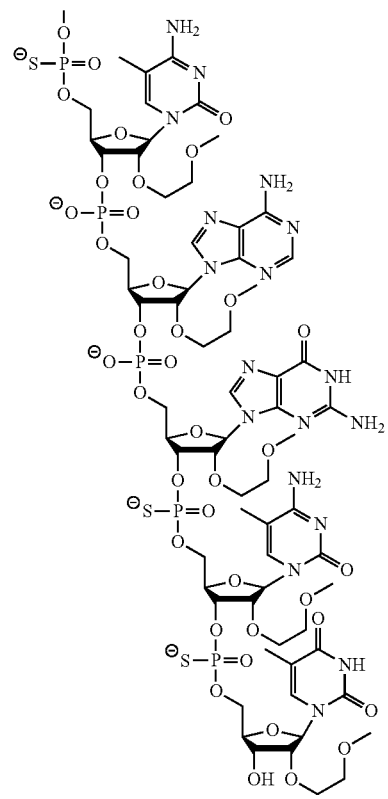

(SEQ ID NO: 36), or a salt thereof.

14. A pharmaceutical composition comprising the compound of claim 1 and a pharmaceutically acceptable carrier or diluent.

15. The compound of claim 11, wherein the nucleobase sequence of the modified oligonucleotide comprises at least 16 contiguous nucleobases of the nucleobase sequences selected from SEQ ID NOs: 36 and 37.

16. The compound of claim 11, wherein at least one internucleoside linkage of the modified oligonucleotide is a phosphorothioate internucleoside linkage.

17. The compound of claim 11, wherein the modified oligonucleotide consists of 20 linked nucleosides having a nucleobase sequence comprising at least 16 contiguous nucleobases of the nucleobase sequences selected from SEQ ID NO: 36 and 37, wherein the modified oligonucleotide comprises:
a gap segment consisting of ten linked 2'-deoxynucleosides;
a 5' wing segment consisting of five linked nucleosides; and
a 3' wing segment consisting of five linked nucleosides;
wherein the gap segment is positioned between the 5' wing segment and the 3' wing segment, and wherein each nucleoside of each wing segment comprises a 2'-O-methoxyethyl sugar.

18. A method of treating, preventing, or slowing progression of a disease, disorder or condition related to excess iron accumulation in an individual comprising administering the compound of claim 1 to the individual.

19. The method of claim 18, wherein the disease, disorder, or condition is β-thalassemia.

20. The pharmaceutical composition of claim 14, wherein the pharmaceutically acceptable carrier or diluent is phosphate buffered saline.

21. The compound of claim 10, wherein the 20 linked nucleosides have a nucleobase sequence identical to SEQ ID NO: 36.

22. The compound of claim 21, comprising a conjugate group conjugated to the modified oligonucleotide, wherein the conjugate group comprises at least one GalNAc.

23. The compound of claim 12, comprising a conjugate group conjugated to the modified oligonucleotide, wherein the conjugate group comprises at least one GalNAc.

24. The modified oligonucleotide of claim 13, which is a sodium salt of the formula.

25. The compound of claim 11, wherein the conjugate group has the formula:

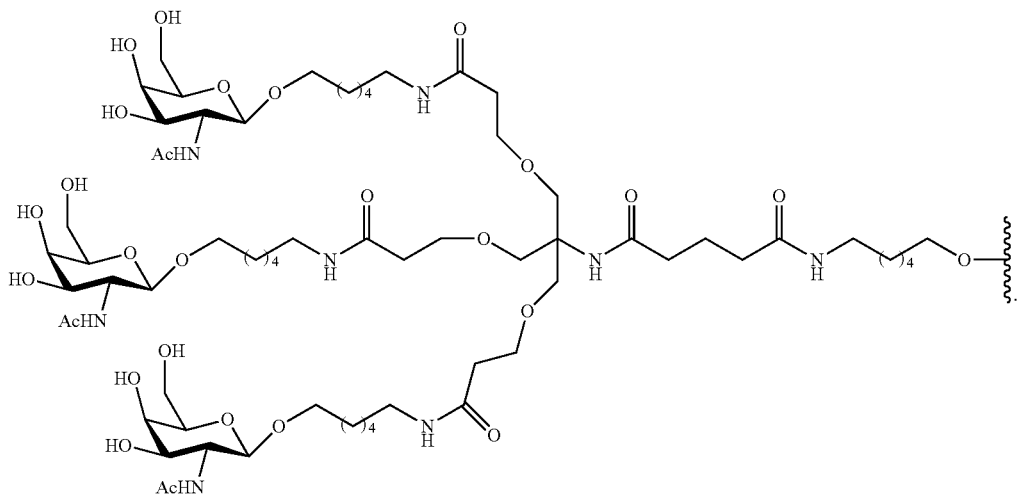

26. The compound of claim 23, wherein the conjugate group has the formula:

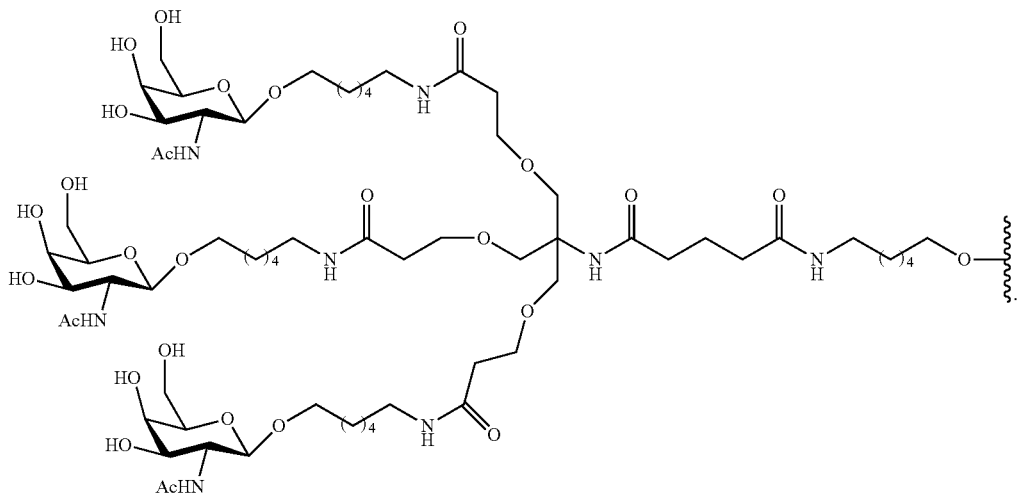

27. The pharmaceutical composition of claim 14, wherein the pharmaceutically acceptable diluent is phosphate buffered saline (PBS).

28. A pharmaceutical composition comprising the compound of claim 13 and a pharmaceutically acceptable carrier or diluent.

29. The pharmaceutical composition of claim 28, wherein the pharmaceutically acceptable diluent is PBS.

* * * * *

SEQUENCE LISTING

```
<160> NUMBER OF SEQ ID NOS: 95

<210> SEQ ID NO 1
<211> LENGTH: 3212
<212> TYPE: DNA
<213> ORGANISM: Homo sapiens

<400> SEQUENCE: 1
cttgagccag acccagtcca gctctggtgc ctgccctctg gtgcgagctg acctgagatg      60
cacttccctc ctctgtgagc tgtctcggca cccacttgca gtcactgccg cctgatgttg     120
ttactcttcc actccaaaag gatgcccgtg gccgaggccc cccaggtggc tggcgggcag     180
ggggacggag gtgatggcga ggaagcggag ccggagggga tgttcaaggc ctgtgaggac     240
tccaagagaa aagcccgggg ctacctccgc ctggtgcccc tgtttgtgct gctggccctg     300
ctcgtgctgg cttcggcggg ggtgctactc tggtatttcc tagggtacaa ggcggaggtg     360
atggtcagcc aggtgtactc aggcagtctg cgtgtactca atcgccactt ctcccaggat     420
cttacccgcc gggaatctag tgccttccgc agtgaaaccg ccaaagccca gaagatgctc     480
aaggagctca tcaccagcac ccgcctggga acttactaca actccagctc cgtctattcc     540
```

```
tttggggagg gacccctcac ctgcttcttc tggttcattc tccaaatccc cgagcaccgc    600
cggctgatgc tgagcccega ggtggtgcag gcactgctgg tggaggagct gctgtccaca    660
gtcaacagct cggctgccgt cccctacagg gccgagtacg aagtggaccc cgagggccta    720
gtgatcctgg aagccagtgt gaaagacata gctgcattga attccacgct gggttgttac    780
cgctacagct acgtgggcca gggccaggtc ctccggctga agggggcctga ccacctggcc    840 tccagctgcc tgtggcacct gcagggcccc aaggacctca tgctcaaaact ccggctggag    900 tggacgctgg cagagtgccg ggaccgactg gccatgtatg acgtggccgg cccctggag     960 aagaggctca tcacctcggt gtacggctgc agccgccagg agcccgtggt ggaggttctg    1020
gcgtcggggg ccatcatggc ggtcgtctgg aagaagggcc tgcacagcta ctacgacccc    1080
ttcgtgctct ccgtgcagcc ggtggtcttc caggcctgtg aagtgaacct gacgctggac    1140
aacaggctcg actcccaggg cgtcctcagc accccgtact ccccagcta ctactcgccc     1200 caaacccact gctcctggca cctcacggtg ccctctctgg actacggctt ggccctctgg    1260
tttgatgcct atgcactgag gaggcagaag tatgatttgc cgtgcaccca gggccagtgg    1320
acgatccaga acaggaggct gtgtggcttg cgcatcctgc agccctacgc cgagaggatc    1380
cccgtggtgg ccacggccgg gatcaccatc aacttcacct cccagatctc cctcaccggg    1440
cccggtgtgc gggtgcacta tggcttgtac aaccagtcgg accccctgcc tggagagttc    1500
ctctgttctg tgaatggact ctgtgtccct gcctgtgatg gggtcaagga ctgccccaac    1560
ggcctggatg agagaaactg cgtttgcaga gccacattcc agtgcaaaga ggacagcaca    1620
tgcatctcac tgcccaaggt ctgtgatggg cagcctgatt gtctcaacgg cagcgacgaa    1680
gagcagtgcc aggaaggggt gccatgtggg acattcacct tccagtgtga ggaccggagc    1740
tgcgtgaaga gcccaaccc gcagtgtgat gggcggcccg actgcaggga cggctcggat    1800
gaggagcact gtgactgtgg cctccagggc ccctccagcc gcattgttgg tggagctgtg    1860
tcctccgagg gtgagtggcc atggcaggcc agcctccagg ttcggggtcg acacatctgt    1920 ggggggggccc tcatcgctga ccgctgggtg ataacagctg cccactgctt ccaggaggac    1980
agcatggcct ccacggtgct gtggaccgtg ttcctgggca aggtgtggca gaactcgcgc    2040
tggcctggag aggtgtcctt caaggtgagc cgcctgctcc tgcacccgta ccacgaagag    2100
gacagccatg actacgacgt ggcgctgctg cagctcgacc accggtggt gcgctcggcc    2160 gccgtgcgcc ccgtctgcct gcccgcgcgc tcccacttct tcgagcccgg cctgcactgc    2220
tggattacgg gctggggcgc cttgcgcgag ggcggcccca tcagcaacgc tctgcagaaa    2280
gtggatgtgc agttgatccc acaggacctg tgcagcgagg tctatcgcta ccaggtgacg    2340
ccacgcatgc tgtgtgccgg ctaccgcaag ggcaagaagg atgcctgtca gggtgactca    2400
ggtggtccgc tggtgtgcaa ggcactcagt ggccgctggt tcctggcggg gctggtcagc    2460 tgggggcctgg gctgtggccg gcctaactac ttcggcgtct acacccgcat cacaggtgtg    2520
atcagctgga tccagcaagt ggtgacctga ggaactgccc cctgcaaag cagggcccac    2580 ctcctggact cagagagccc agggcaactg ccaagcaggg ggacaagtat tctggcgggg    2640 ggtggggag agagcaggcc ctgtggtggc aggaggtggc atcttgtctc gtccctgatg    2700
tctgctccag tgatggcagg aggatggaga agtgccagca gctgggggtc aagacgtccc    2760
ctgaggaccc aggcccacac ccagcccttc tgcctcccaa ttctctctcc tccgtcccct    2820
tcctccactg ctgcctaatg caaggcagtg gctcagcagc aagaatgctg gttctacatc    2880
ccgaggagtg tctgaggtgc gccccactct gtacagaggc tgtttgggca gccttgcctc    2940
```

```
cagagagcag attccagctt cggaagcccc tggtctaact tgggatctgg gaatggaagg    3000
tgctcccatc ggaggggacc ctcagagccc tggagactgc caggtgggcc tgctgccact    3060
gtaagccaaa aggtggggaa gtcctgactc cagggtcctt gccccacccc tgcctgccac    3120
ctgggccctc acagcccaga ccctcactgg gaggtgagct cagctgccct ttggaataaa    3180
gctgcctgat caaaaaaaaa aaaaaaaaaa aa                                  3212

<210> SEQ ID NO 2
<211> LENGTH: 47001
<212> TYPE: DNA
<213> ORGANISM: Homo sapiens

<400> SEQUENCE: 2
tgggtggaat cacttgaggt caggagttcg agaccagcct ggctaacatg gtgaaacccc      60
atctcttcta aaattatgaa aattagccgg gcatggtggt gggcgctgta atcccagcta     120
cctgggaggc tgaggcagga gaattgcttg aacccgggag gcggaggttg cagtgagccg     180
aaatcacacc actgcactct agcctgggtg acggagtgag actccatctt aaaaaaaaaa     240
aaaaaaaaaa aaagaacga ggtaggaatt caaataattc ccagctaaac agaaaatagc     300
atcaaacccc acccctgcct cccctttctc ctctccagtc cccagagtat atgggcccag     360 cctcctttc tctctctcag gccagcagct cctttagtct cgcctgtcca ggtaagcacc     420
tggactcacc cttgtgagcc cctgcactca cctgcaccgg cctctgcaca gtccccagtc     480
cttggctgtc cctacctcat gctctcgggg accagggggt gtaaccaggc aggcatgtca     540
ccaggcaacg ggcctcgggg gagagctcag atctcccgca cctgcctgcc agcctctggg     600
gtgcccatgc gggggtgggg gaagatgggg cggggcaggc actgccttct cctacctcct     660
gcctgtttac ctgtacttag tcacagtgct gtccaggacc cagcaggagg agttccatgg     720
agcctgaggc cacaggccac aggggacaag ggccagacac cctggtcatg gctctaggcc     780
attgatccag cctgggctgg ctgggtgggg gtggggaggc cttggcctgg acaaacagag     840
gctcctgagg cctgtgtgca ggcccggcac ctatctgccg ctcccaaagg taagcggggg     900
cctccaggac aggggaccgg gatctataaa tgacctagtg acagtgtcca ccctaagagc     960
tgggcctggc tccctgcagc ctgagccacc taccctgctc cgaggccagg cctgcagggc    1020
ctcatcggcc agagggtgat cagtgagcag aaggtgaggg gcccacagag ctggggaggg    1080
gagggaccac gcagggtgac accaggtgtg tggacaggca cagcatcagt gctgggtggt    1140
tggtggcctg ggattcaggt ggcagggaca ggaggaaggg agaggccacc ctaccctgc     1200 ctcgcaggac tggacatgct gcccctcca cacccggtac cccacctggg ccttctggtg     1260
taggagacag gcccggagcc ccacattgca cctatgtact gacttaagcc caggaccctg    1320
ggctcacagg ctcagagttg gcatgtatgt gtatgtgtgt tcgtgtgtgt gtctgtgtag    1380
gaagggcgtg catctatgaa tttttgtgtc atgaatagat gtgcgtatat ccctccgcgt    1440
gtctccatct gtgtacatct gtgggtctgt gagtgtgttt atatgtgtgg aagggacccc    1500
cacccagtcc cccacactct caggactcta gggcctaatg gtttcactga aagatgcccc    1560
tatgccccta gccagagtc cctgctctgc tctgctctgc cctggctgag ggacctcggg    1620
taagtcatgt tacctctctc tacctcagtt tccccagcca ttaaatagag tcagcaaagt    1680
aggcacccca ggctgttgga ggctgcagtg gagtttgcag cactgcccag cacagggctg    1740
gcacatggta ggagttcata cgcagtggtt gaatccggat ctgcattgct gggggagtcg    1800
```

```
cggccccgcc ccaaggagct cagcctccag caggcagacc cgagaccctc caatggccag    1860
aagggcagga gggagtgagg agcaggtgcc agggtgggt ccatggtgct cagagctggg     1920
ggactgcttc aggcccctgt ggcaattgga gcacagtccc cgcttccagg agttcaatgt    1980
gaggggcaaa gagagagtgc ccacaggtaa gctgcacatc gcgaggggca gccgccccctt   2040 ctagggcact ctgggagagc tgcgaagagg tgaggtctga actgaggtga cagggctgc    2100 ataagagctg gccaggttgg gaggtggggg cccaggcaga aggaagagtg tggggacgcc    2160
tggccgtgaa caagcactga cagggctcaa ggtccacgag ggctcttggt gccggctggc    2220
tgctcttaat cctaaaatgt ttgctaccat cccattgtta aaatttctca ccaatggaag    2280
tccagtgtcc ttggggtgcg acggggaaaa gagagggtgg gaaaaaagga ggcaggagaa    2340
gttggccagg ccacatatgc acacagcacc ttggacttct gtaggagga aggagctggg     2400 accttgtcat tcattcattt aacaattact gagtgtccgc tgagtaccag actctgctct    2460
catgcagctt acagacaggg aggaggcaga taaatgacat atttgcatat caggcaattt    2520
aggcctctgt aattgctata aagaaaaatg caggagagac gggagtgccc agggaaggcc    2580
tctctggaga ggtgacatct gaccctttgg aggaggtaaa ggaggagcc acgaggccag     2640 cagaaaggaa aacatcccag gcccagcaag gagcaaacct cccattcagc aaagaggaca    2700
ggaaaactga gaccctgggt ctttagggac tgtgttctag gtggatggaa gccgtgcgag    2760
gcttgtgggc agggcacatg gtgacaacac gcagtggcca ttgtgtgaga actcactggg    2820
taggggggtg ggtgattggc tattgcagga gtcgaggtga cagatgacgg tggcctggat    2880
gatggtggga gtcatggggg gccaagaagg ggctggcttt gggggcatt tggaaggtag     2940 ggccacaggc ttttccaaag gtgctggacc ctgggaatgg gggagccgtt gtattataag    3000
atagtaaaga caagagtggc accgtcatct tcacaactgt ccactgcccc tcctcctgct    3060
gggcaggaaa cccaagagga tgggaatgag gtctcttaga gtcaccatgt gccaccctgt    3120
cgccaccaca gagcctggca ccaagcaggt gctagacaaa gatagggtga ctgagcattg    3180
aacctgggac cccacaggcc cacaccattg tccatgcccc agtgccaggc ctcacaagtc    3240
ctccttcctg gaggcagcaa gatagaaagc cctgtaccag gggcctagag acttggcagt    3300
ttcattcact cattctttct gatccttcac tcatgtgacg ggctgtgcgg cgttccatgg    3360
ggaaccccag aggtgagcaa gatgctggcc ctgcctgttc tgtagggac agaggcaaga    3420 cccaaagcca aggcatattc ttgatctgat caagggctgc ccaggggagg gggcagctta    3480
actagccagg gcccagaac ccagtgcctg gcaggtcgcc tggtaagagt tccccacagt    3540
ccaggcaggg ggactcagct gcacaaaggc agggtctcgt gggcctgggg caccatgtgc    3600 atgatgaag ttatagccac gaggagggtg gacagcagcc tggccatgga gggtcttgga   3660
tgtcgcagca aggggtttgg atgataagtg gctgggagct gtgaaaggat cctgagcagg    3720
tgagcgattg agctggggag ggaggatgcg ctggaagacg caatggaggc aggggaccta    3780
gtgaggaggc cgccccaggg gtttgggtgg gaagttatga tgagcccggg ggaattaatt    3840
tcccactact gccatttgga ccatggcttg ggttttttaca gagggtgtcc tgaaaatgag    3900
cctctctgtg ctgctcaaag tcctcccaga tggatgcgag gggcatttag agggaggcaa    3960
aatctgcata gagaaggacg cctggcttgg aggatgagag gggaggggag gcccaccaag    4020 cacccccacca tgagctgccc ctcttcgggc ttcctctaat ggaccacga cctgctccga    4080 gcctcagttt ccctctcttt acactgatta tctgagaggt agtagggctc agtgatcagg    4140
gcgtcactct gaagtcaatc tgcttgactt tgcagcctgg ctgtgctgct gaccagctgt    4200
```

-continued

```
gtgaccttag ccaagctgct caacctctct gtgccttgac tctcccatct gtaaagtagg    4260
agtgatcaga gtacctgtcc ccacaggatc tgtgtaaggc ttacatgaga aagtgcacat    4320
aaagcaacag agacaattga aataaatgtc acctgttacc acctctatgc ccccgagtcc    4380
ccatggctct atgactcatc ccaaaatagc tcctttgtga tccagactca agagtaaaac    4440
agggccaggt atggtggctc acatctgtaa tctcaacact tcaggaggcc aaggtgaggg    4500
gatcgcttga ggccaggtgt ttgagacctg gtctctacaa aaaataaaac tataaaatta    4560
gccaggtgtg ctggtgcacc tgtagtccca gctacttggg aggctgaggt gggaggatca    4620
ctcgaaccca ggagttggag gctggggtga gctatgatcg tgctaccata ctccagcctg    4680
ggtgacagag tgagatcctg tcccttaaac aaaaggggtg cgacgggaat atggtgtcct    4740
cctctggcag agggagggga cgagggactg aaagaagggc aaggagccaa cccatcacct    4800
gggatcttcc caatccagca aaccttctca gattttgagg acagccacct cagtcagagg    4860
tggccagccc aggacagaca ggcagctctg cgctggggac tcaaacctgc catgtggcct    4920
catgcaagag tctcagcacc ctgttactgg tctgtttctt gcctgtttct cactagggat    4980
gctgtgaaca tttgaggaag tgggcggggc tgtcccaccc gttgccggac gtttaccatt    5040
taccattccc tggccttggc cccataaaag ccagtagggc ccactccaca tgcaggaatg    5100
tcctagctta gttgtggagg gggatgtcat gcccagtgag ggtcccctgc agtccctccc    5160
ttccttgtat ctgatggggg ccgctcaaca gagtcactgt ggcttgacac caaagaccct    5220
tagctgggaa cgatgccaag gggagctgga gggagccagg aagctgggag aagggccagg    5280
gcccttcaca tccacctggg aggactttga gcattactaa agagcccgt ttttggaaac     5340 ccgctgtgta aaatcccaag atacagccca aaggaagccc cgcctgcatc tggggtgcat    5400
tttatttatt tttttatgtt tttttttttc tcaagcagag tcttgctctg tcacccaggc    5460
tggagtacaa tggcatgatc tcagctcact gcaacctccc ctgaccaggt tcaagtgatt    5520
ctcctgcctc agcctcccga gtagctggga ttacaggtgc ccaccaccac agccggctaa    5580
tttttgtatt tttcatagtg acagggtttc accatattgg ccaggctgat ctcgaactcc    5640
tgacctcagg tgatccactc acctcagcct cccaaagtgt tgggattaca ggcgtgagcc    5700
acggcacccg gcctggggt gcattttaaa gctacacggt atttatggat atagtaagag     5760
gagatgaact tcgcagtagt ctggagcctt tgctctcccg gtgggtgggt caaaggcttt    5820
ctctgtactg tggggaaacc tgcgtcaaag gccaaataca ttgggatgtt tgcttgaaag    5880
ggtctcaaaa tagagttgga accctggagc gtggagaggg cgacattca gttgctattt      5940 aatcatgatt tgttaattaa cagctcattt atgggaggca tcttagattc gtggaaaaag    6000
cagggagtca gacatctaga ctcaacctcc acttccctgc tgtgtgatct tgggcaagcg    6060
gcttagcctc tctgggcttc agggtttttt taatctgtaa aatgcgtctg ggagtgaatg    6120
tcaggtattc aaatcacact gggaaaatgg ggctaggaaa agccctagac tgagttagtg    6180
ctagaacact ctgggtctca gtttccttat ctgttcaatg ggtgcagaac tggaggttta    6240
agtgagataa agcaggtgaa gtacccacgt ggtgtgggct ggaggaagaa aacatgggac    6300
aatggttcca catccctggg tgacctgaaa attaagtgtg agatgtctca tgagggcacg    6360
aaatgaatat tagttttgt tcccttcctc tgccacaaga ctttgagagc agaaaggtga    6420
gagagacggt actctgtgaa ggaaggcagg tccccgcccc agcgcagtgc cagctcaggg    6480
gattctgggg cggggctaa gtgcatggac tgtgtgggcg tggtgggaag ctccgtgaac    6540
```

```
cagaaccagg agcaagaaac agcattcctt gcgtggacgg gaaatgaggg caagaggtca    6600
gatgtctaca gaagtctgca ccccatgtac ttcagttctg tctgtgggtg cagcctctag    6660
ggaggtgggt gtttaggtac tgagacctcc gtctgtcctc tgaccatagg gaagccagtg    6720
ggaagcaaag gtggggttct tgagccagac ccagtccagc tctggtgcct gccctctggt    6780
gcgagctgac ctgagatgca cttccctcct ctgtgagctg tctcggcacc cacttgcagt    6840
cactgccgcc tgatgttgtt actcttccac tccaaaaggc agggaagtcc tgcttccgtg    6900
ccccaccggt gctcagcaga ggctcccttg caaatgcgag gctgtttcca actttggtct    6960
gtttccctgg caggatgccc gtggccgagg ccccccaggt ggctggcggg caggggacg     7020 gaggtgatgg cgaggaagcg gagccggagg ggatgttcaa ggcctgtgag gactccaaga    7080
gaaaagcccg gggctacctc cgcctggtgc ccctgtttgt gctgctggcc ctgctcgtgc    7140
tggcttcggc gggggtgcta ctctggtatt tcctaggtaa cgttgtggga ccgcctggga    7200
gaggcacctg ggaggactt ggggtgactg tagcaggcac agcaggacag gactgggttc      7260
caggctcagc cgtgcttagc atattgctgt gtgaccttgg gcaagtcact tctgttctct    7320
gggtctccct ccctgtcctt ccagctggag atgctgtcag accctggctc caggtcctat    7380
ggctcgggtc tgcttcctgc ttgggcaaag tgccccaaag ctccccacca ggtggggaaa    7440
gtgggccctc ctagcaccca gttcttgtga gccagccagc ccacagagca taaacatcgc    7500
cttcccttgc ctgcagtcct cctggggttgc ccctgaggct tggagccaac ccagccctaa    7560
agaaggaggc ccagaggcac caatggtacc tggtaccaat tagtgcctct gctcacttga    7620
gcctagccta ggttctcctc taggctgggg accacagctc tatcccctct gggtctccag    7680
ggtccagcat gaatggggga cggagcaggc agctggagag cagccagcct tggggccctc    7740
tgccatgtcc ttaattatgg ctggcccctc cctgatgtca cagccctcag tcagtccct      7800 ggtgcccggg gagcaattgg cctgtgctct gggcccattc atccaggcct ccgttcattc    7860
attcatggaa taaatgctct tgagcatcta ttatctttct ctaagattga tggagtctct    7920
cctcttcctt ctgcctttga cagtgggaag taatggagaa accaaatcgg actgtgcctc    7980
tacactgtac actgtagaag gcccattcat ttgttcattt actcagtgcc aagcacctcc    8040
tgtgtgccag gttctgggga tagcccctgt ccttgtgatt tagccaaggc atcagacctg    8100
acatttacgc taaagcatag catgtgatgg gacagaggaa gctgagggct gggaagccac    8160
aggagggaca acccagatgc ctgcgtgatc agaagcatcc cattaaacat cctgcaaagg    8220
atagctagtg ctcttactgg ctgaatctcc tggtggaatt ccaggcctgt tgaaagcaac    8280
ctggggacca actttgtagc agtggagaga aatccatgta ggcctagatc caagggtca     8340 gggttgggag tgtctggaac cagcatctgg gagtgacact attgggaacc ccaggtctga    8400
cacgggcctg cttgcaatga cttatagtga ttctacccag agttgagcaa cgcaggcagt    8460
agacgccatg tgcatttcac caccagcagg aagccagtgc cccagatagc acagggctgt    8520
gggggcctcc tcaggtagcg ggctaattag tctacagggt aaaccacggg gcactgggct    8580
ggagggccag gaactcacct gccaattatt tctctttgca gaggagttta attccccctg    8640
attatgctcc tgggtaaat caccccccac cccaggagag tgctccatg gggctgagga      8700 cccaagggt gagtgctccc aagcctctgc tgggggaagc caactccccc acagagggat     8760
taagggttga aggaggcact ttgggagctg tttgaaagac tcctcccgcc ttgaccaggc    8820
tgtgctcctg ggactgggcg ctgggcaagg aagtggatca gagacacgcc ctgccctgtc    8880
tggaagagga ggtgcacaag tgaccagtga cactggagca ggacaggccc caagcgagga    8940
```

```
ggacagcctg gcccgaggag agggtgtggc tggcttccta aggatggtag caggacccTt    9000
aataccacca accatatttc ctgggtcctt tccctttcct gctctcccag gcaagagttt    9060
tatgtgttct caagccccca gcacccgcct gcccctgtct cctgcttcag tgagaaaaca    9120
aaacagctta gaagagaagc cccatatatg ttggcccacc tgcccTccca gctgcatcac    9180
gtgcactcct cctgggaccc cgatcccgcc ccctctgccc acacaatggc ccagcaccag    9240
caaggatgcc ctctctcccc cagtgtccct tggggtgcct cccccatttc tctgctcctt    9300
gaaagagctg tcagtccaca cacccagtct ctctgtgccc tttccaacct ggctccctct    9360
gccccccaac tccaatggcc attgtcaagc tcgccaacat cccaggttgc taaatccaat    9420
gtccacttct cagtcatcat tgcacttgac ccgggggctc accccCacct ccagaagccc    9480
tttcctccct agactttggg ccgccaccgg gtccttTccg ctcagcaggt tgcttTTtct    9540
gtgtccctgc tgatgggtgg ggcctctcct ttctctctcc acccgcttct ttcgtgatct    9600
catctgctac ccttagcttc aagtgccctt tatacccTga taacacccac atttgcattt    9660
ctagcctggg cctctccctt gagcttgtct ctagagctgc ccctgctctt cctcttaatg    9720
tctaaggagc atctcggacc ctatgctttc agaccatgag gtctctgcat aatttccccc    9780
agacctgtac ctccaacatc ccagtccaag accacttctt tctggcacct tccccttact    9840
cctttctttc ttttccaccc agccccactt tgccagcaaa cctggtcatc tctaactcca    9900
aaacacatca aaagcagctg acgccaatca cttcccaccc tctcctctgc cacagctggg    9960
gccaggctct gtcccccTgg acatctctcc cctggagccc tgcaggcgtg tcctcgatgc   10020
tctccctgcc tctgccctgc ctccttagag cctttctcaa cagcagaggg accatttgat   10080
aaagcaaacg aaatcctcta acttcgctgc ttaaaacctc gcttggggcc aggcgcgtgg   10140
ctcacgcccg taatcccagc actttgggag gccgaggcag atggatcacc tgaggtcagg   10200
agttcgagac cagcctgacc aatatgcaga aaccctgtct ctactaaaaa tacaaaatta   10260
accgggcgtg gtggtgcatg cctgtaatcc cagctacttg cgaggctgag gcaggagaat   10320
cgcttgaacc cggGaggcag aggttgtggt gagcggagat tgagccattg cactccaagc   10380
taggcaacaa gagcgaaact ctgtctcaaa aacaaaacaa aacaaaaaca aaagaaaac   10440
aaaaaaacca cctcccattc ctcccatctt acccagggtg aaagcccgag tcctcccagg   10500
cctggaaagc cctacccagc ctctcccctt ccccatctca taccctcctg ctgtcctgtt   10560
gctcactctt tgctgctcct gaaacacacc aggcctttgc acttgcccct gctgggaca    10620
ttctttccac agatgtacat caccttcttc cctgacctcc atatcgcagc ccgtcccatg   10680
ccctgattcc caccgcactg accacctcta acctgttata cacgatgtgt ggtttaccgt   10740
ctgattcctt gctagtctac aagctattaa gggcagtttt ttcttgatag ttctgtccgt   10800
tgttttgctc atatagtccc aagtactttg gctcagttcc tacacatagc aggctctcaa   10860
gaggtattta ctgagtaaat ggataggggt gtaaaccagg gctgtgagtc tacccTcttc   10920
acttcagcca aaatagcctt tgcaaaacag aagtctgatg acatcattcc tgattttaaa   10980
cttttcatgg ttaccctTgt tcatcgggta aagacccaat gggccctgcc ctgcggaggc   11040
cccagctcct tgccgcccct ccccatctct gactgctcca gccaaacagg ctTtcagccc   11100
gggtcctcac catggtcccc gtgctaccgg cccgtgccc catgctgctc cctctgctgg   11160
aaggtacttc cctcccTctt ctcttaccaa tttacagtTt cccCatccct acatctcagc   11220
tggagggtca ctccactctg gcccaggctg agtgtcctcg tcacatcccc tcaacagcac   11280
```

```
catgtggcac tgctccctga tggcactgcc cacagacaga tgccacatgc tgtgtggttg    11340
ccagagccac gcctttctta cccaccactg tcagcttcac aaggggaggc acatctgtct    11400
tggttaactg gcgtacccca tgtagtaggt ggttagcaca cactgtggga tccctgggtg    11460
acctcacgag tggaaggatg cctagtggtg ctgacccatg accttggcct cctgggccta    11520
tgtggatttc ctggccttca tgtcattggt gtcctggact ggtcactgtg tcagcctctc    11580
cctgggaacc tgtaggacac catccatctg ggagcctttc acctccctgg taccttgcag    11640
ccagtttgtc atccaataaa ctttagatga ccatgatgac aatgggagtg acaaagatga    11700
tgatgatgac attgatggtg ccatggagac ccaagacact gaggctgagc tgagggtgtg    11760
ggtggcagga gaaggcatgg aagagacagg agactttccc acctgcttcc tccactaacc    11820
ctgctggttc cttcctgggc agggtacaag gcggaggtga tggtcagcca ggtgtactca    11880
ggcagtctgc gtgtactcaa tcgccacttc tcccaggatc ttacccgccg ggaatctagt    11940
gccttccgca gtgaaaccgc caaagcccag aagatggtag gaaaggatct ggggatgag     12000 agggagggaa tatgggggtg aaaagagagg ggtggggtct gatcacatgg agccagttgg    12060
tcaacccatc tggagcattc acagggacca cagccctgct ccaggcacca tggaagcaga    12120
tgaggttgag ggtcatggga aagttagtgg atgtttgggt caatagcact cggattagat    12180
cctgatcatg cctcttacca ggggtggagc atgaccttgg gaaaggtccc acagtgcagc    12240
tgacactatt gagggcccgc tcctgcccct ccgttacagg acggtggccc gctcctcccc    12300
ctccgttaca ggacggtggc ccgctcctcc cctccgttac aggacggtgc cgctcctg     12360 cccctccgtt acaggacggt ggccgctcct gcccctccgt tacaggacgg tggcccgctc    12420
ctccccctcc gttacaggac ggtggccctc tcctcccct ccgttacagg acggtggccc     12480
tctcctcccc ctccgtaaca ggacggtggc cctctcctcc cctccgttac aggacggtg     12540 gcccgctctt cccctccgt tacaggacgg tggccgctcc tgcccctccg ttacaggacg     12600
gtggcccact cctgccccctc cgttacagga cagtggccgc tcctgcccct ccgttacagg    12660
acggtggccc gctcctgccc ctctgttaca agacggtggc ccgctcctgc ccctccgtta    12720
caggacggtg gccactcctg cccctctgtt acaggatggt ggctcactgc acggaggctg    12780
gtctactgcc tgccactctc aggctgcagg accactgccc agcaaggcag gccagaagtg    12840
ccggggagtt attcccagga gcaaccctga accatgagcg ctggagtggg tggatcaata    12900
ccgcagcttc tttggccctg gcaggggaaa tagttcacag aatgttccag gctgtctccc    12960
agagatgccc tattcggctg agctcagatg ctctcagctc tacactgcgc attcatggcc    13020
ctgtgttggt tgcccacttt ccagtctctc cctcccaact actgtttccc agaatcacct    13080
ccaaataaac cacttgcccc accttgtcaa tggagggtct gcttctgagg acccagcct    13140 gaggctgccc gtttcctcct ccatgaggta ggggtgataa acacaggacc cggctgcaga    13200
tttgttgtgg gttgcagtga agttgagata acacgaacac tattcccacg ctgcgcaaat    13260
gcttaagagc ctgtaatcct gccagcagcg ctgtagttgg agatgcgcaa aaactaccca    13320
tcagagctgc tggcttgtcc caggccatgg gaggaggtgc agaggggacc caggagccga    13380
gtgggggttc tcagagttga ggagtgactt ttggcaaggg gcagagggt catcagcagt     13440 gcaggtggag gtgagagtcg ggtgtagtgg aaacagaaag aaggggatgg ggtgtgagat    13500
tcatgcatgc cccggcccgg ccactcagca ctgtgtgacc gtgatcaagc ctgtccacct    13560
tggagaatca tgcatggagc ggggctgcca gtaggagcaa agggcacctc caggtaggaa    13620
gtgggcctgt ctgccctgca gagggtccca ggggctgttg tcttcccttc tcacagctca    13680
```

```
aggagctcat caccagcacc cgcctgggaa cttactacaa ctccagctcc gtctattcct    13740
ttgggtgagt tgtccttgcc cctgaccagc tcctgcaaga agctgagatt caaagaatgg    13800
gaggggcctc tgtaggcttc tgatgcaatg ccttcatgtt tcaaatgggg aaactaaggc    13860
atagagaggg aacttggctt cctgcatgtc accctccctt cactgggctc atctgtagaa    13920
tggaaacatg ggtgtgatag gtttgcacca gacaatgact gtgatggctg atcaagggcc    13980
tgacaccatc aggcgaggcg atgttggagg ggcatgggt taaaagcatt ggctccaggg    14040
cccgactgcc ccgtccacat ctggttctgc tacttgcggc atagtttatg agacacaagt    14100
tcacctctca tgcctcagtt ttctcattcg taaaataagg attatgagag cgcctccttc    14160
agaggtcgct aggaggcttc tgcgtgaaga cggacagcaa tggctgaggt gcggaaagtg    14220
ctcgatgtgc atgagcaggg gtggagctgg ggccagacct cagaatcctt ccctggcctc    14280
tctcacttct gcctgcctta gggagggacc cctcacctgc ttcttctggt tcattctcca    14340
aatccccgag caccgccggc tgatgctgag ccccgaggtg gtgcaggcac tgctggtgga    14400
ggagctgctg tccacagtca acagctcggc tgccgtcccc tacagggccg agtacgaagt    14460
ggaccccgag ggcctagtga tcctgggtca gtactgcgag tggaaacgtg ggggttggcct    14520 catgaggttg ggggaaacaa gctgtggtgt ggcccgggga ggctgcctgc caggcctggg    14580
gtgctgtcag ggtgggcccc ccaggagagc ccccaggtg aggtagcagt gccattgcat    14640
tcaaggagcc aggaaagaag ggtgggatgg gggcatttag ggtaaatctc agacaaggct    14700
ggctccaagg gtctcctcta atttttatttt cattgtattt tctttctttt ttttttttt    14760 ttgttcttgt ttatttgttt gttcatttcc ttttatcaga agccagtgtg aaagacatag    14820
ctgcattgaa ttccacgctg ggtacgctat ttttttttcc cctccccatt ttcctttga    14880 gttggcattt gtcttgactt tgttgtgtat caggggaca catggcttct gttgtgtgtg    14940
cagggagccc tggccaagag tcacccaggg gatgccatgg tggactcagc gatgtgtccc    15000
aagcaagtct tggagcctgt aggggagag gaggtggcga cgtgcatgcg tgtatttgtg    15060
tgtgtcttgt agacgggtgt gcatgcgttc ctgtgtgggt gtgaggatga gtcaggttta    15120
gtggtccacg aacgtgactc tcctctatca ttcacttcaa cctgcccaca agctagtttc    15180
cactgatggt agaaaatcat cttgccaatt cacggtttgt cagtcacgtt ggttttaaaa    15240
cttggtcttt tggaggtagc ggtgccattg cattcaagaa cgctccttcc ctctttttcct    15300 ttccttccca gtcaggctca tcagccctcc ctccctacct ggtgccgtat tgctagagtc    15360
accttgcatt tctccaagcg gacccacaat ctttcagctg accagcacag tcaccacgct    15420
gcacaaggca ggaggtgctg tccaagttgt agtttgtgtg agttgtgcag tgcaccaact    15480
ggctgctgga ctctatggcc cctaaattct cagattcctc ccacactatc tagtgttgtc    15540
acccagagcc aaggtggggg tgagcgtctc aaccccttct cagggaggga ggcagagttt    15600
aaatccttgt tataccttc cttaccttcc cgtcttccca tcctgctggt caaatgcttg    15660
cttctttgtt ggatggaggt gatgaggtca aagtacagtt ttcaaagagg tgaaatcatg    15720
attctcatac aaagatagag tgaccatgtg tcaaatattt atttggctga ttaatgggg    15780 aacgagtaga atggtaaaga atgcaagaaa ctgatctatt tgtctatcta tctatctatc    15840
tatctatcat ctctgttgat atctgtctgc ttgtctatct agttatctaa ctagctagct    15900
gtctattatc tatctgtctg tctctctgtc tctgtctgtc tagctagcta gctgtctgtt    15960
tatatctatc tatctatcta tctatctatc tatctatcta tctatctatc atcaatcatt    16020
```

```
aatggaaaaa gagaattgct agaataagat taccaagtta gatacaaacc tggttaaggt    16080
cctaccaggc aagaaaactc aaacctttgg agttgtcttt tctagtgaat taaaatcatt    16140
gacagcttat tacagtcttc tgaaagttaa catctacctc tacagagtct gaggttgata    16200
atctacaacc aatagtaagt cagagatatt actcctgaga gcctcagggg gacttaatca    16260
gatgatgctt ggagacagag actggctcat tgcagcctgg acaccgaatc tggtcaattg    16320
ctgcctgatt ttgtatagcc catgagccaa gaatgacata tatatatata taacagagtc    16380
tcactctgtc atccaggctg gagtgcagtg ccgcgatctt ggctcattgc aacctccacc    16440
tcccaggttc aagcaattct cctgcttcag cctcctgagt agctgggact acaggtgcct    16500
gccaccatgc ctggctaatt tgtatatttt tagaagagat gaggttttgc cgtgttggcc    16560
aggctggtct cgagctcctg acctcaggtg atccacctgc ctccacctcc caaagtgctg    16620
ggattacagg tgtgagccac cacgcctggc tccataggcc attttttcaat tattaaaaaa    16680
tataaaagtc agccaggcat ggtggctcat gcctgtaacc cagcactttg ggaggcagag    16740
gcaggcagat cacctgaggt caggagtttg agaccagcct ggccaagaag gcgaaacccc    16800
gtctcttcta aaatataaaa aattagccgg gcatggtggt gcgcacctgt agtcctaacc    16860
agtcaggagg ctgaggcagg agaatcactt gaacccggaa gatggagctt gcagtgagct    16920
gagattgtga ggttgtgcca ctgtactcca gcctgggcga cagagtgaga ctccatctca    16980
aaaaaaaaaa aaaaaaaaa aaaaaagaa agaaagaaag gaaaggaaaa ggtcctatgg    17040
aaagttatt tttctcctgc aatagaagtg ctatgtaata gcctcatgtt gcctcgtgcc    17100
tctgtgtccc catgttcctg gcagttgttc tgtaattatc tgtgctcagt gggtgttcgt    17160
ttcatgaatg aatgattgaa caaatgaatg aaagcatgaa tgaggagact ggttcagtgc    17220
atgtccagag cacagagtct caggggggcag agataacaac tcaaatcctt gaagtcgact    17280
ttatgagcac ttccttcatg ccaggcccca ttcctgcgct gaggacacca ggatgaccgt    17340
gtcctcaccc ctgccctcgg aggagcttta agcccatga gggagacaga cacataaaca    17400
gattctcata acaccaggtg ccagtgtgag aatagaggcc ccagaggcag tggagagagg    17460
gaattgttcg ttccaaagca gaagaggggg caaatcaaga gcctcacaca gagtcccaga    17520
tctacaggag ggaggggttg ctcctgactg ggggatcctg gaagacttca tggagggggc    17580
atcagatttg ggcatgggcc gggcgtggtg gcacaagcct gtaatcccag cactttggga    17640
ggccaagttg agcggatcac ctgaggtcag gagttcgagg ccagcctggc caacatggca    17700
aaacccatc tctactgaaa atacaaaatt agctggtcat ggtggcccat gcctgtaatc    17760
ccagctactt gggaggctga ggcaggagaa ttgcttgaac ccaggaggtg gaggttgcag    17820
tgagccaaga ttgcaccatt gcactccagc ctgggcagca agagcaaatt ccattaaaaa    17880
aaaaattagc tggacatggt ggtgtgcacc tgtagtccta gctactcggg ggtgggggtg    17940
gggggctaag gtgggaggat cacccgagct caggaggtcg aggctgcaat gagctgttgt    18000
gatcgcatca ctgcgctcca gcctgagtga caggctgtct caacaataaa ataaaataat    18060
tttcaaaaga aaagaaaatt caggcatggg ggtaggcagg aatttgtcag ggcgagaaga    18120
agaaagggtt ccctgagcag agggaatggc agggcaaag gctgggggag gggaacaccc    18180
aaggcgtgtt cagttaattc ctcccagccc cgagaggtgc caggctccct gaaggtgttt    18240
ctgattaaca agaggttagc acacacctct ccacggaatt cgtctcaaaa aaaaaaaaa    18300
gggtaattat taaagtggca agagcaaaga atctgcttgg agcaagattt aaagaacaca    18360
aaccctagg aagagccagc catctttccc cagctgctgg tggaggccct gtcccttccc    18420
```

```
taggcagaca ttgttgttct ctctctgggg aggtcagctc cccactgcag tcagcatggc    18480
caggggtcag ggagaagggg ctgagccaca ggtggcagca tcagagcaaa gtgtattcac    18540
ctccattccc ttcctggtcc tcagcactgc ccagaggagg tcataggaca gggattatta    18600
ttacatccat ttgacagaac ttggaatggc taagccactg ccccagactc agttaactac    18660
ccagaggtag tgaacatcta cctctacaga gtctgaggtt gataatctgc aaccaatagt    18720
aagtcagagt tattactcct gagagcctca gggggactta atcagacaat gattggggac    18780
agagactggc tcactgcagc ctggacaccg aatctggtcc actgctgcct gattttgtat    18840
ggcccatgag ccaagaatga catcatcaca cagctgatga gtgttggtgc taggtgggga    18900
gggtagtgcc cctccctcct tctctccagt tccctcccca tacccccct ccctggggg     18960 cccagcagat ggcactagcc tgggggcct gccctcaggc tgaccaagct gacagggga    19020 ctttgcttg cctgtggcct tccaaagaag acgatttaaa gcagagaaaa cagactgaaa    19080
actcaggttt tataatttca tgtcaccagg ctgcctccca catcccaggt tcattcctaa    19140
atccccactg ctcctggaa gaacaccagg cttctggcga ggtttaaatg agatactgga    19200
tgctccacgg gagagaacat gttcactggc agaccctggt gcctagatcg aacacacagt    19260
cggtgcacag tcactgtttt gaatgaatga atgaatgaat gaatgatgca ggtggtactg    19320
ctttgtaagt tctagcagtg catcagagct tacggattag atggaagagc agagactcac    19380
tggtgtgtgg ggtagggggg tggggtatga tggtgaaaca gttgtgaagt gaggcagccg    19440
tgagatgggc taggtctgag cctcaggcgg ggccagctgc aggatgaaaa gtcacaggcc    19500
tttctcccca gccctacctg ctccgtctcc ctcacaccca cctgaggaac caggcactgc    19560
ctttattgag cccctactgt gcaaggtgct gtgctgggca ttcaaacgtg tatcatccta    19620
cagcctctgc tggcggccct gcaagggtgg tgttatcgtc ccattctata gatgaggaaa    19680
gcaaggccca ggaaagatta ggtggtggct gggcaaaccc agatgtgtct ggcccaggtc    19740
tgtgcaatgg acacaatcat tgaaagtatc tcatacagct gttgtgggca ttgagcgaga    19800
cagtgaggga aggcattcag ttcagttttct ggcctgtagc aaatgcttga taagcacctg    19860
ttttattctg atggcttcac catcattagc tcaaagctca tgtcctcccc ccagggcagc    19920
ctcccagact cctccttagg gcactcccctt ctctctaccg gaagtgaagc cctcatccct    19980
tcttctcctc attgcctgtg gcctcgctgg tctccacagc agccagagga gtgtgtggtc    20040
caagccagcc catgtccagc cttgcccaac cttctgtggc tccctatggc tgcaggagaa    20100
agcagcgccc atcctcggaa tggcctgggc caggcctccc tgccttcagc ttgtcctcta    20160
gatacacgtg ccctgtgtgt acttttctca aagctgcccg gctcgcccca gcctctttgc    20220
tcacgcaggg accccagga tgcccccagc ccacaggccg ggtttgaagc cgtcacctcc    20280
tgagctattc ttgcctgttc tgtgtctgtc tgtccccgct gtcatccatg tccccaggca    20340
gcgactggat ttttacctgg gcactgagaa ggcgtgaagc tcagtgtgtg tccattccat    20400
gagtgaatga ctgaaccaat gaacaaatgc atgaatgagg atactgacag ggaaagagaa    20460
ggatggggta gagcatgtct ggctatcccc acccggctcc cctgcccagc ccatcctgcc    20520
tggtggagga ccttgaggga cctggctccc cagggtcccc tccttctggc tcacaggaat    20580
caggggctgt gccctctcc ccgctccagg ttgttaccgc tacagctacg tgggccaggg    20640
ccaggtcctc cggctgaagg ggcctgacca cctggcctcc agctgcctgt ggcacctgca    20700
gggccccaag gacctcatgc tcaaactccg gctggagtgg acgctggcag agtgccggga    20760
```

```
ccgactggcc atgtatgacg tggccgggcc cctggagaag aggctcatca cctcgtgagt    20820
ccctgggaag gagggcagga gggagggctg gaaaagggag tggttgatgg gggagttgaa    20880
agtcacacac agcattctta gacaagggag ggtaggacct tgggcctggg tatctgggag    20940
acaggacggc tagcttagag gggataggggg agaggaggct ggagatggtt gtgtactggg    21000
ggcgcttccc ctccgcgagc ctcagtttcc ccatctgtaa caaagccgtt gttgtagatg    21060
actcctgaag tcagctctgg gaggcaccgt ggcttgttgg gatgtttcag agtcggctg     21120 cagcctggac tttcaacctc tgggctcgtt cctaaatcct gactgcttcc tggtagaaca    21180
cccaccctct ctgcttccca ggcttctggt ggggtttaaa tgagatacta gattccccat    21240
gggaggggat gtcttcactg ccgggccctc gtgcctagac caaacgcaca gtaggtgtgc    21300
agtatctatt ttgagtgaac gaatgaatga tgtaggtggt actgctttgc aagttctagc    21360
aatgcatcag agctcacgga ttaaatgtaa gagcagagag gcttactggt gtgtgggggcg   21420 ggggtgtggg gatgtgacgg ggaacccccct gtctcctagc tgcgtgccct aaggcaagtt   21480
actttgcctc ttagaacctg cttaccttgc cggatcattg gaggatttaa atcagactat    21540
ctgtgccatg atccttacac atagtgagtg cctagcactt acacgctagc cattattgtt    21600
atcattatat atgctctaac tgggactggg ccgcaaaagg cattgagtgc caggagccat    21660
ttggactttg atatttggta agtggggagc tattgaaagt tcttgagcac agaagtaggg    21720
ctttagggca taagatatgg agtggagtac agaagtgatc aggatcagag ggcaggtggt    21780
tgggggtggg gaggagggac tggaaatggc cttgacctct gggagcctgg tcctcccaca    21840
ggatggggag atgggtgtta gcctacaaag cactgcagga ggtggggaag atgctctggg    21900 ctggcagtt ctcagcgatt gtttattgag cacttacttt gtgctgggcg tcaggctgat    21960
gcctcttctg tctcacttgg gctgtggcca gcctccaggc agatggggat gggaccagtg    22020
tgttcagatc aagcgcagtc tttgaatgtg agctggcaga ggttcttgcc acacccctcc    22080
cccagggcct ctccaagctg ctctctcctt gtcacccctc ctgctgtcct gctgggtgtg    22140
acctcgatct gcggcatgtg cgtgggctga gtttctggag ggctctggga agtgcagaga    22200
agccagacac catctgactt ccaggtccaa aaagggtggg gacacttagg ggtttcccct    22260
ggggcttctc caggtgcctc tcagcctggg aggggacctg actgccaggc ccagctctgt    22320
tcctactcac tgtggctcct ggtggctctc tcatcccaga cccttggaga agctctaaaa    22380
tgacaggtca gacaacattt ggggttctca agcttgtacc ccagacacct gctagggaat    22440
gggggtgagg gggactttgg tggtgatggg aagacagagc aggtggcccc ttgctcagtt    22500
tcaaccatgt gctttgattc tgcgttccat atttcattta taagaagggc tctgccgcta    22560
ggtaaataaa ataaaacccc ccaacaatga aagctaaagc ccccattaaa ggtgacctcc    22620
aggtctcttc catcctaata tcgtatctcc cacctcccag ggaagatgag ccggtaaggc    22680
caaaaaggac gtggctgtat ggagggtgg ggggcaccgg tgtggttggg gagacttggg    22740
tgctgcagca ggaagatcaa gctggaatgg taggaagaag ggacgagggc ctgggggtg     22800 agggggtgg tgcctgctac tggaggccac ctccctcccc tggcaagagg ccaggggaaa    22860
tgccccatcc ccgaccctg gcaccaaga ccctcccagg gagacccttg gggttatgcc       22920
caccatgcct ccagctggct gcaggctgct tgggtgccat gtgtagcgat tttgaggctg    22980
tgcttggagg agctcaggta ctcgcttgcc aaggtgcctg aaatccctcc agcagcaccc    23040
cttcctcctg tcaaggccca ggtgcccacg cacagtctgc aggcagggag gctattgggt   23100
tgcccattca gagggaggtg gggccgttag tttcttataa attgacccat cagatgcgct    23160
```

```
ggactccaga gagtgttgcc attgacactg ggaagtttgg gggaggttgg tgagagggtg   23220
aaggggagct ggggaacccc tgtctgagac aggcagacca ggggcaccta catatgtggg   23280
agggtaccag ccatcacaga cagtgcctag cgcaggccta tctctgccat ggactgccgg   23340
tagggcctca gtttccctat ctggaaatca agcagctgac cccaacagtg tcaccagtct   23400
tttcagggct gacattccag atttctaaaa gcccagaagt ctaagatacg gttatttgtt   23460
ccgagcctcc caggcgccaa gctctgggca gatttctggg gcaccctggg ggtcacgaga   23520
ccacacctgc cttctccctg cctatccttg agcacagcca ggagtcgcgg tgccagaaac   23580
ggtggtccct gcagatgcca gtctagtctt cctgccaggg acgctagggg tcacagatga   23640
ttctgtagca gggtggaggg gtctgggggag ggagcatggg actcgagcca gccgtcatca   23700
tcaaactgta agctccagaa gtctggggaa cctcctggcc tctctcaccc gaggagctag   23760
cctggtcctt ggagggcctt cagtctgtcc tctggggctg gggagacaca gaattctccc   23820
cacagacaca cagtggtctc tggtaggaga cccggaccca gaacccagat gtccagactc   23880
ccgtccaccc tcccccagca gccgcctgcc gccctccctg ccactcccct cccagacccc   23940
agcccagcct tgccacctttt ctgttctgcc agggtgtacg gctgcagccg ccaggagccc   24000
gtggtggagg ttctggcgtc gggggccatc atggcggtcg tctggaagaa gggcctgcac   24060
agctactacg accccttcgt gctctccgtg cagccggtgg tcttccaggg tgagaggtca   24120
ggggtccctg gggcagggga ggggtggtgg tagaatccaa gggccctcca ctgggctcac   24180
tgctcacctt ttttgcccaa attgaggatg ggatggggag agggaagatt ctggaagctc   24240
ctgctgctct ccactcccca ccccggcccc cctcttcctt ccgtcgtttg cacttccacc   24300
cccctcttcc ccttgaccgt cctaccattc gcagtctctg tcttcctggc atcgctccct   24360
tgcttccctc ctctttctct gtccttcctt ctctctcctt ttctcttttc tgtgctgacc   24420
gcctctcctc cctcctcact cgcctggacc tgtgtcccct cccctctgcc cctcaccccc   24480
tccctgccct ctccccttgg cacccaccgg tggctgggcc tggaacacgg gtctgtttgc   24540
agcaggacta agaactcctt ggattccgcc ctagacagtc cgcttacagc caagagggcg   24600
cagggagctt ggggaggtgt gatggcagca cagccaggcc atggccactg gtgtggcagg   24660
tctcccactg ccttcccagc ccccaccctc ctcctgcttc gggacctccc tccttgcccc   24720
cttcccagga agggcacgtc ccaccccgca tgggacagct gtcctgggcc tggaccagcc   24780
atacttctgc gcaggaggcc caaactttgc catttctgga gctcaggagg ggaggatggc   24840
agagaggagg ccatagagtg ttggcagctg cttctgcctc acctctctcc ccactcttct   24900 ccctccccact cagggtccca gccctcttct cggtttatcc ccaaactgtc tggcatagac   24960
ctgggtccca gctggccaa actggagcgc taaatgggta gcagagctgt tcccttggga   25020
gtctgacaca ggctcgaggc gggagggaac aaagggcttt ggggccctg gcccaatgga   25080 gagatggcca gggcaggtga gcatgctcct gtcctgaccc ctggacccct cagcctctca   25140
cggtgtagcc tcaaccaagc cactccttttt ctccgaacct catcttggaa aaggggaaca   25200
gctctctctc ccccagccac caccgtgagg cctgtgcagg tgtgaatgca ttttgtaaac   25260
tggcgagtgc tgtcccgcaa atatcaataa ctaacacgga tcgagcactt actacatgcc   25320
aggctgtttg aatgtttatg tctttttaat ccactctact accctatgag gtgtgtgcta   25380
ttactgtcct cattttacag atgaggaaac tgagacccag attcacacaa tcacattcaa   25440
ccacagcaat ttgctggcag aggtggtagg ggtggtgggg ttacaagctg cgccagcctg   25500
```

```
ctgggaggtg cagccagggg acccctgtgt aacagctgct ctcctggtcc agcctgtgaa   25560
gtgaacctga cgctggacaa caggctcgac tcccagggcg tcctcagcac cccgtacttc   25620
cccagctact actcgcccca aacccactgc tcctggcacc tcacggtgag accccaccct   25680
gcctgcccac ctgccctctg ccgcaagcac actacaggtc cctggtgacc cgggatgaga   25740
gggggcagtg tcccgcctct gctgaagcgc ccacaggctg agccctgggt acacatcctg   25800
ccagggtgga gagggctgtg ggcgaggtct ccctctgtgg gtcacagcaa tgcctgtttg   25860
ttgagtgact gacagacttt agccccacct gggattctgt gtttccttct ctttgttgtt   25920
agggaggtgg gttcaccaac ctggccacac cccatgggcc acctgatggc ccgctcctcc   25980
ctcccaggtg ccctctctgg actacggctt ggccctctgg tttgatgcct atgcactgag   26040
gaggcagaag tatgatttgc cgtgcaccca gggccagtgg acgatccaga acaggaggta   26100
ccacttcctc tcctccctct ggcttccttt cctccctccc cctccctctc ttccctcctc   26160
aatagtgacc ccctcattgg aagcccaagt ccccaatctc agaggggcag caaggggagc   26220
gagcagaggc tggggctggt gtcaggcctg ttgcccttga ccttgtcctc gtcccagcct   26280
ccgccctggc cccggcttcc ctctggcta ccccagaggt ctcagacacg tttggtcatc   26340
agacaccttg gatgtttatt ctaattacag caaaattgtc tcatcttctt gggtgctgta   26400
accccctctg gcaccctcaa tccttcaata aaatgtttcc agagccaaag gactcatggg   26460
cactttggtg ccttccctct aaacccaagg cgtaccatca gaggtgcctc tcccttatca   26520
cgaacccctg ctgcacagcc aggcccaatc ccattgcaca gggtaacatg gaaatcatgg   26580
gtgccctgga tccccgaat ccccaacggg gcacttgccc tcttccctgc tcttgccctt   26640
gctccctctg gtaactaagt ttccgacaaa gaagtgagtc cttacagaga tgtgagcaag   26700
agacagtggg gttaggctaa gcgactaccg ttgccaggt cactatggca tgaggccagt   26760
aggtgcccac tgggcctggc caccaggaag ccatgggtgg tgccgacagc ttcagaggcc   26820
tgggctgggc aaggaggcag ggaaacagag acagggtgta tggacaggtt ttcatttgtc   26880
tgggaagaaa agagaactag gaaattcaag gaaggggaca tttaagacgg gagaggttcc   26940
atatctcaaa tgtgtggatc atcccagcat ccccagaggg agagaaggag gctcaggtgc   27000
aggtaatatt gtttagagtg gggagggtgg gcaaggggag agggaggccc tcccatggct   27060
ccattgttgg ggagcagagg tttggggaga gagaagagga atattgaagc agcgatggca   27120
gagccaggga gacccttcc ctgggaatcc ggggtgaaaa cggtcatcgt gtcagcgtca   27180
ggaaagagga gactctatcc ttcatcgcag gttgggcctc tgccctccct tccaacctcg   27240
gaattctggg ggcctaatgg gttcagagtc tagtatgaaa gatttgtcat ttcttgattt   27300
cacagagttt gaatatctaa gatgccagtc ttggaagatg ccaaaattgg aaggctctgg   27360
ggctctagaa ttcttggatt tctggggtgt gtgttcccaa tcaccaacac ttgtaatttg   27420
cttgttggct gatcctattc aaaaggatca tccagacaaa aggtgacgaa gaatgacaag   27480
gtttgcttga ctccttttg caatttatct gggactagga ttaaagaaa ggagaagaaa   27540
tactcatggc atgatctagg gctatgctgt tggggtaac atgggagtg actttgggcc   27600
tgtgctgttg ggggtgatat ggcgaagcag tgccttcagg gctttgcatt tggtggtgat   27660
atgctgatgg agtgtgacat caggcctgtg ctgctggggt gacatgctgg ttcagtgatg   27720
tcaggcctgt gctgtctgga gagcagaagg cttctgtagc atgatggggg cacctctggg   27780
aacggctgcc ctgaccctc atggagctca cttgaagcct ccttgctact cacctaggct   27840
ggggatggct ggcttcaccc ccgctcacag gaacccgcag ggtgaccctg agatggatcc   27900
```

```
atgattcaca gttctgcgaa tgatgagaac atgttttcct gcctccctcc ctaccgcaga   27960
gctgaacttt atgtctcagg gaggcccaca aggagaagg aacagtcttg ggtctgacac    28020
tccctgtctc atccctcacc cccttggcga ctccatttgc cagaggcggg gccccagcat   28080
tcaggggttg tgggggttc ggtggcctgg agttaggtgc taagacaggc gttcagtgca    28140
ttggcccaac aacttgtgtg gtcattggcg ccgttcctgt ttcccagaga aggaaatcaa   28200
ggctcagcag gattaggtgg cacgcagatg ggtccacaga tggggtctct cccatacccc   28260
caacagccac aaacagcagg ccaaaggatg ctccacccca tgcttcctgt gggaaggccc   28320
tcctccctcc ctgatgcagt tgggcaaggg tctgggtact ggggagacag ggacttcgtg   28380 agctacccctt gggtaatgac agagagagtg tggaacacgg atgggagagt cttttcccta  28440
atccaaagga atgatgcctt gatggtgaat ttgaggcact aggacagctt ccaacagggt   28500
ggagggatct cgccagagtc tgagcaccac tgagctatag aatgtgtggg ctgaactggt   28560
cctagcaccc aacctatggt acaggtgggg aaactgggac cagcgagggc taaggacttg   28620
gcctcttgtc cctgtctttt ctgcctttca gtggtggaga tgggcttcag ggtgtagcca   28680
agcggtggct gggtggtgag gatgaggcct gacagctccc tgtgcccca tagctccccc    28740 tctctctgtt cagtcctccc tcgccacacg ggggtggaag tgctcagcag gggctggcat   28800
cagggtttgc atggatccct agatgcaccc ccttccttgt ctgtgaaacg aggggttcag   28860
gccagcccag ggccccaatc tttgattgct tacccatcag gaagctattg tctcccatac   28920
aagttgtgtt tattaattcc tggccaaacg ccattccaag tcaggctggt gaggtggaaa   28980
gcgcttaagt gtcgaagcca gacaggccag ggctcagcac ctgtctcctc tgcttcctac   29040
ctgggcgagg acttacatct cccaacctca ggtaactcat ctgaaaaaag ggcgtgaaag   29100 agaccccccac cctgggaaga ctaagtgaga caacgcgtgg agaacattgc acacgcgggc  29160
ttaggtcaag tgcaacaaac ctgcgttcat caccggctct cactctgctc tgggcaggca   29220
caagctgagg ggtttatggt gctggctctt tcagcctcaa caacccagcg aggaagcagg   29280
tgcctgtact gccttcacag accagtgaga cacccaagac acagagagat gaagtaattt   29340
gcacaaagtc acccagctct ttgagccaga gttaaggcca ggcagcctga tctggagtgc   29400
acgtgggtgc acagatgcat gtctgtgtgc gtgcgtacat ccatgcatgt ctgtgcacgt   29460
gtacgtgcat gtgtgtgtgg tccacgtgtg cgattcttcc ctctgagcct ctagcggccc   29520
atgccagctg gtgactccct cagccaaggc atccccagcc aacccactgg catctgggtg   29580
gggggatcga cagtttctgt ggctgtccca ccagttccag agcggcctgg gaagtcccag   29640 cccttctcttc tcagactttc attaagggtc cagggtcccc aggggcagac tcttgtcccc   29700
tccccgcaga ctcctcctgt gtgaatgaat gtggaaggga aggcagaggt ggcgcctgca   29760
aaccatccgc actgggccac tgtgccctct agttatgatc atgggcgata gtgatcatcc   29820
catgtagatg ctgagaaatt cttagaatga gcatttgttg gaaatctgct tgtgtgggtg   29880
gcaaagacat gagaggtcta gggaagagca gattttcaga caaggcactt tagggagggg   29940
gaggtacagc cctttggccc agaatgccca ttgatggaga gggcgggtca ggggagaggg   30000
tatcttaacc ctcaagtgcc agcgtagtga tgaggaaagg ctggcctggt gggcccccca   30060
tggactaagc atccttaggc acttcacctg actcctctga gactgtggtg cctccttcac   30120
ccctgacctg cctgctttct acctagcttc tcccggtgcc cacttgagcc cagctgaggc   30180
ctcaggccct tgagtggcct gggggtggta gagggacttg gcccgtgaga tctggccatg   30240
```

```
gctgctccat ttcgcagaag ccactctcac gggctgccac cgaagcacgg gcttccccct   30300
ttccgggaac ctgcctcctg ccagcttcct ctcctgtgac atcacttctc ttgtgattcg   30360
ccccaccatt tccactcact cccagccagt ggggacaggc agaaccatgg gttccctagg   30420
ccagctggag ccaccccga cccggcctgg cctggctatg gggtggccct tgtgttctcc    30480
ggagcgctag tggccagcac aggcggcagc cacagacact tagtaggaac ttcagtgtgg   30540
ctgacctgag ctgggctggc cgtgcaggag agtgcaagct gcttcctcca tgagctcaca   30600
gcctgacgtc agcaagtgct tcaaagaagt catttcctat gcatgcctta aaccatgcca   30660
caagggagat acgatcaccc ctgttttaca aatgtgaaaa ctaaagcttg ctgagggtga   30720
cccaaggtca cacagcttgt tcctggggca aagccaggct gccaattcag ctctgcagcc   30780
ccaggtctag agctctggca atgccaggtg ctgctctcct cccctcttca gcacttgcct   30840
tctgtgaccc tccttcccct ttaatctgtc tgtaggtaag ggcacggggg tgtgcattca   30900
tccacccacg cacccttctt tccttcttcc ttcttgtgtt ctccccaccc ttccatccat   30960
ccatccatcc atccatgcat ctatccctcc aggcagtaca tcctgacagg gtccctgtct   31020
acctcctgga tgaggcaaga aggaaatatt ccccatatcc agagaggtga ggaagcaagg   31080
caggccacac ggtgcaaaaa tgtgccttca gacactcagt actttgtagc caagatgaac   31140
tggcaggcat cgcagcagtc aggcttctgg tgcttcttgg agagggctag aggggagcac   31200
ttgttggacg ggaggcactg gagagccaga gaatgtgcac cctcccccag agagttctgc   31260
agcagaaaca gaaaactcag atgggccaag gggccaggcc agggctagag tctatgatgg   31320
ggggtagggt agtccagtgg tgttttcggg gcttttctt ctttctctct ttctcttct     31380 ttctttcttt ctttctttct ttcttcttt cttctttt cttctttct ttctctttt         31440 ctccttctcc ttctccttct tcctcttctt tctcttct cttcttctt ccttattctc       31500 cttttcctt cttctccctt cctcttctcc ttcttctcct tctcttcctt ctcctcctcc     31560
tcttctttct tcttctcctt ctcctcttcc tcctcctcct tcttcttctc ctcctccttc   31620
tcctcattct ctttctcctt tcttcctctt catctttct tcttcttctc ctccgcctcc    31680
tccttcctct tcctcttcct cttcctcttc tccttctaaa ggagcaggaa tctggattat   31740
tatgtgaaat tagctcgcga ctcaatgaag caatttctac atggtgcata aacagattgt   31800
ctttacgctg agtgactccg cttgggccac tagatttcag ccgctgcctt gaattcctct   31860
ctggcgcttt ctaagcagac gcttgttcca gggattccac cacctctacc cgtgctccag   31920
gcctccagag tgagaaccaa acactgccca gacagacagg ttcccgggta cacggtgagg   31980
ccctggggaa aggttgctgc cagctacaga ctggttctag gactctccct ggaggttgag   32040
agaacttcct gtagcaggca caggtgtctt tgccttacag cccctgccca aggcttgggt   32100
gacactacag gtcctcaacg cagttgcttc tagggtgaaa cgttccactc cctccaacc    32160 ccggcttggg ttccttctct gtctccccac aatctccctg tgactgtggg aagggacacc   32220
ccaaggccca tgggatgcgc ttgactcctc attccccgca ctagtccttc caaccccctg   32280
gctcccctgt ctacttcctg aggtccttct gtgaggaaaa caatccatga taactttata   32340
gacaaacaga caccaaaacc tgcgtttcct gggttttaca agagcaagag gccaggctt    32400 gctcaggggc gcccctggc ggtgcctcgt ccccaccgg ccctgctggg ctggggaac      32460 catggtcggg ggtggcggct cccaacctgt tctgcctcag gacccagtca ctctccgcaa   32520
aatgactgag taccctaaag agttttgct tatacaggtt atagatctat acttgcagca    32580
ttagaaattg aaacaaaatt ttaaaatgtt tattaattct tttaatataa ttataagccc   32640
```

```
attacacatt tgaatataaa taacattcta tgaaaattag ttgcatcctc caaaagtaaa   32700
aacatttagt gacaagagtg ctgtcatttt acatttttgt acatttcttt aacaactggc   32760
ttcacagact acaggcggga ccttcgaatc tgcctccgag ttcaatcagt cccgatgtca   32820
cacatcagtc tctggaaaac tcgcctgtca ccttatgaga gaatgagggc aaaaaaggca   32880
aatgatatct gagtgttact ataaacatga cttttggacc cccaggggtc ccctgactgt   32940
gctttgagaa ctgctggttg gtgtaagggt aagatcgtgg tcactgtggc cagatagact   33000
taggggggtg ccagagtcta ggccaggcgt gtggaggaca tggggcatgt aggggggctca   33060 gacctcagag ctcctgttgc agtgggaatt cggagccctc ccctcaagca agctaggtga   33120
gctcttctgg gtcctgaggc aagattctgg ctccaccttg gctcctgcac tcttgagcct   33180
catctgtaaa atgggatgag agcaattcct ccctccctgg gtggaggtgc tgcttgaacc   33240
tcagaatccc cgtgcaatga ggccttgtga tgccatagcc aatgaggctc agcccagcc    33300 acacacctgg agatgttaaa acagcctcaa agctcatctt cagctgttcg gtggctaagg   33360
aattgattaa cttattgaac ggttaagtgc ttaccacatt ctagaagttc tggggaagtg   33420
cctggccctt gggaatcatg gccggctccg cagggtgttg gatttgctgt gggatgtccc   33480
cactggcctt caggggcatt cctgatgctc tctggatttc catctgcttt ctctgccagg   33540
ggcattttca gctctccctg cagattttca acctgcaccc tgagtgtgtt tcccccatct   33600
gcaaagcact ctgatttgct ctgtggaggg catttctatg agctgatgaa gctgtcccca   33660
tctgttctgc aagggtgtcc cacctgggat gaaaaggaac cccggctgc tgtggaggga    33720 gggtcccact gtcctggggg agtggctgca cccactctgt gaagtcatgc cgctgcccac   33780
ttgctctgtg gggtgaggtg caccggactc tctgcaggag gaaccctgg gcccatgccc    33840 tggagatggg agggctccta cctgttctct ggtaggagag aaagactcag cctctctgga   33900
gattccccca cctgctctgt ttgaacaacg gtatcttctt ggtggtggta tggcaggggt   33960 gcagggcgg tgttgtccag cagggatgtg agggtgctcc cacagctggg ggtggtccca    34020
ccccgtgtgg ccatgcacag agaaggtgct gcccatcagc actaagctac tggtcatggg   34080
agaaggactg gtccttccct caagcccaca gtgtcacagg gaggcaggag ggttggtgcc   34140
taaatgggga gcactgctgc cccctcgtcc cacaccaagc tcaaggcaga tgaccgtgca   34200
catctgtgga cagtggggca gtcaagggct tttgcctcaa ctgacacatt gaagcctttt   34260
gtcagattca agatcaacag aaataatttt tcctttcttt cttctctctt ctttcttttc   34320
ttttcttttt tctttccctc cctctctccc tttcttctt tctctttctc tttcttcttt    34380 ctttcttttct tcctttctttt ctctttcttt ctttcttttt ccctccctcc cttccttcct  34440
tctttccctc cctccttcct tcctaccttc tgtctctttc tttctttttt tgacgtactt   34500
tcgttcttat tgcccaggct ggagtgcaat ggcacgatct cggctcaccg caacctctgc   34560
ttcctgggtt caagcgattc tcctgcttca gcctcccgag tagctgggat tacaagcatg   34620
tgccaccatg cctggctaat tttgtatttt tagtagcaac ggggtttctc catgttggtc   34680
agtctggtct cgaactcccg acttcaggtg atccacccac ctcagcctcc caaagtgctg   34740
ggattatagg tgtgagccac tgcgcccagc caatttttct tgttttataa gggaggaagg   34800
tgaggctcaa agaaggaccc tgacttgcta gaacctcaca gttcacaggt gactgtgact   34860
agaattgagt tttttatctg gcaggcaatg gggagccatt gaagattttt gagcagggca   34920
gtggcatagc caggctagtt tctagaagat gactctgggg gtgcactcat ctaagggaga   34980
```

```
aatcagggca gaggaggcac agcgggcgtg cagctccccc tgcccctctg gctgcctgtc    35040
cttgctctgt ctgtgcacgg gacccaggag accagccagt gcagccctga gtcgtctctg    35100
actcccccca ggctgtgtgg cttgcgcatc ctgcagccct acgccgagag gatcccccgtg   35160 gtggccacgg ccgggatcac catcaacttc acctcccaga tctccctcac cgggcccggt    35220
gtgcgggtgc actatggctt gtacaaccag tcggaccgtg agtatgggca gccgggggaa    35280 cccccctgcag tgactcgctg cctcttggcc atccctggaa ccaccaaggg ggctgtgggc   35340
agctgcttat gaggctgaac aaaaggagag agagagtgtg tgtgtgtgtg tatgtgcttg    35400
cacaaattta tgcagctttg tgtgcccacg tgtgcaaggc agccacaagg gtttgcagga    35460
atacacactc atacatatcc acgtgtgtgt tgtgtattct gtgtgtgtgt ctggatatgt    35520
atgtctgctt ggactgtgta cacaggtgcc caggaccacg tctgtgggtg cctgtccatg    35580
cgcgtgtgag tgaacaggtg catgcgtgtc tttgtgcgcc ttcgcggcta cgcatggcct    35640
aatggcgccc tgcctgcctc cacggtcccc tgtggttttg cagcctgccc tggagagttc    35700
ctctgttctg tgaatggact ctgtgtccct gcctgtgatg gggtcaagga ctgccccaac    35760
ggcctggatg agagaaactg cggtgagtaa cccgcccgcg catccctcct ctccctgccc    35820
atcccttctc cttcctcacc tttcctgctc tgagctgagt ggagacccca cttctacatg    35880
cagcttccat tatgagcacc caggaagtgg ggttctctca ctgtgccggg gtggcaaaat    35940
gagacagacc agcaatgcag cctccccgag accacctcgt gggacagtgg cagggagaag    36000
tggggagcca ggtctcctga cttccagctc agggccatca cccccagccc ctgtcccagc    36060
cagccttcca ggaaggaaca gaatgggtga gggagatgtc cccctcctct gccctgtcaa    36120
aggtttaaat atgtgggaag agggaagcga gatgttcatg gtgggggat gatcctgcca     36180 cggtgctggg ggaggtacct catattcaga aactgaacat ctggcttcaa gttctggctc    36240
agccaagtga ccttggacaa gtcacctcat ctgtttccac cagtgaaatg gggtatctca    36300
cagggttgct gtgaaacttt gggtgtaaaa tagcagagaa agaggccggg cgcagtggct    36360
catgcctgta atcctagcac tttgggaggc ggagtcgagc ggatcacctg aggtcaggag    36420
ttcaagatca gcctggccaa catggtgaaa ccccgtctct actaaaaata caataattag    36480
ctgggcgtgg tagcaggagc ctgtaattaa tctcagctac tcgggagtct gaggcaggag    36540
aatcgcttgg acctgggagg ttgcagtgag atcatgccat cgcactccag ccttcgtgac    36600
aagagcgaga cataaaaata aagtagcaga gaaagagatt tgtgattggt aacgtgcaat    36660
acagcacacc ttctacaggc atcgccaagc cccggctggc tcctctggct tcctcccacc    36720
tgtcccctct ctgtgtcccc acacagtttg cagagccaca ttccagtgca aagaggacag    36780
cacatgcatc tcactgccca aggtctgtga tgggcagcct gattgtctca acggcagcga    36840
cgaagagcag tgccaggaag gtagggcagg cctagccgag tgtctggagg gacaccaaag    36900
gcagtctagg cctgctacat gcttcagcaa aagtttctag cttctcctct caacaccccac   36960 caacccctct gtatttacat ctgtatgtct gtccattcat ccatccatcc atccatccat    37020
ccatccatcc atccatccat ccatcttctg gtctccaatc accgtctgtc cattgattca    37080
tacagctacc catttatcta tgcatctact gacctgtgca accatcaatc tccctatcat    37140
caaactgtca atctacccat ttattggttt ggctgactac tggtctatat ggccactgtt    37200
ccatccatcc atccatccat ccatccatcc acccacccat ctaccacccc acccatccac    37260
ccatccatca tccatccgtc catcatccat ccatccatca tccgtctatc catccatcca    37320
tccatccatc atccatccat ccacccatcg tccatccgtc catcatccat ccatccatcc    37380
```

```
atcatccatc catcatccat ctatccatcc atcatccttc cacccatccg tcatccaccc    37440
atcgatcatc catctgtcca tcatccatcc atacatcatc catctatcca tccatccatt    37500
catccatcca tcatccatgc atccatccatc catcatccat ccatccatcc atcatccgtc    37560
tatccatcca tccatcatcc atccatccat ccatcatcca tccgtccatc atccatccat    37620
ccatcatcca tctatccatc catccatccg tccatcatcc atccatccat catccatcca    37680
tcatccatcc gtccatcacc catccatcca tcatccatcc atccatcatc catccatcca    37740
tcatccatcc gtccatcatc catccatcca tcgtccatca tccatccatc catccatcat    37800
ccatccatcc atcatccatc catccatcca tcatccatcc attcatccat catccatcca    37860
ttcatccatc atccatctgt ccatcgtcta tccatccatc atccatcatc catccatcca    37920
tccatccatc catccatcat ccatccatcc atcatccatc aatccatcaa tccatcatcc    37980
atccatccat catccatcga tccatcatcc atccatccat gcacccatcc atcatccatc    38040
catccatcca tcatccatcc attcatccat catccatcca tccatcatcc atccatccat    38100
catccatcca tccatgcaac catccatcat ccatccatcc atccatccatc catccatcat    38160 ccatccatcc atccatcatc catccatcca ttcatccatc atccatccat ccatcatccg    38220
ttcatccatc atccatccat tcacccatca tccatccatc catcatccat ccatcatccg    38280
tccatccatc atctgtccat catccatcca tccatccatc atccaaccat ccatcatcca    38340
tccatccacc atccatccat tcatccgtca gccatccatc catccatgca cccatccatc    38400
atccatccat ccatccatcc atccatccatc catcatccat ccatcatcca cccatccatc    38460
atccatccat ccatctaccc atccatccac ccatccatcc acccatccac tgatctccct    38520
agccccctgt ctgtccactg gtccttatat ccacacgttt atccaacctt ctagctgtct    38580
gtcagtctcc ctaatggacc accactccac ccattggctt gtctgctcag tcttctgtct    38640
gggtctattt atccatccat ccatctaccc atccaactga ccaactgacc aacacttgca    38700
ggctacccag cgataggcaa ggtgcagtaa ggaagtgaga ataaaacagc agagatgcag    38760
gccctgcctt ccaaggctca tctgttagta ggaggatatg atgggtgact ctcctgcctt    38820
gtaggaagat tggagggcag ggaggaggtc agacatgaaa agcttcctgg aggaggtagg    38880
tgtttggccc ttggtgagag ctaaaactta aataggcagg aggaaaggag agaggcaaag    38940
accaagtggt ggagtggaaa gttctttaca gtgaagagca gggaggaaaa tgtgacaac     39000 cgggcagggc cagagcctgg gagattgcca ggctaggtgc ggaccctggt ctaaaagtgg    39060
aggcacagtt ctgccttcaa gttccacact ggaggggggag gcatgatctt gtggtcagga   39120
tctccagtct gagaatggag acaccacttt gtgctcaata ggccagtctg agtggagggg   39180
ctgtgggggg cggggggaca tggcctgctt ttaggagacc ctaaaggaga ctcaggaaaa   39240
gactctctag tcacctcctg gctcttctgg ctccatcgtt cctgcacccc actttggaag    39300
gtttccttgg ggctcagaga cccaccttct gtgccctgcc ccatcccct ctgtcccagg    39360 ggtgccatgt gggacattca ccttccagtg tgaggaccgg agctgcgtga agaagcccaa    39420
cccgcagtgt gatgggcggc ccgactgcag ggacggctcg gatgaggagc actgtggtga    39480
gccctgcctg gctgccgggg ccctggagct tgggagggag ggggtgccca cagcaggaag    39540
ctggagggaa atctcactgt tgtccctgg tctctctcta tctcatcctc tgccccttg    39600 cctgggtcct gatggtctct ccccctccat cattctcctg ttctctgtct ctccatctct    39660
ttcctttgcc cttcctctct gtctgcttct ccccttcccc tcctcctctg tccacccac    39720
```

```
cacctgcccc catccccaga ctgtggcctc cagggcccct ccagccgcat tgttggtgga   39780
gctgtgtcct ccgagggtga gtggccatgg caggccagcc tccaggttcg ggtcgacac   39840
atctgtgggg gggccctcat cgctgaccgc tgggtgataa cagctgccca ctgcttccag   39900
gaggacaggt gagcgggagg gtgtggggc ctaggcagta agagacaagg gcagggaagg    39960
cccggtggga ggtgcactgt gtctgagctc tttgcagata gagggaaggg tggtggaccc   40020
cccagacagg ctactgtgat gtgagttcta gtcctggctc caccaggacc ttctgggtcc   40080
ccggacacat tgttccacct ctctgccatc tacttttggt atcttgcttt aagttgggcc   40140
agtaattcat tcattcatct cattcactca ttcagcaaca cttgtgctcc tactatgtgc   40200
cagggctgtg ctagatgctg gggattcagt aaaggacaga actgcccaac ctggtcataa   40260
gctatgacac tcccccgaggt gtgacacgag gtagcaggtg gggctgggga gccccagggg  40320
gacatctcat caggcctcat ggccatcttt cccatctgct tggtgggctg aaacctcccc   40380
caatccaccc ccagacagat ctgggctcca gatcccgccc ccaggccctg cacagggatc   40440
cccttttgta tcctctctgg gacgcagggc gctctgacca cctagctctc tttaacccca   40500
tctcaggctc cccactgccc tcaggtagag ggtagagacc cgaaggctgc ccatctgcca   40560
cccaggcagc tgactgccgc agtccaattc ctccacgctc aactcccacc cgctcccac    40620
taggacccac cagcctcagg gaattcagag cagcctgggt ctgtaaagca cacaggaaaa   40680
aagaaatctg tgtcggggc ctggcactgt gctacatttt ttagatacac ggtcttattg    40740
gattctctca agaacattcg agtagaaaat gccattccca tttgcagatg aggtggcaga   40800
ggcttagaga ggcacaccca tgtctaggga gggatgaagc tggggcgtgg aacccaggca   40860
ggccgagtgg gtgaaggctg aacgctgtac caccagctag gcgaccttca gggagggaag   40920
ggagggctgg gtgtggaggg cactgtcccg ggcggggatc tggctatctt gagggtccct   40980
ggatggggag aggcagcttc ctcccacctc acctcacccc accccacccc accccacccc   41040
accccagcat ggcctccacg gtgctgtgga ccgtgttcct gggcaaggtg tggcagaact   41100
cgcgctggcc tggagaggtg tccttcaagg tgagccgcct gctcctgcac ccgtaccacg   41160
aagaggacag ccatgactac gacgtggcgc tgctgcagct cgaccaccg gtggtgcgct   41220
cggccgccgt gcgccccgtc tgcctgcccg cgcgctccca cttcttcgag cccggcctgc   41280
actgctggat tacgggctgg ggcgccttgc gcgaggcgg tgagcagcgg ggacttgcgg    41340
cgggaggcgg agggagaccg tgcggatctg cgccgtaaca cctggcctgg agaagggcgg   41400
ggctgggggt cccggggctc caccccatag gccctctagt gctgggattc aaattgggct   41460
gaattttacg gtagaaaacc accatttaat gcggcctgta ggcccctgcc cctcccctcc   41520
tagctcttcc cttccttctg gaagggcgtt atgtgtgggg caaggggca ggtctgggac    41580
gccactgccc acgtgcaagc tccacctgct gttccttggg ctgcaagggt ggaaggctct   41640
taattactag cactttccac atccaggctg gatttaggg gaacttgact tcatataatc    41700
cacccaacag ccctacgggc ggatgctgtg gccctatttt atggatggag aaaccaaggc   41760
tcagagacat gttgctgtaa gtcacacagc cagagaggac tggagcaaag attagaaccc   41820
agggctggct gcctccagag cccctgctct tcctgctact gctctcagaa acagggtctc   41880
tcccctttct acgttcactg accagagtcc ctggcggcca ccgcacagtt ttggggacac   41940
agacccagct ggcaaaccta cagacatgcc ctgcagcgtt agtgttggtg gcttcaaaaa   42000
tgtgtacagt gacttacaat ctggaagcag gcggggccgc agagatattt taaggatggg   42060
gaaactgagg ctcagaggaa cagtgactta cccaaggga tggcagtggt catggcaaag    42120
```

```
caaaggctgg ttcattcact attccttcac tcattcagtc actcaatgac actttctgag   42180
caccaagtac gtaccaggcg tggggttagg ggaagggtac ataaggatga agagagaaca   42240
ttctcggggg agacagacag tggtaagagc tgacatggat ggggagatgc aggaacagtg   42300
gagacacaga ggaggctcct gcccagctag ggtcagggga ggcttccagg ggagggttgt   42360
ttaagctgag gcctggaaga tgagttggca acattcagac aaaggggaaa gacattcagg   42420
tgaagacaca ggtgccaaga caggaagatg tgagaacatc cgcagcctgc cagaggggct   42480
gaggtggggg gcaggcgtgc ctgggcgagg agcaaccaga atggcagaca gggccttggg   42540
cgaggagcaa ccagaatggc agacagggcc ttgccggcca gcataaggat cttaggccag   42600
gagttctccc tcctacctgc accttagaac catacgggga gtttcaagaa aaactgcgta   42660
tcaaggctcc ccgggggact gtgatatgca gccctcgtgg agaagcgcta gggcagactg   42720
cagagttggg gcactgcaga gttctaagga aaccatgaag ggatcagatg tgggcttcgg   42780
agacatctgc aggtgctgta acagagcagc gaggagccag ccagagccca gaggtgcctc   42840
agcagacaga ggtgggggac aagaagctgg aggaagacac tcatccacac gggctttttt   42900
cttttttctt tttttgtttt ttttgagaca gagtttcgct cttgttgccc aggctggagt   42960
gcaatggcgc gatctcggct cggatccccc tcctcccggg ttcaagcggt tctcctgcct   43020
cagcctcctg agtaactggg attacaggca tgtgccacca cacccagcta attttgtatt   43080
tttagtacag acagggtttc tccatgttgg tcaagctggt ctcaaactct tgacctcagg   43140
tgttccgtcc gcctcagcct cccaaagtgc tgggattaca ggcatgagcc accgtgcccg   43200
gccctccaca tgggctttgg tcgggggctg tcaccatgaa ccccacagag aaagagctag   43260
aataaagtga cagggaggca gaggggcagg tgcgacccta gcaggggtaa gggtgggcag   43320
agcaggagag aagtaggctc ctgagatgca aagggaataa tgttagggag aatagagaac   43380
aggggctcca ggctcctgag atctcacttc tgcccttgac cacggacagg ccccatcagc   43440
aacgctctgc agaaagtgga tgtgcagttg atcccacagg acctgtgcag cgaggtctat   43500
cgctaccagg tgacgccacg catgctgtgt gccggctacc gcaagggcaa gaaggatgcc   43560
tgtcaggtga gtccccgggg catggagggg agagaggagg gagaaaggat gctgcccaca   43620
tcaccagggt ctggcccttt gctcacatca gcctgctgaa gcctcccatc ctcccagcaa   43680
ggtggtgatg ccacccccta ctttacagaa gaggagactg gggcttagaa aggttgagga   43740
gcttgcccaa ggttgcagag ccacagatca gaagagatgc tgtgatgggc aggtgttagg   43800
ctcaaaccca gttctgctcc ttgcccacca caaggcacta ggcccagggt cccacagtga   43860
ggtggatgca tggaagaaga aaggggtgtc agccacagaa gggaggcgga ggcagagtgg   43920
gggcgtgggg acacagccac agttccagga ggtcccaggc tggctggagg ccggggaggg   43980
ctggcttggg ctctctccat ttagcaggcg aggggaaagc agagctttaa gactgaacgt   44040
gactctggca cccagtcaat tcccaacagt caggacttaa tccctatggc tcttcacctg   44100 gaaaagggggg tgcccttacc ctgcttcagt cctttctcct ttcccccttt cagggtgact   44160
caggtggtcc gctggtgtgc aaggcactca gtggccgctg gttcctggcg ggctggtca   44220 gctgggcct gggctgtggc cggcctaact acttcggcgt ctacacccgc atcacaggtg   44280
tgatcagctg gatccagcaa gtggtgacct gaggaactgc cccctgcaa agcagggccc   44340 acctcctgga ctcagagagc ccagggcaac tgccaagcag ggggacaagt attctggcgg   44400
ggggtggggg agagagcagg ccctgtggtg gcaggaggtg gcatcttgtc tcgtccctga   44460
```

```
tgtctgctcc agtgatggca ggaggatgga gaagtgccag cagctggggg tcaagacgtc   44520
ccctgaggac ccaggcccac acccagccct tctgcctccc aattctctct cctccgtccc   44580
cttcctccac tgctgcctaa tgcaaggcag tggctcagca gcaagaatgc tggttctaca   44640
tcccgaggag tgtctgaggt gcgcccact  ctgtacagag ctgtttggg  cagccttgcc   44700 tccagagagc agattccagc ttcggaagcc cctggtctaa cttgggatct gggaatggaa   44760
ggtgctccca tcggagggga ccctcagagc cctggagact gccaggtggg cctgctgcca   44820
ctgtaagcca aaaggtgggg aagtcctgac tccagggtcc ttgccccacc cctgcctgcc   44880
acctgggccc tcacagccca gaccctcact gggaggtgag ctcagctgcc ctttggaata   44940
aagctgcctg atccaagccc cgctgctgga gtttgaatgg acccaggca  ccagcctcat   45000 gcccttgact ggagcagccc ctgcttcctg ctcagcctgt ttgacaagtg tccagaaggc   45060
caaggtgggc tcagtggcag tgggcgtggc cactgagggc tggggcctgc agggcagctg   45120
cccaggtccc agaagaaatg ccaggaaggc aatcatttgg ggaccctcag gtcagaggga   45180
tgtgaggagc aatcgtctcc ttttggaacc ttaggaggaa actgaggctc agagaggcgg   45240
ttaagacatc ctcatagtgg cactgggggt taggagtgga ggtggcatag actcctgtct   45300
cccagctccc tgtctgccaa ggccccgtcc agtgcgacac tcccttcctt tgcattcttt   45360
gagccactga ataaagcctt gggctccaac catgtgccag cactatgctg gggccacagg   45420
ggtgaaggac ctggctcctg accccaggag cagtggggat gatccagtgg aaggggccg   45480 gaggggagcg tggactgggc aagtcaaggc aagctgcctg gaggctgtga cttgagct    45540 ggggttcaga ggtggtccag gtgggaatat ccgggaagga tattccaggc agggaagagc   45600
acgtgcaaag gcacagtccc ggaagaatga ggcacgctag gacccagcaa gccgagtgag   45660
tgttagaaca gagctcgaga ggatgactca agaattcaga ggggcgaact gaggcgggat   45720
agcagagcct ggggttgagc caaggatttg atcttgaaag ctctggggag ccacggtggg   45780
ctctatagca taggagtgac atgagaggat tcacattttg gaaccagcct tggcaccagt   45840
gtgcagggag cggcaggcag ggaggctggt taggaggcca ccgcaggatt ccaggatgga   45900
gaggatgggc cgggactgag cagcgccatg ggatggactg gaggatgatt ttagacccct   45960
gggggcagtt gtgatggagg cagggggctc gctggaggtg agggtggacg tcaagtgtg   46020 gacaactctt tctagacgcc taactgggag cggaagggag agaggagct  tcagaggggc   46080 cccagactga agaggggttt ttccaacatg ggcgctgctg ccaggtctgt gggtgaatga   46140
ggcagaaggg gaaccaggga cggggagcac ccacctgggt cctgccagga cgagccggag   46200
cagctgggtg ggcagggagc gtctccagag caggtgggca gaacacatgc agaatacctt   46260
gggtgatctg gaatcaccct gggccctacc tcagtcttca tcggaatcct ggagggcggg   46320
ggacgtgtca tctgttctcc taacaagcct cctggtgact cttttgcaag gatagttgga   46380
ccctaaaaat gagtccagct ttggagtgga gtgtcctcag gggaagtggc gaggccctcc   46440
aggcttgagc tggcaagagg gtgcccccgc cccagcctgt ggaaggcctg cgccttaggg   46500
gctcactgcc cggcaggatt tcctcgagca gcggggagga ctgaggagtt gaaggaactg   46560
gccagggtgg gtgagggtc  tggggtctgg gctgggtcca gcagggtcag agaagggaga   46620
gggcggggtg tttatatttc ctaggatttt gggcagaggg gtggcagcaa tagggaggga   46680
tggcggtggc ccaggtgtca gagtagaagt ggaggggggcg cgctgagagg tttaggatgt   46740
ggcagaggca gcccagggct ctccctagag ttctgttttc tggctcccgg ccaggtaggg   46800
caggtgctct ggtatccggc cccagggcaa aggatatagc cagttcccca agccctccct   46860
```

| | | | | |
|---|---|---|---|---|
| gcaacacaca | caggaaaatg | acaacagggc | agcgtccctg | ggcttttggg acaaagccgc | 46920 |
| gttcctttgg | accagactac | cacaccttta | gtttagcccc | gtccccaaaa gtggcccaga | 46980 |
| gaaagagggc | aacagccagg | c | | | 47001 |

<210> SEQ ID NO 3
<211> LENGTH: 2691
<212> TYPE: DNA
<213> ORGANISM: Homo sapiens

<400> SEQUENCE: 3

| | | | | | |
|---|---|---|---|---|---|
| ggacaaacag | aggctcctga | ggcctgtgtg | caggcccggc | acctatctgc cactcccaaa | 60 |
| ggatgcccgt | ggccgaggcc | cccaggtgg | ctggcgggca | ggggacgga ggtgatggcg | 120 |
| aggaagcgga | gccagagggg | atgttcaagg | cctgtgagga | ctccaagaga aaagcccggg | 180 |
| gctacctccg | cctggtgccc | ctgtttgtgc | tgctggccct | gctcgtgctg gcttcggcgg | 240 |
| gggtgctact | ctggtatttc | ctagggtaca | aggcggaggt | gatggtcagc caggtgtact | 300 |
| caggcagtct | gcgtgtactc | aatcgccact | tctcccagga | tcttacccgc cgggaatcta | 360 |
| gtgccttccg | cagtgaaacc | gccaaagccc | agaagatgct | caaggagctc atcaccagca | 420 |
| cccgcctggg | aacttactac | aactccagct | ccgtctattc | ctttggggag gacccctca | 480 |
| cctgcttctt | ctggttcatt | ctccaaatcc | ccgagcaccg | ccggctgatg ctgagccccg | 540 |
| aggtggtgca | ggcactgctg | gtggaggagc | tgctgtccac | agtcaacagc tcggctgccg | 600 |
| tcccctacag | ggccgagtac | gaagtggacc | ccgagggcct | agtgatcctg gaagccagtg | 660 |
| tgaaagacat | agctgcattg | aattccacgc | tgggttgtta | ccgctacagc tacgtgggcc | 720 |
| agggccaggt | cctccggctg | aaggggcctg | accacctggc | ctccagctgc ctgtggcacc | 780 |
| tgcagggccc | caaggacctc | atgctcaaac | tccggctgga | gtggacgctg gcagagtgcc | 840 |
| gggaccgact | ggccatgtat | gacgtggccg | ggcccctgga | aagaggctc atcacctcgg | 900 |
| tgtacggctg | cagccgccag | gagcccgtgg | tggaggttct | ggcgtcgggg gccatcatgg | 960 |
| cggtcgtctg | gaagaagggc | ctgcacagct | actacgaccc | cttcgtgctc tccgtgcagc | 1020 |
| cggtggtctt | ccaggcctgt | gaagtgaacc | tgacgctgga | caacaggctc gactcccagg | 1080 |
| gcgtcctcag | caccccgtac | ttccccagct | actactcgcc | ccaaacccac tgctcctggc | 1140 |
| acctcacggt | gccctctctg | gactacggct | tggccctctg | gtttgatgcc tatgcactga | 1200 |
| ggaggcagaa | gtatgatttg | ccgtgcaccc | agggccagtg | gacgatccag aacaggaggc | 1260 |
| tgtgtggctt | gcgcatcctg | cagccctacg | ccgagaggat | ccccgtggtg gccacggccg | 1320 |
| ggatcaccat | caacttcacc | tcccagatct | ccctcaccgg | gccggtgtg cgggtgcact | 1380 |
| atggcttgta | caccagtcg | gacccctgcc | ctggagagtt | cctctgttct gtgaatggac | 1440 |
| tctgtgtccc | tgcctgtgat | ggggtcaagg | actgccccaa | cggcctggat gagagaaact | 1500 |
| gcgtttgcag | agccacattc | cagtgcaaag | aggacagcac | atgcatctca ctgcccaagg | 1560 |
| tctgtgatgg | gcagcctgat | tgtctcaacg | gcagcgacga | agagcagtgc caggaagggg | 1620 |
| tgccatgtgg | gacattcacc | ttccagtgtg | aggaccggag | ctgcgtgaag aagcccaacc | 1680 |
| cgcagtgtga | tgggcggccc | gactgcaggg | acggctcgga | tgaggagcac tgtgactgtg | 1740 |
| gcctccaggg | cccctccagc | cgcattgttg | gtggagctgt | gtcctccgag ggtgagtggc | 1800 |
| catggcaggc | cagcctccag | gttcgggtc | gacacatctg | tgggggggcc ctcatcgctg | 1860 |
| accgctgggt | gataacagct | gcccactgct | tccaggagga | cagcatggcc tccacggtgc | 1920 |

| | |
|---|---:|
| tgtggaccgt gttcctgggc aaggtgtggc agaactcgcg ctggcctgga gaggtgtcct | 1980 |
| tcaaggtgag ccgcctgctc ctgcacccgt accacgaaga ggacagccat gactacgacg | 2040 |
| tggcgctgct gcagctcgac cacccggtgg tgcgctcggc cgccgtgcgc ccgtctgcc | 2100 |
| tgcccgcgcg ctcccacttc ttcgagcccg gcctgcactg ctggattacg ggctggggcg | 2160 |
| ccttgcgcga gggcgcccta cgggcggatg ctgtggccct attttatgga tggagaaacc | 2220 |
| aaggctcaga gacatgttgc tgccccatca gcaacgctct gcagaaagtg gatgtgcagt | 2280 |
| tgatcccaca ggacctgtgc agcgaggtct atcgctacca ggtgacgcca cgcatgctgt | 2340 |
| gtgccggcta ccgcaagggc aagaaggatg cctgtcaggg tgactcaggt ggtccgctgg | 2400 |
| tgtgcaaggc actcagtggc cgctggttcc tggcggggct ggtcagctgg ggcctgggct | 2460 |
| gtggccggcc taactacttc ggcgtctaca cccgcatcac aggtgtgatc agctggatcc | 2520 |
| agcaagtggt gacctgagga actgcccccc tgcaaagcag ggcccacctc ctggactcag | 2580 |
| agagcccagg gcaactgcca agcaggggga caagtattct ggcggggggt ggggagaga | 2640 |
| gcaggccctg tggtggcagg aggtggcatc ttgtctcgtc cctgatgtct g | 2691 |

<210> SEQ ID NO 4
<211> LENGTH: 1732
<212> TYPE: DNA
<213> ORGANISM: Homo sapiens

<400> SEQUENCE: 4

| | |
|---|---:|
| gttcttgagc cagacccagt ccagctctgg tgcctgccct ctggtgcgag ctgacctgag | 60 |
| atgcacttcc ctcctctgtg agctgtctcg gcacccactt gcagtcactg ccgcctgatg | 120 |
| ttgttactct tccactccaa aaggatgccc gtggccgagg ccccccaggt ggctggcggg | 180 |
| caggggacg gaggtgatgg cgaggaagcg gagccagagg ggatgttcaa ggcctgtgag | 240 |
| gactccaaga gaaaagcccg gggctaccctc cgcctggtgc ccctgtttgt gctgctggcc | 300 |
| ctgctcgtgc tggcttcggc gggggtgcta ctctggtatt tcctagggta caaggcggag | 360 |
| gtgatggtca gccaggtgta ctcaggcagt ctgcgtgtac tcaatcgcca cttctcccag | 420 |
| gatcttaccc gccgggaatc tagtgccttc cgcagtgaaa ccgccaaagc ccagaagatg | 480 |
| ctcaaggagc tcatcaccag cacccgcctg gaacttact acaactccag ctccgtctat | 540 |
| tcctttgggg agggaccccct cacctgcttc ttctggttca ttctccaaat ccccgagcac | 600 |
| cgccggctga tgctgagccc cgaggtggtg caggcactgc tggtggagga gctgctgtcc | 660 |
| acagtcaaca gctcggctgc cgtcccctac agggccgagt acgaagtgga ccccgagggc | 720 |
| ctagtgatcc tggaagccag tgtgaaagac atagctgcat tgaattccac gctgggttgt | 780 |
| taccgctaca gctacgtggg ccagggccag gtcctccggc tgaaggggcc tgaccacctg | 840 |
| gcctccagct gcctgtggca cctgcagggc cccaaggacc tcatgctcaa actccggctg | 900 |
| gagtggacgc tggcagagtg ccgggaccga ctggccatgt atgacgtggc cgggcccctg | 960 |
| gagaagaggc tcatcacctc ggtgtacggc tgcagccgcc aggagcccgt ggtggaggtt | 1020 |
| ctggcgtcgg gggccatcat ggcggtcgtc tggaagaagg gcctgcacag ctactacgac | 1080 |
| cccttcgtgc tctccgtgca gccggtggtc ttccaggcct gtgaagtgaa cctgacgctg | 1140 |
| gacaacaggc tcgactccca gggcgtcctc agcacccgt acttccccag ctactactcg | 1200 |
| ccccaaaccc actgctcctg gcacctcacg gtgccctctc tggactacgg cttggccctc | 1260 |
| tggtttgatg cctatgcact gaggaggcag aagtatgatt gccgtgcac ccagggccag | 1320 |
| tggacgatcc agaacaggag gtaccacttc ctctcctccc tctggcttcc tttcctccct | 1380 |

```
ccccctccct ctcttccctc ctcaacagtg acccoctcat tggaagccca agtccccaat    1440
ctcagagggg cagcaagggg agcgagcaga ggctggggcg ggtgtcaggc ctgctgccct    1500
tgaccttgtc ctcgtcccaa cctccgccct ggccccggct tccctctgg  ctaccccaga    1560 ggtctcagac acgtttggtc atcagacacc ttggatgttt attctaatta cagcaaaatt    1620
gtctcatctt cttgggtgct gtaaccccct ctggcaccct caatccttca ataaaatgtt    1680
tccagagcca aaggaaaaaa aaaaaaaaaa aaaaaaaaaa aaaaaaaaaa aa            1732
```

<210> SEQ ID NO 5
<211> LENGTH: 3143
<212> TYPE: DNA
<213> ORGANISM: Homo sapiens

<400> SEQUENCE: 5

```
gagccaccta ccctgctccg aggccaggcc tgcagggcct catcggccag agggtgatca      60
gtgagcagaa ggatgcccgt ggccgaggcc cccaggtgg  ctgcggggca ggggggacgga    120 ggtgatggcg aggaagcgga gccagagggg atgttcaagg cctgtgagga ctccaagaga    180
aaagcccggg gctacctccg cctggtgccc ctgtttgtgc tgctggccct gctcgtgctg    240
gcttcggcgg gggtgctact ctggtatttc ctagggtaca aggcggaggt gatggtcagc    300
caggtgtact caggcagtct gcgtgtactc aatcgccact tctcccagga tcttacccgc    360
cgggaatcta gtgccttccg cagtgaaacc gccaaagccc agaagatgct caaggagctc    420
atcaccagca cccgcctggg aacttactac aactccagct ccgtctattc ctttggggag    480 ggaccctca  cctgcttctt ctggttcatt ctccaaatcc ccgagcaccg ccggctgatg    540
ctgagccccg aggtggtgca ggcactgctg gtggaggagc tgctgtccac agtcaacagc    600
tcggctgccg tccctacag  ggccgagtac gaagtggacc ccgagggcct agtgatcctg    660
gaagccagtg tgaaagacat agctgcattg aattccacgc tgggttgtta ccgctacagc    720
tacgtgggcc agggccaggt cctccggctg aaggggcctg accacctggc ctccagctgc    780
ctgtggcacc tgcagggccc caaggacctc atgctcaaac tccggctgga gtggacgctg    840
gcagagtgcc gggaccgact ggccatgtat gacgtggccg ggccctgga  aagaggctc     900 atcacctcgg tgtacggctg cagccgccag gagcccgtgg tggaggttct ggcgtcgggg    960
gccatcatgg cggtcgtctg gaagaagggc ctgcacagct actacgaccc cttcgtgctc   1020
tccgtgcagc cggtggtctt ccaggcctgt gaagtgaacc tgacgctgga caacaggctc   1080 gactccagg  gcgtcctcag caccccgtac ttccccagct actactcgcc ccaaacccac   1140
tgctcctggc acctcacggt gccctctctg gactacggct ggccctctg  gtttgatgcc   1200 tatgcactga ggaggcagaa gtatgatttg ccgtgcaccc agggccagtg gacgatccag   1260
aacaggaggc tgtgtggctt cgcatcctg  cagccctacg ccgagaggat ccccgtggtg   1320
gccacggccg ggatcaccat caacttcacc tcccagatct ccctcaccgg gcccggtgtg   1380
cgggtgcact atggcttgta caaccagtcg gacccctgcc ctggagagtt cctctgttct   1440
gtgaatggac tctgtgtccc tgcctgtgat ggggtcaagg actgccccaa cggcctggat   1500
gagagaaact cgcgtttgcag agccacattc cagtgcaaag aggacagcac atgcatctca   1560
ctgcccaagg tctgtgatgg gcagcctgat tgtctcaacg gcagcgatga agagcagtgc   1620
caggaagggg tgccatgtgg gacattcacc ttccagtgtg aggaccggag ctgcgtgaag   1680
aagcccaacc cgcagtgtga tgggcggccc gactgcaggg acggctcgga tgaggagcac   1740
```

```
tgtgactgtg gcctccaggg cccctccagc cgcattgttg gtggagctgt gtcctccgag    1800
ggtgagtggc catggcaggc cagcctccag gttcggggtc gacacatctg tgggggggcc    1860
ctcatcgctg accgctgggt gataacagct gcccactgct tccaggagga cagcatggcc    1920
tccacggtgc tgtggaccgt gttcctgggc aaggtgtggc agaactcgcg ctggcctgga    1980
gaggtgtcct tcaaggtgag ccgcctgctc ctgcacccgt accacgaaga ggacagccat    2040
gactacgacg tggcgctgct gcagctcgac cacccggtgg tgcgctcggc cgccgtgcgc    2100
cccgtctgcc tgcccgcgcg ctcccacttc ttcgagcccg gcctgcactg ctggattacg    2160
ggctggggcg ccttgcgcga gggcggcccc atcagcaacg ctctgcagaa agtggatgtg    2220
cagttgatcc cacaggacct gtgcagcgag gcctatcgct accaggtgac gccacgcatg    2280
ctgtgtgccg gctaccgcaa gggcaagaag gatgcctgtc aggtgactc aggtggtccg    2340 ctggtgtgca aggcactcag tggccgctgg ttcctggcgg ggctggtcag ctggggcctg    2400
ggctgtggcc ggcctaacta cttcggcgtc tacacccgca tcacaggtgt gatcagctgg    2460
atccagcaag tggtgacctg aggaactgcc ccctgcaaa gcagggccca cctcctggac    2520
tcagagagcc cagggcaact gccaagcagg gggacaagta ttctggcggg gggtggggga    2580
gagagcaggc cctgtggtgg caggaggtgg catcttgtct cgtccctgat gtctgctcca    2640
gtgatggcag gaggatggag aagtgccagc agctgggggt caagacgtcc cctgaggacc    2700
caggcccaca cccagcccct ctgcctccca attctctctc ctccgtcccc ttcctccact    2760
gctgcctaat gcaaggcagt ggctcagcag caagaatgct ggttctacat cccgaggagt    2820
gtctgaggtg cgccccactc tgtacagagg ctgtttgggc agccttgcct ccagagagca    2880
gattccagct tcggaagccc ctggtctaac ttgggatctg ggaatggaag gtgctcccat    2940
cggaggggac cctcagagcc ctggagactg ccaggtgggc ctgctgccac tgtaagccaa    3000
aaggtgggga agtcctgact ccagggtcct tgccccaccc ctgcctgcca cctgggccct    3060
cacagcccag accctcactg ggaggtgagc tcagctgccc tttggaataa agctgcctga    3120
tcaaaaaaaa aaaaaaaaaa aaa                                           3143

<210> SEQ ID NO 6
<211> LENGTH: 528
<212> TYPE: DNA
<213> ORGANISM: Homo sapiens
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t

<400> SEQUENCE: 6
aaaaaggcag ggaagtcctg cttccgtgcc ccaccggtgc tcagcagagg ctcccttgca      60
aatgcgaggc tgtttccaac tttggtctgt ttccctggca ggatgcccgt ggccgaggcc     120
ccccaggtgg ctggcgggca gggggacgga ggtgatggcg aggaagcngg agccggaggg    180
gatgttcaag gcctgtgagg actccaagag aaaagcccgg ggctacctcc gcctggtgcc    240
cctgtttgtg ctgctggccc tgctcgtgct ggcttcggcg ggggtgctac tctggtattt    300
cctagggtac aaggcggagg tgatggtcag ccaggtgtac tcaggcagtc tgcgtgtact    360
caatcgccac ttctcccagg atcttacccg ccgggaatct agtgccttcc gcagtgaaac    420
cgccaaagcc canaagatgc tcaaggagct catcaccagc acccgcctgg gaacttacta    480
```
caactccagc tccgtctatt cctttgggga gggacccctc acctgctt          528

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
ccatcacctc cgtccccctg          20

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
tccgcttcct cgccatcacc          20

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
ttttctcttg gagtcctcac          20

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
gcttttctct tggagtcctc          20

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
ccgggctttt ctcttggagt          20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
ggctttggcg gtttcactgc          20

<210> SEQ ID NO 13
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 13
gagcatcttc tgggctttgg                                              20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
ccttgagcat cttctgggct                                              20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
agtgcctgca ccacctcggg                                              20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
cagcagtgcc tgcaccacct                                              20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
tcctccacca gcagtgcctg                                              20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
agctcctcca ccagcagtgc                                              20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
cagcagctcc tccaccagca                                              20
```

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
gctgtgcagg cccttcttcc                                               20

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
gtagtagctg tgcaggccct                                               20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
acggcaaatc atacttctgc                                               20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
gcacggcaaa tcatacttct                                               20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
ccctgggtgc acggcaaatc                                               20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
caaacgcagt ttctctcatc                                               20

<210> SEQ ID NO 26
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 26
tgcaaacgca gtttctctca                                            20

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
gatcacacct gtgatgcggg                                            20

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
ctcctgccac cacagggcct                                            20

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
acctcctgcc accacagggc                                            20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
tgccatcact ggagcagaca                                            20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
atcctcctgc catcactgga                                            20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
tccattccca gatcccaagt                                            20

```
<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
cttccattcc cagatcccaa                                              20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
accttccatt cccagatccc                                              20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
caaagggcag ctgagctcac                                              20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
ctttattcca aagggcagct                                              20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
agctttattc caaagggcag                                              20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
aggcagcttt attccaaagg                                              20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 39
gatcaggcag ctttattcca                                               20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
aggagcggcc accgtcctgt                                               20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
ggcaggagcg gccaccgtcc                                               20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42 tcccctgag gctctcagga                                                20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
taagtccccc tgaggctctc                                               20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
aagactgttc cttctccttt                                               20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
cagcttgtgc ctgcccagag                                               20

<210> SEQ ID NO 46
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 46
agtctatctg gccacagtga                                              20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
ggtccttctt tgagcctcac                                              20

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
cctcaggtca ccacttgctg                                              20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
gccacctcct gccaccacag                                              20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
atgccacctc ctgccaccac                                              20

<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51
ctccatcctc ctgccatcac                                              20

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
```
gcagctgagc tcacctccca                                          20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
ggcagctgag ctcacctccc                                          20

<210> SEQ ID NO 54
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 54
ggcagcttta ttccaaaggg                                          20

<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55
caggcagctt tattccaaag                                          20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
atcaggcagc tttattccaa                                          20

<210> SEQ ID NO 57
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 57
ccactggccc tgggtgcacg                                          20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
tccactggcc ctgggtgcac                                          20

<210> SEQ ID NO 59
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 59
cttttggctt acagtg                                                    16

<210> SEQ ID NO 60
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 60
gctgagctca cctccc                                                    16

<210> SEQ ID NO 61
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 61
tattccaaag ggcagc                                                    16

<210> SEQ ID NO 62
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 62
ctttattcca aagggc                                                    16

<210> SEQ ID NO 63
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 63
agctttattc caaagg                                                    16

<210> SEQ ID NO 64
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 64
tcaggcagct ttattc                                                    16

<210> SEQ ID NO 65
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 65
atcaggcagc tttatt                                                    16
```

```
<210> SEQ ID NO 66
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 66
gatcaggcag ctttat                                                        16

<210> SEQ ID NO 67
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 67
attccaaagg gcagct                                                        16

<210> SEQ ID NO 68
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 68
cttacagtgg cagcag                                                        16

<210> SEQ ID NO 69
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 69
tggcttacag tggcag                                                        16

<210> SEQ ID NO 70
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 70
ttggcttaca gtggca                                                        16

<210> SEQ ID NO 71
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 71
gctttattcc aaaggg                                                        16

<210> SEQ ID NO 72
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 72
caggcagctt tattcc 16

<210> SEQ ID NO 73
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 73
tttgatcagg cagctt 16

<210> SEQ ID NO 74
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 74
ttttgatcag gcagct 16

<210> SEQ ID NO 75
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 75
tttttgatca ggcagc 16

<210> SEQ ID NO 76
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 76
acatcaggga cgagac 16

<210> SEQ ID NO 77
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 77
cagctttatt ccaaag 16

<210> SEQ ID NO 78
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 78
gcagctttat tccaaa 16

<210> SEQ ID NO 79

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 79
aggcagcttt attcca                                                         16

<210> SEQ ID NO 80
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 80
tgatcaggca gcttta                                                         16

<210> SEQ ID NO 81
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 81
ttgatcaggc agcttt                                                         16

<210> SEQ ID NO 82
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 82
ggcagcttta ttccaa                                                         16

<210> SEQ ID NO 83
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 83
ttattccaaa gggcag                                                         16

<210> SEQ ID NO 84
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 84
tttattccaa agggca                                                         16

<210> SEQ ID NO 85
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 85
```
ggcagctgag ctcacc                                                    16

<210> SEQ ID NO 86
<211> LENGTH: 19
<212> TYPE: DNA
<213> ORGANISM: Artificial sequence
<220> FEATURE:
<223> OTHER INFORMATION: Primer

<400> SEQUENCE: 86
tgataacagc tgcccactg                                                 19

<210> SEQ ID NO 87
<211> LENGTH: 20
<212> TYPE: DNA
<213> ORGANISM: Artificial sequence
<220> FEATURE:
<223> OTHER INFORMATION: Primer

<400> SEQUENCE: 87
tcaccttgaa ggacacctct                                                20

<210> SEQ ID NO 88
<211> LENGTH: 21
<212> TYPE: DNA
<213> ORGANISM: Artificial sequence
<220> FEATURE:
<223> OTHER INFORMATION: Probe

<400> SEQUENCE: 88
agttctgcca caccttgccc a                                              21

<210> SEQ ID NO 89
<211> LENGTH: 15
<212> TYPE: DNA
<213> ORGANISM: Artificial sequence
<220> FEATURE:
<223> OTHER INFORMATION: Primer

<400> SEQUENCE: 89
tcgccgcttg ctgca                                                     15

<210> SEQ ID NO 90
<211> LENGTH: 17
<212> TYPE: DNA
<213> ORGANISM: Artificial sequence
<220> FEATURE:
<223> OTHER INFORMATION: Primer

<400> SEQUENCE: 90
atcggccgtg atgtcga                                                   17

<210> SEQ ID NO 91
<211> LENGTH: 23
<212> TYPE: DNA
<213> ORGANISM: Artificial sequence
<220> FEATURE:
<223> OTHER INFORMATION: Probe

<400> SEQUENCE: 91
ccatggtcaa ccccaccgtg ttc                                            23

<210> SEQ ID NO 92
<211> LENGTH: 21
<212> TYPE: DNA

<213> ORGANISM: Artificial sequence
<220> FEATURE:
<223> OTHER INFORMATION: Primer

<400> SEQUENCE: 92
caaagcccag aagatgctca a                                            21

<210> SEQ ID NO 93
<211> LENGTH: 22
<212> TYPE: DNA
<213> ORGANISM: Artificial sequence
<220> FEATURE:
<223> OTHER INFORMATION: Primer

<400> SEQUENCE: 93
ggaatagacg gagctggagt tg                                           22

<210> SEQ ID NO 94
<211> LENGTH: 22
<212> TYPE: DNA
<213> ORGANISM: Artificial sequence
<220> FEATURE:
<223> OTHER INFORMATION: Probe

<400> SEQUENCE: 94
accagcaccc gcctgggaac tt                                           22

<210> SEQ ID NO 95
<211> LENGTH: 42001
<212> TYPE: DNA
<213> ORGANISM: Macaca mulatta
<220> FEATURE:
<221> NAME/KEY: misc_feature
<222> LOCATION: (26913)..(27448)
<223> OTHER INFORMATION: n is a, c, g, or t
<220> FEATURE:
<221> NAME/KEY: misc_feature
<222> LOCATION: (31066)..(31221)
<223> OTHER INFORMATION: n is a, c, g, or t

<400> SEQUENCE: 95
acttggcctt ggaaacctct tgtgcgtctt ccctatgcag cttttctcag ttcagactgg      60
ctcaggagct gcgggtgacc agcggctacc gtcatggaca gcacagggct acggaaccag    120
gtaggaattc atgctgcgta tggtggtaat catgcctgta atcctagcat tttggaaggc    180
cgaggtgggt gggatcacct gaggtcatga gttcgagacc aggctggcca acatggtgaa    240
accccgtctc tactaaaaat ataaaattta gccaggcatg gtggtgggca cctgtaatcc    300
cagttactca ggagactgag gcaagagaat tgcttgaacc tggggaagtg gaggttgcag    360
tgagctgaaa tcgtaccact gcactctagc ctggttaaca gagtgagact ctatccccca    420
cccccgcaaa aaaaaaaaa aaaaaaaag aaaaaagga acaaggtagg aattcaaata       480
aacagaaaat agcatcaaac cccacccctg cctctccttt ctcctctcca gtccccagag    540
tacatgggcc cagcctcctt tactctctct caggcctgta gctcctttag tttctcccgt    600
ccaggtaagc acctggcctt acctgtgtga gcccctgcac tcacctgcac tgggctctgc    660
atagtcccca gtccttgacc cccccccacc tcatgctctt ggggaccagg ggctgtaacc    720
aggcaggcat gtcaccaggc aacaggcctt gggggagagc tcagatctcc cgcacctgcc    780
tgccagcctc tggggtgccc atgggcgggg ggatgggaca ggccggccct gccttctcct    840
gcctcctgcc tgtttacctg tactcagtca cagtgctgtc ctgggccagc aggaggagc     900 cccatggagc ctggggccac aggccacagg ggacaagggc cagacaccct ggccatggct    960

```
ctaggccatt gatccaggcc gggctggcac ggtgggggta gggaggcctt ggcctggaca      1020
aacaaaggct tctgaggcct gcgtgcaggc ccagcaccta ccgccactc ccaaaggtaa       1080 gcgggggcct ccagaacagg ggaccaggat ctataaatga cttagtgaca gtgtccaccc      1140
taagagctgg gcctggctcc ctggggcctg agtcacctac cctgctccaa ggccaggcct     1200
gcagggcctc atcggccaga gggtgatcag tgagcagaag gtgaggggcc cacagagctg     1260
gggaggggag ggaccatgca gggtgacacc aggtgtgtgg acaggcacag catcagtgct    1320
gggtggttgg tggcctggga ttcaggcggc agggacagga ggaaggcaga ggccacccta    1380
cgcctgcctc gcaggactgg acgtgctgcc ccctccatac ccggtacccc acctgggcct    1440
tctggtgtag gagacaggcc cagagcccca cattgcacct gtgtactgac ttaagcacgg    1500
gaccctgggc tcgaaggctc agagttggcg tgtgtgtgtg tgtgtgtgtt cgtgtgtgtg    1560
ttcgtgtgtg tgggggaagg gcatgcatct gtgaatttt gtgtcatgaa tatccctcgc     1620
gtgtctccac ctgtgtacat ctgtgggtct gtgaatgtgt ttatatgtgt ggaagggagc    1680
cccgcccagt ctcccacact cgcaggtctc tagggcctaa tgacttcact gaaagatgca    1740
cctacaaccc tagcccagag tccccgctct gctctgctct gccctggcta agggaccctcg   1800 ggtaagtcat gttactgctc tctacctcag tttccccagc cattaaacag agttagcaaa    1860
gcacacaccc caggctgttg gaggctgcag tggagttcgc agcgccgccc agcgcagggc    1920
tggcacatgg taggagttca cacgcagtgg ttgaatacag atctgcattg ccggggagtg    1980
gcggccccgc cccaaggagc tcagcctcca gcgggcagac tccagacccg ccaatggcca   2040
gaagggcagg agggagtgaa gagcaggtgc cagggtgggg tccaggtgct cagagctgcg   2100
ggactgcttc aggcccctgt ggcaattgca gcacagtccc cgcttccagg agctcaatgt    2160
gaggggcaga gagggtgccc ataggtgaac cgcacatcgc gaggcacagc tgctccttct   2220
agggcactct gggagagctg caaagaggtg aggtctgagt ggaggtgaca gaggctgcat   2280
aagagctggc caggctggga ggtgggggtc caggcagaag gaagagtgtg gggatgcctg   2340
gccgtgaaca agcactgaca gggctcaagg tccaggaggg ctcttggtgc tggctggctg    2400
ctcttaatcc gtaaatgttt gccaccatcc cattgttaaa atttcttacc aagggaagga   2460
agtccagtgt ccccggggtg tgacggggag aagagagggt gagaaaaaag gaggcaggag   2520
aaggtggcca ggcacatat gcacacagca ccttggagtt ccgtggggag gaaggagctg    2580
ggaccttgtc attcatttgt tcaacaatta ctgagtgtcc gctgagtacc agactctgct    2640
ctcacgcagc ttagacaggg aggagacaga taaacaacgt atttgcatat caggcaattt    2700
aggcctcagt cattgctata agaaaaaag caggagagac aggggagtgc ccagggaagg   2760
cctctctgga aaggtgacat gtgacacctt ggaggaggta aaggagggag ctatgaggca   2820
agcagaaagg aaagcatccc aggctcagca aggagcaaac tcccattcag cgaagaggac   2880
agaaaaccta gccctgggc cttgtgggac tgagttctag ttggatggaa gccgtgggag    2940
gctcgtggac agggcacata gtgacaacac gcagtgtttt ttttgtattt ttagtagaga   3000
cggggtttca ccttgttagc caggatggtc tctatctcct gacctggtga tccgcccgcc   3060
tcggcctccc aaagtgctgg gattacaggc ttgagccacc gcgccccggc ctgggtggga   3120
agttatgatg agcctggggg agttaatttc ctactaccac catttggact atggcttggg   3180
tttttacaga gggtttcctg aaaacgaacc cctctgtgct gctcaagtcc tcccagatgg   3240
atgcgagggg tattgagagg gaggcaaaat ctgcatagag aaggaggcct ggcttggagg   3300
```

```
atgagaggggaggggaggcc cacgaagcac ttcaccctga gctgcccctc ttcggggctc    3360
ctctaatgga cccatgacct tctctgagcc tcagtttccc tctctttaca ctgattatct    3420
gagaggtagt agggcaccag ggatactgtg aacatttgag gaagtgggca gggctctccc    3480
acccattgcc cattgccgga catttatcat ttaccattcc ctggccttgg ccccataaaa    3540
gccagtaggg cccatcccac atgtgggaat atcctagctt agggtgtgga gggggggtgcc   3600 atgcctaatg agggtcccct gcagtcctc ccttccttgt atctgatggg gaccgctcaa     3660
cagagtcact gtggctggac accaaagacc cttagctggg aaggatgcca aggggagctg    3720
gagggagccg ggaagctggg agaagggcca ggacccttca tatccacctg ggaggatttt    3780
gagcgtcact aaagagccgc attttggaa acccactttg taaaatccta agacacagcc     3840
caaagggagc ccccgcctgc atctggggtg cattttattt ttttaacgg tttgtttgtt     3900 tgttttttat cagagtcttg ctctgtcacc caggctggag tataatggca tgatcttggc    3960
tcactgcaac ctcccttgcc caggttcaag tgattctcct gcctcagcct cccgagtagc    4020
tgggattaca ggcgcccacc accatgcccg gctaatttttt gtattttttca tagtgacagg  4080 gtttcaccat attggccagg ctgatctcga actcctgacc tcaggtgatc cacccacctg    4140
aggtgttggg attacaggcg tgagccaccg cgcccggccc tggggtgcat tttaaagcta    4200
ctcagtattt gtggatacag taagagaaga tgagcttccc agtagtgtgg agcccttgct    4260
ctcctggtgg gcgggtcaaa ggctttctct gtactgtcgg gaaacctgcc tgaaaggcca    4320
catacattgg gatatttgct tcaaagcctc tcaaaataga gttggaaccc tggaacatgg    4380
agaggggtga cattcagttg ctatttaatc atgatttgtt aatcaacagc tcagttatgg    4440
gaggcatctt agattagtgg aaaaagcagg gagtcagaca tccagactca acctccgctt    4500
tcctgctgtg tgaccttggg caagtggctt agcctctctg ggcttcatgg tttttttttt    4560
tttaatctgt aaaatgcatc tgagagtgaa tgccaggtat tcaactcaca atggaaaaat    4620
gcagctagga aaagccctag actgcgttat tgctagaaca ctctgggtct cagtttcctc    4680
atctgttcaa tgggtacaga actggaggtt taagtgagat aatgcgggtg aagtacccat    4740
gtggtgtggg cttgaggaag aaaacatggg acaatggttc cacatccctg ggtgacctga    4800
agattaagtg tgaaatgtct catgagggca cgaaatgaat attagttttt gttcccttcc    4860
tctgctgtga gagtttgaga gtagaaaggt gagagacg gtactctgtg aaggaaggca     4920
ggtccctggc ccagcacagt gccagctcag gggattctgg ggcaggggct aagtgcatgg    4980
gctgtgtggg cgtggtggga agctctgcga accagaacca ggagcaagaa acagcattcc    5040
ttgcgtggaa gggaaatgag ggcaaaaggt ccgatgccta cagaagtcta caccccatgt    5100
acttcagttc tgtctgtggg tgcagcctct agggaggtgg tgttcaggc actgagacct     5160 ccatctgtcc tctgaccaca gggaagccag cgggaagcaa aggtggggtt cttgagccac    5220
acccagtcca gctctggtgc ctgccctctg gggtgagctg ccttgagatg cacttcgctc    5280
ctctgtgaac tgtctcggca cccacttccg gtcactgccg cctgatgttg ttactcttcc    5340
actctgaaag gcagggaagt cctgcttctg tacccacca gtgctcagca gaggctccct     5400
tgcaaatgcg aggctgattc caacttcggt ctgtttctct ggcaggatgc ctgtggccaa    5460
gcccccccag gtgctggtg gcagggggga cggaggtgat ggcgaggaag cggagccaga    5520
ggggatgttc gaggcccgtg aggactccaa gagaaaagcc cggggctacc tccgcctggc    5580 gccctgtgg ctgaccctgg ttgtgctgac ttcagtgggg gtgctactct ggtatttcct    5640
aggtaatgtc gtgggactgc ctgggagagg cacctgggga ggacttagta gcaggcacag    5700
```

```
caggacagaa cggggttcca ggctcagcca tgcttagcat gttgctgtgt gatcttgggc    5760
aagtcacttc tcctctctgg gtctccctcc ctgtcctgcc agctggagac gctgtcagag    5820
cctggctcca ggtcctatgg ctcaggcctg cttcccgctt gggcaaagtg ccccaaggct    5880
ccctaccagg tggggaaaat gggctctcct agcagtcagt tcttgtgaac cagcattccc    5940
cagagcataa acattgcctt cccttgccta cagtcctcct gggttgcccc tgaggcttgg    6000
agccaaccca ggcctgaaga aggaggccca gaggcactca tggtgcctgg taccaattag    6060
tgcctctgct cacttgagcc cagcctgcat tctcctctag ggtggggacc acagctctat    6120
cccttctggg tctccagggt ccagcatgaa tgggggatgg agcgggcagc tggagagcag    6180
ctagccttag gggcctctcc catgtcctta attatggctg cacacaacc ctcagtcagt     6240 gtcctggtgc ttggggagca actggcctgt gctctgggtc catccatcca ggcttccatt    6300
cattcattca ttgaataaat gctcttgagc atctattatc tttctctaag attgatggag    6360
tctatcttct tccttctgcc tttgacagtg ggaagtaacg gagaaaccaa actagactgt    6420
gcctatacac tgtacactgt agaagcccca ttcattcgtt catttattca gtgccaagca    6480
cctcctgtgt gccaggtact ggggtcagcc cctgtccttg tgattagcca aggcgtcaga    6540
cctgacactt acgctaaagc acggcatgtg ctgggacaga gaaagctgag ggctgggagg    6600
ccacggcagg gacaatccag ctgcctgcgt gatcagaggc atcccattaa acatcctgca    6660
aaggttagct agtgctttta ctggccgaat ctcctggtgg aattccaggc tgttgaaag     6720 caacctgggg accaaccttg cagcagtgga gcgaaatcca cgtaggccta gatccaaggg    6780
ggtcagggtt ggtggtgtct ggaaccagcc tctgggagtg acgctgttgg gaaccccagg    6840
tctgacatgg gcctgcttgc aatgacttac agtgattcta cccagagttg agcaacgcag    6900
gcagtagacg ctgtgtgcat ttcaccaccg gcaagaagcc agtgccccag atagcacagg    6960
gctgtggggg cctcctcagg tttcgggcta atgagtctta agggtaaacc atggggcact    7020
gggctggagg ggcaggaact cacctgccaa ttatttctct ttgcagagga gtttaattcc    7080
ccctgattat gctcctgggg taaatcatcc ccaccccagg agaggtgctc catggggctg    7140
aggacccaag gggtgagtgc tcccaagcca actcccccac agagggatta aggggttggag   7200 gaggcacttc gggagctgtt tgaaagactc ctcccgcctg gaccaggctg tgctcctgag    7260
actgggtgct gggcaaggag gtggatcaga gacatgcccc gccctgtctc gaagaggagg    7320
tacacaagtg gccggtgaca ctggtgcaca ggcccaagc gaggagggca gcctggcccg      7380
aggagagggt ggggccgact tctcaaggag gatggtagca gagcccttaa taccaccaac    7440
cgtatttcct gggtcctttt cctttcctgc tctcccaggc aggagttttg tatgttctca    7500
agcccccagc acccgcctgc cctgtgtct tgcttcagtg agaaaacaga atggcttaga      7560
agagaagccc cacacatgtc ggcccacctg ccctcccagc tgcatcacgt gcactcctcc    7620
ggagcccccg atcccgcccc ctctgcgcac acaatggccc ggcaccagca agggtgccct    7680 cttctccccca gcagcagcgt ctatcagtgt cccttggggt gcctcccccta tttctctgct   7740 ccttgaagga gctgtcagtc cacacaccta gtctctctgt gcccttttcca acctggttcc    7800 ccctgccccc caactccaac ggccattgtc aagctcacca ggttgctaaa tccaatgtcc    7860
agttctcagt cttcattgca cttgacccgg gggctcactc ccacctccag aagcccttttg    7920 ctctcttgac tttgggccgc cactgggtcc ttttgctca gcgggttttg ctttttctgt      7980
gtccctgctg atggggggggg gggcctctcc tttctctctc caccacttct ttcgtgatct    8040
```

```
catctgctac ccttagcttc gagtgccctt tataccctga tgacacccac atttgcattt     8100
ctagcctggg cctctccctt gagcttgact ctagagctgc ccctgctctt cctctcatat     8160
gtctaaggag catctcaaac cccaggagtt cagaccgtga ggtctctgca taatttcccc     8220
cagacctgca cctcccacat cccagtccaa gaccacttct ttctggcacc ttcccttac      8280
tcctctcttt cttttccacc ccagccccaa tttgccagca aacctggtca tctctgactc     8340
caaaatacat caaaaacggc tgaagccaat cacttcccac cctctcctct gccgcagccg     8400
gggccaggct ctgtcccctt ggacatctct gccctggagc cctgcaggtg tgtcctcgat     8460
gctctgcctg cctctgtcca gcgttcttag agcctttctc aacgtaacag cagagggacc     8520
atttgatgaa gcaaaccaaa tcctctaatt tccctgctta aaatctcacg tggggccagg     8580
cacgtggctc acgcccgtaa tcccagcact ttgggaggcc gaggtggatg gatcacctga     8640
ggtcgggagt tcgagaccag cctgaccaac agggagaaac cctgtctcta ctaaaaatgc     8700
aaaattaaca gggcgtggtg gcacatgcct gtaatcccag ctactcgaga ggctgaggca     8760
ggagaatcac ttgaacccgg gaggcagagg ttgtggtgag ccaacgtcgc accattgcac     8820
tccagcctgg gcaacaagag cgaaactccg tctcaaaacc aaaccaaaca aaaccaaacc     8880
aaaacaaaat acctcccgtt cctcccatct tacccagggt gaaagcccag gtcctcccag     8940
gcctgacaag ccctacccgg cctctcccct tcccaatctc ataccctcct gctgtcccct     9000
tcccaatctc ataccctcct gctgtcccct tcccaatctc ataccctcct gctgtccgct     9060
tcccaatctc ataccctcct gctgtcccct tcccaatctc ataccctcct gctgtcccct     9120
tcccaatctc ataccctcct gctgtcctgt tgctcactct tgctgctcc tgaaccacac      9180
caggcctttg cacttgcccc tgcctgtgat actcttttcca cagatgtaca tcaccttctt    9240
ccctgacctc catactgcag cccgcccac gccctggttt ccaccgcact gatcacctct      9300
aacctgttat acgctatgtg tggtttactg tctgattcct tgctagtctg caagctatta    9360
agggcagttt ttcttgatt gttctgttcg ttgttttgct catatagtcc caagtgcttt     9420
ggctcagttc ctacacatag caggctctca ggaagtattt gttgagtgga taaataggg      9480
tgtaaaccag ggctatgagt ctaccctctt cacttcagcc aaaatagtct ttgcaaaaca    9540
gaagtatgat ggcatcactc ctgatttaa acctttcacg gtttctcttg ttcttcgggt     9600
aaagacccag tgggccctgc cctgcggagg ccccagctcc ttgccacccc tccccatccc    9660
tgattgctcc agtcaaacag gctttcagcc cgggtcctca ccatggtccc cgtgccacca    9720
gtcctgtgcc ccatgctgct ccctctgttt gaaggtactt ctcttcctct tctcttacca    9780
atttacggtt tccccatccc tacataccag ctggagggtc actccactct ggcccagcct    9840
gagtgtcctc gtcacgtccc ctcaacagca ccgagtggca ctgctccctg atggcactgc    9900
ttacagatgg gtgccgcgtg ctgtgtgttt gccagcgcca cgcctttctt atccaccgtc    9960
agcttcatga ggggagacac atctgtcttg gttaactagc gtaccccatg tagttggtgc   10020
ttagcacaca cctgtgggat ccctggatga gctcacgaat ggaaggatgc ctagtggtgc   10080
tgacccacag ccttggcctc ctgggcctat gtggatttcc tggccttcct gtcgttggtg   10140
tcctggactg ctcgctgtgt cagcctctcc ctgggaacct gtaggacacc atccatctgg   10200
gagcctctca cctccctggc accgtgcaac cagtttgtca tccaataaac tttggatgac   10260
catgatgaca atggcagtaa caaagatgat gatgatgagg atgatggtgc tgtggagacc   10320
caagacactg aggctgagcg gagggtgtgg ggtggcagga aaggcatgga agagacaggg   10380
gccttttccca tccgcttcct ccattaaccc tgctggttcc ttcctgggca gggtacaagg   10440
```

```
cggaggtgac ggtcagccag gtgtactcag gcagcctgcg cgtgctcaat cgccacttct    10500
cccaggatct tacccgccgg gaatccagtg ccttccgcag tgaaaccgcc aaagcccaga    10560
agatggtagg aaaggatttg ggggatgaga gggagggaat gtgagggtga aaagagagca    10620 gtgggggtctg atcacatgga gccagttggt caacccatct ggagcactca cggggaccac   10680
agccctgctc caggcaccat ggaagcagat gaggttgagg gtgatgggaa agttagcgga    10740
cgcttgagtc aatcgcactc ggattagatc ctgatcctgc ctcttaccag gggtggagca    10800
tgaccttggg aaagctcccg cagtgcagct gacactgtca agggcccgat cctgcccttc    10860
cattacagga cgtggcctgc tcctgcctct ccgttacagg acggtggttc actgcacaga    10920
ggctggtcta ctgcctgcca ctctcaggct gcaggatcag tgcccagcaa ggcaggccag    10980
aagtgccagg gagttattcc caggaacacc cctgagccat gagcgctgga gtgggtggat    11040
caataccaca gcttctttgg ccctggctgg gggaacggtt cagagagtgt tccaggctgt    11100
ctcccagaga tgccctgctg ggctaagctc agaagctctc agctttacac tgcacattca    11160
tggccccgtg ttggttaccc actttccagt ctctccctcc caactactgt ttcccggaat    11220
cacctccaaa taaaccactt gccccacctt gtcaatggag ggtctgcttc tgggggaccc   11280
agcctgaggc tgcctgtttc ctcctccatg aagtgggagt gataacaaca ggacccggct    11340
gcagatttgt tgcgggttgc agtgaagttg agataacacg aacactattc ccacgccgcg    11400
caaatgcttg agagcctgta atcctgccag cagcgctgta gttggagatg tgcaaaaaat    11460
ccagccagct gtgctaccca tcagagctgc tggcttgtcc caggccacgg gaggaggtgc    11520 ggagggggacc caggagctga gtggggtttt tcagagttga ggagtgactt ttggcaaggc    11580 gcagagggg catcggcagt gcgggtggag gtgagagtca ggtataggg aaagggaaag    11640 atggggaggt tcatgcatgc cccggcctgg ccactcagca ctgtgtgact gtgatcaagc    11700
ctgtccacct tggaggctcc tgcatggagc ggggctgccg ggaggagcaa agggcaccct    11760
gaagtaggaa gtggccctcc ttgcagaggg tcccaggagc tcctgtcttc ccttcttaca    11820
gctcaaggag ctcatcgcca gcacccgcct gggaacttat tacaactcca gctccgtcta    11880
ttcctttggg tgagttgtcc ttgcccctga caagctcctg caagaagctg agacacaaag    11940
agtgggaggg gactctatag gcttctgatg caatgccttc atgtttcaaa tgggaaaact    12000
aaggcacgga gagggaactt ggcttcctgc atgtcaccct cccttcactg ggctcatctg    12060
tagaatggaa acatgggtgt gataggtttg caccaggcaa tgactgtgat gggtgatcaa    12120
gggcttgaca ccatcaggcg aggccatgtt ggagggcgat ggggttacga gcattggctc    12180
cagggcctgg ctgccctgtt cgcatctggt tctgctgctt gccttgaagc atagtctatg    12240
aggcacaagt tcaactctcg tgcctcagtt ttctcattca taaataagg atgatgagag    12300 cgcctccttc agaggttgct aggaggcttc tgtgtgaaga cggacagcaa tggctgggt    12360 gtggaaagtg ctcaatgtgc atgagcaggg gcggggcagg ggccagacct cagaatcctt    12420
ccctggcccc tctcatttct gcctgcctta gggagggacc gctcacctgc ttcttctggt    12480
tcattctcca aatccccgag caccgccggc tgatgctgag cccgaggtg gtgcaggcac    12540 tgctggtgga ggagctgctg tccacagtca acagctcggc ggctgtcccc tacagggccg    12600
agtacgaagt ggaccccgag ggcctagtga tcctaggtcg gtactgggag tggaaacgtg    12660
gggttggcct cgtgaggttg ggagaaacaa gctgtggtgt ggcctgggga gctgcctgc    12720 cagggctggg gtgccctcag ggtgggcccc ccaggagggc ccccaggtga ggtagcagag    12780
```

```
ccattgcatt caaggagcca ggaaggaaag gtggggtagg ggtgcttagg gtcaatctca   12840
gacaaggctg gctccaagag tctcctctaa ttttattttc attgtatttt cttttattta   12900
ttttgtcctt gtttatttgt ttattcattt ccttttatca gaagccagtg tgaaagacat   12960
agctgcactg aattccacgc tgggtacgct actttttcc cctccccact ttccttttga    13020
gttggtgttt gtattgactt tgttgtgtgt caggggaca catggcctct gtcgtgggtg    13080
cagagagccc tggcccagag tcacccaggg gatgccatgg tggactcagt gatgtgtccc   13140
cagcaagtct tggaaactgt aggggagag gaggtggctt tgtgcacgca tgtattttgt    13200
gtgtgtcttg tagacaagtg tgcatgtgtt cctgtgtggg tgtgagaatg agtcagattt   13260
agtggtccac aaacgtgact ctccttctct atcattgact tcaacctgcc cacaagccat   13320
ttttccactg atggtagaaa atcacctcgc caattcacgg tgtgtcaggt cttttggagg   13380
tagcggtgcc attgcattca aaaacactcc ttccacctttt cctttccttt cccagtcagg  13440
ctcatcagcc ctccctccct acctggtgcc atattgctag agtcaccttg catttctcca   13500
agtggaccca caatctttca gctgaccagc agagtcaccg cgctgcacaa ggcaggaggt   13560
gctgtccaag ttgtagtttg tgtgagttgt gcagtgcacc aactgggctg ctggactgta   13620
cggcccctaa attctcagat tcctcctaca gtatctagca ttgtcaccca gagccaaggt   13680
gggggtgagc gtctcaaccc cttctcaggg agggaggcag agtttaaatc cttgttatac   13740
ttttccttaa cttccccttt tcccatcctg ctggtcaaat gtttgctttg ttggatggag   13800
gtgatgagct caaagtacag ttttcaaaga ggtgaaatca tgattctcat acaaagatag   13860
agtgaccacg tgtcaaatat gtatttaact gattaacagg ggaaccagcg gaatggtaaa   13920
gaatgcaaga aactgatctg tctgtctgtc tatctatcta tctatctatc tatctatcta   13980
tctatctatc tatcttttcta tctgtctatc atccctctct tgatatctgt ctgtctacag   14040
ttgttctgta attatctgtg ctcagtgggt gttcgtttca tgagtgaatg atttaacaaa   14100
tgaatgaaag catgaatgag gagactggtt cagtgtgcgt ccagggcaga gtctcaggga   14160
gcagcggtaa caacttaaac ccttgaagtg gactttctga gcacttcctt tatgccaggc   14220
cccattcctg tgctgaggac accaggacga ccgtgtcctc accctgccc tcggaggagc    14280 ttcaagcccc atgagggaga cagagcacat aaacagactc tcataacatc aagtgccagt   14340
gtgaaaatag agggcccaga ggcagtggag agagggaatt gtttgttcca aagcagagga   14400
ggggtaaatc aagagcctca cacagagtcc cagatctaca ggaggaaggg gtgctcctga   14460 ctggggatc ctggaagact tcatggaggg ggcatcagat ttgggcatgg gctgggcgtg    14520
gtggcacacg cctgtaatcc cggcactttg ggaggccgag ttgagcagat cacctgaggt   14580
caagagttcg aggccagcct ggccaacatg acaaaatccc gtctctacta aaaatacaaa   14640
attagtgggg cgtggtggcc catgcctgta atcccaggta cttgggaggc tgaggcagga   14700
gaatttcttg aacccaggaa gtgtaggttg cagtgagctg agattacacc attgcattcc   14760
agcctgggcg acaagagcaa actccattta aaaaaaaaaa aaaaaattag ccgggcatgg   14820
tggtgtgcac ctgcagtcct agctactcgg gggtggagga ggggaggcta aggtgggagg   14880
atcacccgag ctcaggaggt tgaggctgca atgagctgtt gtgatcacaa cactgcactc   14940
cagcctgggt gacaggctgt ctcaacaata aaataaaata atttttaaaa gaaaagaaa    15000 ttcaggcgtg ggggtaggca gggatttgtc agggtgagaa ggagaaaggg ttccctgggc   15060
agagagaatg gcagggcaa aggccaaggg agagcaacac ccaaggcatg ttcagttact    15120
tcctcccagc cccgagaggt gccaggctcc ctgacggtac ttctgattaa caagaggtta   15180
```

```
gcacacacct ctccactgaa ttcacctaaa aaaaaaaaaa aagagtaatt attaaagtgg    15240
caagaacaaa gaatctgctt agagcaagat ttaaagaaca caaaaccta ggaagagcca     15300 ggcatctttc cccagctgct ggtggaggct ctgtcccttc cctaggcaga tactgttggt    15360
ctctccctgg ggagctcggc tccccactgc agtcagcaca gccaggggtc agggagaagg    15420
agctgagcca caggcggcag catcagagca aagtgtattc accttcattc ccttcctggt    15480
cctcagcact gcccggagga ggtcatagga cagggattat tatcacatcc atttgacaga    15540
acttggaatg gctaagccac tggcccagac tcagttaact acccagaggt agtgaacatc    15600
tacctctaca gagtccgagg ttgataatct acaatcaata gtaagtcaga gttattattc    15660
ctgagagcct ccgggggact taatcagacg atgcctgggg acagagactg gctcactgca    15720
gcctggacac cgaatctggt ccactgctgc ctgaccaaga atgacatcat cacacagctg    15780
atgagtgttg gtgctaggtg gggagggtag tgcccctcct tccttctctc cagttttctc    15840
cccctccccc ctccccgggg ggcccagcag atggctagcc tagggagctg ccctcagtct    15900
gtccaagctg aaaggggggac ctttgcttgt cggtggcctt ccaaataaga cgatttaaag   15960
cagagaaaat agactgaaaa ctcaggtttt ataatttcat gtcaccaggc tgcctcccac    16020
atcccaggtt cattcctaaa tccccactgg ctcctggaag aacaccaggc ttctagtgag    16080
gtttaaatga gatactggat gctccatggg agagaatatg ttcactgcca gaccctggtg    16140
cctagatgga acacacagta ggtgcacagt cactgttttg aatgaatgaa tgaatgaatg    16200
aatgatgcag gtggtactgc tttgtaagtt ctagcagtgc atcagagctt atggattaga    16260
tggaagagca gaggctcact ggtgtgtggg gtaggggtgt agggtgtaat ggtgaaggag    16320
ttgtgaagcg aggcagccgt gagatgggct aggtctgagc ctcaggcggg gccagcggca    16380
ggatgacaag tcacaggcct ttcttcccag ccctacctgc tccgtttccg tcacacccac    16440
ctgaggaaca ggcaatgtct ttactgagcc cctactgtgc aaggcgccgt gctgggcact    16500
caaatgtgcg tcatgtcaca acctgctgat gaccctgcaa gggtggtgtt attgtcccat    16560
tctacagatg aggaaaccaa ggcccaggaa agattaggtg gtggctgggc aaacctagat    16620
gtgtccggcc caggtctgtg caatgggcac aatcattgaa cgtatctcat agagctgttg    16680
tgggcattca gtgagacact gagggaaggc attcagctcg gtttctggcc tgtagcaaat    16740
gcttgataag cacctgtttt attctgacga cttcaccatg attagctcaa agctcacgtc    16800
ctcccctcaa ggcagcctcc cagactcctc cttgggcag tcccttctct ctaccagaag     16860
tgaagccctc atcccttgc ctcctcattg cgtgtggaat cgctgttctc cacagtgttg     16920
ctcgcagcag ccagaggagt gtgtggtcca agccagccca tgtctagcct tgctcaacct    16980
tctgtggctc cctatggctg caggagaaag cagcgtcggt cctgggagtg gcctggtccg    17040
ggcctccctg ccttcagctt gtcctctaga cacatgtgcc ctgtgtgtac ttttctcaaa    17100
gctgcctggc tcgcccagc ctctttgctc acgcggggac ccccaggacg cccccagcct    17160
ataggctggg tttggaacca tcacctcctg agctattctt gcctgttctg tgtctgtttg    17220
tctccgctgt catccatgtc cccaggcagt gactgtatct ttacctgggc actgagaaac    17280
catgaagctc agtgggtgtc cgttccatga gtgaatgact gaaccaatga acaaatgcgt    17340
gaatgaggat actggcaggg aaagagaagg atcgggtaga gcgtgtctgg ctgtccccac    17400
ctggctcccc tgcccggccc atcctgcctc ggaaggacc ttgaggaacc tggctcccca    17460
gggtcccctc cttctgggtc acaggaatca ggggctttgc ccctcttccc gctccaggtt    17520
```

```
gttaccgcta cagctacgtg ggccagggtc aggtcctccg gctgaaggga cccgaccacc   17580
tggcctccag ctgcctgtgg cacctgcagg gccccgaaga cctcatgctg aaactccggc   17640
tggagtggac gctggccgag tgccgggacc gactggccat gtatgacgtg gctgggcccc   17700
tggagaagag gctcatcacc tcgtgagtcc ctgggaagga gggcgggagg gagggctgga   17760
aaggggaatg gctgattagg gggttaaaag tcacacacaa cattcttaga caagtggggg   17820
taggaccttg ggcctgggta tctgggagac aggacggcta gtctagaggg gataggagag   17880
aggaggctgg agatggttgt gtagtgcgag cgcttcccct ccccgagcct cggttttccc   17940
atttgtaaca aagctgttgt tctagatgac ccgtacagac agctctggga ggcactgtgg   18000
cttgttggga tatttcagag cctggctgca gcctggacgt tcaacctctg ggctcattcc   18060
taaatcctga ctgcttcctg gcagagcacc cacccctccct gcttccaggt tgctggtggg   18120
gtttaaatga gacactagat tcgcaatggg aggggatatc ttcactgccg ggccctggtg   18180
cctagatcaa acgcacagtt ggtgtgcagc atctattttg agtgaaccaa tgaatgatgt   18240
aggtggtact gctttgcaag ctctagcaat gcatcagagc tcatggatta aatgtaagag   18300
cagagaggtt tactggtgtg tggggtgggg gtgtgggggt gtgatgggga acccctgcc   18360 tcctagctgt gtgccctaag ttactttgcc tctcagaacc ttcttacctt gcatcttgcg   18420
ggatcattgg aggatttaaa tcagactatc tgtaccatga tccttacaca tagtgagtgc   18480
ccagtaaatg ctagccatta ttgttatcat tatatatagt ctaactggga ctgggccaca   18540
aaaggcgttg agtaccaggc gccgtttgga atttgataag tggggagcta ttgaaagttc   18600
tgagatctgc ggcatgtgcg tgagctgagt tcctggaggg ctctgggaag cacagagaag   18660
ccagacacca tctgacttcc aggtccaaaa agggtgggga cacttagggg cttcccctgg   18720
ggcttctcca ggtgccccct agcttgggag gggacctgac tgccaggccc aactctgttc   18780
ctagtcactg tggctcctgg tggctccctc atcccagacc cttggagaag ctctaaaatg   18840
acaggtcaga caacatttgg ggttctcaag ctcgtacccc agaaacctgc tagggaatgg   18900
gagtgagggg gcctttggtg gtgacaggaa gacagagcag gtggcccctc gtccaggttc   18960
aaccatgtgc tttgtttctg cgttccatgt ttcattgaca agggctctgc tgctaggtaa   19020
ataaaataac cccccccaac aatgaaagca aaagcccccct ttaaaggtga cccccaggtc   19080
ttttccatcc tgtatcgta tctcccacct cccaggaag atgagccagt aaggcccaaa   19140
aggacatggc tgtgtgggag ggtgggggggg ggcgcggtct ggctggggag actagagcac   19200
tgcaggaaga ccaagctgga atggtaggaa gaagggacga gggcctgggg ggcgagcggg   19260
gtggtgcctg ctactggagg ccacctccct cctctggcga gaggccaggg gaactgcccc   19320
atctccggac tctgggcacc aagaccttcc caggagacc ccctgggctt atgcacacca   19380
cgccttcaac cggctgcagg ctgctcggat gccacgtgtg gtgattttgc ggctgtcctg   19440
ggaggagctc aggtactcgc ttgccaaggt gccccaaatc cctccagcgg cacccccttcc   19500 tcctgtcaag gcccaggtgc ccacgcacag tcagcaggca gggaggctat tgggttaccc   19560
actcaggggc aggcagggct gttagtttct tataaattgg cccatcagat gcgctgggcc   19620
tccagagggt attgtcattg acactggaa gtttggtgga ggttggtgag agggtgaagg   19680
ggcgctgggg aaccgtgtc tgagacagga agaccagggg catctgtgta tgtgggaggg   19740
taccagtcat cacaggcaat gcctagcgca ggcctgtctc tgccatggac tgccggtgag   19800
gcctcagttt cccccatctgg gaatcaagaa gctgacttca acagtgtcac tggagtcttt   19860
tccgggctga cattccagac ttctaaaagc ccagaagtct aagatacggt tatttgttcc   19920
```

```
gagcccccca ggcaccaagc tctgggcaga tttctggggc accctggggg tcaccagacc    19980
acacctgcct tctccctgtc gcatccttga acacggccag gagttgcagt gcaggcagcc    20040
agaaggggtg gcccctgcag atgccagtct agtcttcctg ccagggatgc tagggggccac   20100 aggtgattcc gtagcagggt ggaggaggct ggggagggag catgagactt gagccagcca    20160
tcatcattga actgtaagct ccagaagtct ggggaacctc caggcctctc tcacccaagg    20220
agctggcctg gtccttggag ggccttcagt ctgtcctctg aggccaggga gatacagact    20280
ccccatggac acacagcggt ctctagtagc agacctgggt ccagaaccca gatatccaga    20340
ctctcatcca ccatcccgga gcagctgcct gccaccctcc ctgccactcc cctcccagac    20400
cccggcccag ccttgccgct tttctgttct gccagggtgt atggctgcag ccgccaggag    20460
cctgtggtgg aagtcctggc atcgggggcc atcatggcgg tggtctggaa gaagggcctg    20520
cacagctact acgacccctt tatgctctcc gtgcagtcgg tggtcttcca gggtgagggg    20580
tgaggggact ctggggcagg ggaggggtgg tggtagaacc ccagggccct ccactgggct    20640
cactgctcac cttttttgccc aacttgggga cgggatggag agggaaggtt ctggaagctc   20700
ctgctgctct ccactcccca ccctggcccc actcttcctt ccgccatttg cacttccacc    20760
ccgctctgcc ccttgaccct tctacccgtt cgcagtctct gtcttcccgg catcgctccc    20820
tcacttctct cctctttccc tctccatcct tcttcctcct tttctctttt ctgtgctgac    20880
tgcctctcct ccctcctcac cctcctggac ctgtgtcccc tcccctctgc ccctccctgc    20940
cctcttccct cggcacccac cagtggctgg gcctggaaca ccggtctgtt tgcagcagga    21000
ctcagaactc cttggattct gccctagaca gtccgcttac ggccaagagg gcacagggag    21060
cttggggagg catgatggca gcacagccag gccagggcca ccgtgtgac aggtcccccca    21120 ctgccctccc agcccccacc ctcctcctgc ttcaggacct ccccccttgc ccccttccta    21180
ggaagggcac gtcccactct gcactggaca gctgtcctgg gccggggcca gccatacctc    21240
tgggcaggaa gctcaaactt tgccatttct ggagcttggg aggggaagat ggcagagagg    21300
aagccacaga gtattggcag ctgcttctcc cccgacccct gtccccagtc tgctccctcc    21360
cactcagggt ccctgccctc ttctcagttt atccctaaac tctctggcag ggaccagggt    21420
ccccagctgg ccaagctgga gctctaaatg ggtagcagag ctgttctctt gggagtctga    21480
cacaggctca aggcaggagg gaacaaacgg ctttgggggc cctggcccca tggagagatg    21540
gccagggcag ctgagcgtgc tcctgtcctg accccctggac ccctcagctt ctcactgtgt   21600
agcctcaacc aagccactcc ttttctccaa acctcatctt ggaaaagggg aacagctctc    21660
tctctcccag ccgccaccgt gaggcctgcg caggtgtgaa tgcattttgt aaactggcgg    21720
gtgctgtccc gcaaatgtca ataactaaca cggatcgaac acttactaca tgccaggctg    21780
tttgaatgtt ttatgtcttt ttaatcctct ttactaccct atgaggtgtg tgctattatt    21840
gtccccattt tacagatgag gaaactgaga cccaagttca cacagttaca cttaaccaca    21900
gcactttgct ggcagaggtg gtaggggtgg tggggttaca agctgcgctc gcctgctggg    21960
aggtgcagcc aggggacccc gtgtaacggc tgctctcctc gtccagcctg cgaggtaaac    22020
ctgacgctgg atgacaggct ggactcccag ggcgtcctca gcacccgta cttccccagc     22080 tactactcgc cccgaaccca ctgctcctgg cacctcacgg tgagacccca cctgcctgc     22140 ccacctgtcc tctgccccaa gcacagcacc ggtcctggt aacccgggat gagagcgggc     22200
agtgtcctgc ttctgctgaa gcgcccacag gctgagccct gggtaccaat cctgctaggt    22260
```

-continued

```
ggagaggggt atgggcgagg tctccctctg tggatcacag caatgcctgt tgttgagtg    22320
actgacagac tttagcccca cctgggattc tatgtctcct tctctttgtt gttagggagg   22380
tgggttcacc aatctggcca caccccatgg gccacctgat ggcccgctcc tccctcccag   22440
gtgccctctc tggactacgg cttggccctc tggtttgacg cctacgcact gcggaggcag   22500
aagtatgatt tgccgtgcac ccagggccag tggacgatcc agaacaggag gtactacttc   22560
ctctcctccc tccagcttcc tttcctccct cccctccct ctcctccctc ccctacaggt    22620
gacccctca ttggaagccc aagtcccag cctcagaggg acagcaggga gagccagcag    22680
aggctggggc tggtgttggg cctgttgtcc tcgtcccggt ccccgctgt ggccccagct    22740
tcctctctag ctaccccagc agtctcagac actcttggtc atcagacacc ttggatgttg   22800
gttctaatta cagcaaaata gtctcatctc cttgggtgct gtaaccccct ctggcaccct   22860
caattcttca ataaatgat tccagagcca aaggactcat gggcacttcg gtgccttccc    22920
cctaaacccca aggtgtacaa tccaaggac ctctcccctta ttatgacccc ctgatgcaca   22980
gccaggtcca atcccattgc acagggtaac atggaaatca cgggtgccct ggatcccccg   23040
aatccccaac agggcacttg ccctcttccc tgctcttgcc cttgcccct ctggtaacta    23100
agtttctgac aaagaagtga gtccttccag ggatgtgagc aagagacagc agagttaggc   23160
tgagcgacca ccgtcaccag ggtcactatg gcatgaggcc aataagtgcc ccctgggcct   23220
ggccaccagg aggccatggg tgttgccagc agcttcagag gctgggtg gcagggagg     23280
caggaaaaca gagacagcgt atatggacag tttttcattt gtctgggaag aaagagaac    23340
taggcaattc aaggaagggg catttaagac aggagaggtt ccgtatctca aatgtgtgga   23400
tcatcccagc atccccagag ggagagaagg aggctcaggt acaggtaata ttgtttagag   23460
ggtggagggt gggcaagagg agaggggaggc cctcccacgg ctccattgtt ggggagcaga  23520
ggtttgggga gagagaagag gaatattgaa gcagcgatgg cagagccagg gagacccttc   23580
ccctgggaat ccaggtgaa aacgtcatc gtgtcagcgt caggaaagag gagactaccc     23640
ctcatcacag actgggctct gccctccctt ccaaccccag aattctgggg gcctaatggg   23700
ttgagagtct agtacgcaag attcatcatt tcttggtttc acagagtttg aatatccaag   23760
atgccagtct tggaagatgc caaaattgga aggctctggg gctctagaat tcttggattt   23820
ctggggtctg agttcccatt caccaacact tgtaatttgc ttgttggttg atcctattca   23880
aaaggatcat ccagacaaaa ggtgacagag aatgacaagg tttgcttgac tccctttttg   23940
caattatct gggactagga ttaaaggaaa ggagaagaat tacccatggt atgatttagg    24000
actatgctgt tgggggtgac atgggaagtg actttgggcc tgtgctgctg ggggtgacat   24060
ggggtgtgac ttcaggcctg tgctgttggg ggtgacatgg ggtgtgactt caggcctgtg   24120
ctgttggggg tgacatggtg aagcagtggc ttcagggctt tgcatttggt gatgatatgc   24180
tgatggagtg tgacatcagg cctgtgctgc tggggtgaca tgctggtccg gtgacatcag   24240
gtctgtgctg tctggagaga aggcatctgt agcatgatgg gggcacctct gggaatggct   24300
gccctgaccc tcatggagct cccttgggc tgccttgctg ctcacttagg ctgaggatgg    24360
ctggcctcac ccccgctcac aggaaccccg agggtgaccc tgagatggat ccatgattca   24420
cagttctgcg aatgatgaga acatgttttc ctgcctcccg ccctaccccca gagctgaact  24480
ttatgtctca gggaggctca gaaaggagaa ggaacagtct tgggtctgac accccccatct 24540
catccctcac ccccatggca attccatttg ccagaggtgg ggcccccagca ttcagggggtt 24600
gtgggggagtt cagtggcctg gagttagggg ctaagacagg tgttcagtgc attggcccaa  24660
```

```
caacctgtgt ggtcattggc accgttccca tttcccagag aagaaaatca aggctcggca    24720
ggattaggta acacgcagat aggtccacag ttggggtctc tcccataccc caccagccac    24780
aaacggcagg ccaaaggatg ctccacccca tgcttcctgg gggagggccc tcctccctcc    24840
ctgatgcagt cgggcaaggg tctgggtact ggggacacag ggacttcgtg agctaccctt    24900
gggtaatgac agagagagtg tggaacacgg atgggagaat cttttcccta atccaaagga    24960
atgatgcctc aatggtgaat ttgaggcgct aggacagctt ccaatggggt ggagggatct    25020
ccccagagtc tctgagcacc attgagctat agaacgtgtg ggctggactg gtcctagcac    25080
ccaacctatg gtacaggtgg ggaaactggg atcagcgatg gttaaaagga cttggccttt    25140
tgtccctgtc ttttctgcct ttcagtggtg gagatggacg tcagggtgta gctaagcggt    25200
ggctgggtgg tgaggatgag gcctggcagt tccccgtgcc cccacagctc ccctctctct    25260
gtccaggcct cccttgccat atggggtgg aagtgctcag tggaatctgg cgtcagggtt    25320
tgcatggatc tctagatgcg ctcccttcct tgtctgtgaa acaaggggtt caggccagcc    25380
ccaacctttg attacttacc catcagggag atgctgtctc ccatacaagt tgcgtttatt    25440
aattcctggc caagggccat tccaagtcag gctggtgagg cagaaagtgc tttagtgtcg    25500
aaaccagaca ggccaaggct cagcacctgt ctcctctgct tcctacctgg gcgaggactt    25560
agatctccca gcctcaggta actcatctga aaaaaggtcg tgaaagagac ccccgccctg    25620
ggaagactaa gtgagacagt gcatggagaa cactgcacac gtgggtgtgg gtcaagtgca    25680
gcgaccctgc gttcctcacc ggccgtcact ccgctctggg caggcacaag ctgaggggtt    25740
tacggtgctg gctctttcag cctcaacaac ccagcgagga atcacgtgcc tgtacagact    25800
tcatagacca gtgagacacc caagacagag acacgaagta atttgcacaa agtcacccag    25860
cttgttgagc cagacctaag gccaggcagc ctgatccgga gtgcacgtgg gtgcacagat    25920
gcatgtctgt gtgcgtgcgt ccatgcatgt ctgtgcacgt gtgtgtgcat gtgtgtgtgg    25980
tccacgtgtg cgattcttcc ctctgggcct ctagtggccc atgccagctg gtgactccct    26040
cagccatccc cagccaaccc accggcatcc ggatggggg atggatggtt tctgtggctg    26100
tcccaccagc tgcagagtgg cctgggaagt cccagccctt tcttctcaga ctttcattaa    26160
gggtccagga tccccagggg cagactcttg tccctcccc gcagactcct cctgtgcgaa    26220
tgactgtgga agggaaggca gaggtggtac ctgcgaacca tctgcactgg gacaccgtgc    26280
cctctagtta tgatcatggg cgatagtgat catcccatgt agatgctgag aaattcttag    26340
aatgagcgat gttggaaatc tgcttgtgtg ggtggcaaag acatgagagg tctagggaag    26400
agcagatttt cagacaaggc actttaggga gggggaggtg cagtccttg cccagaatg     26460 cccattgatg gagagggtgt gtcagggag agggtatctt aaccctcaag tgccagcgta    26520
gtgatgagga aaggctggcc tgggcctccc acgggctgag catccttagg cacctcacct    26580
gactcctctg agcccgtggt gcctccttca ccccgaccta cctgctgtct acctagcttc    26640
tcctggtgcc cacttgagcc cagctgaggc ctcatgccct tgagaggcct gagggtggta    26700
gaaggacttg gcctgtgaga tctgacctcg gctgctccgt ttcgcagaag ccactctcac    26760
gggctgccac caaagcacag gcttccccct ttctgggaac ctgcctcctg ccagcttcct    26820
ctcctgtgac atcacttctc ttgtgagagg ccccaccatt tccactcact cccagccagt    26880
ggggacaggc agaatcatgg gttccctagg ccnnnnnnnn nnnnnnnnnn nnnnnnnnnn    26940
nnnnnnnnnn nnnnnnnnnn nnnnnnnnnn nnnnnnnnnn nnnnnnnnnn nnnnnnnnnn    27000
```

-continued

```
nnnnnnnnnn nnnnnnnnnn nnnnnnnnnn nnnnnnnnnn nnnnnnnnnn nnnnnnnnnn    27060
nnnnnnnnnn nnnnnnnnnn nnnnnnnnnn nnnnnnnnnn nnnnnnnnnn nnnnnnnnnn    27120
nnnnnnnnnn nnnnnnnnnn nnnnnnnnnn nnnnnnnnnn nnnnnnnnnn nnnnnnnnnn    27180
nnnnnnnnnn nnnnnnnnnn nnnnnnnnnn nnnnnnnnnn nnnnnnnnnn nnnnnnnnnn    27240
nnnnnnnnnn nnnnnnnnnn nnnnnnnnnn nnnnnnnnnn nnnnnnnnnn nnnnnnnnnn    27300
nnnnnnnnnn nnnnnnnnnn nnnnnnnnnn nnnnnnnnnn nnnnnnnnnn nnnnnnnnnn    27360
nnnnnnnnnn nnnnnnnnnn nnnnnnnnnn nnnnnnnnnn nnnnnnnnnn nnnnnnnnnn    27420
nnnnnnnnnn nnnnnnnnnn nnnnnnnngg tcacacagct tgttcctggg gcaaagtcag    27480
gctgtcagtt cagctctgca gccccaggtc cagagctctg gccatgctgg gtgatgctct    27540
cctcccctct tcagcacttg ccttctgtga ccctccttc cctttaacct gtttgtagat     27600
aagggcatgg tggtgtgcac tcatccaccc atgcacctt ccttccttat tccttcttgt     27660
gttctcccca ccccttccatc catccaccca tccatgcatt tatccctcca ggcagtactt    27720
cctgacaggt cccttcctga cagggtacct cctggatgag gcaagaagga aatattcccc    27780
atattcaacg aggtgaggaa gcaaggcagg ccacacggtg caaaaatgtg ccttcagaca    27840
ctcagtactt tgtagccgag atgaattggc aggcatcgca gcagtcaggc ttctggtgct    27900
tcttggagag ggctagagag gagcacttga tggacaggag gccctggaga gccagagaat    27960
gtgcaccctc tcccagaaag ctctgcagca gaaacagaaa actcagatgc gccaagggc     28020 caggccaggg ctagagccta tgacgggggt agttttccag gctcttttct ttctttcctt    28080
ccttccttct ttccttcctt ccttctttct tttttctttc tttcttttct tttctttctt    28140 tcccttctt tctttctttc cttccttctt tctttccttc tttctcttct tcttcttcct     28200
ccttctcctc ctccaccatc acctcctcct tctccttctt ctccttttcc cttcttctcc    28260
ttttcccttc tcccttcctc ttctctgtt tctcctcctc ctcttctttc ttcttcttt      28320 tcttcttcct cttcttctcc ttctcctcct ccttctcctt tcttcctctt catctttctt    28380
cctcctcctc ctccttcttc ctccttcttc tcctcttcct cttctccttc tccttctaga    28440
ggagcaagaa tctggattat tatgtgaaat tagctcgaga ctcaatgaag caatttctac    28500
acgctgcata aacacattgt ctttatgctg agtgactccc cctgggccac tagatttcag    28560
cccctgcctt gaattcctct ctggtgcttt ctaagcagaa gcttgtccta ggggtccacc    28620
accactaccc ctgctccagg cctccagagt gagaaccaaa tgccacccag gcagacagtt    28680
tcccgggtac gcggtgaagc cttggggaaa ggttgctgcc agctacaggc tggttctagg    28740
actctcccgg gaggttaata gagagaactt cctgtagcag gcacaggtgc ctttgcctta    28800
cagcccctgc ccaaggcttg ggtgacactg cagccctcca cgcagttgct tctagggtga    28860
aacgttccac tccccctccaa cccggcttg ggttccttct ctgtctctcc acaatctccc    28920
tgtgactgtg ggagggacac cccaaggccc atgggatgtg cttgactcct cattcccgg     28980 accagtcctt tgcaacccct ggctcccctg tctacttcct gaggtccttc tgtgaggaaa    29040
acaatccatg ataactttat aaacagacat caaaaccagg gtttcctggg ttttacgagg    29100
gcaagagggc cgggtttgct cagggcgcc cctggcggt gcctcatccc ccaccggccc      29160
tgctgggctg ggggaaccac ggtgggaggc agcgactccc aacctgctct gtctcaggac    29220
ccagttactc tctgcaaaat gagcacccta aagagttgtt gcttatacag gttatagatc    29280
tatacctgta gcattagaaa ttggaacaaa attttaaaat gtttattaat tcctttaatg    29340
taattatcag cccattacac atttgaatat aaataatatt ctatgcaaat tagttgcatt    29400
```

```
ctccaaaagt aaaaacattt agtggcaaga gtactgtcct tttacatttt tgtacatttc   29460
tttaacaact ggcttcacag accacaggcg ggaccttcga atctgcctcc gagttccatc   29520
agtcccgatg tcacacatca cgtagtctct ggaaaactcg tctgtcacct tatgagagaa   29580
tgagggcaaa aaaggcaaat gacatctgaa tgttactaaa aaaaaatgac ttttggaccc   29640 caggggtcc cctgactgtg ctctgagaac tgctggttgg tgtaagggta agatcgtgat    29700
cactgtggcc agatagactt atgggggtgc cagagtctag gccaagtctg tggaagacat   29760
gggggatgta gggggctcag acctcagagc tactggtgca gtgggaatca ggatccctcc   29820
cgccaagcaa gctaggtgag ctcttctggg ccctgaggcc agattctgac gacaccttgg   29880
ctcctgcgct catgagcctc atctgtaaaa tgggatgaga gcaattcctc cctccctggg   29940
cggaggtgct gcttgaaact cagaatcccc atgcaacgag gccttgtgat gccatagctg   30000
atgaggctca gccccagcca cacaccttga gatgttaaaa cagcctcaaa gctcatcttc   30060
agctgttcag tggctggtga attgattaac ttattgaacg gttaagtgct taccacgttc   30120
tagaagttct ggggaagtgc ctggcccctg ggaatcatgg ctggctccaa ggggtttgga   30180
tttgctgtgg ggtatctcca tcggccctca ggggtattcc tgatgctctc tggatttcct   30240
tctgctttct ctgccagggg catttcagc tctccctgca gatttcagc ctgcgccctg     30300 tgtgtgtttt ccccatctgc aaagcgctct gatttgctct gtggcaggca tttctatgag   30360
ctgaggaagc tgtccccgtc tgttctgcaa gcgtgtccca cctgggatga aaaggaaccc   30420
ccggcggctg tggagggagg gttccactgt tctcagggag tggttacacc cactctgtga   30480
aggcacgccg ctgcccactt actctggggg acgaggtgcg ccggactctc tacaggagga   30540 gccctggac ctatgaccta gagatgggag ggctcctacc tgttctctgg taggagagaa    30600
agactcagcc tctctggagg ttcccccacc tgctctgttt aaacaagtgt atcttcttgg   30660
tggtgttgtg gcaggggagc aggggcggtg ttgtccagca gggatgtgag ggtgctccca   30720
cagctggggg tggtcccacc ccgtgaggcc atgcacggag aaggtgctgc ccatcagcac   30780
taagttactg gtcatgggag aaggactggt ccttccctca aacccacagt gtcacaagga   30840
ggcaggaagg atggtgccta aacgggagc actgctgccc cctcgtccca caccaacctc    30900
aaggcgaata accttgcaca tctgtggaca gtaggccagt caagggcttt tgcctcgact   30960
gacacattga agccttttgt cagattcaag gtcaacagaa ataattttc cttccctccc    31020 tccctccctc cctccctccc ttccttcctc tctctctctc tcccgnnnnn nnnnnnnnnn   31080
nnnnnnnnnn nnnnnnnnnn nnnnnnnnnn nnnnnnnnnn nnnnnnnnnn nnnnnnnnnn   31140
nnnnnnnnnn nnnnnnnnnn nnnnnnnnnn nnnnnnnnnn nnnnnnnnnn nnnnnnnnnn   31200
nnnnnnnnnn nnnnnnnnnn ntcctgcctc agcctccaga gtagctagga ttacaggcat   31260
gcgccaccac accccggcta attttgtatt tttagtagcg acggggtttc tccatgttgg   31320
tcaggctggt ctcaaactcc tgacctcagg tgatccaccc acctcggcct ctcaaaatgc   31380
tgggattaca ggtgtgagcc actgctcctg gccaattttt cttgttttat gagggaggaa   31440
agtgaggctc aaagaaggac cctgacttgc tagaacctca cagttcacag gtcactgtga   31500
ctagaattga gttttatctg gcaggcaatg ggaagccatt gaagaatttt gagcagggga   31560
gtgatatagc caggctactt tctagaagat aactctgggg gtgaacagtc acccaaggga   31620
gaaatcaggg cagaggaggc gcagtggggg tgcagctccc cctgcccctc tggctgccct   31680
gtccttgctc tgtgcacggg acccaggaga ccagccagtg cagccctgag ttgtgtctga   31740
```

```
tttcccccag gctgtgtggc ctgcgcatcc tgcagcctta cgccgagagg atccccgtgg   31800
tggccacggc cggcatcacc atcaatttca cctcccagat ctccctcaca gggcctggtg   31860
tgcgggtgca ctatggcttg tacaaccagt cggaccgtga gtatgggcag ccgggggaac   31920
cccctgcagt gactctctgc ctcttggcca tccctggaac caccaagggg gctgtaggca   31980
gctgcttatg aggccgaaca aaaggagaga gagagagaga gagagagaga gagagagtgt   32040
ttgtgcttgc acaaatttat gcagctttgt gtgtgcccac gtgtgcaagg cagccacacg   32100
ggtttgcaag aatacacact catacatagc ctgtgcgtgt gtctggatat gtatgtgtgt   32160
tctgtgcgtg tgtctggata tgtatgtctg cttggaatgt gtacacgggt gcccaggaac   32220
acatggcgcc tgtccatgtg tgtgtgagtg aacaggtgca ttcatgtctt tgtgcgcctt   32280
tggggctatg catggcctaa cggcgccctc cctgcctcca cggtcccctg tggtttcgca   32340
gcctgccctg gagagttcct ctgctctgtg aacggactct gcgtccctgc ctgtgatggg   32400
gtcaaggact gccccaacgg cctggatgag agaaactgcg gtgagcaacc cgcccgcgca   32460
tccctcctct ccccgccaat ccctcctccc tcctcacctt ccctgctctg agctgagtgg   32520 agacccccact cctacatgta gcttccatta tcaacaccca ggaagtgggg ttctctcact   32580 gtgcggggt ggcaagatga caccacctcg tgggacagtg gcaggacaa gtggggagcc   32640 aggtctcctg acttccagct cagggctatc accccacc ctgtcccagc cagccttcca   32700 ataaggaac agaatgggtg agggagatgt cccctcctc tgccctgtca aggtttaaa   32760 tatgtgtttt tccaaaggaa gcaagatgtt catggccggg gggatgatcc tgccacggtg   32820
ctgggggagg tgcctgatat tcggaaactg aacatctggc ttcaagttct ggctcagcca   32880
agtgaccttg acaagtcac ctcatctgtt tccaccaatg aaatggggta tctcacaggg   32940
ttgctgtgaa actttgggtg taaaatagca gagaaagagg ccgggcgcag tggctcacgc   33000
ctgtaatccc agcactttgg gaggccgagt agagcggatc aactgaggtc aggagttcaa   33060
gatcagcctg gtcaacatgg tgaaacccta tctctacaaa aagtacaata attagctggg   33120
tgtagtggca ggagcctgca atcccagcta cttgggagtc tgaggcagga gaatcgcttg   33180
aacctgggag gttgcagtga gattgtgcca ttgcactcca gccttcatga caagagtgag   33240
attctgtctc aaaaaaataa taataataaa ataaataaa ataaaattaa aataaagtag   33300
cagtgagaga tttgtgatcg gtaatgtgca atacagcaca ccttccacag gcatcgccaa   33360
gccccagctg gctcctctgg cttcctccca cctgtcccct ctctgtatct ccacacagtt   33420
tgcagagcca cattccagtg ccaagaggac agcacgtgca tctcactgct taaggtctgt   33480
gacgggcagc ctgactgtct caacggcagc gatgaagagc ggtgccagga aggtagggca   33540
gggcctggct gagtgtctgc agggacacca aaggcagtct aggcctgcta catgcttcag   33600
caaaggtttc tagcttcttg tcccaacacc caccaacccc tctgtattta cacctgtata   33660
tctatccatc catccatcca tccatccatc catccatcca tccactcatc tatcttctgg   33720
tctccaatca ccctgtctgt ccatcgattc atacagctac ccatttatcc atgcatctac   33780
tgacctttgc aaccactgat cttcctatca tcaaactgtc aatctaccca cttattagtt   33840
tggctgacta cctgcctgta atggccactg ttccatccat ctgtccatcc atccatccat   33900
catccatcca tcatccatcc atcatccatt catccatcca tccacccatc catcatccat   33960
ccatccatcc atccatccat catccatcca tcatccatcc atccacccat ccatcatcca   34020
tctatccatt catccatcaa tctatccatc atccatccat ccatccatcc atccatccat   34080
acatccatcc atcatccatc catccatcat ccatccaccc atccatcatc catccatcca   34140
```

```
tcatccatcc atccatctac ccatccatcc atccatccat ccatccatcc atccacccat    34200
ccacctaccc atccactgat ctccctagca ccctgtctat ccactggtcc ttacatccac    34260
acatttatcc aaccttctag ctgtctgtca gtctccctaa tggaccacca ctccacccat    34320
tggcttttct gctcaatctt ctgtctgggt ctatttatcc atccatccat ctacccaccc    34380
aactgaccaa ctgaccatca cttgcagact atccagcaat aggcaaggtg cagtgaggaa    34440
gtgggaataa aacagcagag atgcggcccc tgccttccaa ggcttatctg ttaggacgat    34500
acgatgagtg actctcctgc cgtgtaggca gattgtgggg cagggaggag gtcagacatg    34560
aaaagcttcc tggaggaggt aggcgtttgg cccttggtga gagctaaaac ttaaatgggc    34620
aggaggaaag gagagcggca aagaccaagt ggtggagtgg aaagttcttt acagtgaaga    34680
gcagggagga aaaggtggca accgggcagg gccagagcct gggagactgc caggctaggt    34740
ggggactctg gtctgaaagt ggaggcatag ttctgctttg aagttccaca ccagaggggg    34800
aggcatgatc ttgtggtcag gagctccagt ctgagaatgg agacactgct ttgcactcaa    34860
cagaccagtc tcagtggagg ggctgggggt gcggggaca tggcctgctt ttaggaaacc     34920
ctaaaggaga ctcaggaaaa gactctccag tcacctcctg gatcttctgg ctccatcgtt    34980
cctgcaccct actttggaag tctcctttgg ggctcagaga cccaccttct gtgccctgtc    35040
cccatcccct ctgtcccagg ggtgccctgc gggacattca ccttccagtg tgaggaccag    35100
agctgcgtga agaagcccaa cccacagtgt gatgggcggc ccgactgcag ggacggctca    35160
gacgagcagc actgtggtga gccctgcccg gctgcctggg gccctggagc ttgggaggga    35220 gggggtgcc cacagcagga cgctggaggg aaatctcacc cctgttccct ggtctctctc     35280
tatcccaccc tctgcccct cacacctggg tctttatgat ctctcccct ccattgttct      35340 cctgttctct gtctctccat ctctttcctt tgcccttcct ctctgtctgt ctgcttctcc    35400
ccttcccctc ctcctctgtc cacccccacca cctgccccc atcccagac tgtggcctcc    35460 agggcccctc cagtcgcatt gttggtgggg ccgtgtcctc cgagggtgag tggccatggc    35520
aggccagcct ccaggttcgg ggtcgacaca tctgtggggg cgccctcatc gctgaccgct    35580
gggtgataac agctgcccat tgcttccagg aggacaggta aggggaggg tgtggggcc     35640 taggccataa gaggcaaggg cagggaaggc tgggtgggcg gtgcactgtg tctgagctct    35700
ttgcagatag agggaagggt ggtgaacccc tcagacaggc tactgtgatg tgggttctag    35760
ttctggctcc accaggacct actgggtccc tggacacatt gttctacctc tctgccatct    35820
actttcggta tcttgcttta agttgggcca gtgattcatt cattcatctc attcactcat    35880
tcagcaacac ttgttgtgct cttactatgt gccaggggct atggtagatg ctggggatac    35940
agtaaaggac agaactgccc tacctggtca taagctatga cactccccca ggtgtgcat     36000 gaagtagcag ggagccccca ggggacatct catcaggcct catggccatc tttcccatct    36060
gcttggtggg ctgaaacctc ccccaatcca cccgcagaca gatctgggct ccagatcctg    36120
cccccagaac ctgcacaggg atcctctttt gtatcctctc tggggcacag gttgctctga    36180
ccacctagct ctcttaaacc ccatcccagg ctccgcactg ccctcaggta gagagacccg    36240
aaggctgccc gcctgccacg caggcagctg actgcggcag tccaattcct ccacggtcaa    36300
cgcccacccc ctcccacca ggacccacca acctcgggga actcagagca gcctgggtcc    36360
gtaaagtgct aaggaaaaaa gaaatttgtg tcgagggcct ggccctgtgc tacatttttt    36420
agatatacgg tcttactgga ttctctcaag aacagtcgag tagaaaatgc cgttcccatt    36480
```

```
ttgcagatga ggtggcagag gcttagagag gcacacacat gtctagggag ggataaagct    36540
ggggcctgga acccaggcag gccgagggggg tgaaggctga aagctgtacc accagctagg    36600
cggccttcag ggagggaagg gagggctggg tgtggagggc actgtcccag gcggcagttg    36660
gctatcctga gggtccctgg atggggagag gcagcttccc cccacccac cccaccccac     36720
cccaccccac cccagcatgg cctccccggc gctgtggacg gtgttcctgg gcaaggtgtg    36780
gcagaactcg cgctggcctg gagaggtgtc cttcaaggtg agccgcctac tcctgcatcc    36840
gtatcacgaa gaggacagcc acgactacga cgtggcgctg ttgcagctcg accacccggt    36900
ggtgcgctcg gccgccgtgc gtccagtctg cctgcccgcg cgctcccact tcttcgaacc    36960
cggcctgcac tgctggatca ctggctgggg cgccctgcgc gaaggcggta agcggccggc    37020
acgtacggcg ggaggcggag ggagaccgtg cggagccaga ccgtgcggag ccgcttcgcc    37080
acacccggcc tggagaaggg cggggctggg gggtcccggg gctccacccc acaggccctt    37140
tactcctggg attcaaattg gctgaattt tacggtacaa aaccacccttt taatgcggcc     37200
cataggcccc cgcccctgcc ctcctagctc ttgccttcat tctggaaggg cattatgtgt    37260
ggggcaaagg ggcaggtctg gggggccact gcccacgtgc aagctccacc tgctgctcct    37320
tggcctgcaa gggcggaggc tcttaattat tagcactttc cacatccagg ctgaatttta    37380
ggggaacatg acttcacgta atccatccaa tagccctggg gcggaagctg tggccccatt    37440
ttatggatgg agaaaccaag gctccacaca cagccagaga ggactggagc agagattaga    37500
acccaggact ggctgcctcc agagcccccg ctcttcctgc tactgctctc agaaacaggg    37560
tctctccct ttctaccttc actaaccaga gctggctgtc cctggcggcc accgtacagt      37620
tttggggaca cagacccagc tggcaaacct acagacatgc cctgcagcct tagtgttggt    37680
ggcttcacaa atgtgtacag tgacttacaa tctggaggca ggcagggctg cagagatatt    37740
ttaaggatgg gaaaactgag gctcagagga acagtgactt acccaagggg atggcagaag    37800
tcatggcaaa gcaaaggctg gttcattcac tattccttca ctcattcagt cactcaatga    37860
cactttctga gcaccagcta tgtaccaggt atggggttaa gggaagggta catcaggatg    37920
gagagagaac attctcgggg gagacagtga taagagctgg catggatggg gaggtgtagg    37980
gacagtggag acacagaggc ggctcctgcc taggtagggt caagggaggc ttctagggga    38040
gggttgttta agctgaggcc tgaagatga gttggcaaca tccagacaaa gggaaaagac     38100
attcaggtga agacacaggt gccaagacag gaagacctga gaacatccgc agcctgccag    38160
aggggccaag gtgggggca ggtgtgcctg ggcaaggagc agccagtgta aggatcttgg      38220
gccaggagtt ctccctccta cctgcacctt agaaccatgc gtggttcaag aaaaacccttt   38280
gtatcaaggc ttcccagggg actgtgatat gctgccctcc tggagaagca ttggggtgga    38340
ctgcagagtt ggggctctgc agagttgtaa ggaaacggtg aaggggtcag atgtgggctt    38400
tggaaacatc cccaggtgct ataacatagc agcgaagagc cagccagagc ccagaggtgc    38460
ctgaacagac agaggtgggg gacaagacgc tggagtaaga cactcatcca cacgggcttc    38520
tttttttttt gagatggagt ttcactcttg ttgcccaggc tggagtgcaa tggtatgatc    38580
ttggctcact acaacctctg cctcctgggt tcaagcgatt ctcctgcctc aacctcctga    38640
gtaactggga ttacaggcat gcaccaccac acacagctaa ttttgtattt ttagtagaga    38700
cagggtttct ccatgttggt caggctggtc ttgaactctt gacctcaggt gatctgtccg    38760
ccttggccac ccaaagtgct gggattacag gcgtgagcca cttcgcctgg ctctccacat    38820
gggctttggt caggggctct gtctccatga accccacaga gaaagagcta gaataaagtg    38880
```

```
acaggGAGGC AGAGGGGCAG GTGCAACCCC AGCAGAGGTA AGGGTGGGCA GAGCAGGAGA   38940
gaagcaggct cctgagatgc aaaggagcgt tagggagaac aggtgctcca ggttccttag   39000
atctcacttc tgcccttgac cacggacagg ccccaccagc aatgctctgc agaaagtgga   39060
cgtgcagttg atcccacagg acctgtgcag cgaggcctat cgctaccagg tgacgccacg   39120
catgctgtgt gccggctacc gcaagggcaa gaaggatgcc tgccaggtga gtaccccag    39180 tgtgggaggg agaaagaaag gatgctgctc acatcatcag ggtctggccc tatgctcaca   39240
tcagcctgct gaagcctccc atcctcccag aaaggtggcg atggccgccc tcactttaca   39300
gaagaggaga ctgggggttg aagggttga ggagcttgcc caaggttgca gagccatgga    39360
tcagaagaaa tgctgtgacg ggcaggtgtt aggctcaaac ccagttctgc tccttgccca   39420
tcacaaggca ctaggcccag ggtcccacag tgaggtggat gcaaggaaga agaaaggcgt   39480
gtcagccaca aagggcggt ggagacagag tgggggtgtg gggacacagc cacagttcca    39540
ggagggccca ggctggctgg aggacaaaga gggttggctt ggactctctc catttagcag   39600
gcgaggaaaa agcagagctt taagactgaa cgtgagtctc tggcacccag tcaattccca   39660
acagtcagga cttaatcccc atggcccctc gcctggaaag ggggtgccct taccctgctt   39720
cagtcctttc tcctttcccc ctttcagggt gactcgggtg gtccgctggt atgcaaggca   39780
ctcagtggcc gctggttcct ggcagggctg gtcagctggg gctgggctg tggccggcct    39840 aactacttcg gcgtctacac ccgcatcaca ggtgtgatcg gctggatcca gcaagtggtg   39900
acctgaggaa ctgccccct gcagagcagg tcccacctct tggactcaga gagcccaggg    39960
caattgccaa gcaggggac aagtattctg ggggagggg ggcgcgagca ggccctgtgg     40020
tggcaggagg tggcatcttg tcttgtccct gatgtctgct ccagtgatgg caggaggatg   40080
gaggagtgcc agcagctggg ggtcaagacg tccctaggg acccaggccc acacccagcc    40140
cttctgcctc ccgattctct ctcctctgtc cccttcctcc actgctgcct attgcaagga   40200
agtggctcag cagcaagaat gctggctcta cgtccccagg agtgtctgag ctgtgcccca   40260
ctctgtacag aggctgcttg ggcagccttg cctctagaga gcagatgcca gcttcggaag   40320
cccctggtct aacttgggat ctgggaatgg aaggtgcccc cataggaggg gaccctcaca   40380
gccccgggga ctgccaggtg ggccggctgc caccgtaagc caaaaaaggt ggggaagccc   40440
tgactccaag gtccttgccc cacccctgcc tgccacctgg cccctcacag cccagaccct   40500
caccggcagg tgagctcagc tgcccttttgg aataaagctg cctgatccaa gcccctctgc   40560
tggagtttga atgggaccc gggcaccagc cttacgccct tgactgaagc agtccctgct    40620
tccagctcag cctgattgac aagtgtccag aaggccaagg tgggctcagt ggcagcaggc   40680
gtggccactg agggccactg agggctggga cctctgggc agctgccag gtcctaggag     40740 aaatgctggg aaggcaatcg tttggggacc ctcaggtcac agggagggat gtgaggagca   40800
atggtctcct tttggaacct taaaggaaac aggctcagag aggcggttaa gacatcctca   40860
tggtggcact gggggttagg agtggaggtg gcatagactc cggtctccca gttccccgtc   40920
tgccatggcc ccctccagcg cgacactcat tcccttttgaa ttctttgaat cattgagtag   40980
gcactgtgct ggcgccacag gggtgaagga cctggctcct gaccccagaa gcaatgggga   41040
tgatccagtg ggaagggat ggaggggagc gcagaccggg caagtcaagg caagctgcct    41100
ggaggctgtg agacttgagc tgggggttcag aggtagtcaa ggtgggaata tccgggaggg   41160
atattccagg caggggaaga gcatgtgcaa aggcacagag tcccggaaga atgagacaca   41220
```

```
ctaggaccca gcaagccgag tgagtgttac aacagagctt gagagggaa ggactgaaga    41280 attcagaggg gcaaaccgag gcgggatagc agagcctgga gttgagccaa ggatttgacc    41340
ctgcaagttc tgtggagcca tggtaggctc tatagcatag gggtgacatg agtggactca    41400
cattttggaa ccagccttgg caccagtgtg cagggagtgg caggcaggga ggctgggtag    41460
gccactgcag gattccggga aggagaggat gggccgggac tgagcggcgc cacgggatgt    41520
actggaggat gatttcggac ccctgagggc agttgtgacg gagccggggg acccgctgga    41580
ggtgagggtg ggtgctcaag tgtggacaac tctttctgga agcctaactg ggagcggaag    41640
ggacagaggg cgcttcagag gggccctaga ctgaagaggg gtttttccag catgggcgct    41700
gctgccaggt ctgtgggtga atgaggcaga aggggaacca gggacgggaa gcacccacct    41760
gggtcctgcc aggaggagcc ggggcagctg ggcgagcagg gggcgtctcc agagcaggtg    41820
ggcagaacac atgcagaatc ccttgggtga tctggaatca ccgtgggccc taccccagtc    41880
ttcgtcggaa tcctggaggg gtggggatg tcatctgttc tcctaacaag cctcctggcg    41940
actcttttgc aaggatagtt ggacccccaaa agtgaggcca gctttgaagt ggagcgtcct    42000
c                                                                   42001
```